United States Patent
Zeiger et al.

(10) Patent No.: US 9,234,244 B2
(45) Date of Patent: Jan. 12, 2016

(54) DIAGNOSTIC TOOL FOR DIAGNOSING BENIGN VERSUS MALIGNANT THYROID LESIONS

(75) Inventors: Martha Allen Zeiger, Bethesda, MD (US); Nijaguna B. Prasad, Columbia, MD (US); Steven K. Libutti, Potomac, MD (US); Christopher B. Umbricht, Towson, MD (US)

(73) Assignees: The United States of America, as represented by the Secretary, Department of Health and Human Services, Washington, DC (US); The Johns Hopkins University, Baltimore, MD (US)

(*) Notice: Subject to any disclaimer, the term of this patent is extended or adjusted under 35 U.S.C. 154(b) by 608 days.

(21) Appl. No.: 12/675,209

(22) PCT Filed: Aug. 27, 2008

(86) PCT No.: PCT/US2008/010139
§ 371 (c)(1),
(2), (4) Date: Jul. 26, 2010

(87) PCT Pub. No.: WO2009/029266
PCT Pub. Date: Mar. 5, 2009

(65) Prior Publication Data
US 2010/0285979 A1    Nov. 11, 2010

Related U.S. Application Data

(60) Provisional application No. 60/966,271, filed on Aug. 27, 2007.

(51) Int. Cl.
*C12Q 1/68* (2006.01)

(52) U.S. Cl.
CPC ........ *C12Q 1/6886* (2013.01); *C12Q 2600/106* (2013.01); *C12Q 2600/112* (2013.01); *C12Q 2600/136* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,965,188 A | 10/1990 | Mullis et al. | |
| 5,556,752 A | 9/1996 | Lockhart et al. | |
| 5,578,832 A | 11/1996 | Trulson et al. | |
| 5,593,839 A | 1/1997 | Hubbell et al. | |
| 5,599,695 A | 2/1997 | Pease et al. | |
| 5,631,734 A | 5/1997 | Stern et al. | |
| 2007/0037186 A1* | 2/2007 | Jiang et al. | 435/6 |

FOREIGN PATENT DOCUMENTS

| | | |
|---|---|---|
| EP | 0721016 | 7/1996 |
| EP | 0728520 | 5/2001 |
| EP | 0799897 | 6/2006 |
| WO | WO 95/22058 | 8/1995 |
| WO | WO 97/02357 | 1/1997 |
| WO | WO 97/27317 | 7/1997 |
| WO | WO 97/29212 | 8/1997 |
| WO | WO 2005100608 | * 10/2005 |

OTHER PUBLICATIONS

Promega Catalog. 1997, p. 78.*
Rosen et al. Surgery. 2005. 138: 1050-1057.*
Liu et al. Clinical Immunology. 2004. 112: 225-230.*
Coleman, R. Drug Discovery Today. 2003. 8: 233-235.*
Saetre et al. Molecular Brain Research. 2004. 126: 198-206.*
Ito et al. AntiCancer Research. 2002. 22(4):2385-2389.*
Hanke et al. Clinical Chemistry. 2007. 53: 2070-2077.*
Palmer et al. BMC Genomics. 2006. 7:115.*
Min et al. BMC Genomics. 2010. 11:96.*
GeneCard for HMGA2, available via url: <genecards.org/cgi-bin/carddisp.pl?gene=HMGA2 >, printed Jul. 17, 2012.*
Ito et al. Cancer Letters. 2003. 200: 161-166.*
Beige et al. Genes Chromosomes and Cancer. Oct. 2007. 47: 56-63.*
Free Dictionary definition for "measuring", available via url: < thefreedictionary.com/measuring>, printed on Mar. 18, 2014.*
Barden et al., "Classification of follicular thyroid tumors by molecular signature: results of gene profiling", Clin. Cancer Res., May 2003, 9(5), 1792-1800.
Berlingieri et al., "Inhibition of HMGI-C protein synthesis suppresses retrovirally induced neoplastic transformation of rat thyroid cells", Molec Cell Biol. 2005:15, p. 1545.
Caraway et al., "Diagnostic pitfalls in thyroid fine-needle aspiration: a review of 394 cases", Diagn. Cytopathol., 1993, 9(3), 345-350.
Cerutti et al., "Molecular profiling of matched samples identifies biomarkers of papillary thyroid carcinoma lymph node metastasis", Cancer Res., Aug. 15, 2007, 67(16), 7885-7892.
Chee et al., "Accessing genetic information with high-density DNA arrays", Science, Oct. 25, 1996, 274(5287), 610-614.
Dudoit et al,. "Comparison of discrimination methods for classification of tumors using DNA microarrays", Journal of the American Statistical Association, 2002, 97, 77-87.
Eberwine, "Amplification of mRNA populations using aRNA generated from immobilized oligo(dT)-T7 primed cDNA", Biotechniques, Apr. 1996, 20(4), 584-591.
Fedor et al., "Practical methods for tissue microarray construction", Methods Mol Med. 2005, 103, 89-101.
Finley et al., "Advancing the molecular diagnosis of thyroid nodules: defining benign lesions by molecular profiling", Thyroid., Jun. 15, 2005, (6), 562-568.
Gharib et al., "Fine-needle aspiration biopsy of the thyroid. The problem of suspicious cytologic findings", Ann Intern Med., Jul. 1984, 101(1), 25-28.
Goellner et al., "Fine needle aspiration cytology of the thyroid 1980 to 1986", Acta Cytol., Sep.-Oct. 1987, 31(5),587-590.
Goellner, "Problems and pitfalls in thyroid cytology", Monogr Pathol., 1997, (39), 75-93.

(Continued)

*Primary Examiner* — Carla Myers

(57) ABSTRACT

The present invention relates to the use of genes differentially expressed in benign thyroid lesions and malignant thyroid lesions for the diagnosis and staging of thyroid cancer.

6 Claims, 24 Drawing Sheets

(56) References Cited

OTHER PUBLICATIONS

Golub et al., "Molecular classification of cancer: class discovery and class prediction by gene expression monitoring", Science, Oct. 15, 1999, 286(5439), 531-537.
Gordon et al., "Using gene expression ratios to predict outcome among patients with mesothelioma", J. Natl. Cancer Inst., Apr. 16, 2003, 95(8), 598-605.
Hacia et al., "Detection of heterozygous mutations in BRCA1 using high density oligonucleotide arrays and two-colour fluorescence analysis", Nat Genet., Dec. 1996, 14(4), 441-447.
Hamberger et al., "Fine-needle aspiration biopsy of thyroid nodules. Impact on thyroid practice and cost of care", Am. J. Med., Sep. 1982, 73(3), 381-384.
Huang et al., "Gene expression in papillary thyroid carcinoma reveals highly consistent profiles", PNAS USA., Dec. 18, 2001, 98(26), 15044-15049.
Jarzab et al., "Gene expression profile of papillary thyroid cancer: sources of variability and diagnostic implications", Cancer Res., Feb. 15, 2005, 65(4), 1587-1597.
Kozal et al., "Extensive polymorphisms observed in HIV-1 Glade Bprotease gene using high-density oligonucleotide arrays", Nat Med., Jul. 1996, 2(7), 753-759.
Lockhart et al., "Expression monitoring by hybridization to high-density oligonucleotide arrays", Nat Biotechnol., Dec. 1996, 14(13), 1675-1680.
Mazzaferri et al., "Long term impact of initial surgical and medical therapy on papillary and follicular thyroid cancer", 1994, 97, 418-428.
Mazzaferri, "Management of a solitary thyroid nodule", N. Engl. J. Med., Feb. 25, 1993, 328(8), 553-559.
Mechanick et al., "Progress in the preoperative diagnosis of thyroid nodules: managing uncertainties and the ultimate role for molecular investigation", Biomed Pharmacother, Sep. 2006, 60(8), 396-404.
Miller et al., "Optimal gene expression analysis by microarrays", Cancer Cell, Nov. 2002, 2(5), 353-361.
Needleman et al., "A general method applicable to the search for similarities in the amino acid sequence of two proteins", J. Mol Biol., Mar. 1970, 48(3), 443-453.
Pearson et al., "Improved tools for biological sequence comparison", PNAS USA, Apr. 1988, 85(8), 2444-2448.
Radmacher et al., "A paradigm for class prediction using gene expression profiles", J. Comput Biol., 2002, 9(3), 505-511.
Ramaswamy et al., "Multiclass cancer diagnosis using tumor gene expression signatures", PNAS USA, Dec. 18, 2001, 98(26), 15149-15154.
Ravetto et al., "Usefulness of fine-needle aspiration in the diagnosis of thyroid carcinoma: A retrospective study in 37,895 patients", Cancer, Dec. 25, 2000, 90(6), 357-363.
Raychaudhuri et al., "Basic microarray analysis: grouping and feature reduction", Trends Biotechnol., May 2001, 19(5), 189-193.
Rosen et al., "A six-gene model for differentiating benign from malignant thyroid tumors on the basis of gene expression", Surgery, Dec. 2005, 138(6), 1050-1056.
Sauter et al., "Predictive molecular pathology", N. Engl J. Med., Dec. 19, 2002, 347(25), 1995-1996.
Schulze et al., "Navigating gene expression using microarrays—a technology review", Nat Cell Biol., Aug. 2001, 3(8), E190-E195.
Sherman, "Thyroid carcinoma", Lancet, Feb. 8, 2003, 361(9356), 501-511.
Simon et al., "Analysis of gene expression data using BRB-ArrayTools", Cancer Inform, Feb. 4, 2007, 3, 11-17.
Simon et al., "Pitfalls in the use of DNA microarray data for diagnostic and prognostic classification", J. Natl Cancer Inst., Jan. 1, 2003, 95(1), 14-18.
Siraj et al., "Genome-wide expression analysis of Middle Eastern papillary thyroid cancer reveals c-MET as a novel target for cancer therapy", J. Pathol., Oct. 2007, 213(2), 190-199.
Smith et al., "Comparison of biosequences," Adv. Appl. Math., 1970, 2, 482.
Staudt, "Gene expression profiling of lymphoid malignancies", Annu. Rev. Med., 2002, 53, 303-318.
Suen, "How does one separate cellular follicular lesions of the thyroid by fine-needle aspiration biopsy?", Diagn Cytopathol., Mar. 1988, 4(1), 78-81.
Tatusova et al., "Blast 2 Sequences, a new tool for comparing protein and nucleotide sequences", FEMS Microbiol Lett., May 15, 1999, 174(2), 247-250. Erratum in: FEMS Microbiol Lett, Aug. 1, 1999, 177(1), 187-188.
Vallone et al., "Neoplastic transformation of rat thyroid cells requires the junB and fra-1 gene induction which is dependent on the HMGI-C gene product", EMBO J., Sep. 1, 1997, 16(17), 5310-5321.
Van de Vijver et al., "A gene-expression signature as a predictor of survival in breast cancer", N. Engl. J. Med., Dec. 19, 2002, 347(25), 1999-2009.
Van't Veer et al., "The microarray way to tailored cancer treatment", Nat. Med., Jan. 2002, 8(1), 13-14.
Wang et al., "High-fidelity Mrna amplification for gene profiling", Nat Biotechnol., Apr. 2000 18(4), 457-459.
West et al., "Predicting the clinical status of human breast cancer by using gene expression profiles", PNAS USA, Sep. 25, 2001, 98(20), 11462-11467.
Wright et al., "A random variance model for detection of differentialgene expression in small microarray experiments", Bioinformatics, Dec. 12, 2003, 19(18), 2448-2455.
Yarden et al., "Human proto-oncogene c-kit: a new cell surface receptor tyrosine kinase for an unidentified ligand", EMBO J., Nov. 1987, 6(11), 3341-3351.

* cited by examiner

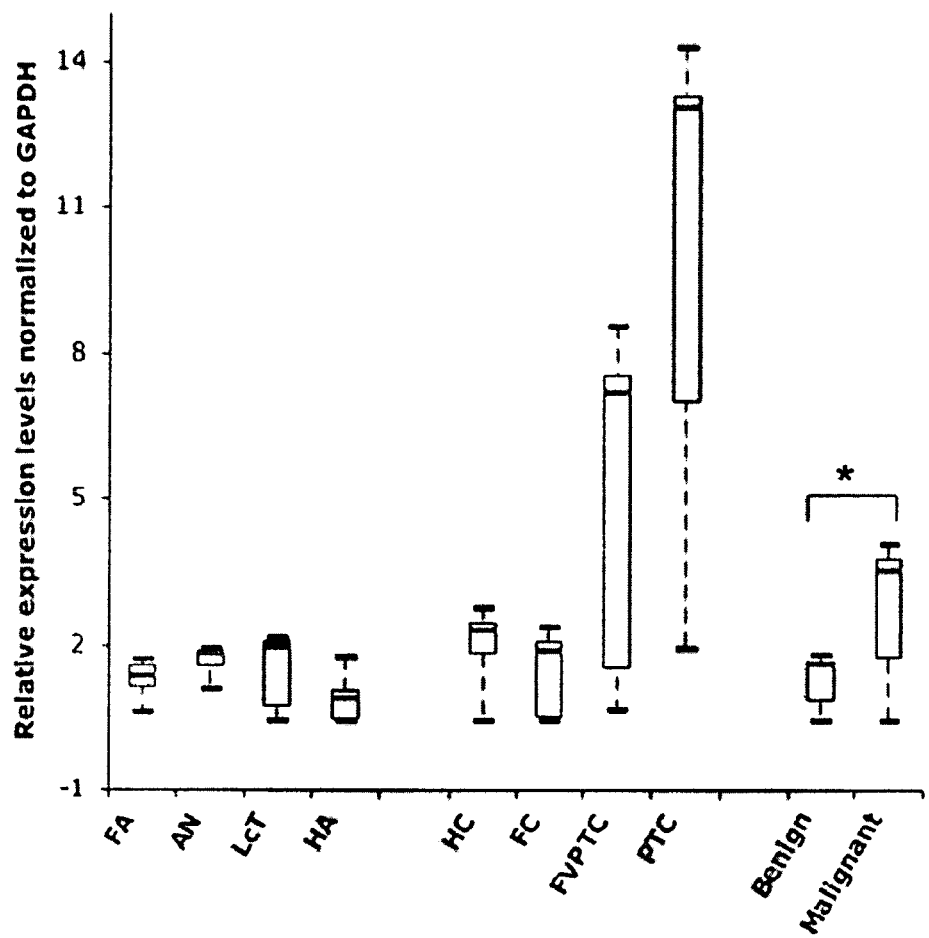
FIG. 9 (cont...)

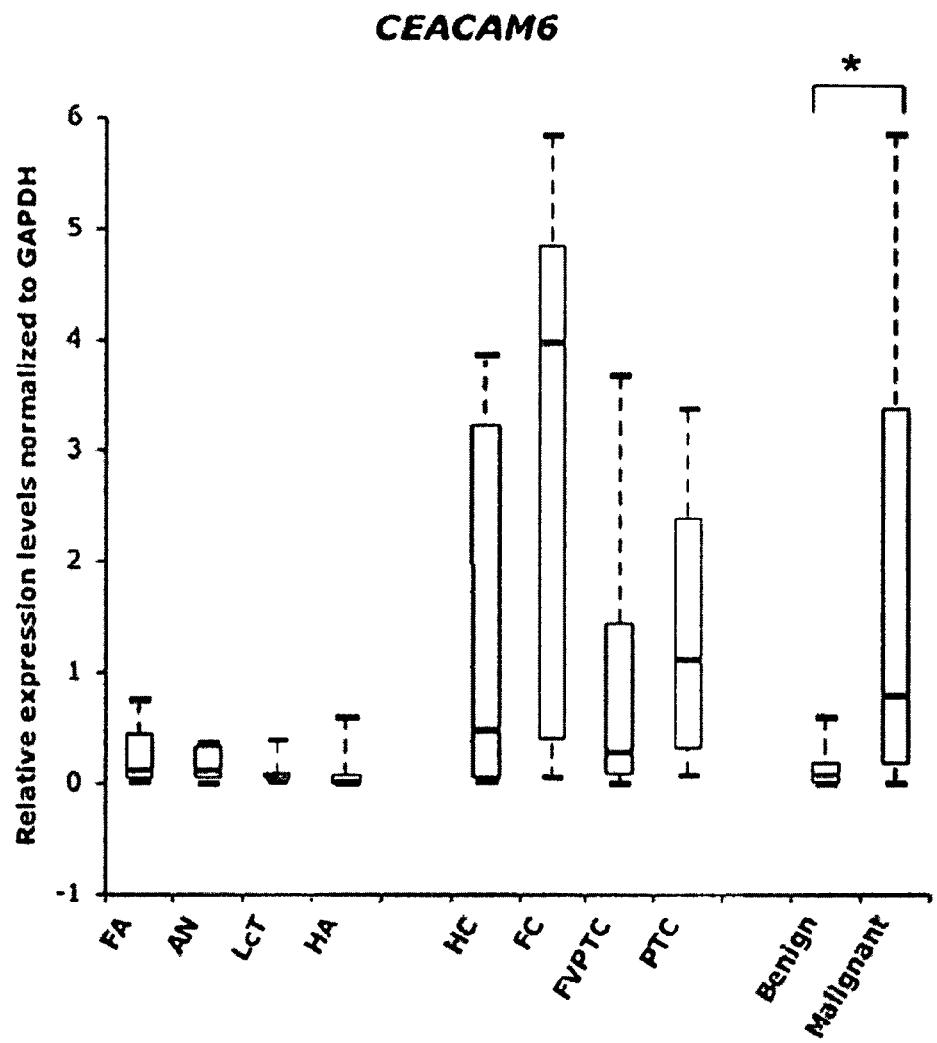
FIG. 9 (cont...)

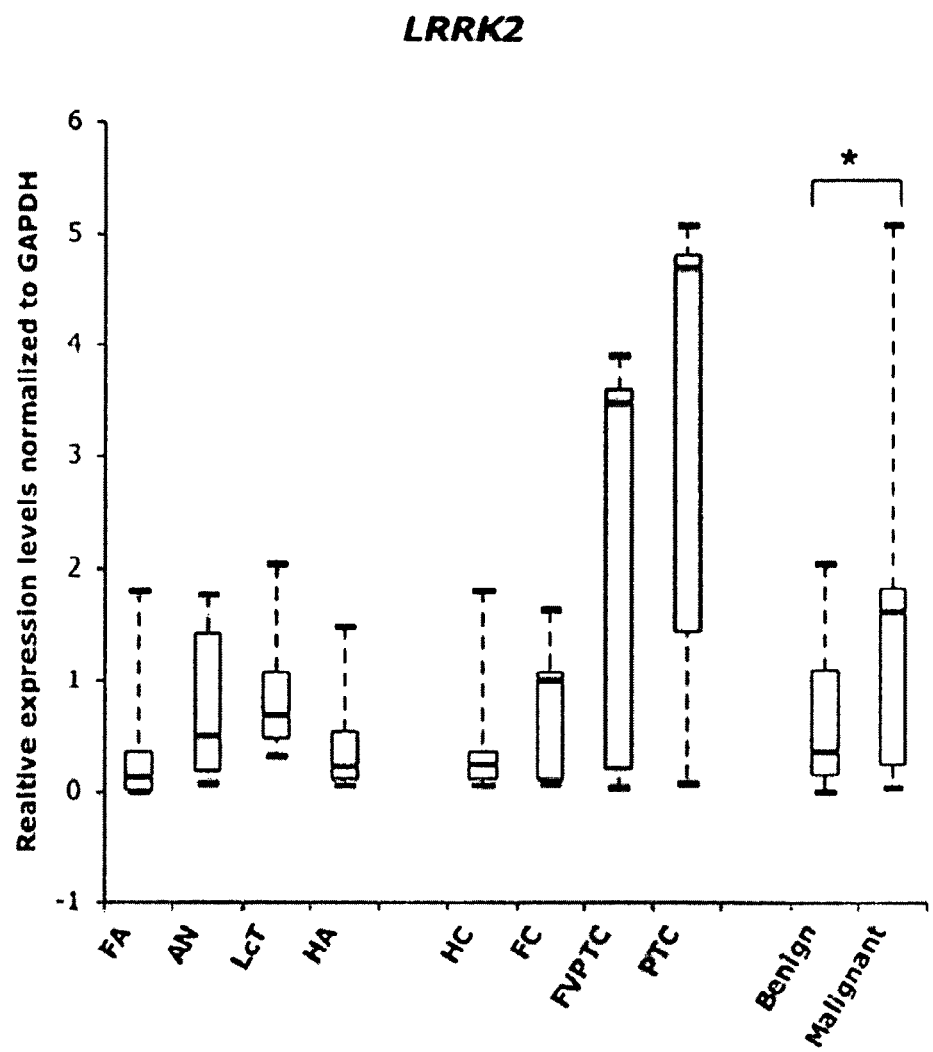
FIG. 9 (cont...)

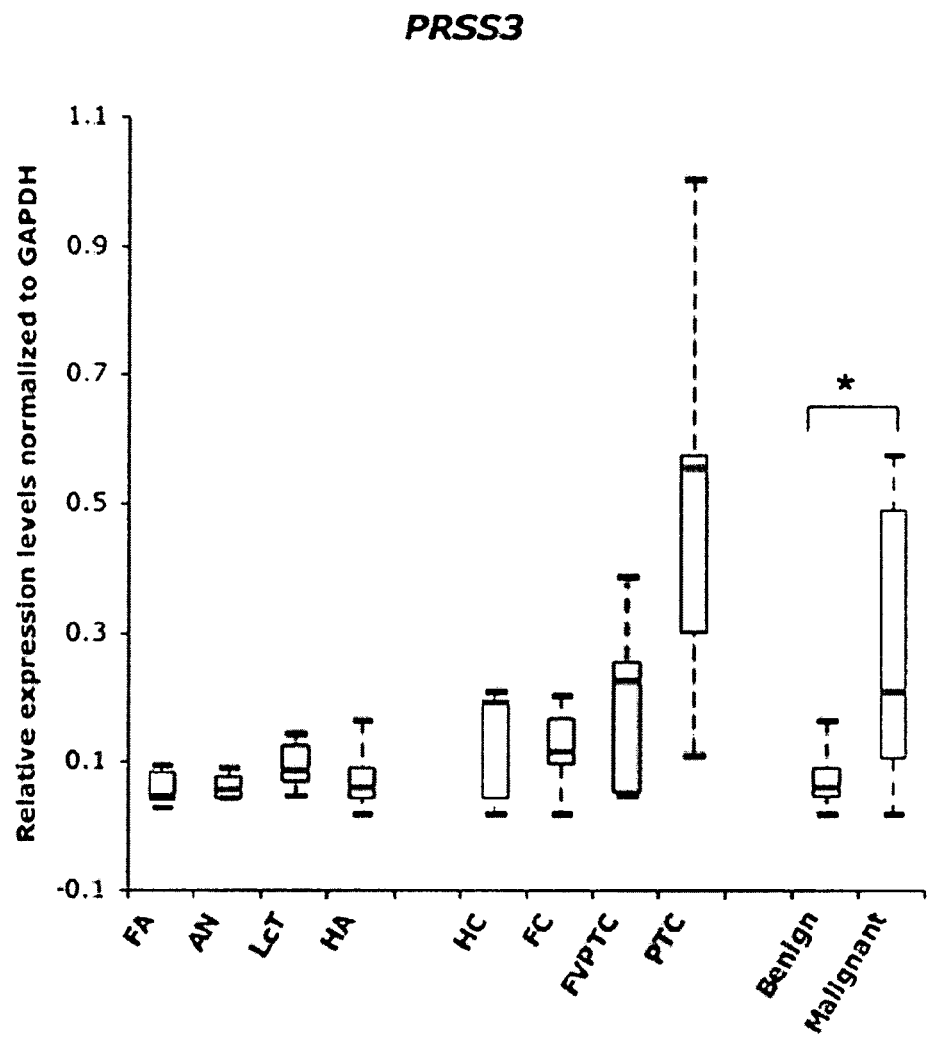
FIG. 9 (cont...)

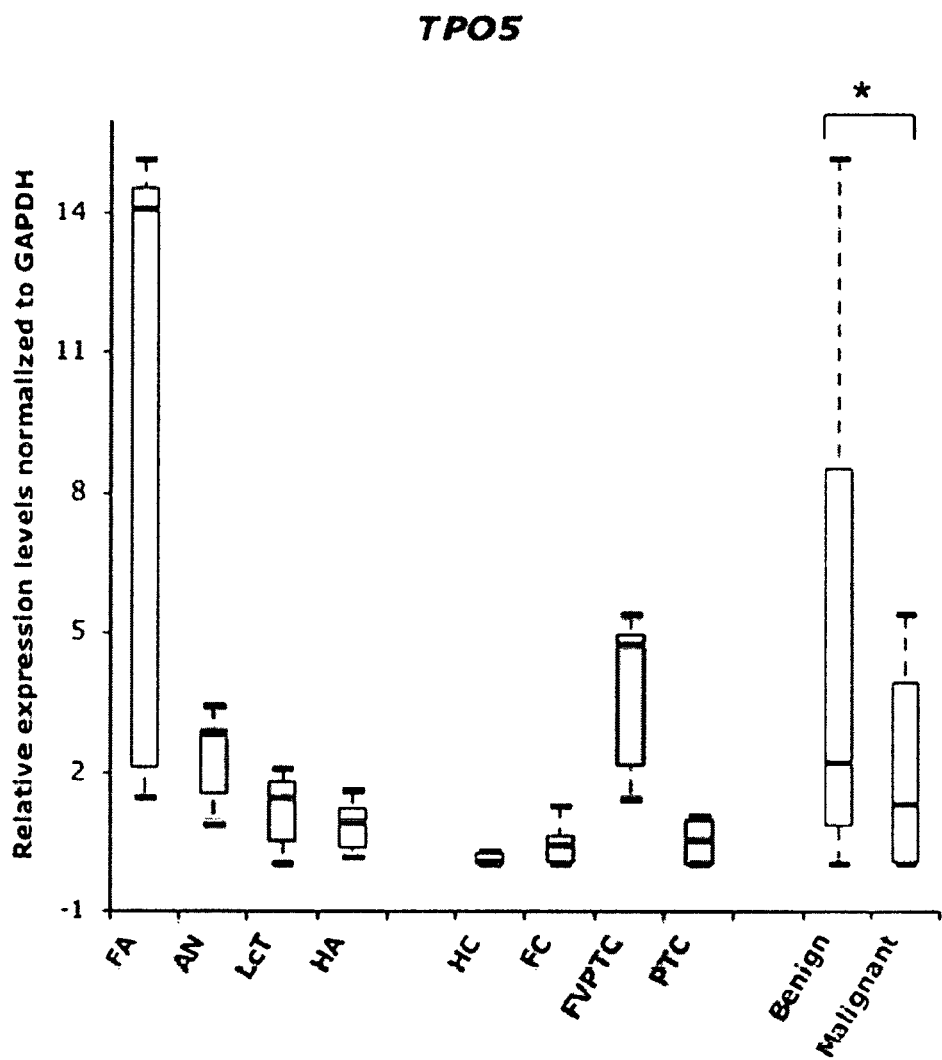
FIG. 9 (cont...)

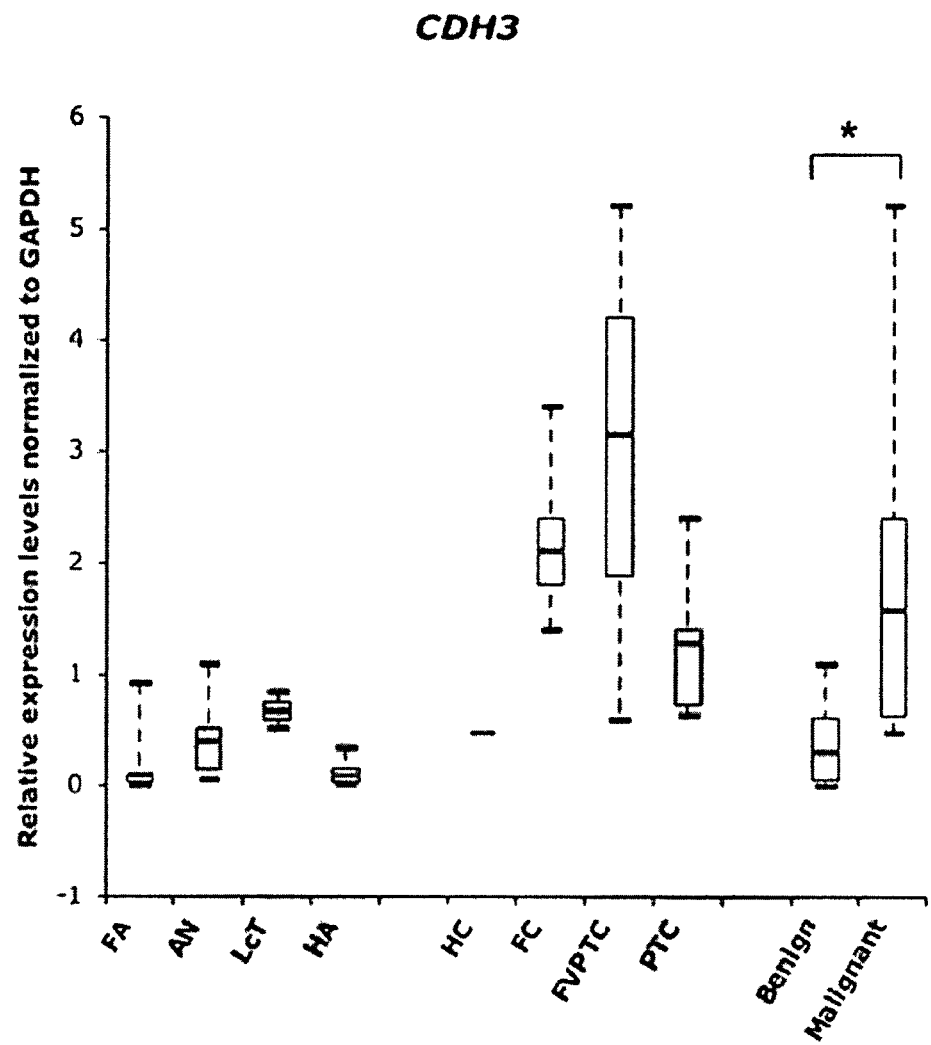
FIG. 10 (cont...)

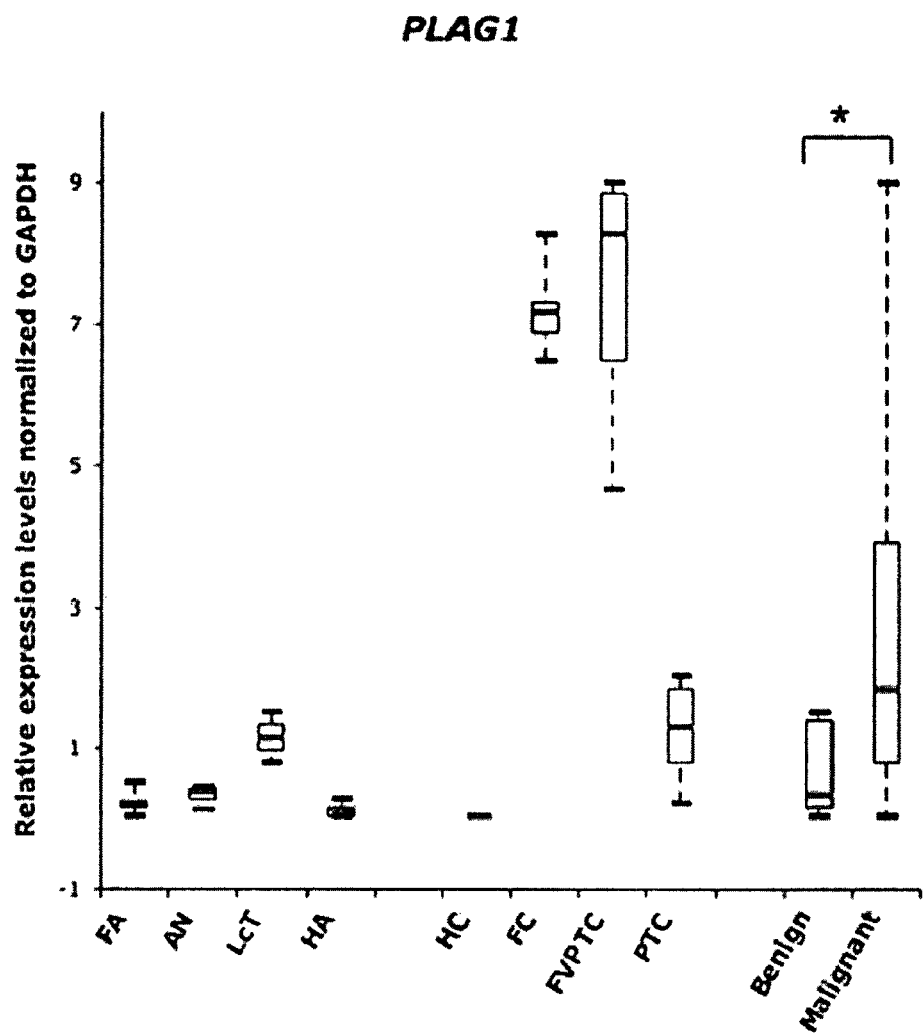
FIG. 10 (cont...)

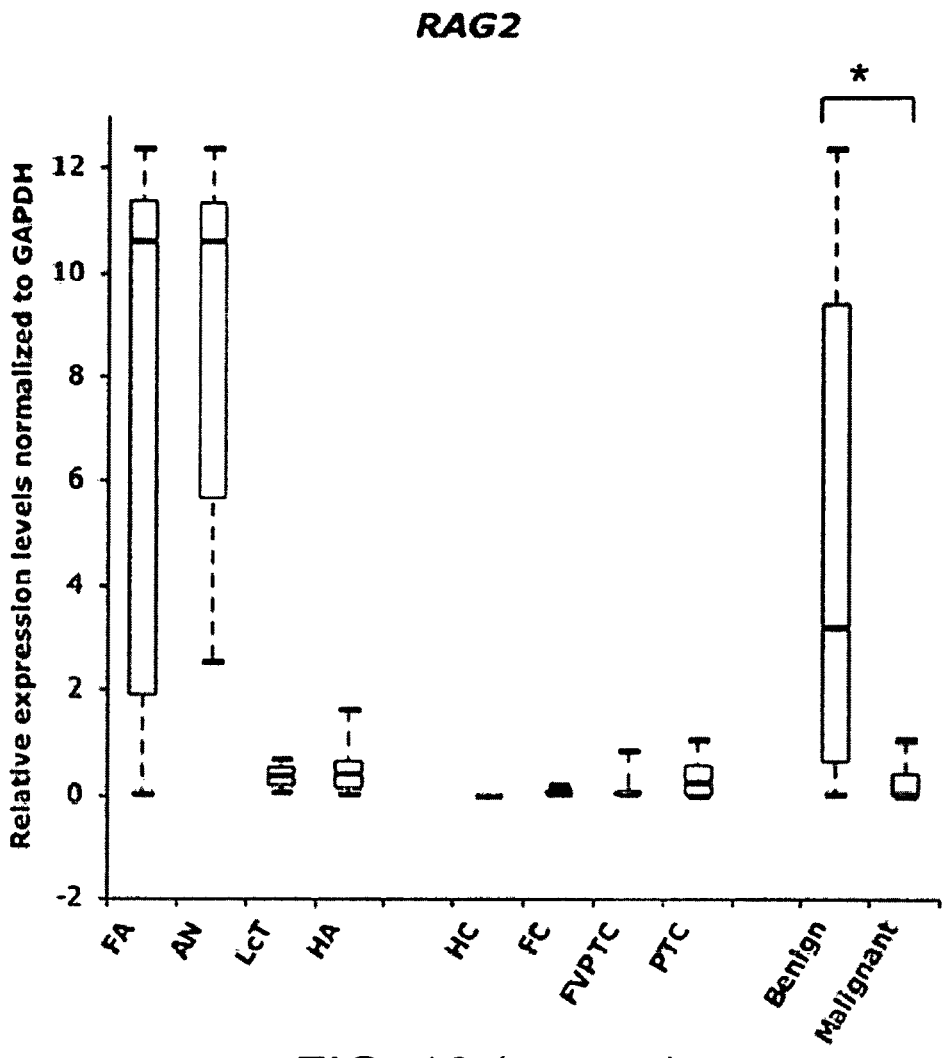
FIG. 10 (cont...)

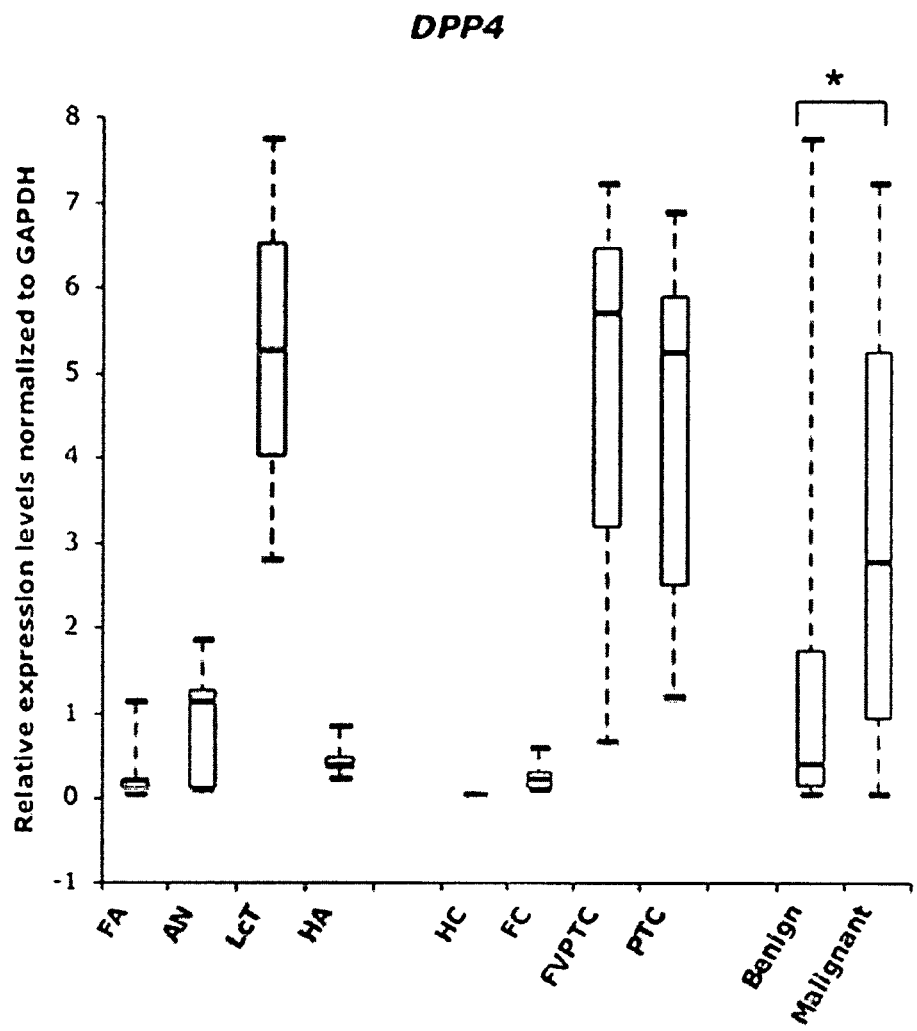
FIG. 10 (cont...)

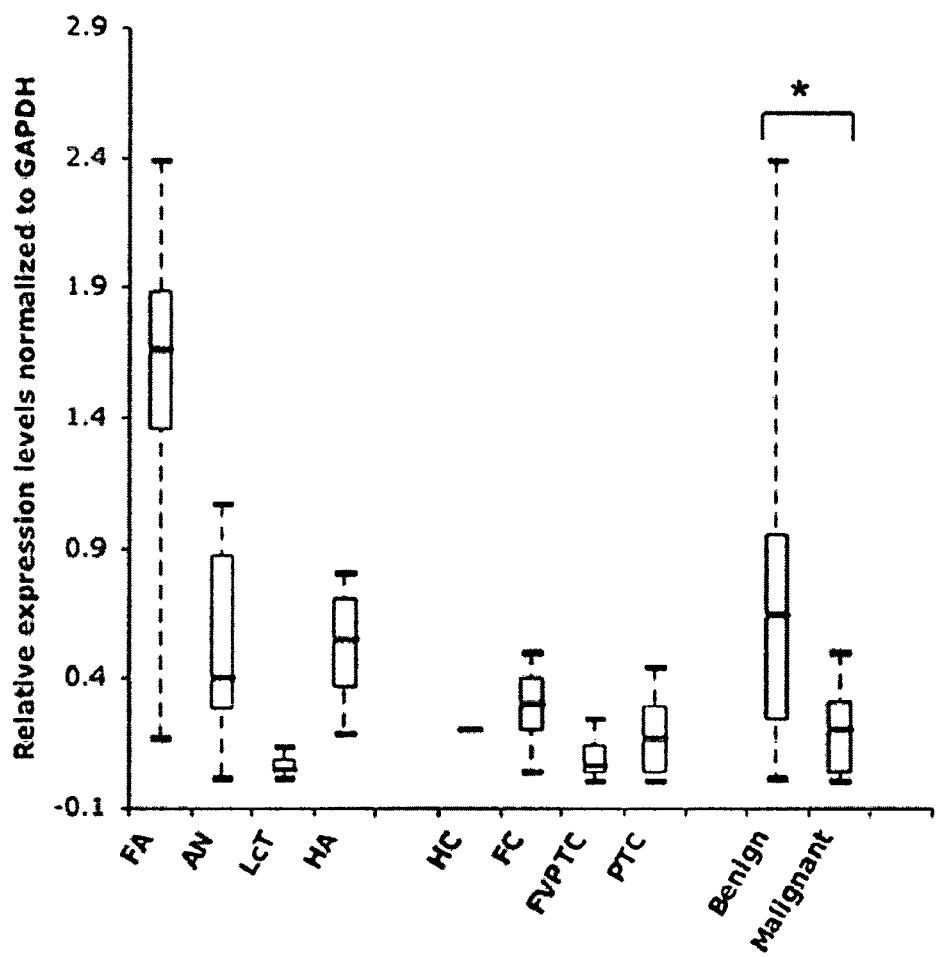
FIG. 10 (cont...)

SEQUENCE LISTING

<160> NUMBER OF SEQ ID NOS: 60

<210> SEQ ID NO 1
<211> LENGTH: 22
<212> TYPE: DNA
<213> ORGANISM: Artificial Sequence
<220> FEATURE:
<223> OTHER INFORMATION: Synthetic construct

<400> SEQUENCE: 1
ggctgactgg caaaaagtct tg                                              22

<210> SEQ ID NO 2
<211> LENGTH: 26
<212> TYPE: DNA
<213> ORGANISM: Artificial Sequence
<220> FEATURE:
<223> OTHER INFORMATION: Synthetic construct

<400> SEQUENCE: 2
ttggttccct taagttctca gagttt                                          26

<210> SEQ ID NO 3
<211> LENGTH: 23
<212> TYPE: DNA
<213> ORGANISM: Artificial Sequence
<220> FEATURE:
<223> OTHER INFORMATION: Synthetic construct

<400> SEQUENCE: 3
tggccctgtc actcccatga tgc                                             23

<210> SEQ ID NO 4
<211> LENGTH: 18
<212> TYPE: DNA
<213> ORGANISM: Artificial Sequence
<220> FEATURE:
<223> OTHER INFORMATION: Synthetic construct

<400> SEQUENCE: 4
aagggctcgc atgcaaag                                                   18

<210> SEQ ID NO 5
<211> LENGTH: 25
<212> TYPE: DNA
<213> ORGANISM: Artificial Sequence
<220> FEATURE:
<223> OTHER INFORMATION: Synthetic construct

<400> SEQUENCE: 5
cacagtagca ctctgagttg aagca                                           25

<210> SEQ ID NO 6
<211> LENGTH: 25
<212> TYPE: DNA
<213> ORGANISM: Artificial Sequence
<220> FEATURE:
<223> OTHER INFORMATION: Synthetic construct

<400> SEQUENCE: 6
tttgtccctg cttgtactag tgagg                                           25

<210> SEQ ID NO 7
<211> LENGTH: 22
<212> TYPE: DNA
<213> ORGANISM: Artificial Sequence

```
<220> FEATURE:
<223> OTHER INFORMATION: Synthetic construct

<400> SEQUENCE: 7
gcaatcctct tacctccgct tt                                              22

<210> SEQ ID NO 8
<211> LENGTH: 24
<212> TYPE: DNA
<213> ORGANISM: Artificial Sequence
<220> FEATURE:
<223> OTHER INFORMATION: Synthetic construct

<400> SEQUENCE: 8
ggaatcggag acagaagaga gctt                                            24

<210> SEQ ID NO 9
<211> LENGTH: 28
<212> TYPE: DNA
<213> ORGANISM: Artificial Sequence
<220> FEATURE:
<223> OTHER INFORMATION: Synthetic construct

<400> SEQUENCE: 9
ctgggaccac agatgtatcc tccactcc                                        28

<210> SEQ ID NO 10
<211> LENGTH: 22
<212> TYPE: DNA
<213> ORGANISM: Artificial Sequence
<220> FEATURE:
<223> OTHER INFORMATION: Synthetic construct

<400> SEQUENCE: 10
atggcagtgc agtcatcatc tt                                              22

<210> SEQ ID NO 11
<211> LENGTH: 25
<212> TYPE: DNA
<213> ORGANISM: Artificial Sequence
<220> FEATURE:
<223> OTHER INFORMATION: Synthetic construct

<400> SEQUENCE: 11
gcattcatac agctgcttac catct                                           25

<210> SEQ ID NO 12
<211> LENGTH: 23
<212> TYPE: DNA
<213> ORGANISM: Artificial Sequence
<220> FEATURE:
<223> OTHER INFORMATION: Synthetic construct

<400> SEQUENCE: 12
tttggtccct gcctaggacc ggg                                             23

<210> SEQ ID NO 13
<211> LENGTH: 16
<212> TYPE: DNA
<213> ORGANISM: Artificial Sequence
<220> FEATURE:
<223> OTHER INFORMATION: Synthetic construct

<400> SEQUENCE: 13
ccggcccaag ctccat                                                     16
```

<210> SEQ ID NO 14
<211> LENGTH: 21
<212> TYPE: DNA
<213> ORGANISM: Artificial Sequence
<220> FEATURE:
<223> OTHER INFORMATION: Synthetic construct

<400> SEQUENCE: 14
ttgtgtaacc gtcggtcatg a                                        21

<210> SEQ ID NO 15
<211> LENGTH: 29
<212> TYPE: DNA
<213> ORGANISM: Artificial Sequence
<220> FEATURE:
<223> OTHER INFORMATION: Synthetic construct

<400> SEQUENCE: 15
tgtttggtgg aatccatgaa ggttatggc                                29

<210> SEQ ID NO 16
<211> LENGTH: 20
<212> TYPE: DNA
<213> ORGANISM: Artificial Sequence
<220> FEATURE:
<223> OTHER INFORMATION: Synthetic construct

<400> SEQUENCE: 16
gagagcgtga tccccctaca                                          20

<210> SEQ ID NO 17
<211> LENGTH: 23
<212> TYPE: DNA
<213> ORGANISM: Artificial Sequence
<220> FEATURE:
<223> OTHER INFORMATION: Synthetic construct

<400> SEQUENCE: 17
accaagagtg cacctcagtg tct                                      23

<210> SEQ ID NO 18
<211> LENGTH: 33
<212> TYPE: DNA
<213> ORGANISM: Artificial Sequence
<220> FEATURE:
<223> OTHER INFORMATION: Synthetic construct

<400> SEQUENCE: 18
tcacttccaa atgttcctgt agcataaatg gtg                           33

<210> SEQ ID NO 19
<211> LENGTH: 24
<212> TYPE: DNA
<213> ORGANISM: Artificial Sequence
<220> FEATURE:
<223> OTHER INFORMATION: Synthetic construct

<400> SEQUENCE: 19
tgccaaggag ctttgtttat agaa                                     24

<210> SEQ ID NO 20
<211> LENGTH: 20
<212> TYPE: DNA
<213> ORGANISM: Artificial Sequence
<220> FEATURE:
<223> OTHER INFORMATION: Synthetic construct

```
<400> SEQUENCE: 20
atgacggcat gtaccaacca                                              20

<210> SEQ ID NO 21
<211> LENGTH: 29
<212> TYPE: DNA
<213> ORGANISM: Artificial Sequence
<220> FEATURE:
<223> OTHER INFORMATION: Synthetic construct

<400> SEQUENCE: 21 ttggtccct cagttctatg ctgttgtgt                                     29

<210> SEQ ID NO 22
<211> LENGTH: 26
<212> TYPE: DNA
<213> ORGANISM: Artificial Sequence
<220> FEATURE:
<223> OTHER INFORMATION: Synthetic construct

<400> SEQUENCE: 22
gcacctgctg aaatgtatga cataat                                       26

<210> SEQ ID NO 23
<211> LENGTH: 28
<212> TYPE: DNA
<213> ORGANISM: Artificial Sequence
<220> FEATURE:
<223> OTHER INFORMATION: Synthetic construct

<400> SEQUENCE: 23
tttgctaagt tggagtaaat atgattgg                                     28

<210> SEQ ID NO 24
<211> LENGTH: 36
<212> TYPE: DNA
<213> ORGANISM: Artificial Sequence
<220> FEATURE:
<223> OTHER INFORMATION: Synthetic construct

<400> SEQUENCE: 24
attgttcagc taattgagaa gcagatttca gagagc                            36

<210> SEQ ID NO 25
<211> LENGTH: 26
<212> TYPE: DNA
<213> ORGANISM: Artificial Sequence
<220> FEATURE:
<223> OTHER INFORMATION: Synthetic construct

<400> SEQUENCE: 25
tgaagaatgt catggtggta gtatca                                       26

<210> SEQ ID NO 26
<211> LENGTH: 26
<212> TYPE: DNA
<213> ORGANISM: Artificial Sequence
<220> FEATURE:
<223> OTHER INFORMATION: Synthetic construct

<400> SEQUENCE: 26
atgactcctc aggtgaattt gtgtag                                       26

<210> SEQ ID NO 27
```

```
<211> LENGTH: 29
<212> TYPE: DNA
<213> ORGANISM: Artificial Sequence
<220> FEATURE:
<223> OTHER INFORMATION: Synthetic construct

<400> SEQUENCE: 27
ctggtatgga gggattctgc taggaccag                                    29

<210> SEQ ID NO 28
<211> LENGTH: 21
<212> TYPE: DNA
<213> ORGANISM: Artificial Sequence
<220> FEATURE:
<223> OTHER INFORMATION: Synthetic construct

<400> SEQUENCE: 28
tgagtgtccc ccggtatctt c                                            21

<210> SEQ ID NO 29
<211> LENGTH: 21
<212> TYPE: DNA
<213> ORGANISM: Artificial Sequence
<220> FEATURE:
<223> OTHER INFORMATION: Synthetic construct

<400> SEQUENCE: 29
cagccgcttt cagattttca t                                            21

<210> SEQ ID NO 30
<211> LENGTH: 27
<212> TYPE: DNA
<213> ORGANISM: Artificial Sequence
<220> FEATURE:
<223> OTHER INFORMATION: Synthetic construct

<400> SEQUENCE: 30
cctgccaatc ccgatgaaat tggaaat                                      27

<210> SEQ ID NO 31
<211> LENGTH: 19
<212> TYPE: DNA
<213> ORGANISM: Artificial Sequence
<220> FEATURE:
<223> OTHER INFORMATION: Synthetic construct

<400> SEQUENCE: 31
gctggtgctc atggcactt                                               19

<210> SEQ ID NO 32
<211> LENGTH: 19
<212> TYPE: DNA
<213> ORGANISM: Artificial Sequence
<220> FEATURE:
<223> OTHER INFORMATION: Synthetic construct

<400> SEQUENCE: 32
ccctccccag gcttcctaa                                               19

<210> SEQ ID NO 33
<211> LENGTH: 24
<212> TYPE: DNA
<213> ORGANISM: Artificial Sequence
<220> FEATURE:
<223> OTHER INFORMATION: Synthetic construct

<400> SEQUENCE: 33
```
aagggctttg cctgacaaca ccca                                          24

<210> SEQ ID NO 34
<211> LENGTH: 21
<212> TYPE: DNA
<213> ORGANISM: Artificial Sequence
<220> FEATURE:
<223> OTHER INFORMATION: Synthetic construct

<400> SEQUENCE: 34
gacgatccgg gtaaagttcc a                                             21

<210> SEQ ID NO 35
<211> LENGTH: 20
<212> TYPE: DNA
<213> ORGANISM: Artificial Sequence
<220> FEATURE:
<223> OTHER INFORMATION: Synthetic construct

<400> SEQUENCE: 35
aggttgagga gtgggtcgaa                                               20

<210> SEQ ID NO 36
<211> LENGTH: 22
<212> TYPE: DNA
<213> ORGANISM: Artificial Sequence
<220> FEATURE:
<223> OTHER INFORMATION: Synthetic construct

<400> SEQUENCE: 36
aggccgcgaa gccagtggaa tc                                            22

<210> SEQ ID NO 37
<211> LENGTH: 22
<212> TYPE: DNA
<213> ORGANISM: Artificial Sequence
<220> FEATURE:
<223> OTHER INFORMATION: Synthetic construct

<400> SEQUENCE: 37
tcaccagggc tgcttttaac tc                                            22

<210> SEQ ID NO 38
<211> LENGTH: 26
<212> TYPE: DNA
<213> ORGANISM: Artificial Sequence
<220> FEATURE:
<223> OTHER INFORMATION: Synthetic construct

<400> SEQUENCE: 38
ggaatcatat tggaacatgt aaacca                                        26

<210> SEQ ID NO 39
<211> LENGTH: 27
<212> TYPE: DNA
<213> ORGANISM: Artificial Sequence
<220> FEATURE:
<223> OTHER INFORMATION: Synthetic construct

<400> SEQUENCE: 39
ttgccatcaa tgaccccttc attgacc                                       27

<210> SEQ ID NO 40
<211> LENGTH: 3084
<212> TYPE: DNA

<213> ORGANISM: Artificial Sequence
<220> FEATURE:
<223> OTHER INFORMATION: Synthetic construct: C21orf4

<400> SEQUENCE: 40

```
gctcccgggg ctgaggtgga gccgcgggac gccggcaggg ttgtggcgca gcagtctcct      60
tcctgcgcgc gcgcctgaag tcggcgtggg cgtttgagga agctgggata cagcatttaa     120
tgaaaaattt atgcttaaga agtaaaaatg gcaggcttcc tagataattt tcgttggcca     180
gaatgtgaat gtattgactg gagtgagaga agaaatgctg tggcatctgt tgtcgcaggt     240
atattgtttt ttacaggctg gtggataatg attgatgcag ctgtggtgta tcctaagcca     300
gaacagttga accatgcctt tcacacatgt ggtgtatttt ccacattggc tttcttcatg     360
ataaatgctg tatccaatgc tcaggtgaga ggtgatagct atgaaagcgg ctgtttagga     420
agaacaggtg ctcgagtttg cttttcatt ggtttcatgt tgatgtttgg gtcacttatt      480
gcttccatgt ggattctttt tggtgcatat gttacccaaa atactgatgt ttatccggga     540
ctagctgtgt tttttcaaaa tgcacttata ttttttagca ctctgatcta caaatttgga     600
agaaccgaag agctatggac ctgagatcac ttcttaagtc acattttcct tttgttatat     660
tctgtttgta dataggtttt ttatctctca gtacacattg ccaaatggag tagattgtac     720
attaaatgtt ttgtttcttt acattttat gttctgagtt tgaaatagt tttatgaaat       780
ttctttattt ttcattgcat agactgttaa tatgtatata atacaagact atatgaattg     840
gataatgagt atcagttttt tattcctgag atttagaact tgatctactc cctgagccag     900
ggttacatca tcttgtcatt ttagaagtaa ccactcttgt ctctctggcc gggcacggtg     960
gctcatgcct gtaatcccag cactttggga ggccgaggcg ggcgattgc ttgaggtcaa     1020
gtgtttttgag accagcctgg ccaacatggc gaaaccccat ctactaaaaa tacaaaaatt   1080
agccaggcat ggtggtgggt gcctgtaatc ccaactacct aggaggctga ggcaggagaa   1140
tcgcttgaac ccgggggca gaggttgtag tgagctgagt ttgcgccact gcactctagc    1200
ctgggggaga aagtgaaact ccctctcaaa aaaagaagg accactctca gtatctgatt    1260
tctgaagatg tacaaaaaaa tatagcttca tatatctaga atgagcactg agccataaaa   1320
ggttttcagc aagttgtaac ttattttggc ctaaaaatga ggttttttttg gtaaagaaaa  1380
aatatttgtt cttatgtatt gaagaagtgt actttatat aatgattttt taaatgccca    1440
aaggactagt ttgaaagctt ctttaaaaa gaattcctct aatatgactt tatgtgagaa    1500
gggataatac atgatcaaat aaactcagtt ttttatggtt actgtaaaaa gactgtgtaa   1560
ggcagctcag caccatgctt ctcgtaaaag cagcttcaaa tatccactgg ggttatcttt   1620
tgacgacttg ccattatctg atgttacaca attcaatagc aagcaagttt gagacaatcg   1680
cagtttaaaa gcatgaacca tttaacaaaa agtggaataa ttaaagataa agcacttctt   1740
cccaaaggga attatcacct agtgaaaat tatgcatttc atctactcag ttaccgactg    1800
caagtctctc ctcgctctag ctctcaagct ttgggtgaat attcctgtga aatatatctt   1860
caacttgaaa gttcatactc caatcaaaaa ctccttttac tgagtttgca gtactgtatt   1920
tgcactgttt gtattcctct gggcccttat tgctactttt gctttccttt gttacacaga   1980
ttttgtgttg cactttttct ccagaggggt gttgtagagc cttggttgta tgaataatac   2040
cagtggtagt gtccacggct ctaatgtaag cccattggc atcactcctc tcctctctct    2100
tgagaggatt tcttgtgcac agagtatgaa gcagttgtgg agcgctgtgc ctttgtcaag   2160
ataccatctt gtttgatgac ttctttcttt gctgtttttt tcttcaaaat gttagtaagc   2220
```

```
tctgtcatgc ttctagcaaa ttgtaagact aattatttgt ttccacctca taacctgttg    2280
caataaatat tacttctcat acagtttaat attgttgttt gttggagaaa atgaaccata    2340
aaaattgatt tgctgttcag ttttcaatta ttcaagtata cccaattaaa gatgcagtta    2400
tgtttataaa ataagaagaa atagacttgt aaaatgctta tgtgagggtt attgaaggtt    2460
tccctgaaga ctgactggaa atggtggctg ttttttttcta tttctgactc tgccatgaat    2520
tttttttttt ttttttttaaa gacaatatct cactctgttg cctaggctgg agtgcagtgg    2580
tgcaaccaca gctcactgca ccttcaaatg ctggagctca ggcaatcctc ttacctccgc    2640
tttccaagca gctgggacca cagatgtatc ctccactcct cgctggccac catcctgctg    2700
cccaacagaa gaagctcttc tgtctccgat ttcctgaacg gtctaaggac caggaagaaa    2760
caggctcctg ccagcaccga cagcaacgaa aatgttccca cggagatcag gatgacttgc    2820
tgaagctcag tggaggctaa aaagaggaca cgaaagtgaa cagaatgatc ttcctacgca    2880
caacacaaac atcagttaat gttccatcca tgctgcttaa agagcattcc tgtcctagta    2940
aaatgggcaa gtccctctac cccccaccct cacctggtat gcttacatta atagctaaag    3000
tcaatcctgt aatgaaataa agcaagtggt agctgtctgg tagcctccac tactgcaaat    3060
ctcaagaaaa aaaaaaaaaa aaaa                                          3084
```

<210> SEQ ID NO 41
<211> LENGTH: 158
<212> TYPE: PRT
<213> ORGANISM: Artificial Sequence
<220> FEATURE:
<223> OTHER INFORMATION: Synthetic construct: C21orf4

<400> SEQUENCE: 41

```
Met Ala Gly Phe Leu Asp Asn Phe Arg Trp Pro Glu Cys Glu Cys Ile
1               5                   10                  15

Asp Trp Ser Glu Arg Arg Asn Ala Val Ala Ser Val Val Ala Gly Ile
            20                  25                  30

Leu Phe Phe Thr Gly Trp Trp Ile Met Ile Asp Ala Ala Val Val Tyr
        35                  40                  45

Pro Lys Pro Glu Gln Leu Asn His Ala Phe His Thr Cys Gly Val Phe
    50                  55                  60

Ser Thr Leu Ala Phe Phe Met Ile Asn Ala Val Ser Asn Ala Gln Val
65                  70                  75                  80

Arg Gly Asp Ser Tyr Glu Ser Gly Cys Leu Gly Arg Thr Gly Ala Arg
                85                  90                  95

Val Trp Leu Phe Ile Gly Phe Met Leu Met Phe Gly Ser Leu Ile Ala
            100                 105                 110

Ser Met Trp Ile Leu Phe Gly Ala Tyr Val Thr Gln Asn Thr Asp Val
        115                 120                 125

Tyr Pro Gly Leu Ala Val Phe Phe Gln Asn Ala Leu Ile Phe Phe Ser
    130                 135                 140

Thr Leu Ile Tyr Lys Phe Gly Arg Thr Glu Glu Leu Trp Thr
145                 150                 155
```

<210> SEQ ID NO 42
<211> LENGTH: 2822
<212> TYPE: DNA
<213> ORGANISM: Artificial Sequence
<220> FEATURE:
<223> OTHER INFORMATION: Synthetic construct: Hs. 145049

```
<400> SEQUENCE: 42
gtttctctga atagcagagg catcaaattt tggtggggaa tgagaggagt attagggaa      60 agtttgaaaa tagctctcct ggagatggag ggcacacaga gtggtcctca ggctcacctt    120
gactgagttg attcacagtt atcctgcatc agaccattag atttctttag tgctatgatt    180
ataataggga ttttgaatc accaaaaaca gttttagat gtttatgttc tttgttttac     240
tatcaatgtt gtgctggtta agggagagaa aagttcaaga agatcttaca tatttgaaag   300
gaaattggta ctcttgaagg ctatgcaaca tgagtctttg aacaagaatt ccttgctact   360
ttgattcatt catcaaatac tgagtgcctg tgtgccaggc acaggtgaac tctggggatt   420 cagggggtaac taaaacagat tgcaaccctg cccttgtgaa gctttcagtc tagaagggag  480
acgtgaaaca aattttagct tcaaaagcaa catctatttt tgcctgttag catgcattta   540
ttttaaaagt catattagag ttacctggtt ccgcttcaga gcagactggg aaaatcaggc   600
ttacaatgga atcagatgct gtgggcctaa aacagctctt taaaaatcta tttttttagg   660
ccaggtgcgt tggctcacac ctgtaatccc agcactttgg gaggccaagg tgggtggata   720
tgaggtcagg aggtcgagac cagcctggtc aatatgatga aaccttacct ctactaaaaa   780
taaaaaatta gccgggcatg gtggcacatg cctgtagtcc cagctactcg ggaaactgag   840
gcagaagaat cgcttgaacc cgggaggcgg aggttgcagt gagccgggat cacgtcactg   900
tactccagcc tgggcaagag tgagacaccg tctcaaaaaa aaaaaaaatt tttttttaaa   960
tggaatcaga gaaaccaaca aaatatgtaa catgtataaa tgcctgagga gatcagttat  1020
tgagaaatcc atttacaatg ctggaggaga ggggatggcc aggaaagaag tgcaacaaat  1080
aaatggaaga tgaccctaaa atgcaccag tgacagtcag tcaatccatc agaccacctc   1140
acatgcaggg tagaaacatg gagtgtgcgg cagcatcctc ctcacatccc tttgtgagca   1200
cggctgctcc ggaatactga ccatctgggc tagcacgact tagcagaggg ttctgcagga   1260
tgtgctattt taaagcagct gggtgcaact tgtgaaaacg ggaatctaga gcagaacatg   1320
taatcagcga tggctgggat tggtggacag gattgacagg agtatttgag gctctaccag   1380
gcctgtctac aggacagctt catcaaaggg acatttttta acctgttatt ttaaatgcca   1440
catatatgtt gtaatgctga agcatacagg tagaatttct ggatcgtaac tactagtgac   1500
ttctgaggtt tacagttaga aaatgttctc aaaggtttat cagttatgta ttgatgattg   1560
gtaatctaga ccctctggag gctgtagaat gtgaaaagat acagctgagc tgacaagttt   1620
tagggcacta tcttctggaa tgaaatcggc caagaaaatg gttcaagggc atgggggtta   1680
gagaatgttt cttttaccta aaaatgttaa gccaactatg gaagattggg gtcgtggggg   1740
catgaaatac aaaattatga taatttatac agaactaggt ttctttatgt tctgcaagaa   1800
ggtttttatt agctaatttg ggagggggg catgctgcag tattttttt cctgggaaca    1860 tgcatttctg atgggaagtt attttgttta caagagttgg ttttacacac aaccctgaat   1920
gaatgtgtct atggcctaaa aatggtagac ctgtatttcc ttcccgaggc aggctgattc   1980
gtttcctgat tccttctgtc tgagattacc tgatgctgac cagacttatt tttcctttcc   2040
tgaatcttca cagctgagtt tatggcaccc atccaagacc ttcccatttg aatgactaga   2100
tttctattct atccccgatc atcctttga aatagttcta gtgataaact cagagaaatt   2160
caatatattg attgaatttt attttttcgc tttgtatcta caacagaaat tgatttgttc   2220 attttattt caaatctctt catggcaagt tgggctaatg gacttgcac tcaagaaagg     2280 tttgtttacc agttttgtag ccatgtttgg caaatcttag caactagaaa ccccgtcctt   2340
```

```
tcttttcctt ctttatatgt tcttgcagtt actcttgtat tgcaagatttt tctgactttta      2400 agctttgaga ctactgcatc ttaaaagaag aactaggctg actggcaaaa agtcttgcca      2460
gtggccctgt cactcccatg atgctttggt tttgagagtt gggaaaactc tgagaactta      2520
agggaaccaa actcaggaat cccaaaattg gtggcattgt gccattcgtt taggggctga      2580
acataggacc tgtctgaaac tgagtgagct agatgcattt gggtttgaat ttttgtcaca      2640
tactgaaatg taagtcagcc ctaaataatc aaaacacttt attttatttt tcttttttta      2700
aataggaact ttctgaagaa aaagtggtgt gtaaacatt tgatatttaa gacaataaag      2760 ttttatcat aaaaaaaaaa aaaaaaaaaa aaaaaaaaaa aaagaaaaa aaaaaaaaaaa      2820 aa                                                                        2822
```

<210> SEQ ID NO 43
<211> LENGTH: 152
<212> TYPE: PRT
<213> ORGANISM: Artificial Sequence
<220> FEATURE:
<223> OTHER INFORMATION: Synthetic construct: Hs. 145049

<400> SEQUENCE: 43

```
Met Val His Ser Pro Arg Ser Leu Val Ala Asn Pro Ser Gln Val Leu
1               5                   10                  15

Phe Phe Leu Ser Phe Leu Phe Phe Phe Leu Arg Gln Ser Phe Ala
            20                  25                  30

Leu Val Ala Gln Ala Gly Val Gln Trp Arg Asn Leu Gly Ser Leu Gln
        35                  40                  45

Pro Pro Pro Pro Gly Phe Lys Gln Phe Ser Cys Leu Ser Leu Leu Ser
    50                  55                  60

Ser Trp Asp Tyr Arg His Ala Pro Pro Cys Pro Ala Tyr Phe Val Phe
65                  70                  75                  80

Leu Val Asp Met Gly Phe Pro His Val Gly Gln Thr Gly Leu Glu Leu
                85                  90                  95

Leu Thr Ser Gly Asp Pro Pro Ala Ser Ala Ser Gln Ser Ala Gly Ile
            100                 105                 110

Thr Gly Gly Ser His Arg Ala Gln Pro Thr Ser Ser Asn Pro Tyr Gly
        115                 120                 125

Ile Val Phe Phe Phe Leu Pro Val Lys Thr Phe Ser Gly Met Ser Gln
    130                 135                 140

Glu Ala Gly Asp Cys Arg Glu Thr
145                 150
```

<210> SEQ ID NO 44
<211> LENGTH: 4597
<212> TYPE: DNA
<213> ORGANISM: Artificial Sequence
<220> FEATURE:
<223> OTHER INFORMATION: Synthetic construct: Hs. 296031

<400> SEQUENCE: 44

```
aatggtacga ttgagagatg agtgctatgg agaaaaatcc agccagaaag ggagatgcag        60
aagatagcac cagatcttct caatgttgtt ttcatcatgg acaggtgcgt tccttagaag       120
atgaagtgtt agtgattcct gagttttct caccttcacg tcgattgatc tgaatttgga       180
gagtctgttt tctgtgtctg gctctgcact caactttgta ggggaccctg tcgaggtccc       240
cacactgtgg cttcaggtag acagagcaga tgggagccca tttcagttca ttgtcttgct       300
```

```
gaccaatggg gaactgtggt caggtgagag gaggcagctt ttacaatcag acttcattga    360
atagtgtggg ctgctgtttc cttgtaacaa aacccccataa tgatggcagt ttccggatgt    420 gtcttttag gacttcagaa cttattattt gaatagaagt ttaaagcatc tggatgatga     480
tgctgtagct aaaacagctg cttgtcagaa gagaccctat ttaacacttc taaacttgtt    540
tcagaggtgg aggaaaggat aatctgggaa ggcctccctc tcaagtccac aggttggtat    600
cagctgtgtt catcccccaa aaggaaaata aaatgacaac aatatttggg tcacagaatt    660
cctgagaaac ctctgtttct atcttcatgt ctttaagata gggacatgaa ttccccatga    720
tctgggtgat agggttagag tggccaggac actgttactt tgtgtgtgac acaggtggct    780
cctcatgaca gttcctccat gccttagaac atgttgtctg tctggtcatc cctgggggta    840
gagctgagtg acccagcagt gggagattta acaactggag aagaagatgg gatgtgttta    900
attatcccca gaggtagggc caatttgtca ccctttaaat agacttattt gcatataaac    960
taaagcacct tagggcatca ttaccgaaag tgtctaagca aatgtctgat atagttacgt   1020
gcctgcatta aaagaaagca gcccccttat cttgccttaa tatccttaca gtgttttaat   1080
aagttcataa tgcatcctgt atgtgcattt tttggtataa aacaccgaaa ggtggagaat   1140
tgacttcagt tctctccatc ctttcccctt aagtgttggt ggcgctgcag gggcaacgtg   1200
cctcccattg gaagtggtga cttcctcttt gatagaggtt tgcctgtctc ttgaaaatga   1260
aaagaagcgg agattgatct ctggagtccc atggtccagt ttggactatt gggaatattt   1320
tttatgggat gttaaaaaca atattagaga cgtgagatag taaatttgtg gtaataccgg   1380
atccaggaag cttacagtga agagtatgaa cttaacctga aaagtatttc tctgttctat   1440
aaatctctca gtgacatttg gattaatcaa gcataattaa atgtagttag attttgtca   1500 gattgtagtt caaaataata ttcatctatg gagagggtaa tatattatgt agaaattta    1560 ttaagcactt tagttaagca aacactaagg agaacaaaat caacctcagg aaggttaatt   1620
actaaaaaaa tcacaaagta tagtagatta tgtaaatcat tttaatttg aataccatgg   1680 cttgagcttt aatttacata gagacgtatt ttggatttgt ttttcacatt atattttcta   1740
gtacaggatt gcaattgcat tcttgaaaag ttctactcat tttaggattc cattaagttt   1800
gcttaacttt tttcatgtta taattttccaa agcaaagaa ttacaattgt attctagcta   1860 attatttaa tgtttcacta actttgtgtg tattgtaaga ccatatttt atttctatac    1920 aaatgatgat tttaagagaa gtatcaggag agagaatgta tatgaaagca tcgcgtccac   1980
gcctggcttt gcaataagtg ttcattaaa agaaagacat ttacaaaggt aaaacataag    2040
agtttagact atagcgataa atcttttat tttagtaatt tctttaaagg gaaaagtaaa    2100
gagatcaaaa tgatttata tgtatttttt ttgtactcag agaattacat tttcactacc    2160
cccgcctgtc tcagggaata gcctttgata agaatcccat ggagatctct ggaactctat   2220
tacagtgtgt tcagatttgt tagttcatat gtaaatttca gagctagagc ttcaaaacta   2280
gagtattgta atctcaggaa cataagatta tccaagaagc ctgaaccttg ctcttttcat   2340
gataaatgac atccaaattt cctttgtcta ggagataagc atagatccct tttatcatgc   2400
ttctctgaga ttttcacaga acaaccctgc aatttgattt tgttgataa ttttgctttt    2460 tggcttttca gtgaggactc tatttttccat tggaactgac tccttttgggg ataataagct   2520 ttcacttaaa agaacattcc attagatagt tctaacttca atgaacctaa aagtggcttc   2580
ttaatttgaa taatctggat aacttttgca aatgggtcaa aacagcacaa gtatcaacaa    2640
tcacgtatgt actgagtaat atttgccctc cagttagcaa agtcaagaaa tgtctaactc   2700
```

```
tggcacacag cactggtttt aactactctt tagttcatct ttgccttcca aattggttga      2760
aaatggcaag cttagaatgg aatgcatatt aataacagaa ccacttaatg ttttaaaata      2820
ttcatacctt gagattcttt ttgagagaaa aagaaatct taacatccaa ttctagttgt      2880
tttggctttt cacatatgct agacatgaaa aaggcagtta caaaagtgaa atccgattgg      2940
aagtcagtgg tgtccgccat tgagccgtgc taaatgtcgt gtcacaaaag gagtttgtga      3000
aaacaggatg agtagaaaat gttatactgt tgtttctatc gtggcaccgc tttcttataa      3060
attccatttg cttttgtca tctgaactgt tacaaccatg ggaaacctca gtccatattt      3120
ttaaaagcac tatatactta caggaaaaac cgacttatgc cttcattgaa aaatgttga      3180 agttaatatc ccaaatgttt aatgagcatg ttttagaata tttacagcta aagtctgtca      3240
ctttagggat ttgacaaaac ttgagactgc ctgccaccga agagggacca ggcagaatct      3300
tctcagcctt gtaaccagcg ttaaaaaaat ataaggggct tgatgagatc ctagatctgc      3360
tccttttctc ctaggtgcct gggtaactcc tggggaaagc atcatattaa gtccttttca      3420
agcaaggtgt gtgattttga ccaatgaatt gagctgatat gtgatttga ccaatgaatt      3480 gtgcatctat ttaaaaatta ccaagtgtat cttgactctt gagtggacag tcaaggcaaa      3540
gtttacttag gaaatgtaaa gtatggagtg ttttaaaaaa ttcaaattga gtttattcac      3600
tgttggagga attgaattct attgcctccc tcatttcaat tatgttcatt gttacaattg      3660
tgctgctctg ttctcattgt gatgcttagt tctcgtgtag aactgagtgc tacattgtga      3720
ttagaaactg gagttgtgct tgagtcagtc ctggaaaaca ggaccccattt ttaagaagaa      3780 cggaacatac cactttggca ttctggctga ccctaatttc tgcagagttc cttggtgtta      3840
aaatcatttg aggtcatagt tgctgcttat ggtttatata cacccatct gctgctctaa      3900 gttcacatcc tctcaaaagc atgcaagtgc ttgaaattta atatttccc agatctaaaa      3960 caacttgtga ctacctaaga aatgcttgaa ccaaataaga aacagcactg tggaataaaa      4020
tataccattg tgaacatatc tgatgctgca atgaaatgta aagttcctta ctttgctgat      4080
ttttcatcat aactccttga ctcataaaag cggtgtctaa actgggaaca gctgctaata      4140
gggtaaaagt attatacatc aaataaaagt tcattacaat atttgtactc ataagtcaaa      4200
atctgacctg gttcgctttg tgcctctgtc agcctactta cagtgataaa tgtacacaca      4260
agtccagtgt tgccaaggag ctttgtttat agaaagaagc ttggtcccct cagttctatg      4320
ctgttgtgtg gcctggttgg tacatgccgt catgatgaag gatgactttg gtttgagata      4380
atttgtcact ccacattcca tggagaaag tgtttcattt tgatgttgga aaacatgac      4440 cagagaagca tgtgactcag ataatgttcc ccggaagttg cagagcaatc tgtggtgtct      4500
gtcatagccc aactagtcct ggagcacatg gacaattctg taccccaata atcagaacaa      4560
taaaatggta gttgtgattc aaaaaaaaaa aaaaaaa                              4597
```

<210> SEQ ID NO 45
<211> LENGTH: 5084
<212> TYPE: DNA
<213> ORGANISM: Artificial Sequence
<220> FEATURE:
<223> OTHER INFORMATION: Synthetic construct: KIT

<400> SEQUENCE: 45

```
gatcccatcg cagctaccgc gatgagaggc gctcgcggcg cctgggattt tctctgcgtt        60
ctgctcctac tgcttcgcgt ccagacaggc tcttctcaac catctgtgag tccaggggaa       120
```

-continued

```
ccgtctccac catccatcca tccaggaaaa tcagacttaa tagtccgcgt gggcgacgag     180
attaggctgt tatgcactga tccgggcttt gtcaaatgga cttttgagat cctggatgaa     240
acgaatgaga ataagcagaa tgaatggatc acggaaaagg cagaagccac caacaccggc     300
aaatacacgt gcaccaacaa acacggctta agcaattcca tttatgtgtt tgttagagat     360
cctgccaagc ttttccttgt tgaccgctcc ttgtatggga agaagacaa cgacacgctg      420 gtccgctgtc ctctcacaga cccagaagtg accaattatt ccctcaaggg gtgccagggg     480
aagcctcttc ccaaggactt gaggtttatt cctgaccca aggcgggcat catgatcaaa      540
agtgtgaaac gcgcctacca tcggctctgt ctgcattgtt ctgtggacca ggagggcaag     600
tcagtgctgt cggaaaaatt catcctgaaa gtgaggccag ccttcaaagc tgtgcctgtt     660
gtgtctgtgt ccaaagcaag ctatcttctt agggaagggg aagaattcac agtgacgtgc     720
acaataaaag atgtgtctag ttctgtgtac tcaacgtgga aaagagaaaa cagtcagact     780
aaactacagg agaaatataa tagctggcat cacggtgact tcaattatga acgtcaggca     840
acgttgacta tcagttcagc gagagttaat gattctggag tgttcatgtg ttatgccaat     900
aatacttttg gatcagcaaa tgtcacaaca accttggaag tagtagataa aggattcatt     960
aatatcttcc ccatgataaa cactacagta tttgtaaacg atggagaaaa tgtagatttg    1020
attgttgaat atgaagcatt ccccaaacct gaacaccagc agtggatcta tgaacagaa     1080 accttcactg ataaatggga agattatccc aagtctgaga tgaaagtaa tatcagatac     1140 gtaagtgaac ttcatctaac gagattaaaa ggcaccgaag gaggcactta cacattccta    1200
gtgtccaatt ctgacgtcaa tgctgccata gcatttaatg tttatgtgaa tacaaaacca    1260
gaaatcctga cttacgacag gctcgtgaat ggcatgctcc aatgtgtggc agcaggattc    1320
ccagagccca caatagattg gtattttgt ccaggaactg agcagagatg ctctgcttct     1380
gtactgccag tggatgtgca gacactaaac tcatctgggc caccgtttgg aaagctagtg    1440
gttcagagtt ctatagattc tagtgcattc aagcacaatg gcacggttga atgtaaggct    1500
tacaacgatg tgggcaagac ttctgcctat tttaactttg catttaaagg taacaacaaa    1560
gagcaaatcc atccccacac cctgttcact cctttgctga ttggtttcgt aatcgtagct    1620
ggcatgatgt gcattattgt gatgattctg acctacaaat atttacagaa acccatgtat    1680
gaagtacagt ggaaggttgt tgaggagata aatggaaaca attatgttta catagaccca    1740
acacaacttc cttatgatca caaatgggag tttcccagaa acaggctgag ttttgggaaa    1800
accctgggtg ctggagcttt cgggaaggtt gttgaggcaa ctgcttatgg cttaattaag    1860
tcagatgcgg ccatgactgt cgctgtaaag atgctcaagc cgagtgccca tttgacagaa    1920
cgggaagccc tcatgtctga actcaaagtc ctgagttacc ttggtaatca catgaatatt    1980
gtgaatctac ttggagcctg caccattgga gggcccaccc tggtcattac agaatattgt    2040
tgctatggtg atcttttgaa ttttttgaga agaaaacgtg attcatttat tgttcaaag    2100 caggaagatc atgcagaagc tgcactttat aagaatcttc tgcattcaaa ggagtcttcc    2160
tgcagcgata gtactaatga gtacatggac atgaaacctg gagtttctta tgttgtccca    2220
accaaggccg acaaaaggag atctgtgaga ataggctcat acatagaaag agatgtgact    2280
cccgccatca tggaggatga cgagttggcc ctagacttag aagacttgct gagcttttct    2340
taccaggtgg caagggcat ggcttttcctc gcctccaaga attgtattca cagagacttg    2400
gcagccagaa atatcctcct tactcatggt cggatcacaa agatttgtga ttttggtcta    2460
gccagagaca tcaagaatga ttctaattat gtggttaaag gaaacgctcg actacctgtg    2520
```

```
aagtggatgg cacctgaaag cattttcaac tgtgtataca cgtttgaaag tgacgtctgg    2580
tcctatggga ttttttcttg ggagctgttc tctttaggaa gcagcccta tcctggaatg     2640 ccggtcgatt ctaagttcta caagatgatc aaggaaggct tccggatgct cagccctgaa    2700
cacgcacctg ctgaaatgta tgacataatg aagacttgct gggatgcaga tccctaaaa    2760 agaccaacat tcaagcaaat tgttcagcta attgagaagc agatttcaga gagcaccaat    2820
catatttact ccaacttagc aaactgcagc cccaaccgac agaagcccgt ggtagaccat    2880
tctgtgcgga tcaattctgt cggcagcacc gcttcctcct cccagcctct gcttgtgcac    2940
gacgatgtct gagcagaatc agtgtttggg tcacccctcc aggaatgatc tcttcttttg    3000
gcttccatga tggttatttt ctttttcttt aacttgcatc caactccagg atagtgggca    3060
ccccactgca atcctgtctt tctgagcaca ctttagtggc cgatgatttt tgtcatcagc    3120
caccatccta ttgcaaaggt tccaactgta tatattccca atagcaacgt agcttctacc    3180
atgaacagaa acattctga tttggaaaaa gagagggagg tatggactgg gggccagagt      3240
cctttccaag gcttctccaa ttctgcccaa aaatatggtt gatagtttac ctgaataaat    3300
ggtagtaatc acagttggcc ttcagaacca tccatagtag tatgatgata caagattaga    3360
agctgaaaac ctaagtcctt tatgtggaaa acagaacatc attagaacaa aggacagagt    3420
atgaacacct gggcttaaga aatctagtat ttcatgctgg gaatgagaca taggccatga    3480
aaaaaatgat ccccaagtgt gaacaaaaga tgctcttctg tggaccactg catgagcttt    3540
tatactaccg acctggtttt taaatagagt ttgctattag agcattgaat tggagagaag    3600
gcctccctag ccagcacttg tatatacgca tctataaatt gtccgtgttc atacatttga    3660
ggggaaaaca cctaaggtt tcgtttctgt atacaaccct ggcattatgt ccactgtgta     3720
tagaagtaga ttaagagcca tataagtttg aaggaaacag ttaataccat ttttaagga    3780 aacaatataa ccacaaagca cagttttgaac aaaatctcct cttttagctg atgaacttat   3840
tctgtagatt ctgtggaaca agcctatcag cttcagaatg gcattgtact caatggattt    3900
gatgctgttt gacaaagtta ctgattcact gcatggctcc cacaggagtg ggaaaacact    3960
gccatcttag tttggattct tatgtagcag gaaataaagt ataggtttag cctccttcgc    4020
aggcatgtcc tggacaccgg gccagtatct atatatgtgt atgtacgttt gtatgtgtgt    4080
agacaaatat ttggaggggt attttttgccc tgagtccaag agggtccttt agtacctgaa   4140
aagtaacttg gctttcatta ttagtactgc tcttgtttct tttcacatag ctgtctagag    4200
tagcttacca gaagcttcca tagtggtgca gaggaagtgg aaggcatcag tccctatgta    4260
tttgcagttc acctgcactt aaggcactct gttatttaga ctcatcttac tgtacctgtt    4320
ccttagacct tccataatgc tactgtctca ctgaaacatt taaattttac cctttagact    4380
gtagcctgga tattattctt gtagtttacc tcttttaaaaa caaacaaaa caaaacaaaa    4440 aactccccctt cctcactgcc caatataaaa ggcaaatgtg tacatggcag agtttgtgtg    4500
ttgtcttgaa agattcaggt atgttgcctt tatggtttcc cccttctaca tttcttagac    4560
tacatttaga gaactgtggc cgttatctgg aagtaaccat ttgcactgga gttctatgct    4620
ctcgcacctt tccaaagtta acagattttg ggggtgtgtt gtcacccaag agattgttgt    4680
ttgccatact ttgtctgaaa aattcctttg tgtttctatt gacttcaatg atagtaagaa    4740
aagtggttgt tagttataga tgtctaggta cttcaggggc acttcattga gagttttgtc    4800
ttgccatact ttgtctgaaa aattcctttg tgtttctatt gacttcaatg atagtaagaa    4860
```

```
aagtggttgt tagttataga tgtctaggta cttcaggggc acttcattga gagtttttgtc    4920 aatgtctttt gaatattccc aagcccatga gtccttgaaa atatttttta tatatacagt    4980
aactttatgt gtaaatacat aagcggcgta agtttaaagg atgttggtgt tccacgtgtt    5040
ttattcctgt atgttgtcca attgttgaca gttctgaaga attc                     5084
```

<210> SEQ ID NO 46
<211> LENGTH: 976
<212> TYPE: PRT
<213> ORGANISM: Artificial Sequence
<220> FEATURE:
<223> OTHER INFORMATION: Synthetic construct: KIT

<400> SEQUENCE: 46

```
Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

Glu Pro Ser Pro Pro Ser Ile His Pro Gly Lys Ser Asp Leu Ile Val
        35                  40                  45

Arg Val Gly Asp Glu Ile Arg Leu Leu Cys Thr Asp Pro Gly Phe Val
    50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
    210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
    290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
```

-continued

```
                325                 330                 335
Tyr Glu Ala Phe Pro Lys Pro Glu His Gln Gln Trp Ile Tyr Met Asn
                340                 345                 350

Arg Thr Phe Thr Asp Lys Trp Glu Asp Tyr Pro Lys Ser Glu Asn Glu
                355                 360                 365

Ser Asn Ile Arg Tyr Val Ser Glu Leu His Leu Thr Arg Leu Lys Gly
                370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
                420                 425                 430

Phe Pro Glu Pro Thr Ile Asp Trp Tyr Phe Cys Pro Gly Thr Glu Gln
                435                 440                 445

Arg Cys Ser Ala Ser Val Leu Pro Val Asp Val Gln Thr Leu Asn Ser
                450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
                485                 490                 495

Val Gly Lys Thr Ser Ala Tyr Phe Asn Phe Ala Phe Lys Gly Asn Asn
                500                 505                 510

Lys Glu Gln Ile His Pro His Thr Leu Phe Thr Pro Leu Leu Ile Gly
                515                 520                 525

Phe Val Ile Val Ala Gly Met Met Cys Ile Ile Val Met Ile Leu Thr
530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
                565                 570                 575

Pro Tyr Asp His Lys Trp Glu Phe Pro Arg Asn Arg Leu Ser Phe Gly
                580                 585                 590

Lys Thr Leu Gly Ala Gly Ala Phe Gly Lys Val Val Glu Ala Thr Ala
                595                 600                 605

Tyr Gly Leu Ile Lys Ser Asp Ala Ala Met Thr Val Ala Val Lys Met
                610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
                645                 650                 655

Leu Gly Ala Cys Thr Ile Gly Gly Pro Thr Leu Val Ile Thr Glu Tyr
                660                 665                 670

Cys Cys Tyr Gly Asp Leu Leu Asn Phe Leu Arg Arg Lys Arg Asp Ser
                675                 680                 685

Phe Ile Cys Ser Lys Gln Glu Asp His Ala Glu Ala Ala Leu Tyr Lys
                690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                725                 730                 735

Asp Lys Arg Arg Ser Val Arg Ile Gly Ser Tyr Ile Glu Arg Asp Val
                740                 745                 750
```

```
Thr Pro Ala Ile Met Glu Asp Asp Glu Leu Ala Leu Asp Leu Glu Asp
        755                 760                 765

Leu Leu Ser Phe Ser Tyr Gln Val Ala Lys Gly Met Ala Phe Leu Ala
    770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                805                 810                 815

Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
        835                 840                 845

Glu Ser Asp Val Trp Ser Tyr Gly Ile Phe Leu Trp Glu Leu Phe Ser
    850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
        915                 920                 925

Ser Glu Ser Thr Asn His Ile Tyr Ser Asn Leu Ala Asn Cys Ser Pro
    930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975

<210> SEQ ID NO 47
<211> LENGTH: 489
<212> TYPE: DNA
<213> ORGANISM: Artificial Sequence
<220> FEATURE:
<223> OTHER INFORMATION: Synthetic construct: LSM7

<400> SEQUENCE: 47
cgcgacaaga tggcggataa ggagaagaag aaaaaggaga gcatcttgga cttgtccaag    60
tacatcgaca agacgatccg ggtaaagttc cagggaggcc gcgaagccag tggaatcctg   120
aagggcttcg acccactcct caaccttgtg ctggacggca ccattgagta catgcgagac   180
cctgacgacc agtacaagct cacggaggac acccggcagc tgggcctcgt ggtgtgccgg   240
ggcacgtccg tggtgctaat ctgcccgcag gacggcatgg aggccatccc caacccccttc  300 atccagcagc aggacgccta gcctggccgg gggcgcgggg ggtgcagggc aggcccgagc   360
agctcggttt cccgcggact tggctgctgc tcccaccgca gtaccgcctc ctggaacgga   420
agcatttctc cttttttgtat aggttgaatt tttgttttct taataaaatt gcaaacctca   480
aaaaaaaaa                                                            489

<210> SEQ ID NO 48
<211> LENGTH: 103
<212> TYPE: PRT
<213> ORGANISM: Artificial Sequence
<220> FEATURE:
<223> OTHER INFORMATION: Synthetic construct: LSM7
```

<400> SEQUENCE: 48

```
Met Ala Asp Lys Glu Lys Lys Lys Glu Ser Ile Leu Asp Leu Ser
1               5                   10                  15

Lys Tyr Ile Asp Lys Thr Ile Arg Val Lys Phe Gln Gly Gly Arg Glu
            20                  25                  30

Ala Ser Gly Ile Leu Lys Gly Phe Asp Pro Leu Leu Asn Leu Val Leu
        35                  40                  45

Asp Gly Thr Ile Glu Tyr Met Arg Asp Pro Asp Gln Tyr Lys Leu
    50                  55                  60

Thr Glu Asp Thr Arg Gln Leu Gly Leu Val Val Cys Arg Gly Thr Ser
65                  70                  75                  80

Val Val Leu Ile Cys Pro Gln Asp Gly Met Glu Ala Ile Pro Asn Pro
                85                  90                  95

Phe Ile Gln Gln Gln Asp Ala
            100
```

<210> SEQ ID NO 49
<211> LENGTH: 1694
<212> TYPE: DNA
<213> ORGANISM: Artificial Sequence
<220> FEATURE:
<223> OTHER INFORMATION: Synthetic construct: SYNGR2

<400> SEQUENCE: 49

```
ggcggcggca gcggcggcga cggcgacatg gagagcgggg cctacggcgc ggccaaggcg      60
ggcggctcct tcgacctgcg gcgcttcctg acgcagccgc aggtggtggc gcgcgccgtg     120
tgcttggtct tcgccttgat cgtgttctcc tgcatctatg gtgagggcta cagcaatgcc     180
cacgagtcta agcagatgta ctgcgtgttc aaccgcaacg aggatgcctg ccgctatggc     240
agtgccatcg gggtgctggc cttcctggcc tcggccttct tcttggtggt cgacgcgtat     300
ttcccccaga tcagcaacgc cactgaccgc aagtacctgg tcattggtga cctgctcttc     360
tcagctctct ggaccttcct gtggtttgtt ggtttctgct tcctcaccaa ccagtgggca     420
gtcaccaacc cgaaggacgt gctggtgggg gccgactctg tgagggcagc catcaccttc     480
agcttctttt ccatcttctc ctggggtgtg ctggcctccc tggcctacca gcgctacaag     540
gctggcgtgg acgacttcat ccagaattac gttgacccca ctccggaccc caacactgcc     600
tacgcctcct acccaggtgc atctgtggac aactaccaac agccaccctt cacccagaac     660
gcggagacca ccgagggcta ccagccgccc cctgtgtact gagcggcggt tagcgtggga     720 aggggggacag agagggccct cccctctgcc ctggactttc ccatgagcct cctggaactg     780
ccagcccctc tctttcacct gttccatcct gtgcagctga cacacagcta aggagcctca     840
tagcctggcg ggggctggca gagccacacc ccaagtgcct gtgcccagag gcttcagtc     900 agccgctcac tcctccaggg cacttttagg aaagggtttt tagctagtgt ttttcctcgc     960
ttttaatgac ctcagccccg cctgcagtgg ctagaagcca gcaggtgccc atgtgctact    1020
gacaagtgcc tcagcttccc cccggcccgg gtcaggccgt gggagccgct attatctgcg    1080
ttctctgcca aagactcgtg ggggccatca cacctgccct gtgcagcgga gccggaccag    1140
gctcttgtgt cctcactcag gtttgcttcc cctgtgccca ctgctgtatg atctgggggc    1200
caccaccctg tgccggtggc ctctgggctg cctcccgtgg tgtgagggcg gggctggtgc    1260
tcatggcact tcctccttgc tcccacccct ggcagcaggg aagggctttg cctgacaaca    1320
cccagcttta tgtaaatatt ctgcagttgt tacttaggaa gctggggag ggcaggggtg    1380
```

-continued

```
cccatggct cccagactct gtctgtgccg agtgtattat aaaatcgtgg gggagatgcc    1440
cggcctggga tgctgtttgg agacggaata aatgttttct cattcagtct ccagtcattg   1500
gttgagccac agcctagggg ttggaggaag actccactct gggtacaccc ttaggggctg   1560
gctttatgga acttgtagtt tgaacaaggc agtggcaatc cgccccctcc agcctgcctg   1620
gctggccccc ttccctctgt ctggggtcgc attccgcaca agcctttcat caacatctta   1680
aaatagtaac tgtg                                                    1694
```

<210> SEQ ID NO 50
<211> LENGTH: 224
<212> TYPE: PRT
<213> ORGANISM: Artificial Sequence
<220> FEATURE:
<223> OTHER INFORMATION: Synthetic construct: SYNGR2

<400> SEQUENCE: 50

```
Met Glu Ser Gly Ala Tyr Gly Ala Ala Lys Ala Gly Gly Ser Phe Asp
1               5                   10                  15

Leu Arg Arg Phe Leu Thr Gln Pro Gln Val Val Ala Arg Ala Val Cys
            20                  25                  30

Leu Val Phe Ala Leu Ile Val Phe Ser Cys Ile Tyr Gly Glu Gly Tyr
        35                  40                  45

Ser Asn Ala His Glu Ser Lys Gln Met Tyr Cys Val Phe Asn Arg Asn
    50                  55                  60

Glu Asp Ala Cys Arg Tyr Gly Ser Ala Ile Gly Val Leu Ala Phe Leu
65                  70                  75                  80

Ala Ser Ala Phe Phe Leu Val Val Asp Ala Tyr Phe Pro Gln Ile Ser
                85                  90                  95

Asn Ala Thr Asp Arg Lys Tyr Leu Val Ile Gly Asp Leu Leu Phe Ser
            100                 105                 110

Ala Leu Trp Thr Phe Leu Trp Phe Val Gly Phe Cys Phe Leu Thr Asn
        115                 120                 125

Gln Trp Ala Val Thr Asn Pro Lys Asp Val Leu Val Gly Ala Asp Ser
    130                 135                 140

Val Arg Ala Ala Ile Thr Phe Ser Phe Phe Ser Ile Phe Ser Trp Gly
145                 150                 155                 160

Val Leu Ala Ser Leu Ala Tyr Gln Arg Tyr Lys Ala Gly Val Asp Asp
                165                 170                 175

Phe Ile Gln Asn Tyr Val Asp Pro Thr Pro Asp Pro Asn Thr Ala Tyr
            180                 185                 190

Ala Ser Tyr Pro Gly Ala Ser Val Asp Asn Tyr Gln Gln Pro Pro Phe
        195                 200                 205

Thr Gln Asn Ala Glu Thr Glu Gly Tyr Gln Pro Pro Val Tyr
    210                 215                 220
```

<210> SEQ ID NO 51
<211> LENGTH: 2272
<212> TYPE: DNA
<213> ORGANISM: Artificial Sequence
<220> FEATURE:
<223> OTHER INFORMATION: Synthetic construct: C11orf8

<400> SEQUENCE: 51

```
aatgcacagc ggtattgatg agtagatcct tggattcaga ggttggctga aacgcaccat     60
gcctgcttcc atcttttgct ctgtaaagtt gtgaattgct catgcctata gggaggaagg    120
atggcacatg ggattccttc tcaaggcaaa gttaccataa cggtggatga gtacagctca    180
```

```
aaccccaccc aggcattcac gcactacaac atcaaccaga gcagattcca gcctccacat      240
gtacatatgg tcgaccccat cccatatgac actccaaaac cagcgggcca cacgcggttt      300
gtctgcatct cagacacaca ctccagaaca gatggtatcc agatgcctta tggggacatc      360
cttctccaca caggcgattt caccgagctg ggactgccct cagaggttaa gaagtttaat      420
gactggttag gaaacctgcc atatgaatat aaaatagtga ttgctgggaa tcatgaactg      480
acatttgata aggaattcat ggcagacctt gttaaacagg actactaccg tttcccctct      540
gtgtccaaat tgaaaccaga ggactttgac aatgttcagt ccctcctgac aaacagtatt      600
tacttacaag attcggaggt aacagtgaag ggattcagga tatacggtgc accttggacc      660
ccgtggttta atggatgggg cttttaaccta cccagaggtc agtctctgct ggacaagtgg      720
aacctcatcc ctgagggcat tgacatactc atgacacatg gacctcctct aggttttcga      780
gactgggttc caaaggagct tcaaagagtg ggctgtgtgg agctgttaaa cacggttcag      840
aggcgagtcc ggcccaagct ccatgtgttt ggtggaatcc atgaaggtta tggcatcatg      900
accgacggtt acacaacgta catcaatgcc tcgacgtgta cagtcagctt caaccgacc       960 aaccctccaa ttatatttga ccttccaaac ccacagggtt cctgaagctc taaatgccct     1020
attggaatgt gagggaaggt ctataaactg ccatttttct aattataaac ttacattctc     1080
ttacttattt acaaaccctg tgagttcttt ttgtaaattg ttggaacaca atgatgcta      1140 gaggttgtgc ttcttatttt atttttattt aaatgggca tccatttgaa atcagaggaa      1200
cattgtgaat ttgtaaaatg acttctgttt tctcaaaggc catgccattg taaattgtta     1260
gtgttcgcca aggacagcc aagctttctt ttaaaaagtg ataaaagtct tattttaata      1320
tgctttaagc tgaaagaaaa aaaaataaga aacaggcagt gttttaaaaa ccaacacaga     1380
tttgcacaac tgtttaagag tattgtttga aatattttaa ttttcaatgt tttgttgttg     1440 ttgtttctt ggtaatgctt cttttttgca gatgtggtcc caatttatag caatcttctc      1500
aacagaagta ggcatggaaa agacttcttt tcatactctc actataaaga aagctgcatt     1560
gagaagaaaa tggctgtcat ttaaaggatg gtttaactag tgagattcct attgtggtta     1620
tacaaggtct cattgtttgt ttgtttcttt taaattattt cagcttttaa aatacagaaa     1680
tggaatctgt caagagcagg tatttcatac ggttaaaaaa atgaacatgc agactccttt     1740
tcaatatggg tttatatata taagtatttt ttgtgtatta tgactacgtt aggagtttaa     1800
tattgtcaag gacagtacaa ctgcaaaggg atgctgtata gcagcacatc agaagtcgga     1860
aggaactgac acattctctc agagctcaag gtcttaaaga gcttgagtta aatctaggta     1920
cagttacagg catgtataga cttaaatgga tgcaatggaa gctaactaaa ataaggctta     1980
gttgtccttt ctatttaaat accccaagtt gtcttcttac ttcctctccc ctctcccatt     2040
ttgcactgtg tgtcgatgca atcttcgcta gcacaaaata ttgtcgctaa tagtcatttc     2100
tgttttccca ttgtaaatgc tgttgagctt tattctattt tatgttactt tgttaatgaa     2160
atttaggaaa gcagttgttt ctttaaattt attgtgatat tctatatcta gcggccttta     2220
tatgcaaata aaattgcaag atttttaaaa aaaaaaaaaa aaaaaaaaaa aa             2272
```

<210> SEQ ID NO 52
<211> LENGTH: 294
<212> TYPE: PRT
<213> ORGANISM: Artificial Sequence
<220> FEATURE:
<223> OTHER INFORMATION: Synthetic construct: C11orf8

<400> SEQUENCE: 52

```
Met Ala His Gly Ile Pro Ser Gln Gly Lys Val Thr Ile Thr Val Asp
1               5                   10                  15
Glu Tyr Ser Ser Asn Pro Thr Gln Ala Phe Thr His Tyr Asn Ile Asn
            20                  25                  30
Gln Ser Arg Phe Gln Pro Pro His Val His Met Val Asp Pro Ile Pro
        35                  40                  45
Tyr Asp Thr Pro Lys Pro Ala Gly His Thr Arg Phe Val Cys Ile Ser
    50                  55                  60
Asp Thr His Ser Arg Thr Asp Gly Ile Gln Met Pro Tyr Gly Asp Ile
65                  70                  75                  80
Leu Leu His Thr Gly Asp Phe Thr Glu Leu Gly Leu Pro Ser Glu Val
                85                  90                  95
Lys Lys Phe Asn Asp Trp Leu Gly Asn Leu Pro Tyr Glu Tyr Lys Ile
            100                 105                 110
Val Ile Ala Gly Asn His Glu Leu Thr Phe Asp Lys Glu Phe Met Ala
        115                 120                 125
Asp Leu Val Lys Gln Asp Tyr Tyr Arg Phe Pro Ser Val Ser Lys Leu
    130                 135                 140
Lys Pro Glu Asp Phe Asp Asn Val Gln Ser Leu Leu Thr Asn Ser Ile
145                 150                 155                 160
Tyr Leu Gln Asp Ser Glu Val Thr Val Lys Gly Phe Arg Ile Tyr Gly
                165                 170                 175
Ala Pro Trp Thr Pro Trp Phe Asn Gly Trp Gly Phe Asn Leu Pro Arg
            180                 185                 190
Gly Gln Ser Leu Leu Asp Lys Trp Asn Leu Ile Pro Glu Gly Ile Asp
        195                 200                 205
Ile Leu Met Thr His Gly Pro Pro Leu Gly Phe Arg Asp Trp Val Pro
    210                 215                 220
Lys Glu Leu Gln Arg Val Gly Cys Val Glu Leu Leu Asn Thr Val Gln
225                 230                 235                 240
Arg Arg Val Arg Pro Lys Leu His Val Phe Gly Gly Ile His Glu Gly
                245                 250                 255
Tyr Gly Ile Met Thr Asp Gly Tyr Thr Thr Tyr Ile Asn Ala Ser Thr
            260                 265                 270
Cys Thr Val Ser Phe Gln Pro Thr Asn Pro Pro Ile Ile Phe Asp Leu
        275                 280                 285
Pro Asn Pro Gln Gly Ser
    290
```

<210> SEQ ID NO 53
<211> LENGTH: 4828
<212> TYPE: DNA
<213> ORGANISM: Artificial Sequence
<220> FEATURE:
<223> OTHER INFORMATION: Synthetic construct: CDH1

<400> SEQUENCE: 53

```
agtggcgtcg gaactgcaaa gcacctgtga gcttgcggaa gtcagttcag actccagccc      60
gctccagccc ggcccgaccc gaccgcaccc ggcgcctgcc ctcgctcggc gtccccggcc     120
agccatgggc ccttggagcc gcagcctctc ggcgctgctg ctgctgctgc aggtctcctc     180
ttggctctgc caggagccgg agccctgcca ccctggcttt gacgccgaga gctacacgtt     240
cacggtgccc cggcgccacc tggagagagg ccgcgtcctg ggcagagtga attttgaaga     300
```

```
ttgcaccggt cgacaaagga cagcctattt ttccctcgac acccgattca aagtgggcac    360
agatggtgtg attacagtca aaaggcctct acggtttcat aacccacaga tccatttctt    420
ggtctacgcc tgggactcca cctacagaaa gttttccacc aaagtcacgc tgaatacagt    480
ggggcaccac caccgccccc cgccccatca ggcctccgtt tctggaatcc aagcagaatt    540
gctcacattt cccaactcct ctcctggcct cagaagacag aagagagact gggttattcc    600
tcccatcagc tgcccagaaa atgaaaaagg cccatttcct aaaaacctgg ttcagatcaa    660
atccaacaaa gacaaagaag gcaaggtttt ctacagcatc actggccaag gagctgacac    720
acccctgtt ggtgtcttta ttattgaaag agaaacagga tggctgaagg tgacagagcc    780
tctggataga gaacgcattg ccacatacac tctcttctct cacgctgtgt catccaacgg    840
gaatgcagtt gaggatccaa tggagatttt gatcacggta accgatcaga atgcaacaa     900
gcccgaattc acccaggagg tctttaaggg gtctgtcatg gaaggtgctc ttccaggaac    960
ctctgtgatg gaggtcacag ccacagacgc ggacgatgat gtgaacacct acaatgccgc   1020
catcgcttac accatcctca gccaagatcc tgagctccct gacaaaaata tgttcaccat   1080
taacaggaac acaggagtca tcagtgtggt caccactggg ctggaccgag agagtttccc   1140
tacgtatacc ctggtggttc aagctgctga ccttcaaggt gaggggttaa gcacaacagc   1200
aacagctgtg atcacagtca ctgacaccaa cgataatcct ccgatcttca atcccaccac   1260
gtacaagggt caggtgcctg agaacgaggc taacgtcgta atcaccacac tgaaagtgac   1320
tgatgctgat gcccccaata ccccagcgtg ggaggctgta tacaccatat tgaatgatga   1380
tggtggacaa tttgtcgtca ccacaaatcc agtgaacaac gatggcattt tgaaaacagc   1440
aaagggcttg gattttgagg ccaagcagca gtacattcta cacgtagcag tgacgaatgt   1500
ggtacctttt gaggtctctc tcaccacctc cacagccacc gtcaccgtgg atgtgctgga   1560
tgtgaatgaa gcccccatct ttgtgcctcc tgaaaagaga gtggaagtgt ccgaggactt   1620
tggcgtgggc caggaaatca catcctacac tgcccaggag ccagacacat ttatggaaca   1680
gaaaataaca tatcggattt ggagagacac tgccaactgg ctggagatta atccggacac   1740
tggtgccatt ccactcgggc tgagctgga  cagggaggat tttgagcacg tgaagaacag   1800
cacgtacaca gccctaatca tagctacaga caatggttct ccagttgcta ctggaacagg   1860
gacacttctg ctgatcctgt ctgatgtgaa tgacaacgcc cccataccag aacctcgaac   1920
tatattcttc tgtgagagga atccaaagcc tcaggtcata aacatcattg atgcagacct   1980
tcctcccaat acatctccct tcacagcaga actaacacac ggggcgagtg ccaactggac   2040
cattcagtac aacgacccaa cccaagaatc tatcattttg aagccaaaga tggccttaga   2100
ggtgggtgac tacaaaatca atctcaagct catggataac cagaataaag accaagtgac   2160
caccttagag gtcagcgtgt gtgactgtga aggggccgcc ggcgtctgta ggaaggcaca   2220
gcctgtcgaa gcaggattgc aaattcctgc cattctgggg attcttggag gaattcttgc   2280
tttgctaatt ctgattctgc tgctcttgct gtttcttcgg aggagagcgg tggtcaaaga   2340
gcccttactg ccccagagg atgacacccg ggacaacgtt tattactatg atgaagaagg    2400
aggcggagaa gaggaccagg actttgactt gagccagctg cacaggggcc tggacgctcg   2460
gcctgaagtg actcgtaacg acgttgcacc aacccctcatg agtgtccccc ggtatcttcc   2520
ccgccctgcc aatcccgatg aaattggaaa ttttattgat gaaatctga aagcggctga     2580
tactgacccc acagccccgc cttatgattc tctgctcgtg tttgactatg aaggaagcgg   2640
ttccgaagct gctagtctga gctccctgaa ctcctcagag tcagacaaag accaggacta   2700
```

-continued

```
tgactacttg aacgaatggg gcaatcgctt caagaagctg gctgacatgt acggaggcgg    2760
cgaggacgac taggggactc gagagaggcg ggccccagac ccatgtgctg ggaaatgcag    2820
aaatcacgtt gctggtggtt tttcagctcc cttcccttga gatgagtttc tggggaaaaa    2880
aaagagactg gttagtgatg cagttagtat agctttatac tctctccact ttatagctct    2940
aataagtttg tgttagaaaa gtttcgactt atttcttaaa gcttttttt ttttcccatc    3000 actctttaca tggtggtgat gtccaaaaga tacccaaatt ttaatattcc agaagaacaa    3060
ctttagcatc agaaggttca cccagcacct tgcagatttt cttaaggaat tttgtctcac    3120
ttttaaaaag aaggggagaa gtcagctact ctagttctgt tgttttgtgt atataatttt    3180
ttaaaaaaaa tttgtgtgct tctgctcatt actacactgg tgtgtccctc tgcctttttt    3240 tttttttta agacagggtc tcattctatc ggccaggctg gagtgcagtg gtgcaatcac    3300
agctcactgc agccttgtcc tcccaggctc aagctatcct tgcacctcag cctcccaagt    3360
agctgggacc acaggcatgc accactacgc atgactaatt ttttaaatat ttgagacggg    3420
gtctccctgt gttacccagg ctggtctcaa actcctgggc tcaagtgatc ctcccatctt    3480
ggcctcccag agtattggga ttacagacat gagccactgc acctgcccag ctccccaact    3540
ccctgccatt ttttaagaga cagtttcgct ccatcgccca ggcctgggat gcagtgatgt    3600
gatcatagct cactgtaacc tcaaactctg gggctcaagc agttctccca ccagcctcct    3660
tttatttttt ttgtacagat ggggtcttgc tatgttgccc aagctggtct aaactcctg    3720 gcctcaagca atccttctgc cttggcccc caaagtgctg ggattgtggg catgagctgc    3780
tgtgcccagc ctccatgttt taatatcaac tctcactcct gaattcagtt gctttgccca    3840
agataggagt tctctgatgc agaaattatt gggctctttt agggtaagaa gtttgtgtct    3900
ttgtctggcc acatcttgac taggtattgt ctactctgaa gacctttaat ggcttccctc    3960
tttcatctcc tgagtatgta acttgcaatg ggcagctatc cagtgacttg ttctgagtaa    4020
gtgtgttcat taatgtttat ttagctctga agcaagagtg atatactcca ggacttagaa    4080
tagtgcctaa agtgctgcag ccaaagacag agcggaacta tgaaaagtgg gcttggagat    4140
ggcaggagag cttgtcattg agcctggcaa tttagcaaac tgatgctgag gatgattgag    4200
gtgggtctac ctcatctctg aaaattctgg aaggaatgga ggagtctcaa catgtgtttc    4260
tgacacaaga tccgtggttt gtactcaaag cccagaatcc ccaagtgcct gcttttgatg    4320
atgtctacag aaaatgctgg ctgagctgaa cacatttgcc caattccagg tgtgcacaga    4380
aaaccgagaa tattcaaaat tccaaatttt ttcttaggag caagaagaaa atgtggccct    4440 aaaggggggtt agttgagggg taggggggtag tgaggatctt gatttggatc tcttttatt    4500 taaatgtgaa tttcaacttt tgacaatcaa agaaaagact tttgttgaaa tagctttact    4560
gtttctcaag tgttttggag aaaaaaatca accctgcaat cacttttttgg aattgtcttg    4620 attttttcggc agttcaagct atatcgaata tagttctgtg tagagaatgt cactgtagtt    4680
ttgagtgtat acatgtgtgg gtgctgataa ttgtgtatt tctttggggg tggaaaagga    4740
aaacaattca agctgagaaa agtattctca aagatgcatt tttataaatt ttattaaaca    4800
attttgttaa accataaaaa aaaaaaaa                                      4828
```

<210> SEQ ID NO 54
<211> LENGTH: 882
<212> TYPE: PRT
<213> ORGANISM: Artificial Sequence
<220> FEATURE:

<223> OTHER INFORMATION: Synthetic construct: CDH1

<400> SEQUENCE: 54

```
Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45

Gly Arg Val Leu Gly Arg Val Asn Phe Glu Asp Cys Thr Gly Arg Gln
    50                  55                  60

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
                85                  90                  95

His Phe Leu Val Tyr Ala Trp Asp Ser Thr Tyr Arg Lys Phe Ser Thr
            100                 105                 110

Lys Val Thr Leu Asn Thr Val Gly His His Arg Pro Pro His
        115                 120                 125

Gln Ala Ser Val Ser Gly Ile Gln Ala Glu Leu Leu Thr Phe Pro Asn
    130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
                165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
        195                 200                 205

Arg Glu Thr Gly Trp Leu Lys Val Thr Glu Pro Leu Asp Arg Glu Arg
    210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
        275                 280                 285

Ala Asp Asp Asp Val Asn Thr Tyr Asn Ala Ala Ile Ala Tyr Thr Ile
    290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
            340                 345                 350

Glu Gly Leu Ser Thr Thr Ala Thr Ala Val Ile Thr Val Thr Asp Thr
        355                 360                 365

Asn Asp Asn Pro Pro Ile Phe Asn Pro Thr Thr Tyr Lys Gly Gln Val
    370                 375                 380

Pro Glu Asn Glu Ala Asn Val Val Ile Thr Thr Leu Lys Val Thr Asp
385                 390                 395                 400
```

```
Ala Asp Ala Pro Asn Thr Pro Ala Trp Glu Ala Val Tyr Thr Ile Leu
            405                 410                 415
Asn Asp Asp Gly Gly Gln Phe Val Val Thr Thr Asn Pro Val Asn Asn
            420                 425                 430
Asp Gly Ile Leu Lys Thr Ala Lys Gly Leu Asp Phe Glu Ala Lys Gln
            435                 440                 445
Gln Tyr Ile Leu His Val Ala Val Thr Asn Val Val Pro Phe Glu Val
            450                 455                 460
Ser Leu Thr Thr Ser Thr Ala Thr Val Thr Val Asp Val Leu Asp Val
465                 470                 475                 480
Asn Glu Ala Pro Ile Phe Val Pro Pro Glu Lys Arg Val Glu Val Ser
            485                 490                 495
Glu Asp Phe Gly Val Gly Gln Glu Ile Thr Ser Tyr Thr Ala Gln Glu
            500                 505                 510
Pro Asp Thr Phe Met Glu Gln Lys Ile Thr Tyr Arg Ile Trp Arg Asp
            515                 520                 525
Thr Ala Asn Trp Leu Glu Ile Asn Pro Asp Thr Gly Ala Ile Ser Thr
            530                 535                 540
Arg Ala Glu Leu Asp Arg Glu Asp Phe Glu His Val Lys Asn Ser Thr
545                 550                 555                 560
Tyr Thr Ala Leu Ile Ile Ala Thr Asp Asn Gly Ser Pro Val Ala Thr
            565                 570                 575
Gly Thr Gly Thr Leu Leu Leu Ile Leu Ser Asp Val Asn Asp Asn Ala
            580                 585                 590
Pro Ile Pro Glu Pro Arg Thr Ile Phe Phe Cys Glu Arg Asn Pro Lys
            595                 600                 605
Pro Gln Val Ile Asn Ile Ile Asp Ala Asp Leu Pro Pro Asn Thr Ser
            610                 615                 620
Pro Phe Thr Ala Glu Leu Thr His Gly Ala Ser Ala Asn Trp Thr Ile
625                 630                 635                 640
Gln Tyr Asn Asp Pro Thr Gln Glu Ser Ile Ile Leu Lys Pro Lys Met
            645                 650                 655
Ala Leu Glu Val Gly Asp Tyr Lys Ile Asn Leu Lys Leu Met Asp Asn
            660                 665                 670
Gln Asn Lys Asp Gln Val Thr Thr Leu Glu Val Ser Val Cys Asp Cys
            675                 680                 685
Glu Gly Ala Ala Gly Val Cys Arg Lys Ala Gln Pro Val Glu Ala Gly
            690                 695                 700
Leu Gln Ile Pro Ala Ile Leu Gly Ile Leu Gly Gly Ile Leu Ala Leu
705                 710                 715                 720
Leu Ile Leu Ile Leu Leu Leu Leu Phe Leu Arg Arg Arg Ala Val
            725                 730                 735
Val Lys Glu Pro Leu Leu Pro Pro Glu Asp Asp Thr Arg Asp Asn Val
            740                 745                 750
Tyr Tyr Tyr Asp Glu Glu Gly Gly Gly Glu Glu Asp Gln Asp Phe Asp
            755                 760                 765
Leu Ser Gln Leu His Arg Gly Leu Asp Ala Arg Pro Glu Val Thr Arg
            770                 775                 780
Asn Asp Val Ala Pro Thr Leu Met Ser Val Pro Arg Tyr Leu Pro Arg
785                 790                 795                 800
Pro Ala Asn Pro Asp Glu Ile Gly Asn Phe Ile Asp Glu Asn Leu Lys
            805                 810                 815
Ala Ala Asp Thr Asp Pro Thr Ala Pro Pro Tyr Asp Ser Leu Leu Val
```

|  | 820 |  | 825 |  | 830 |  |
|---|---|---|---|---|---|---|

Phe Asp Tyr Glu Gly Ser Gly Ser Glu Ala Ala Ser Leu Ser Ser Leu
835                     840                     845

Asn Ser Ser Glu Ser Asp Lys Asp Gln Asp Tyr Asp Tyr Leu Asn Glu
850                     855                     860

Trp Gly Asn Arg Phe Lys Lys Leu Ala Asp Met Tyr Gly Gly Gly Glu
865                     870                     875                     880

Asp Asp

<210> SEQ ID NO 55
<211> LENGTH: 5858
<212> TYPE: DNA
<213> ORGANISM: Artificial Sequence
<220> FEATURE:
<223> OTHER INFORMATION: Synthetic construct: FAM13A1

<400> SEQUENCE: 55

| | |
|---|---|
| ccttccagcc atgtgggttc agcggaaaga gaagcaaaac cactcttcct aaaatgttag | 60 |
| aagctgctct tcgcttacct tggggccttt gcattgggag ctgtttttca catcaaagaa | 120 |
| tatgtgctga atgaatttt agtattttgc tgtcgtttta atattttcgt ctggtcttcc | 180 |
| tcagttcttc cagacgcttt ctgagagaat gggggcagga gctctagcca tctgtcaaag | 240 |
| taaagcagcg gttcggctga agaagacat gaaaaagata gtggcagtgc cattaaatga | 300 |
| acagaaggat tttacctatc agaagttatt tggagtcagt ctccaagaac ttgaacggca | 360 |
| ggggctcacc gagaatggca ttccagcagt agtgtggaat atagtggaat atttgacgca | 420 |
| gcatggactt acccaagaag gtcttttag ggtgaatggt aacgtgaagg tggtggaaca | 480 |
| acttcgactg aagttcgaga gtggagtgcc cgtggagctc gggaaggacg tgatgtctg | 540 |
| ctcagcagcc agtctgttga gctgtttct gagggagctg cctgacagtc tgatcacctc | 600 |
| agcgttgcag cctcgattca ttcaactctt tcaggatggc agaaatgatg ttcaggagag | 660 |
| tagcttaaga gacttaataa agagctgcc agacacccac tactgcctcc tcaagtacct | 720 |
| ttgccagttc ttgacaaaag tagccaagca tcatgtgcag aatcgcatga atgttcacaa | 780 |
| tctcgccact gtatttgggc caaattgctt tcatgtgcca cctgggcttg aaggcatgaa | 840 |
| ggaacaggac ctgtgcaaca agataatggc taaaattcta gaaaattaca atacctgtt | 900 |
| tgaagtagag tatacagaaa atgatcatct gagatgtgaa acctggcta ggcttatcat | 960 |
| agtaaaagag gtctattata agaactccct gcccatcctt ttaacaagag gcttagaaag | 1020 |
| agacatgcca aaaccacctc caaaaaccaa gatcccaaaa tccaggagtg agggatctat | 1080 |
| tcaggcccac agagtactgc aaccagagct atctgatggc attcctcagc tcagcttgcg | 1140 |
| gctaagttat agaaaagcct gcttggaaga catgaattca gcagagggtg ctattagtgc | 1200 |
| caagttggta cccagttcac aggaagatga agacctctg tcacctttct atttgagtgc | 1260 |
| tcatgtaccc caagtcagca atgtgtctgc aaccggagaa ctcttagaaa gaaccatccg | 1320 |
| atcagctgta gaacaacatc ttttgatgt taataactct ggaggtcaaa gttcagagga | 1380 |
| ctcagaatct ggaacactat cagcatcttc tgccacatct gccagacagc gccgccgcca | 1440 |
| gtccaaggag caggatgaag ttcgacatgg gagagacaag ggactatca acaaagaaaa | 1500 |
| tactccttct gggttcaacc accttgatga ttgtatttg aatactcagg aagtcgaaaa | 1560 |
| ggtacacaaa atactttg gttgtgctgg agaaaggagc aagcctaaac gtcagaaatc | 1620 |
| cagtactaaa ctttctgagc ttcatgacaa tcaggacggt cttgtgaata tggaaagtct | 1680 |

| | |
|---|---|
| caattccaca cgatctcatg agagaactgg acctgatgat tttgaatgga tgtctgatga | 1740 |
| aaggaaagga aatgaaaaag atggtggaca cactcagcat tttgagagcc ccacaatgaa | 1800 |
| gatccaggag catcccagcc tatctgacac caaacagcag agaaatcaag atgccggtga | 1860 |
| ccaggaggag agctttgtct ccgaagtgcc ccagtcggac ctgactgcat tgtgtgatga | 1920 |
| aaagaactgg gaagagccta tccctgcttt ctcctcctgg cagcgggaga acagtgactc | 1980 |
| tgatgaagcc cacctctcgc cgcaggctgg gcgcctgatc cgtcagctgc tggacgaaga | 2040 |
| cagcgacccc atgctctctc ctcggttcta cgcttatggg cagagcaggc aatacctgga | 2100 |
| tgacacagaa gtgcctcctt ccccaccaaa ctcccattct ttcatgaggc ggcgaagctc | 2160 |
| ctctctgggg tcctatgatg atgagcaaga ggacctgaca cctgcccagc tcacacgaag | 2220 |
| gattcagagc cttaaaaaga agatccggaa gtttgaagat agattcgaag aagaagaa | 2280 |
| gtacagacct tcccacagtg acaaagcagc caatccggag gttctgaaat ggacaaatga | 2340 |
| ccttgccaaa ttccggagac aacttaaaga atcaaaacta aagatatctg aagaggacct | 2400 |
| aactcccagg atgcggcagc gaagcaacac actccccaag agttttggtt cccaacttga | 2460 |
| gaaagaagat gagaagaagc aagagctggt ggataaagca ataaagccca gtgttgaagc | 2520 |
| cacattggaa tctattcaga ggaagctcca ggagaagcga gcggaaagca gccgccctga | 2580 |
| ggacattaag gatatgacca agaccagat tgctaatgag aaagtggctc tgcagaaagc | 2640 |
| tctgttatat tatgaaagca ttcatggacg gccggtaaca aagaacgaac ggcaggtgat | 2700 |
| gaagccacta tacgacaggt accggctggt caaacagatc ctctcccgag ctaacaccat | 2760 |
| acccatcatt ggttcccct ccagcaagcg gagaagccct ttgctgcagc caattatcga | 2820 |
| gggcgaaaact gcttccttct tcaaggagat aaaggaagaa gaggagggggt cagaagacga | 2880 |
| tagcaatgtg aagccagact tcatggtcac tctgaaaacc gatttcagtg cacgatgctt | 2940 |
| tctggaccaa ttcgaagatg acgctgatgg attatttcc ccaatggatg ataaaaatacc | 3000 |
| atcaaaatgc agccaggaca cagggcttc aaatctccat gctgcctcaa tacctgaact | 3060 |
| cctggaacac ctccaggaaa tgagagaaga aaagaaaagg attcgaaaga aacttcggga | 3120 |
| ttttgaagac aacttttca gacagaatgg aagaaatgtc cagaaggaag accgcactcc | 3180 |
| tatggctgaa gaatacagtg aatataagca cataaaggcg aaactgaggc tcctggaggt | 3240 |
| gctcatcagc aagagagaca ctgattccaa gtccatgtga ggggcatggc caagcacagg | 3300 |
| gggctggcag ctgcggtgag agtttactgt ccccagagaa agtgcagctc tggaaggcag | 3360 |
| ccttggggct ggccctgcaa agcatgcagc ccttctgcct ctagaccatt tggcatcggc | 3420 |
| tcctgtttcc attgcctgcc ttagaaactg gctggaagaa gacaatgtga cctgacttag | 3480 |
| gcattttgta attggaaagt caagactgca gtatgtgcac atgcgcacgc gcatgcacgc | 3540 |
| acacacacac acagtagtgg agctttccta acactagcag agattaatca ctacattaga | 3600 |
| caacactcat ctacagagaa tatacactgt tcttccctgg ataactgaga aacaagagac | 3660 |
| cattctctgt ctaactgtga taaaaacaag ctcaggactt tattctatag agcaaacttg | 3720 |
| ctgtggaggg ccatgctctc cttggaccca gttaactgca aacgtgcatt ggagccctat | 3780 |
| ttgctgccgc tgccattcta gtgaccttc cacagagctg cgccttcctc acgtgtgtga | 3840 |
| aaggttttcc ccttcagccc tcaggtagat ggaagctgca tctgcccacg atggcagtgc | 3900 |
| agtcatcatc ttcaggatgt ttcttcagga cttcctcagc tgacaaggaa ttttggtccc | 3960 |
| tgcctaggac cgggtcatct gcagaggaca gagagatggt aagcagctgt atgaatgctg | 4020 |
| attttaaaac caggtcatgg gagaagagcc tggagattct ttcctgaaca ctgactgcac | 4080 |

```
ttaccagtct gattttatcg tcaaacacca agccaggcta gcatgctcat ggcaatctgt    4140
ttggggctgt tttgttgtgg cactagccaa acataaaggg gcttaagtca gcctgcatac    4200
agaggatcgg ggagagaagg ggcctgtgtt ctcagcctcc tgagtactta ccagagttta    4260
attttttaa aaaaaatctg cactaaaatc cccaaactga caggtaaatg tagccctcag    4320
agctcagccc aaggcagaat ctaaatcaca ctattttcga gatcatgtat aaaaagaaaa    4380
aaaagaagtc atgctgtgtg gccaattata attttttca aagactttgt cacaaaactg    4440
tctatattag acattttgga gggaccagga aatgtaagac accaaatcct ccatctcttc    4500
agtgtgcctg atgtcacctc atgatttgct gttactttt taactcctgc gccaaggaca    4560
gtgggttctg tgtccacctt tgtgctttgc gaggccgagc ccaggcatct gctcgcctgc    4620
cacggctgac cagagaaggt gcttcaggag ctctgcctta gacgacgtgt tacagtatga    4680
acacacagca gaggcaccct cgtatgtttt gaaagttgcc ttctgaaagg gcacagtttt    4740
aaggaaaaga aaaagaatgt aaaactatac tgacccgttt tcagttttaa agggtcgtga    4800
gaaactggct ggtccaatgg gatttacagc aacattttcc attgctgaag tgaggtagca    4860
gctctcttct gtcagctgaa tgttaaggat ggggaaaaag aatgccttta agtttgctct    4920
taatcgtatg gaagcttgag ctatgtgttg gaagtgccct ggttttaatc catacacaaa    4980
gacggtacat aatcctacag gtttaaatgt acataaaaat atagtttgga attctttgct    5040
ctactgttta cattgcagat tgctataatt tcaaggagtg agattataaa taaaatgatg    5100
cactttagga tgtttcctat ttttgaaatc tgaacatgaa tcattcacat gaccaaaaat    5160
tgtgttttt taaaaataca tgtctagtct gtcctttaat agctctctta aataagctat    5220
gatattaatc agatcattac cagttagctt ttaaagcaca tttgtttaag actatgtttt    5280
tggaaaaata cgctacagaa tttttttta agctacaaat aaatgagatg ctactaattg    5340
ttttggaatc tgttgtttct gccaaaggta aattaactaa agatttattc aggaatcccc    5400
atttgaattt gtatgattca ataaaagaaa acaccaagta agttatataa aataaattgt    5460
gtatgagatg ttgtgttttc ctttgtaatt tccactaact aactaactaa cttatattct    5520
tcatggaatg gagcccagaa gaaatgagag gaagcccttt tcacactaga tcttatttga    5580
agaaatgttt gttagtcagt cagtcagtgg tttctggctc tgccgaggga gatgtgttcc    5640
ccagcaacca tttctgcagc ccagaatctc aaggcactag aggcggtgtc ttaattaatt    5700
ggcttcacaa agacaaaatg ctctggactg gattttttcc tttgctgtgt tgggaatatg    5760
tgtttattaa ttagcacatg ccaacaaaat aaatgtcaag agttatttca taagtgtaag    5820
taaacttaag aattaaagag tgcagactta taattttc                           5858
```

<210> SEQ ID NO 56  
<211> LENGTH: 1023  
<212> TYPE: PRT  
<213> ORGANISM: Artificial Sequence  
<220> FEATURE:  
<223> OTHER INFORMATION: Synthetic construct: FAM13A1

<400> SEQUENCE: 56

```
Met Gly Ala Gly Ala Leu Ala Ile Cys Gln Ser Lys Ala Ala Val Arg
1               5                   10                  15

Leu Lys Glu Asp Met Lys Lys Ile Val Ala Val Pro Leu Asn Glu Gln
            20                  25                  30

Lys Asp Phe Thr Tyr Gln Lys Leu Phe Gly Val Ser Leu Gln Glu Leu
        35                  40                  45
```

Glu Arg Gln Gly Leu Thr Glu Asn Gly Ile Pro Ala Val Val Trp Asn
 50                  55                  60

Ile Val Glu Tyr Leu Thr Gln His Gly Leu Thr Gln Glu Gly Leu Phe
 65                  70                  75                  80

Arg Val Asn Gly Asn Val Lys Val Val Glu Gln Leu Arg Leu Lys Phe
                 85                  90                  95

Glu Ser Gly Val Pro Val Glu Leu Gly Lys Asp Gly Asp Val Cys Ser
                100                 105                 110

Ala Ala Ser Leu Leu Lys Leu Phe Leu Arg Glu Leu Pro Asp Ser Leu
                115                 120                 125

Ile Thr Ser Ala Leu Gln Pro Arg Phe Ile Gln Leu Phe Gln Asp Gly
                130                 135                 140

Arg Asn Asp Val Gln Glu Ser Ser Leu Arg Asp Leu Ile Lys Glu Leu
145                 150                 155                 160

Pro Asp Thr His Tyr Cys Leu Leu Lys Tyr Leu Cys Gln Phe Leu Thr
                165                 170                 175

Lys Val Ala Lys His His Val Gln Asn Arg Met Asn Val His Asn Leu
                180                 185                 190

Ala Thr Val Phe Gly Pro Asn Cys Phe His Val Pro Pro Gly Leu Glu
                195                 200                 205

Gly Met Lys Glu Gln Asp Leu Cys Asn Lys Ile Met Ala Lys Ile Leu
                210                 215                 220

Glu Asn Tyr Asn Thr Leu Phe Glu Val Glu Tyr Thr Glu Asn Asp His
225                 230                 235                 240

Leu Arg Cys Glu Asn Leu Ala Arg Leu Ile Ile Val Lys Glu Val Tyr
                245                 250                 255

Tyr Lys Asn Ser Leu Pro Ile Leu Leu Thr Arg Gly Leu Glu Arg Asp
                260                 265                 270

Met Pro Lys Pro Pro Lys Thr Lys Ile Pro Lys Ser Arg Ser Glu
                275                 280                 285

Gly Ser Ile Gln Ala His Arg Val Leu Gln Pro Glu Leu Ser Asp Gly
                290                 295                 300

Ile Pro Gln Leu Ser Leu Arg Leu Ser Tyr Arg Lys Ala Cys Leu Glu
305                 310                 315                 320

Asp Met Asn Ser Ala Glu Gly Ala Ile Ser Ala Lys Leu Val Pro Ser
                325                 330                 335

Ser Gln Glu Asp Glu Arg Pro Leu Ser Pro Phe Tyr Leu Ser Ala His
                340                 345                 350

Val Pro Gln Val Ser Asn Val Ser Ala Thr Gly Glu Leu Leu Glu Arg
                355                 360                 365

Thr Ile Arg Ser Ala Val Glu Gln His Leu Phe Asp Val Asn Asn Ser
                370                 375                 380

Gly Gly Gln Ser Ser Glu Asp Ser Glu Ser Gly Thr Leu Ser Ala Ser
385                 390                 395                 400

Ser Ala Thr Ser Ala Arg Gln Arg Arg Gln Ser Lys Glu Gln Asp
                405                 410                 415

Glu Val Arg His Gly Arg Asp Lys Gly Leu Ile Asn Lys Glu Asn Thr
                420                 425                 430

Pro Ser Gly Phe Asn His Leu Asp Asp Cys Ile Leu Asn Thr Gln Glu
                435                 440                 445

Val Glu Lys Val His Lys Asn Thr Phe Gly Cys Ala Gly Glu Arg Ser
450                 455                 460

-continued

```
Lys Pro Lys Arg Gln Lys Ser Ser Thr Lys Leu Ser Glu Leu His Asp
465                 470                 475                 480

Asn Gln Asp Gly Leu Val Asn Met Glu Ser Leu Asn Ser Thr Arg Ser
                485                 490                 495

His Glu Arg Thr Gly Pro Asp Asp Phe Glu Trp Met Ser Asp Glu Arg
            500                 505                 510

Lys Gly Asn Glu Lys Asp Gly Gly His Thr Gln His Phe Glu Ser Pro
        515                 520                 525

Thr Met Lys Ile Gln Glu His Pro Ser Leu Ser Asp Thr Lys Gln Gln
    530                 535                 540

Arg Asn Gln Asp Ala Gly Asp Gln Glu Glu Ser Phe Val Ser Glu Val
545                 550                 555                 560

Pro Gln Ser Asp Leu Thr Ala Leu Cys Asp Glu Lys Asn Trp Glu Glu
                565                 570                 575

Pro Ile Pro Ala Phe Ser Ser Trp Gln Arg Glu Asn Ser Asp Ser Asp
            580                 585                 590

Glu Ala His Leu Ser Pro Gln Ala Gly Arg Leu Ile Arg Gln Leu Leu
        595                 600                 605

Asp Glu Asp Ser Asp Pro Met Leu Ser Pro Arg Phe Tyr Ala Tyr Gly
    610                 615                 620

Gln Ser Arg Gln Tyr Leu Asp Asp Thr Glu Val Pro Pro Ser Pro Pro
625                 630                 635                 640

Asn Ser His Ser Phe Met Arg Arg Arg Ser Ser Leu Gly Ser Tyr
                645                 650                 655

Asp Asp Glu Gln Glu Asp Leu Thr Pro Ala Gln Leu Thr Arg Arg Ile
            660                 665                 670

Gln Ser Leu Lys Lys Lys Ile Arg Lys Phe Glu Asp Arg Phe Glu Glu
        675                 680                 685

Glu Lys Lys Tyr Arg Pro Ser His Ser Asp Lys Ala Ala Asn Pro Glu
    690                 695                 700

Val Leu Lys Trp Thr Asn Asp Leu Ala Lys Phe Arg Arg Gln Leu Lys
705                 710                 715                 720

Glu Ser Lys Leu Lys Ile Ser Glu Glu Asp Leu Thr Pro Arg Met Arg
                725                 730                 735

Gln Arg Ser Asn Thr Leu Pro Lys Ser Phe Gly Ser Gln Leu Glu Lys
            740                 745                 750

Glu Asp Glu Lys Lys Gln Glu Leu Val Asp Lys Ala Ile Lys Pro Ser
        755                 760                 765

Val Glu Ala Thr Leu Glu Ser Ile Gln Arg Lys Leu Gln Glu Lys Arg
    770                 775                 780

Ala Glu Ser Ser Arg Pro Glu Asp Ile Lys Asp Met Thr Lys Asp Gln
785                 790                 795                 800

Ile Ala Asn Glu Lys Val Ala Leu Gln Lys Ala Leu Leu Tyr Tyr Glu
                805                 810                 815

Ser Ile His Gly Arg Pro Val Thr Lys Asn Glu Arg Gln Val Met Lys
            820                 825                 830

Pro Leu Tyr Asp Arg Tyr Arg Leu Val Lys Gln Ile Leu Ser Arg Ala
        835                 840                 845

Asn Thr Ile Pro Ile Ile Gly Ser Pro Ser Ser Lys Arg Arg Ser Pro
    850                 855                 860

Leu Leu Gln Pro Ile Ile Glu Gly Glu Thr Ala Ser Phe Phe Lys Glu
865                 870                 875                 880

Ile Lys Glu Glu Glu Glu Gly Ser Glu Asp Asp Ser Asn Val Lys Pro
```

|     |     |     |     |     |     |     |     |     |     |     |     |
| --- | --- | --- | --- | --- | --- | --- | --- | --- | --- | --- | --- |
|     |     |     | 885 |     |     |     | 890 |     |     |     | 895 |
| Asp | Phe | Met | Val | Thr | Leu | Lys | Thr | Asp | Phe | Ser | Ala | Arg | Cys | Phe | Leu |
|     |     |     | 900 |     |     |     | 905 |     |     |     | 910 |

Asp Gln Phe Glu Asp Asp Ala Asp Gly Phe Ile Ser Pro Met Asp Asp
          915                 920                 925

Lys Ile Pro Ser Lys Cys Ser Gln Asp Thr Gly Leu Ser Asn Leu His
        930                 935                 940

Ala Ala Ser Ile Pro Glu Leu Leu Glu His Leu Gln Glu Met Arg Glu
945                 950                 955                 960

Glu Lys Lys Arg Ile Arg Lys Lys Leu Arg Asp Phe Glu Asp Asn Phe
              965                 970                 975

Phe Arg Gln Asn Gly Arg Asn Val Gln Lys Glu Asp Arg Thr Pro Met
            980                 985                 990

Ala Glu Glu Tyr Ser Glu Tyr Lys  His Ile Lys Ala Lys Leu Arg Leu
            995                 1000                1005

Leu Glu  Val Leu Ile Ser Lys  Arg Asp Thr Asp Ser  Lys Ser Met
    1010                1015                1020

<210> SEQ ID NO 57
<211> LENGTH: 3683
<212> TYPE: DNA
<213> ORGANISM: Artificial Sequence
<220> FEATURE:
<223> OTHER INFORMATION: Synthetic construct: IMPACT

<400> SEQUENCE: 57

| | | | | | | |
|---|---|---|---|---|---|---|
| cctggcaggc | ggcggctgca | gggcaggtcc | aggggccaca | tggctgaggg | ggacgcaggg | 60 |
| agcgaccaga | ggcagaatga | ggaaattgaa | gcaatggcag | ccatttatgg | cgaggagtgg | 120 |
| tgtgtcattg | atgactgtgc | caaaatattt | tgtattagaa | ttagcgacga | tatagatgac | 180 |
| cccaaatgga | cactttgctt | gcaggtgatg | ctgccgaatg | aatacccagg | tacagctcca | 240 |
| cctatctacc | agttgaatgc | tccttggctt | aaagggcaag | aacgtgcgga | tttatcaaat | 300 |
| agccttgagg | aaatatatat | tcagaatatc | ggtgaaagta | ttctttacct | gtgggtggag | 360 |
| aaaataagag | atgttcttat | acaaaaatct | cagatgacag | aaccaggccc | agatgtaaag | 420 |
| aagaaaactg | aagaggaaga | tgttgaatgt | gaagatgatc | tcattttagc | atgtcagccg | 480 |
| gaaagttcgg | ttaaagcatt | ggattttgat | atcagtgaaa | ctcggacaga | agtagaagta | 540 |
| gaagaattac | ctccgattga | tcatggcatt | cctattacag | accgaagaag | tacttttcag | 600 |
| gcacacttgg | ctccagtggt | ttgtcccaaa | caggtgaaaa | tggttctttc | caaattgtat | 660 |
| gagaataaga | aaatagctag | tgccacccac | aacatctatg | cctacagaat | atattgtgag | 720 |
| gataaacaga | ccttcttaca | ggattgtgag | gatgatgggg | aaacagcagc | tggtgggcgt | 780 |
| cttcttcatc | tcatggagat | tttgaatgtg | aagaatgtca | tggtggtagt | atcacgctgg | 840 |
| tatggaggga | ttctgctagg | accagatcgc | tttaaacata | tcaacaactg | tgccagaaac | 900 |
| atactagtgg | aaaagaacta | cacaaattca | cctgaggagt | catctaaggc | tttgggaaag | 960 |
| aacaaaaaag | taagaaaaga | caagaagagg | aatgaacatt | aatacctgaa | actataggaa | 1020 |
| aggttaattt | gcctataatt | atatatacat | tccatagtca | tcaaggaata | tattgtgcag | 1080 |
| agagagtatc | cttgactgct | taagtcagcc | agttcagcat | ggataccaac | attagctttt | 1140 |
| cttcttggtt | atatcatctg | ccaaaaatag | agaacttatg | atctattcat | gtgtgtttca | 1200 |
| ggcttatttg | ggagaactaa | tttgaactta | atcaccactt | catctaattt | tagcaaggta | 1260 |
| acagttgccc | agggcagtac | ctgaattaac | tgtccatttc | agtacatgtc | aagtgccttt | 1320 |

```
gttaggtgga gaagaaatgt ctctagagga atataaatac ctgatttctt gtcatcgaga    1380
ttcttgtact gttaaatgaa tattgccttt tactgctctt tatggcttat tggaatagga    1440
gctcatttaa gattgatctt ggagagtttc ttcttgtgat tttagttcat aagtatgtca    1500
cctttcattt tatagtgttc atcattgagt aatggattaa gtgaaaatcc aggagtatcc    1560
atctgcagtt atgtgctgag gtgataattc atccaacata tttgttagca taaatattat    1620
gcttcagttt ctgttgcaaa ttggtgattg tgaaattaca gaaagtgatt ttctagtctg    1680
ctttttttgt ttaattcttg taatgtaagc aataaatatg gagtgtcagt agtctccttc    1740
cacccccagaa atgtgttggt gtaacattct cgtttctttt aacaacctgg aagtaccttt    1800
cttgtgatct tcactgagga attagaacta tgatagaagt taggctgtgg caaatgggac    1860
attcgtagag tgggatagag gtggcagaat gaacctggtg tagggcagga gtatgttgtg    1920
tagttacatc aatttgatgc atgctttcca tctgcactcc agacggcttt ctcagttcca    1980
agattttgca gagagaagga gcaaacccttt tcattggaaa aacagaaaca accctccccc    2040
ccattttttc ccctctattc atcaaacctt tatgtatctt tcatcttcca gttacctcta    2100
ggcatttaga tagtgaaatt tacctttgag atataacaat aagtgattaa ctgttcactt    2160
tcagatgtaa tggcaaacaa ttgttaaaag ttattaactg atcacagatt tgcctggact    2220
tcccttccca gggagggaac agaagttagg aggcaacttt gggatggtgc tagagcatgg    2280
aaagcacaga gaattggaca acaggtctt tttctctttt ctctgatgtt ttacctttaa    2340
aagatccaac atccttaccg ttggtatttt tagtaaggtt atagtaaata gctttacacc    2400
aggatggatt ctgaaatata aattctaaat tatatttgtt ataactatat tttatgttgt    2460
atgttatcag gagccatcag agaatgacct ttttgtgttt ggaacacttg gttccatgaa    2520
aagtatgctt tgtgttttaa ctgttaaaat aatttaaaaa ttaattattt tacataatta    2580
aagaagttaa aaactattaa cattaaataa tttcacaatt tcaacatgtc aaacctatga    2640
agggagatag gaaacaatga gaaacttact tttgctccct tatacagaat tattaactat    2700
attttactaa ctaaaaaact ctagtattct ttacctaaag tcaattggct ggtaagaggg    2760
agagatgcaa aattctccag ctctgaactt ggagctactt cacactctac tcttaatgga    2820
aacttgaact aatgatagat agtattttt tcctctattt aaaatttttg tcttgattag    2880
gagatttttc agttctccat ataataattt tctacaatca gatctatgct gtggcatatt    2940
ttgctttatt taaaaatttt tttttagaga tgagttcttg ctctgtcacc taggctggag    3000
tgcagtggca tgatcatggc tcactgcagc cttgaccttc cagcctgcca gtagctggg    3060
attacagaca ggcatgtgct attacacctg gctaatttt aaagtttttt ttgtaaagat    3120
agggtctttc tatgttgccc aggctcgtct tgagctcctg gcctcaatcg atcttcctgc    3180
caaggttttg gaattacagg tgtgagccac catgcctggc ctgctttgac atattttata    3240
gtgtgttaat tacaaatagt cttcatatgc cagaatataa gagcaagtgt tatctacttt    3300
ttagatggga attgcagaag ctgcatcaaa agtatgcttt gaggtatata tagtgaaaca    3360
gagcctttct gaagagaatt atatcaaact aattacaacc aagaaataat agtatgaagc    3420
ggatgctgtt tggaggacag gaaaattat cgggaaaat acataatccc tctgattcca    3480
ctatccagag atagccatta ttattaatat ttggtatgta catccttata ttattttttt    3540
tttatgcatg atttttgtata tatggttatt tttctttcca taaaaatggt attaaactgt    3600
atatactgtt ttgtagccta catatttcat atagaagtat attgttaaca ttttccatgt    3660
```
caataaatat tctatggctt tct 3683

<210> SEQ ID NO 58
<211> LENGTH: 320
<212> TYPE: PRT
<213> ORGANISM: Artificial Sequence
<220> FEATURE:
<223> OTHER INFORMATION: Synthetic construct: IMPACT

<400> SEQUENCE: 58

```
Met Ala Glu Gly Asp Ala Gly Ser Asp Gln Arg Gln Asn Glu Glu Ile
1               5                   10                  15
Glu Ala Met Ala Ala Ile Tyr Gly Glu Trp Cys Val Ile Asp Asp
            20                  25                  30
Cys Ala Lys Ile Phe Cys Ile Arg Ile Ser Asp Asp Ile Asp Asp Pro
        35                  40                  45
Lys Trp Thr Leu Cys Leu Gln Val Met Leu Pro Asn Glu Tyr Pro Gly
    50                  55                  60
Thr Ala Pro Pro Ile Tyr Gln Leu Asn Ala Pro Trp Leu Lys Gly Gln
65                  70                  75                  80
Glu Arg Ala Asp Leu Ser Asn Ser Leu Glu Glu Ile Tyr Ile Gln Asn
                85                  90                  95
Ile Gly Glu Ser Ile Leu Tyr Leu Trp Val Glu Lys Ile Arg Asp Val
            100                 105                 110
Leu Ile Gln Lys Ser Gln Met Thr Glu Pro Gly Pro Asp Val Lys Lys
        115                 120                 125
Lys Thr Glu Glu Glu Asp Val Glu Cys Glu Asp Leu Ile Leu Ala
    130                 135                 140
Cys Gln Pro Glu Ser Ser Val Lys Ala Leu Asp Phe Asp Ile Ser Glu
145                 150                 155                 160
Thr Arg Thr Glu Val Glu Val Glu Leu Pro Pro Ile Asp His Gly
                165                 170                 175
Ile Pro Ile Thr Asp Arg Arg Ser Thr Phe Gln Ala His Leu Ala Pro
            180                 185                 190
Val Val Cys Pro Lys Gln Val Lys Met Val Leu Ser Lys Leu Tyr Glu
        195                 200                 205
Asn Lys Lys Ile Ala Ser Ala Thr His Asn Ile Tyr Ala Tyr Arg Ile
    210                 215                 220
Tyr Cys Glu Asp Lys Gln Thr Phe Leu Gln Asp Cys Glu Asp Asp Gly
225                 230                 235                 240
Glu Thr Ala Ala Gly Gly Arg Leu Leu His Leu Met Glu Ile Leu Asn
                245                 250                 255
Val Lys Asn Val Met Val Val Ser Arg Trp Tyr Gly Gly Ile Leu
            260                 265                 270
Leu Gly Pro Asp Arg Phe Lys His Ile Asn Asn Cys Ala Arg Asn Ile
        275                 280                 285
Leu Val Glu Lys Asn Tyr Thr Asn Ser Pro Glu Ser Ser Lys Ala
    290                 295                 300
Leu Gly Lys Asn Lys Lys Val Arg Lys Asp Lys Lys Arg Asn Glu His
305                 310                 315                 320
```

<210> SEQ ID NO 59
<211> LENGTH: 6737
<212> TYPE: DNA
<213> ORGANISM: Artificial Sequence
<220> FEATURE:
<223> OTHER INFORMATION: Synthetic construct: KIAA1128

<400> SEQUENCE: 59

```
gctgtggatc ttacaaagcc ttatcagaac caacagctat ccattagagt gcctctacgg      60
tcaagtatgc taacaagaaa ttcccggcag ccagaagtac tcaatgggaa tgaacatttg     120
gggtatggat ttaataggcc ttatgctgct ggtggaaaga agttggcttt accaaatggc     180
ccaggtgtaa cttctacttt aggttataga atggttcatc cctctctact gaaatctagc     240
cgatctccat tttctgggac tatgacagtt gatggaaata aaaattcacc tgctgacaca     300
tgtgtagagg aagatgctac agttttggct aaggacagag ctgctaataa ggaccaagaa     360
ctgattgaaa atgaaagtta tagaacaaaa acaaccaga ccatgaaaca tgatgctaaa      420
atgagatacc tgagtgatga tgtggatgac atttccttgt cgtctttgtc atcttctgat     480
aagaatgatt taagtgaaga ctttagtgat gattttatag atatagaaga ctccaacaga     540
actagaataa ctccagagga aatgtctctc aaagaagaga acatgaaaaa tgggccacca     600
caggatatgt ttgattcccc caaggaaaat gaaaaagcct tcagtaaaac tgatgaatgg     660
atagatataa gtgtctctga caggagtgaa tgtacaaaac atacttctgg gaataatttg     720
gtttcaccag atacagacta cagagctggt tcttcgtttg aactctctcc atctgatagc     780
tctgatggaa catacatgtg ggatgaagaa ggcttggaac ccattggaaa tgtccatcca     840
gttgggagct atgagtcctc tgaaatgaac agcatagata ttttgaataa tcttgaatca     900
tgtgaccttg aggatgatga tcttatgctt gatgtggatc tgcctgagga tgcacctctt     960
gaaaatgtgg agtgtgacaa tatgaaccgc tttgaccgac cagacagaaa tgttcggcag    1020
cctcaggaag gtttttggaa aaggccaccc cagaggtgga gtggacagga gcattaccac    1080
ctcagccacc ctgaccacta tcatcaccat ggaaaaagtg acttgagcag aggctctccc    1140
tatagagaat ctccctttggg tcattttgaa agctatggag ggatgccctt tttccaggct   1200
cagaagatgt ttgttgatgt accagaaaat acagtgatac tggatgagat gacccttcgg    1260
cacatggttc aggattgcac tgctgtaaaa actcagttac tcaaactgaa acgtctcctg    1320
catcagcatg atggaagtgg ttcattgcat gatattcaac tgtcattgcc atccagtcca    1380
gaaccagaag atggtgataa agtatataag aatgaagatt tattaaatga aataaaacaa    1440
cttaaagacg aaataaagaa aaagatgaa aagatccaac tattagaact tcagcttgca     1500
actcagcata tctgccacca aaaatgtaaa gaggaaaaat gcacttatgc tgataaatat    1560
acccaaacac cctggagacg aattcctggt gggtattctg ctccctcctt ctctccttgg    1620
cagggctcct tccaggggat cccacggact gttccaccgc accgcagaca gacctcaagt    1680
actacagcct tccagcagcc ttcccagacc cacagatcac acccagggaa aactaataaa    1740
gccacaacgt atcgaggccc gcagtgaatg ctcaatccaa gacatgcatc agggcggtgc    1800
acatccggaa gaaagcttta cacacgtctt gcaccaagaa agcaactatg gtttggaaga    1860
gcagcctttt tcatcaggcc cacaattaac aatggatgtg ctaagagta caccttctga    1920
agcaaactta aacattactg taaatgctca agagccttat catttggcaa acaatcaaat    1980
tagtgacatg cagtttatac ccacttctct tcagacacct cccgagtcaa gtacagtaga    2040
ccaggctaag agagttggaa gaaatcagtc tccgccagtg ggttatatgt ctcagcccaa    2100
gtccttgcag cttttaaagc catccatatt gagttctttg gtaccgcctc cagtttctga    2160
atcatctcca gtaggactcc ccacttgtaa aaagtcacca ataatcacaa catgtaattc    2220
agcaaaactt cagccaacat ctagtcaaac aaatcttgca aataatcaga atctgaaagc    2280
```

```
atctaagctc cgccccccct caggctcttt caaacaaaaa caaacaaaca gcccccaact    2340
agagcctcaa agcttccagg ccaagacaag catcccaagg ccactaacac aacgaaaaga    2400
aatcatgcag aatccaaatg gcaatttgca ttctggggat tgtttggcct ctaatcgata    2460
ttctcgtctt cctaaaccaa agatacatta agtacatagc catcacctgc caatttgttt    2520
cttaaaaaca atctcttctg taatagcttt atgtgcagct tgcagcttgc tactgtggtg    2580
gaggttccat tgaaagcctg caaatcttaa attaaaatgt ggaagcttct actagtttgg    2640
ctccttcatt ttatatcctg gttgaagtac atgccatttg agcataatta tctcaggtaa    2700
acacgaaagt ttgcttaccc atttcagagg cctgccaaag gcccaaatca tgttatccat    2760
ccctctccag gtcagaaaat tcataatatt ttactgagca ggcaagaagt gtgctttgct    2820
ggtttagtcc tattaaggtc tgtatttatt gtggttgtca gaacctcacc ccttttcact    2880
tgtctctcct gtgaatatgg ctactatttt aactaaagat atggtgataa tggaagatgg    2940
tagtctgtaa gcagagttct ggccagtgtt ttgtatattt aaaaggtcta tgcaaaagct    3000
ttgtgatgaa taaggagat taggctttta atggaaagtc tatgtaagtt ttattttcc    3060 ttgccagggt cagtcagcta atgttactgt tgattcattt cccaaattcc ccagactgaa    3120
aatgtttctt attacatata aatcagttat atattccttt acatcttgtt ttacaaacac    3180
atgtgcatgc acacacacac atacacacac ataccattta tgtttgtatt tgttactggg    3240
taaattttgg agcgcttgag atacacccttg aaacctgtac ctaaagatgt attcatttgt    3300
aacatatgtt ggtgctagag ttttgctggt aattcaggtt tgaacccta ggcttgtgga    3360 tccatgatag ccatttaag gttccacagc attatgtctt taattgtaat atttatattt    3420
attgattttc tgctaatatc tgaagactga aataatgaac ttgaaacatt tgcacaaaac    3480
tttgatgggg tataaatata ccatatatag ggattgtaaa ctattttcta tagcaaaaca    3540
agttaaaata ttttgagaaa aataacaaat ttaaataaga ctatcttgag aaagctggag    3600
ttcataatat tctccccctc ccccatctcc agtctcctag gtttcccttt tctgtgtttt    3660
ttgttttttt ctgtttgttt tttgagacag agtcttgctc cattgcccag gctggattac    3720
agtggcgcaa tctcggctca ctgcaacttc tgcctcccgg gttcaagcga ttctcctgcc    3780
tcagcctcct gagtagctgg gactacaggc atgtgccacc atgcctggct aattttttg    3840 tatttttagt agagatgagg tttcaccttg ttggtcaggc tggtctcgaa ctcctgacct    3900
caagtgatcc acccacctcg tctatggtgt attttgaaa gacaattttt taaaggtaga    3960
tttgggaaaa aaatagaatt gaagatggga aattttgttt tattaaaaag gtgctagaag    4020
atgtttcaaa gacaatattc ttattttaat acgctgtaga aggtaggtgt ggaacctcca    4080
tgctaccatg tgcacaaacc taattatgct ttgggtcact tgtcagttca gtaaatctgc    4140
cttcctcttc tcccaaatca tgtcatcttt aggttgttca cctgcagctg ctttaaatga    4200
attagtatct ttcagataga taaccttaca aggagaatgt tgttttgag cagctgacca    4260 aaaatatatc aaacaggatt atggccaaaa agtcactcaa atttctagag attcctttaa    4320
aagatgtatg ttgatgaaat tgccccttta taagaaaaac aacagcaagt cttttagtag    4380
aaatttgaaa gaagtgtttg ctaccatttt gacccattat tcccttacct atcagatgaa    4440
tttgccattc actggataga aaccattctt ggatttggta agaggtgagc aagacaaatc    4500
ttgtaccata ctcttatgta ccagcacttc tgatggagaa gcagtgaagt tcagaacgtt    4560
cttcacatag tccagatact gttagagtca ggcaaatcag caaagcactt tgttatggag    4620
atgacccatg atggctgcag ttgtaagtgg gcatacatgt tctatcattt tgaaggagaa    4680
```

```
agaaaaccgt tctcacatgt cgcaaatatg tgaatcatac tatattcccc taaagtaaaa    4740
ccagtgactt agtggttttt ggtttattta aagttggtt tagaccctta tgaaacatta     4800
tttacgagtt ggccttatcc ttaagggaaa agttctaaat tttaaattt attttaatt     4860
ccctagtctg agggaaatgt ctttattgtc cattacataa aaatgttgac tccagtaatt    4920
tattttctc tattttttcc tccatgtatt tactccattt ttctctattt tttccttccc    4980
tgatggattt gcagaaatgt taaccaatta gctcaacttt tctctacctt tgttgagtct    5040
taatctttta gaagataggc ttaccgtata tttatgaagc ataatatatt aaaagaaaac    5100
aaatctagga tgcttgcatg acataaagta tttgcctgca gttttcatta aaaactgcaa    5160
gaatatcatg cttgtctgct tcttagtaaa tgttaagtct gaaatggaag tgaggatgta    5220
actctactga ataatcaaag atcatcttag atttggcttg atctgtgttt attgcttcta    5280
ttaatgtaaa tcaactctgt gccaaatcct cctccacaaa ccatttattg tcttagttct    5340
agtggtatca atgaagatag ttacagtata tgaattctaa gtcctgagga agaaattta    5400
tggggtttgt taagtttcac attcgtgaaa gaggaaatta gtagagtatt cagactttga    5460
tatttggctg ttaatgggat gcatatcaaa ttttaaaag aaggcttggc ctaaggagtt    5520
tattggtaca ggtgcagatg attttaaggc attaaaggat tatagagtta tgtcatttag    5580
actgttccta ataactgaga ccatctaaca ttttctttt ggagtctcat ttttatttgt    5640
gcaatatttt caggcatata ggctactgtt cattgtattt atatatatat tagaatttac    5700
taagtacttt aacaagtaaa aatctgaata tgaaagaaaa tatcagattt gcactttaaa    5760
tgagcttaat tgcttgaagt tgtgcctgaa atatcgaatt gcctcctatt gggtgtggct    5820
ttgttgaaat aaatttgtaa ttgttgctgt ttgaagatat cagtacagct gttcacagaa    5880
atatattccc agcatgtcac ttttccatta aagcactaag ttttctttga atgttccatt    5940
gttccgataa gtattttact tttttctcag tacatcagag agagcgtgat cccctacag    6000
ctgtcacttc caaatgttcc tgtagcataa atggtgttac agacactgag gtgcactctt    6060
ggtttctgag cagagttgtc atactggttt cctggtctct agggcactgg ggatgtactt    6120
tgaaatcacc gaacaggctt gcaattaaga tcaataaggc tgcagcacca tttcaattta    6180
cttccatct tacccagtag ttttgtgtt tttaaattcg tttgggtggt tatgtttgca    6240
tgcttaagca cacatttgaa aattaattat agctgtacta cccgatgttt ttccttgggg    6300
atgatggcct tgttcctttt taaattctga tgcttgaatt ctattttcta gtgatttttc    6360
acatctccct ttaagttttt gctgcagcaa tttgagagag tacttttgat taaatgattc    6420
tgatggtggg caccaatcta caactatgtc attaactgaa gatacatgtt ttaatcttgt    6480
tgggaataag cttacccact ttctccttgg taaagcgttt acttaacaaa ataatacccg    6540
agaatgtaag gtctctaagt cattactaac aaagagcaaa ataatatct gcagtattgt    6600
ttttcccatt gattttaagt cagtttagag tacaaactgt atattagaat ttgcctgtaa    6660
aatgaattct aaaaagcaga tgtaaagtct ctcctgaaaa tgttggcata gtaaataaaa    6720
ataaagttca taattat                                                   6737
```

<210> SEQ ID NO 60  
<211> LENGTH: 588  
<212> TYPE: PRT  
<213> ORGANISM: Artificial Sequence  
<220> FEATURE:  
<223> OTHER INFORMATION: Synthetic construct: KIAA1128

```
<400> SEQUENCE: 60

Ala Val Asp Leu Thr Lys Pro Tyr Gln Asn Gln Gln Leu Ser Ile Arg
1               5                   10                  15

Val Pro Leu Arg Ser Ser Met Leu Thr Arg Asn Ser Arg Gln Pro Glu
            20                  25                  30

Val Leu Asn Gly Asn Glu His Leu Gly Tyr Gly Phe Asn Arg Pro Tyr
        35                  40                  45

Ala Ala Gly Gly Lys Lys Leu Ala Leu Pro Asn Gly Pro Gly Val Thr
    50                  55                  60

Ser Thr Leu Gly Tyr Arg Met Val His Pro Ser Leu Leu Lys Ser Ser
65                  70                  75                  80

Arg Ser Pro Phe Ser Gly Thr Met Thr Val Asp Gly Asn Lys Asn Ser
                85                  90                  95

Pro Ala Asp Thr Cys Val Glu Glu Asp Ala Thr Val Leu Ala Lys Asp
            100                 105                 110

Arg Ala Ala Asn Lys Asp Gln Glu Leu Ile Glu Asn Glu Ser Tyr Arg
            115                 120                 125

Thr Lys Asn Asn Gln Thr Met Lys His Asp Ala Lys Met Arg Tyr Leu
130                 135                 140

Ser Asp Asp Val Asp Asp Ile Ser Leu Ser Ser Leu Ser Ser Ser Asp
145                 150                 155                 160

Lys Asn Asp Leu Ser Glu Asp Phe Ser Asp Phe Ile Asp Ile Glu
                165                 170                 175

Asp Ser Asn Arg Thr Arg Ile Thr Pro Gln Glu Met Ser Leu Lys Glu
            180                 185                 190

Glu Lys His Glu Asn Gly Pro Pro Gln Asp Met Phe Asp Ser Pro Lys
        195                 200                 205

Glu Asn Glu Lys Ala Phe Ser Lys Thr Asp Glu Trp Ile Asp Ile Ser
210                 215                 220

Val Ser Asp Arg Ser Glu Cys Thr Lys His Thr Ser Gly Asn Asn Leu
225                 230                 235                 240

Val Ser Pro Asp Thr Asp Tyr Arg Ala Gly Ser Ser Phe Glu Leu Ser
            245                 250                 255

Pro Ser Asp Ser Ser Asp Gly Thr Tyr Met Trp Asp Glu Glu Gly Leu
        260                 265                 270

Glu Pro Ile Gly Asn Val His Pro Val Gly Ser Tyr Glu Ser Ser Glu
    275                 280                 285

Met Asn Ser Ile Asp Ile Leu Asn Asn Leu Glu Ser Cys Asp Leu Glu
        290                 295                 300

Asp Asp Asp Leu Met Leu Asp Val Asp Leu Pro Glu Asp Ala Pro Leu
305                 310                 315                 320

Glu Asn Val Glu Cys Asp Asn Met Asn Arg Phe Asp Arg Pro Asp Arg
            325                 330                 335

Asn Val Arg Gln Pro Gln Glu Gly Phe Trp Lys Arg Pro Pro Gln Arg
            340                 345                 350

Trp Ser Gly Gln Glu His Tyr His Leu Ser His Pro Asp His Tyr His
        355                 360                 365

His His Gly Lys Ser Asp Leu Ser Arg Gly Ser Pro Tyr Arg Glu Ser
    370                 375                 380

Pro Leu Gly His Phe Glu Ser Tyr Gly Gly Met Pro Phe Phe Gln Ala
385                 390                 395                 400

Gln Lys Met Phe Val Asp Val Pro Glu Asn Thr Val Ile Leu Asp Glu
            405                 410                 415
```

-continued

```
Met Thr Leu Arg His Met Val Gln Asp Cys Thr Ala Val Lys Thr Gln
            420                 425                 430
Leu Leu Lys Leu Lys Arg Leu Leu His Gln His Asp Gly Ser Gly Ser
            435                 440                 445
Leu His Asp Ile Gln Leu Ser Leu Pro Ser Ser Pro Glu Pro Glu Asp
        450                 455                 460
Gly Asp Lys Val Tyr Lys Asn Glu Asp Leu Leu Asn Glu Ile Lys Gln
465                     470                 475                 480
Leu Lys Asp Glu Ile Lys Lys Asp Glu Lys Ile Gln Leu Leu Glu
                485                 490                 495
Leu Gln Leu Ala Thr Gln His Ile Cys His Gln Lys Cys Lys Glu Glu
            500                 505                 510
Lys Cys Thr Tyr Ala Asp Lys Tyr Thr Gln Thr Pro Trp Arg Arg Ile
        515                 520                 525
Pro Gly Gly Tyr Ser Ala Pro Ser Phe Ser Pro Trp Gln Gly Ser Phe
        530                 535                 540
Gln Gly Ile Pro Arg Thr Val Pro Pro His Arg Arg Gln Thr Ser Ser
545                 550                 555                 560
Thr Thr Ala Phe Gln Gln Pro Ser Gln Thr His Arg Ser His Pro Gly
                565                 570                 575
Lys Thr Asn Lys Ala Thr Thr Tyr Arg Gly Pro Gln
            580                 585
```

DIAGNOSTIC TOOL FOR DIAGNOSING BENIGN VERSUS MALIGNANT THYROID LESIONS

CROSS-REFERENCE TO RELATED APPLICATIONS

This application is the National Stage of International Application No. PCT/US2008/0010139, filed Aug. 27, 2008, which claims the benefit of U.S. Provisional Application No. 60/966,271, filed Aug. 27, 2007, the disclosures of which are incorporated herein by reference in their entireties.

FIELD OF THE INVENTION

The present invention relates to the use of genes differentially expressed in benign thyroid lesions and malignant thyroid lesions for the diagnosis and staging of thyroid cancer.

BACKGROUND OF THE INVENTION

It is well known that cancer results from changes in gene expression patterns that are important for cellular regulatory processes such as growth, differentiation, DNA duplication, mismatch repair and apoptosis. It is also becoming more apparent that effective treatment and diagnosis of cancer is dependent upon an understanding of these important processes. Classification of human cancers into distinct groups based on their origin and histopathological appearance has historically been the foundation for diagnosis and treatment. This classification is generally based on cellular architecture, certain unique cellular characteristics and cell-specific antigens only. In contrast, gene expression assays have the potential to identify thousands of unique characteristics for each tumor type (3) (4). Elucidating a genome wide expression pattern for disease states not only could have a enormous impact on the understanding of specific cell biology, but could also provide the necessary link between molecular genetics and clinical medicine (5) (6) (7).

Thyroid carcinoma represents 1% of all malignant diseases, but 90% of all neuroendocrine malignancies. It is estimated that 5-10% of the population will develop a clinically significant thyroid nodule during their life-time (8). The best available test in the evaluation of a patient with a thyroid nodule is fine needle aspiration biopsy (FNA) (9). Of the malignant FNAs, the majority are from papillary thyroid cancers (PTC) or its follicular variant (FVPTC). These can be easily diagnosed if they have the classic cytologic features including abundant cellularity and enlarged nuclei containing intra-nuclear grooves and inclusions (10). Indeed, one third of the time these diagnoses are clear on FNA. Fine needle aspiration biopsy of thyroid nodules has greatly reduced the need for thyroid surgery and has increased the percentage of malignant tumors among excised nodules (11, 12). In addition, the diagnosis of malignant thyroid tumors, combined with effective therapy, has lead to a marked decrease in morbidity due to thyroid cancer. Unfortunately, many thyroid FNAs are not definitively benign or malignant, yielding an "indeterminate" or "suspicious" diagnosis. The prevalence of indeterminate FNAs varies, but typically ranges from 10-25% of FNAs (13-15). In general, thyroid FNAs are indeterminate due to overlapping or undefined morphologic criteria for benign versus malignant lesions, or focal nuclear atypia within otherwise benign specimens. Of note, twice as many patients are referred for surgery for a suspicious lesion (10%) than for a malignant lesion (5%), an occurrence that is not widely appreciated since the majority of FNAs are benign. Therefore when the diagnosis is unclear on FNA these patients are classified as having a suspicious or indeterminate lesion only. It is well known that frozen section analysis often yields no additional information.

The question then arises: "Should the surgeon perform a thyroid lobectomy, which is appropriate for benign lesions or a total thyroidectomy, which is appropriate for malignant lesions when the diagnosis is uncertain both preoperatively and intra-operatively?" Thyroid lobectomy as the initial procedure for every patient with a suspicious FNA could result in the patient with cancer having to undergo a second operation for completion thyroidectomy. Conversely, total thyroidectomy for all patients with suspicious FNA would result in a majority of patients undergoing an unnecessary surgical procedure, requiring lifelong thyroid hormone replacement and exposure to the inherent risks of surgery (16).

Several attempts to formulate a consensus about classification and treatment of thyroid carcinoma based on standard histopathologic analysis have resulted in published guidelines for diagnosis and initial disease management (2). In the past few decades no improvement has been made in the differential diagnosis of thyroid tumors by fine needle aspiration biopsy (FNA), specifically suspicious or indeterminate thyroid lesions, suggesting that a new approach to this should be explored. Thus, there is a compelling need to develop more accurate initial diagnostic tests for evaluating a thyroid nodule.

SUMMARY OF THE INVENTION

This invention is based in part on the discovery of genes whose expression levels can be correlated to benign or malignant states in a thyroid cell. Thus, the present invention provides differentially expressed genes that can be utilized to diagnose, stage and treat thyroid cancer. These differentially expressed genes are collectively referred to herein as "Differentially Expressed Thyroid" genes ("DET" genes). Examples of these DET genes are provided herein and include C21orf4 (DET1), Hs.145049 (DET2), Hs.296031 (DET3), KIT (DET4), LSM7 (DET5), SYNGR2 (DET6), C11orf8 (DET7), CDH1 (DET8), FAM13A1 (DET9), IMPACT (DET10), KIAA1128 (DET11).

Examples of additional DET genes provided herein include HMGA2 (DET12), KLK7 (DET13), MRC2 (DET14), LRRK2 (DET15), PLAG1 (DET16), CYP1B1 (DET17), DPP4 (DET18), FNDC4 (DET19), PHLDA2 (DET20), CCNA1 (DET21), CDH3 (DET22), CEACAM6 (DET23), QSCN6 (DET24), COL7A1 (DET25), MGC9712 (DET26), IL1RAP (DET27), LAMB3 (DET28), PRSS3 (DET29), LRP4 (DET30), SPOCK1 (DET31), PDE5A (DET32), FLJ37078 (DET33), FBN3 (DET34), DIRAS3 (DET35), PRSS1 (DET36), CAMK2N1 (DET37), SNIP (DET38), KCNJ2 (DET39), SFN (DET40), GALNT7 (DET41), TGFA (DET42), BAIAP3 (DET43), KCNK15 (DET44) These genes are upregulated in malignant thyroid tumors.

Examples of additional DET genes provided herein include RAG2 (DET45), CLYBL (DET46), NEB (DET47), TNFRSF11B (DET48), GNAI1 (DET49), AGTR1 (DET50), HLF (DET51), SLC26A4 (DET52), MT1A (DET53), FABP4 (DET54), LRP1B (DET55), SLC4A4 (DET56), LOC646278 (DET57), MAN1C1 (DET58), KCNIP3 (DET59), DNAJB9 (DET60), UBR1 (DET61), HSD17B6 (DET62), SLC33A1 (DET63), CDH16 (DET64), TBC1D1 (DET65), SLC26A7 (DET66), C11orf74 (DET67), PLA2R1 (DET68), PTTG3 (DET69), EFEMP1 (DET70), ZMAT4 (DET71), STEAP3 (DET72), DIO1 (DET73), KIT (DET4), TPO (DET74), PTTG1 (DET75), LGI3 (DET76), TMEM38B (DET77), SLITRK4 (DET78), VBP1 (DET79), COL9A3 (DET80), IRS1 (DET81), STARD13 (DET82), LOC654085 (DET83), RPS3A (DET84), SPARCL1 (DET85). These genes are down regulated in malignant thyroid tissue.

Provided is a method of distinguishing normal thyroid tissue from malignant thyroid tumor tissue, comprising a) measuring the expression of one or more nucleic acid sequences selected from the group consisting of DET1, DET2, DET 4, DET 5, DET 7, DET 8, DET 9, DET 10, DET 11, and DET12 in a test cell population, wherein at least one cell in the said test cell population is capable of expressing one or more nucleic acid sequences selected from the group consisting of DET1, DET2, DET 4, DET 5, DET 7, DET 8, DET 9, DET 10, DET 11, and DET12, b) comparing the expression of one or more nucleic acid sequences selected from the group consisting of DET1, DET2, DET 4, DET 5, DET 7, DET 8, DET 9, DET 10, DET 11, and DET12 in the test cell population to the expression of the same one or more nucleic acid sequences(s) in a reference cell population comprising at least one cell which is known to be normal; and c) identifying an increase in expression of one or more nucleic acid sequences selected from the group consisting of DET1, DET2, and DET12, an increase in expression being associated with a malignant thyroid tumor, or d) identifying a decrease in expression of one or more nucleic acid sequences selected from the group consisting of DET 4, DET 5, DET 7, DET 8, DET 9, DET 10, and DET 11, a decrease in expression being associated with a malignant thyroid tumor.

Also provided is a gene expression approach to diagnose benign vs. malignant thyroid lesions. Identification of differentially expressed genes allows the development of models that can differentiate benign vs. malignant thyroid tumors. Results obtained from these models provide a molecular classification system for thyroid tumors and this in turn provides a more accurate diagnostic tool for the clinician managing patients with suspicious thyroid lesions.

The present invention also provides a method for classifying a thyroid lesion in a subject comprising: a) measuring the expression of one or more nucleic acid sequences selected from the group consisting of DET1, DET2, DET3, DET4, DET6, DET7, DET8, DET9, DET10 and DET11 in a test cell population, wherein at least one cell in said test cell population is capable of expressing one or more nucleic acid sequences selected from the group consisting of DET1, DET2, DET3, DET4, DET6, DET7, DET8, DET9, DET10 and DET11; b) comparing the expression of the nucleic acid sequence(s) to the expression of the same nucleic acid sequence(s) in a reference cell population comprising at least one cell for which a thyroid lesion classification is known; and c) identifying a difference, if present, in expression levels of one or more nucleic acid sequences selected from the group consisting of DET1, DET2, DET3, DET4, DET6, DET7, DET8, DET9, DET10 and DET11, in the test cell population and reference cell population, thereby classifying the thyroid lesion in the subject.

Further provided is a method for classifying a thyroid lesion in a subject comprising: a) measuring the expression of one or more nucleic acid sequences selected from the group consisting of DET1, DET2, DET3, DET4, DET5 and DET6 in a test cell population, wherein at least one cell in said test cell population is capable of expressing one or more nucleic acid sequences selected from the group consisting of DET1, DET2, DET3, DET4, DET5 and DET6; b) comparing the expression of the nucleic acid sequence(s) to the expression of the same nucleic acid sequence(s) in a reference cell population comprising at least one cell for which a thyroid lesion classification is known; and c) identifying a difference, if present, in expression levels of one or more nucleic acid sequences selected from the group consisting of DET1, DET2, DET3, DET4, DET5 and DET6, in the test cell population and reference cell population, thereby classifying the thyroid lesion in the subject.

Further provided is a method for classifying a thyroid lesion in a subject comprising: a) measuring the expression of one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 in a test cell population, wherein at least one cell in said test cell population is capable of expressing one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85; b) comparing the expression of the nucleic acid sequence(s) to the expression of the same nucleic acid sequence(s) in a reference cell population comprising at least one cell for which a thyroid lesion classification is known; and c) identifying a difference, if present, in expression levels of one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85, in the test cell population and reference cell population, thereby classifying the thyroid lesion in the subject.

The present invention also provides a method of identifying the stage of a thyroid tumor in a subject comprising: a) measuring the expression of one or more nucleic acid sequences selected from the group consisting of DET1, DET2, DET3, DET4, DET5 and DET6 in a test cell population, wherein at least one cell in said test cell population is capable of expressing one or more nucleic acid sequences selected from the group consisting of DET1, DET2, DET3, DET4, DET5 and DET6; b) comparing the expression of the nucleic acid sequence(s) to the expression of the same nucleic acid sequence(s) in a reference cell population comprising at least one cell for which a thyroid tumor stage is known; and c) identifying a difference, if present, in expression levels of one or more nucleic acid sequences selected from the group consisting of DET1, DET2, DET3, DET4, DET5 and DET6, in the test cell population and reference cell population, thereby identifying the stage of the thyroid tumor in the subject.

Further provided by the present invention is a method of identifying the stage of a thyroid tumor in a subject comprising: a) measuring the expression of one or more nucleic acid sequences selected from the group consisting of DET1, DET2, DET3, DET4, DET6, DET7, DET8, DET9, DET10 and DET11 in a test cell population, wherein at least one cell in said test cell population is capable of expressing one or more nucleic acid sequences selected from the group consisting of DET1, DET2, DET3, DET4, DET6, DET7, DET8, DET9, DET10 and DET11; b) comparing the expression of the nucleic acid sequence(s) to the expression of the same nucleic acid sequence(s) in a reference cell population comprising at least one cell for which a thyroid tumor stage is known; and c) identifying a difference, if present, in expression levels of one or more nucleic acid sequences selected from the group consisting of DET1, DET2, DET3, DET4, DET6, DET7, DET8, DET9, DET10 and DET11, in the test cell population and reference cell population, thereby identifying the stage of the thyroid tumor in the subject.

Further provided by the present invention is a method of identifying the stage of a thyroid tumor in a subject comprising: a) measuring the expression of one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 in a test cell population, wherein at least one cell in said test cell population is capable of expressing one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85; b) comparing the expression of the nucleic acid sequence(s) to the expression of the same nucleic acid sequence(s) in a reference cell population comprising at least one cell for which a thyroid tumor stage is known; and c) identifying a difference, if present, in expression levels of one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85, in the test cell population and reference cell population, thereby identifying the stage of the thyroid tumor in the subject.

Also provided by the present invention is a method of identifying an agent for treating a thyroid tumor, the method comprising: a) contacting a population of thyroid tumor cells from a subject for which a tumor stage is known, wherein at least one cell in said population is capable of expressing one or more nucleic acid sequences selected from the group consisting of DET1, DET2, DET3, DET4, DET5 and DET6, with a test agent; b) measuring the expression of one or more nucleic acid sequences selected from the group consisting of DET1, DET2, DET3, DET4, DET5 and DET6 in the population; c) comparing the expression of the nucleic acid sequence(s) to the expression of the same nucleic acid sequence(s) in a reference cell population comprising at least one cell for which a thyroid tumor stage is known; and d) identifying a difference, if present, in expression levels of one or more nucleic acid sequences selected from the group consisting of DET1, DET2, DET3, DET4, DET5 and DET6, in the test cell population and reference cell population, such that if there is a difference corresponding to an improvement, a therapeutic agent for treating a thyroid tumor has been identified.

The present invention also provides a method of identifying an agent for treating a thyroid tumor, the method comprising: a) contacting a population of thyroid tumor cells from a subject for which a tumor stage is known, wherein at least one cell in said population is capable of expressing one or more nucleic acid sequences selected from the group consisting of DET1, DET2, DET3, DET4, DET6, DET7, DET8, DET9, DET10 and DET11, with a test agent; b) measuring the expression of one or more nucleic acid sequences selected from the group consisting of DET1, DET2, DET3, DET4, DET6, DET7, DET8, DET9, DET10 and DET11 in the population; c) comparing the expression of the nucleic acid sequence(s) to the expression of the same nucleic acid sequence(s) in a reference cell population comprising at least one cell for which a thyroid tumor stage is known; and d) identifying a difference, if present, in expression levels of one or more nucleic acid sequences selected from the group consisting of DET1, DET2, DET3, DET4, DET6, DET7, DET8, DET9, DET10 and DET11, in the test cell population and reference cell population, such that if there is a difference corresponding to an improvement, a therapeutic agent for treating a thyroid tumor has been identified.

The present invention also provides a method of identifying an agent for treating a thyroid tumor, the method comprising: a) contacting with a test agent a population of thyroid tumor cells from a subject for which a tumor stage is known, wherein at least one cell in said population is capable of expressing one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85; b) measuring the expression of one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 in the population; c) comparing the expression of the nucleic acid sequence(s) to the expression of the same nucleic acid sequence(s) in a reference cell population comprising at least one cell for which a thyroid tumor stage is known; and d) identifying a difference, if present, in expression levels of one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85, in the test cell population and reference cell population, such that if there is a difference corresponding to an improvement, a therapeutic agent for treating a thyroid tumor has been identified.

The present invention also provides a method for classifying a thyroid lesion in a subject as malignant or benign comprises receiving gene expression data of one or more nucleic acid sequences selected from the group consisting of the differentially expressed thyroid genes DET1, DET2, DET3, DET4, DET5, and DET6 in a test cell population, wherein at least one cell in said test cell population is capable of expressing one or more nucleic acid sequences selected from the group consisting of DET1, DET2, DET3, DET4, DET5, and DET6; and determining a class of tumor, wherein the determination is made by applying a statistical classifier or predictor model to the gene expression data; and outputting the class of tumor as malignant or benign based on the determination.

The present invention also provides a method for classifying a thyroid lesion in a subject as malignant or benign comprises receiving gene expression data of one or more nucleic acid sequences selected from the group consisting of the differentially expressed thyroid genes DET1, DET2, DET3, DET4, DET6, DET7, DET8, DET9, DET10, DET11, in a test cell population, wherein at least one cell in said test cell population is capable of expressing one or more nucleic acid sequences selected from the group consisting of DET1, DET2, DET3, DET4, DET6, DET7, DET8, DET9, DET10, DET11; and determining a class of tumor, wherein the determination is made by applying a statistical classifier or predictor model to the gene expression data; and outputting the class of tumor as malignant or benign based on the determination.

The present invention also provides a method for classifying a thyroid lesion in a subject as malignant or benign comprises receiving gene expression data of one or more nucleic acid sequences selected from the group consisting of the differentially expressed thyroid genes DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 in a test cell population, wherein at least one cell in said test cell population is capable of expressing one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85; and determining a class of tumor, wherein the determination is made by applying a statistical classifier or predictor model to the gene expression data; and outputting the class of tumor as malignant or benign based on the determination.

The present invention also provides a method for identifying the stage of a thyroid tumor in a subject comprises receiving gene expression data of one or more nucleic acid sequences selected from the group consisting of the differentially expressed thyroid genes DET1, DET2, DET3, DET4, DET5, and DET6 in a test cell population, wherein at least one cell in said test cell population is capable of expressing one or more nucleic acid sequences selected from the group consisting of DET1, DET2, DET3, DET4, DET5, and DET6; and determining the stage of the thyroid tumor, wherein the determination is made by applying a statistical classifier or predictor model to the gene expression data; and outputting the stage of the thyroid tumor based on the determination.

The present invention also provides a method for identifying the stage of a thyroid tumor in a subject comprises receiving gene expression data of one or more nucleic acid sequences selected from the group consisting of the differentially expressed thyroid genes DET1, DET2, DET3, DET4, DET6, DET7, DET8, DET9, DET10, DET11, in a test cell population, wherein at least one cell in said test cell population is capable of expressing one or more nucleic acid sequences selected from the group consisting of DET1, DET2, DET3, DET4, DET6, DET7, DET8, DET9, DET10, DET11; and determining the stage of the thyroid tumor, wherein the determination is made by applying a statistical classifier or predictor model to the gene expression data; and outputting the stage of the thyroid tumor based on the determination.

The present invention also provides a method for identifying the stage of a thyroid tumor in a subject comprises receiving gene expression data of one or more nucleic acid sequences selected from the group consisting of the differentially expressed thyroid genes DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 in a test cell population, wherein at least one cell in said test cell population is capable of expressing one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85; and determining the stage of the thyroid tumor, wherein the determination is made by applying a statistical classifier or predictor model to the gene expression data; and outputting the stage of the thyroid tumor based on the determination.

The present invention also provides a method for identifying the stage of a thyroid tumor in a subject comprises receiving gene expression data of one or more nucleic acid sequences selected from the group consisting of the differentially expressed thyroid genes DET1, DET2, DET3, DET4, DET5, and DET6 in a test cell population, wherein at least one cell in said test cell population is capable of expressing one or more nucleic acid sequences selected from the group consisting of DET1, DET2, DET3, DET4, DET5, and DET6; and determining the stage of the thyroid tumor, wherein the determination is made by applying a statistical classifier or predictor model to the gene expression data; and outputting the stage of the thyroid tumor based on the determination.

The present invention also provides a method for identifying the stage of a thyroid tumor in a subject comprises receiving gene expression data of one or more nucleic acid sequences selected from the group consisting of the differentially expressed thyroid genes DET1, DET2, DET3, DET4, DET6, DET7, DET8, DET9, DET10, DET11, in a test cell population, wherein at least one cell in said test cell population is capable of expressing one or more nucleic acid sequences selected from the group consisting of DET1, DET2, DET3, DET4, DET6, DET7, DET8, DET9, DET10, DET11; and determining the stage of the thyroid tumor, wherein the determination is made by applying a statistical classifier or predictor model to the gene expression data; and outputting the stage of the thyroid tumor based on the determination.

The present invention also provides a method for identifying the stage of a thyroid tumor in a subject comprises receiving gene expression data of one or more nucleic acid sequences selected from the group consisting of the differentially expressed thyroid genes DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 in a test cell population, wherein at least one cell in said test cell population is capable of expressing one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85; and determining the stage of the thyroid tumor, wherein the determination is made by applying a statistical classifier or predictor model to the gene expression data; and outputting the stage of the thyroid tumor based on the determination.

Also provided by the present invention is a kit comprising one or more reagents for detecting the expression of one or more nucleic acid(s) selected from the group consisting of DET1, DET2, DET3, DET4, DET5, DET6, DET7, DET8, DET9, DET10, DET11.

DIFFERENTIALLY EXPRESSED THYROID GENES

Figure 1:
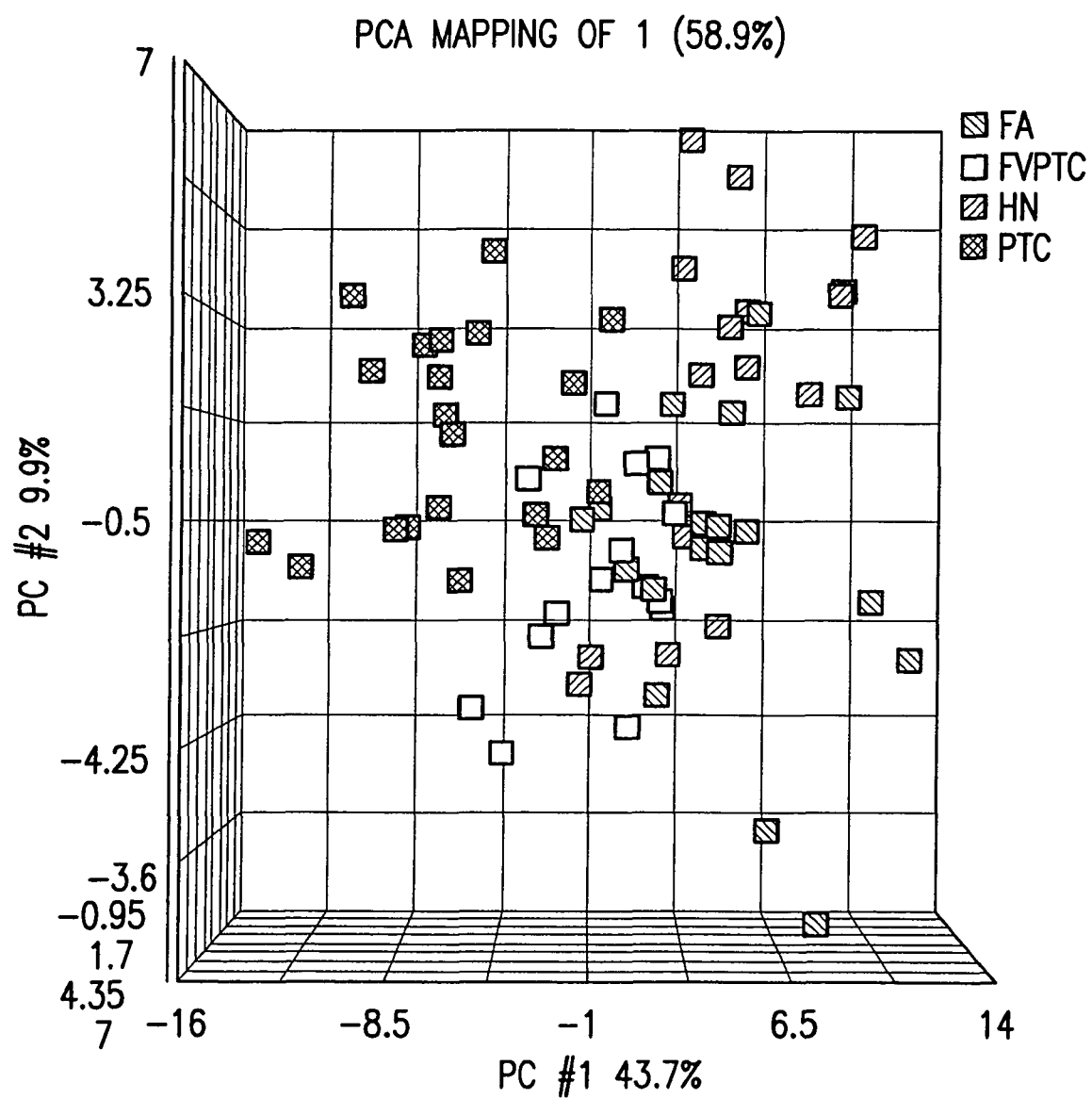
FIG. 1 shows PCA (principle component analysis) organization in a three-dimensional space of all samples divided into four groups: hyperplastic-nodule (HN), follicular adenoma (FA), follicular variant of papillary thyroid carcinoma (FVPTC) and papillary thyroid carcinoma (PTC). Each dot represents how that sample is localized in space on the basis of its gene expression profile. The distance between any pair of points is related to the similarity between the two observations in high dimensional space. The principal components are plotted along the various axes (x,y,z). The % indicates the total amount of variance captured by the PCs; the first PC is the one capturing the largest amount of variance, or information, the second PC, the second largest etc. Three PCs were plotted, thus creating a 3D plot.

One aspect of the invention relates to genes that are differentially expressed in benign and/or malignant thyroid lesions relative to benign thyroid tissue. These differentially expressed genes are collectively referred to herein as "Differentially Expressed Thyroid" genes ("DET" genes). The corresponding gene products are referred to as "DET products" "DET polypeptides" and/or "DET proteins". The DET genes of the present invention include C21orf4 (DET1), Hs.145049 (DET2), Hs.296031 (DET3), KIT (DET4), LSM7 (DET5), SYNGR2 (DET6), C11orf8 (DET7), CDH1 (DET8), FAM13A1 (DET9), IMPACT (DET10), KIAA1128 (DET11), HMGA2 (DET12), KLK7 (DET13), MRC2 (DET14), LRRK2 (DET15), PLAG1 (DET16), CYP1B1 (DET17), DPP4 (DET18), FNDC4 (DET19), PHLDA2 (DET20), CCNA1 (DET21), CDH3 (DET22), CEACAM6 (DET23), QSCN6 (DET24), COL7A1 (DET25), MGC9712 (DET26), IL1RAP (DET27), LAMB3 (DET28), PRSS3 (DET29), LRP4 (DET30), SPOCK1 (DET31), PDE5A (DET32), FLJ37078 (DET33), FBN3 (DET34), DIRAS3 (DET35), PRSS1 (DET36), CAMK2N1 (DET37), SNIP (DET38), KCNJ2 (DET39), SFN (DET40), GALNT7 (DET41), TGFA (DET42), BAIAP3 (DET43), KCNK15 (DET44), RAG2 (DET45), CLYBL (DET46), NEB (DET47), TNFRSF11B (DET48), GNAI1 (DET49), AGTR1 (DET50), HLF (DET51), SLC26A4 (DET52), MT1A (DET53), FABP4 (DET54), LRP1B (DET55), SLC4A4 (DET56), LOC646278 (DET57), MAN1C1 (DET58), KCNIP3 (DET59), DNAJB9 (DET60), UBR1 (DET61), HSD17B6 (DET62), SLC33A1 (DET63), CDH16 (DET64), TBC1D1 (DET65), SLC26A7 (DET66), C11orf74 (DET67), PLA2R1 (DET68), PTTG3 (DET69), EFEMP1 (DET70), ZMAT4 (DET71), STEAP3 (DET72), DIO1 (DET73), TPO (DET74), PTTG1 (DET75), LGI3 (DET76), TMEM38B (DET77), SLITRK4 (DET78), VBP1 (DET79), COL9A3 (DET80), IRS1 (DET81), STARD13 (DET82), LOC654085 (DET83), RPS3A (DET84), SPARCL1 (DET85). The following provides a brief description of DET1-DET11.

C21orf4 (DET1)

C21orf4 is a gene encoding an integral membrane protein of unknown function, located in the q region of chromosome 21. C21orf4 was found to be upregulated in benign thyroid lesions and upregulated in malignant thyroid lesions as compared to normal thyroid tissue. Upon comparing benign tissue with malignant tissue, C21orf4 was found to be upregulated in benign tissue as compared to malignant tissue. An example of a nucleic acid encoding C21orf4 is set forth herein as SEQ ID NO: 40. Nucleic acid sequences for C21orf4 can also be accessed via GenBank Accession No. AP001717, GenBank Accession No. NM_006134 and via Unigene No. Hs.433668. All of the information, including any nucleic acid and amino acids sequences provided for C21orf4 under GenBank Accession No. AP001717, GenBank Accession No. NM_006134 and Unigene No. Hs.433668 is hereby incorporated in its entirety by this reference.

Hs.145049 (DET2)

Hs. 145049, formerly known as Hs.24183, is a sodium-D-glucose transporter. The Unigene cluster identified as Unigene NO. Hs. 24183 has been retired and has been replaced by Hs. 145049. Hs. 145049 was found to be upregulated in both benign and malignant thyroid lesions as compared to normal thyroid tissue. Upon comparing benign tissue with malignant tissue, Hs.145049 was found to be upregulated in benign tissue as compared to malignant tissue. A nucleic acid encoding Hs. 145049 is set forth herein as SEQ ID NO: 42. Nucleic acid sequences for Hs.145049 can also be accessed via GenBank Accession No. NP_060265, via GenBank Accession No. AL832414.1 and via Unigene No. Hs.145049. All of the information, including any nucleic acid and amino acids sequences provided for Hs.145049 under GenBank Accession NP_060265, via GenBank Accession No. AL832414 and via Unigene No. Hs.145049 is hereby incorporated in its entirety by this reference.

Hs.296031 (DET3)

Hs.296031 is a gene of unknown function. Hs. 296031 was found to be downregulated in benign and comparable to normal in malignant thyroid lesions as compared to normal thyroid tissue. Upon comparing benign tissue with malignant tissue, Hs.296031 was found to be upregulated in malignant tissue as compared to benign tissue. A nucleic acid encoding Hs. 296031 is set forth herein as SEQ ID NO: 44. Nucleic acid sequences for Hs.296031 can also be accessed via GenBank Accession No. BC038512 and via Unigene No. Hs.296031. All of the information, including any nucleic acid and amino acids sequences provided for Hs.296031 under GenBank Accession No. BC038512 and Unigene No. Hs.296031 is hereby incorporated in its entirety by this reference.

c-kit proto-oncogene (KIT) (DET4)

KIT is a protooncogene that functions as a transmembrane receptor tyrosine kinase and is involved in cellular proliferation. See Yarden et al. "Human proto-oncogene c-kit: a new cell surface receptor tyrosine kinase for an unidentified ligand" EMBO J. 6(11): 3341-3351 (1987). The Yarden et al. reference is incorporated herein in its entirety for the purpose of describing KIT function as well as for incorporating all KIT protein sequences and nucleic acids encoding KIT provided in the Yarden et al. reference. KIT was found to be downregulated in benign thyroid lesions and downregulated in malignant thyroid lesions as compared to normal thyroid tissue. Upon comparing benign tissue with malignant tissue, KIT was found to be upregulated in benign tissue as compared to malignant tissue. Thus, KIT expression decreases during malignancy. A nucleic acid encoding KIT is set forth herein as SEQ ID NO: 45. Nucleic acid sequences for KIT can also be accessed via GenBank Accession Nos. X06182 and NM_000222 and via Unigene No. Hs.81665. All of the information, including any nucleic acid and amino acids sequences provided for KIT under GenBank Accession No. X06182, GenBank Accession No. NM_000222 and via Unigene No. Hs.81665 is hereby incorporated in its entirety by this reference.

U6 small nuclear RNA Associated Homo sapiens LSM7 Homolog (LSM7) (DET5)

LSM7 is a U6 small nuclear ribonucleoprotein that is involved in tRNA processing. LSM7 was found to be upregulated in benign thyroid lesions and downregulated in malignant thyroid lesions as compared to normal thyroid tissue. Upon comparing benign tissue with malignant tissue, LSM-7 was found to be upregulated in benign tissue as compared to malignant tissue. A nucleic acid sequence encoding LSM7 is set forth herein as SEQ ID NO: 47. Nucleic acid sequences for LSM7 can also be accessed via GenBank Accession No. NM_016199 and via Unigene No. Hs.512610. All of the information, including any nucleic acid and amino acids sequences provided for LSM7 under GenBank Accession No. NM_016199 and Unigene No. Hs.512610 is hereby incorporated in its entirety by this reference.

Synaptogyrin 2 (SYNGR2) (DET6)

SYNGR2 is a synaptic vesicle protein that may play a role in regulating membrane traffic. SYNGR2 was found to be downregulated in benign thyroid lesions and comparable to normal in malignant thyroid lesions as compared to normal thyroid tissue. Upon comparing benign tissue with malignant tissue, SYNGR2 was found to be upregulated in malignant tissue as compared to benign tissue. A nucleic acid encoding SYNG2 is set forth herein as SEQ ID NO: 49. Nucleic acid sequences for SYNGR2 can also be accessed via GenBank Accession No. NM_004710 and via Unigene No. Hs. 433753. All of the information, including any nucleic acid and amino acids sequences provided for LSM7 under GenBank Accession No. NM_004710 and via Unigene No. Hs. 433753 is hereby incorporated in its entirety by this reference.

C11orf8 (DET7)

C11orf8 is a gene involved in central nervous system development and function. C11orf8 was found to be downregulated in both benign thyroid lesions and malignant thyroid lesions as compared to normal thyroid tissue. Upon comparing benign tissue with malignant tissue, C11orf8 was found to be upregulated in benign tissue as compared to malignant tissue. A nucleic acid encoding C11orf8 is set forth herein as SEQ ID NO: 51. Nucleic acid sequences for C11orf8 can also be accessed via GenBank Accession No. NM_001584 and via Unigene No. Hs. 432000. All of the information, including any nucleic acid and amino acids sequences provided for LSM7 under GenBank Accession No. NM_001584 and Unigene No. Hs. 432000 is hereby incorporated in its entirety by this reference.

Cadherin 1, type1, E-cadherin (CDH1) (DET8)

CDH1 is a cadherin protein involved in cell adhesion, motility, growth and proliferation. CDH1 was found to be upregulated in benign thyroid lesions and downregulated in malignant thyroid lesions as compared to normal thyroid tissue. Upon comparing benign tissue with malignant tissue, CDH1 was found to be upregulated in benign tissue as compared to malignant tissue. A nucleic acid encoding CDH1 is set forth herein as SEQ ID NO: 53. Nucleic acid sequences for CDH1 can also be accessed via GenBank Accession No. NM_004360 and via Unigene No. Hs. 194657. All of the information, including any nucleic acid and amino acids sequences provided for CDH1 under GenBank Accession No. NM_004360 and Unigene No. Hs. 194657 is hereby incorporated in its entirety by this reference.

Homo Sapiens Family with Sequence Similarity 13, Member A1 (FAM13A1) (DET9)

FAM13A1 is a gene of unknown function. FAM13A1 was found to be upregulated in benign thyroid lesions and down-regulated in malignant thyroid lesions as compared to normal thyroid tissue. Upon comparing benign tissue with malignant tissue, FAM13A1 was found to be upregulated in benign tissue as compared to malignant tissue. A nucleic acid encoding FAM13A1 is set forth herein as SEQ ID NO: 55. Nucleic acid sequences for FAM13A1 can also be accessed via GenBank Accession No. NM_014883 and via Unigene No. Hs. 442818. All of the information, including any nucleic acid and amino acids sequences provided for FAM13A1 under GenBank Accession No. NM_014883 and Unigene No. Hs. 442818 is hereby incorporated in its entirety by this reference.

Homo Sapiens Hypothetical Protein IMPACT (IMPACT) (DET10)

IMPACT is a gene of unknown function. IMPACT was found to be upregulated in benign thyroid lesions and down-regulated in malignant thyroid lesions as compared to normal thyroid tissue. Upon comparing benign tissue with malignant tissue, IMPACT was found to be upregulated in benign tissue as compared to malignant tissue. A nucleic acid encoding IMPACT is set forth herein as SEQ ID NO: 57. Nucleic acid sequences for IMPACT can also be accessed via GenBank Accession No. NM_018439 and via Unigene No. Hs. 284245. All of the information, including any nucleic acid and amino acids sequences provided for IMPACT under GenBank Accession No. NM_018439 and Unigene No. Hs. 284245 is hereby incorporated in its entirety by this reference.

KIAA1128 Protein (KIAA1128) (DET11)

KIAA1128 is a gene of unknown function. KIAA1128 was found to be upregulated in benign thyroid lesions and down-regulated in malignant thyroid lesions as compared to normal thyroid tissue. Upon comparing benign tissue with malignant tissue, KIAA1128 was found to be upregulated in benign tissue as compared to malignant tissue. A nucleic acid encoding KIAA1128 is set forth herein as SEQ ID NO: 59. Nucleic acid sequences for KIAA1128 can also be accessed via GenBank Accession Nos. AB032954 and via Unigene No. Hs. 81897. All of the information, including any nucleic acid and amino acids sequences provided for KIAA1128 under GenBank Accession Nos. AB032954 and via Unigene No. Hs. 81897 is hereby incorporated in its entirety by this reference.

Differential Expression

As shown in Example 1, in a 6-gene panel c21orf4, Hs.145049, KIT and LSM-7 were upregulated in benign samples as compared to malignant samples (i.e., the expression of c21orf4, Hs.145049, KIT and LSM7 decreases during malignancy). Hs.296031 and SYNGR2 were upregulated in malignant samples as compared to benign samples (i.e., expression of Hs.296031 and SYNGR2 increases during malignancy).

Figure 7:
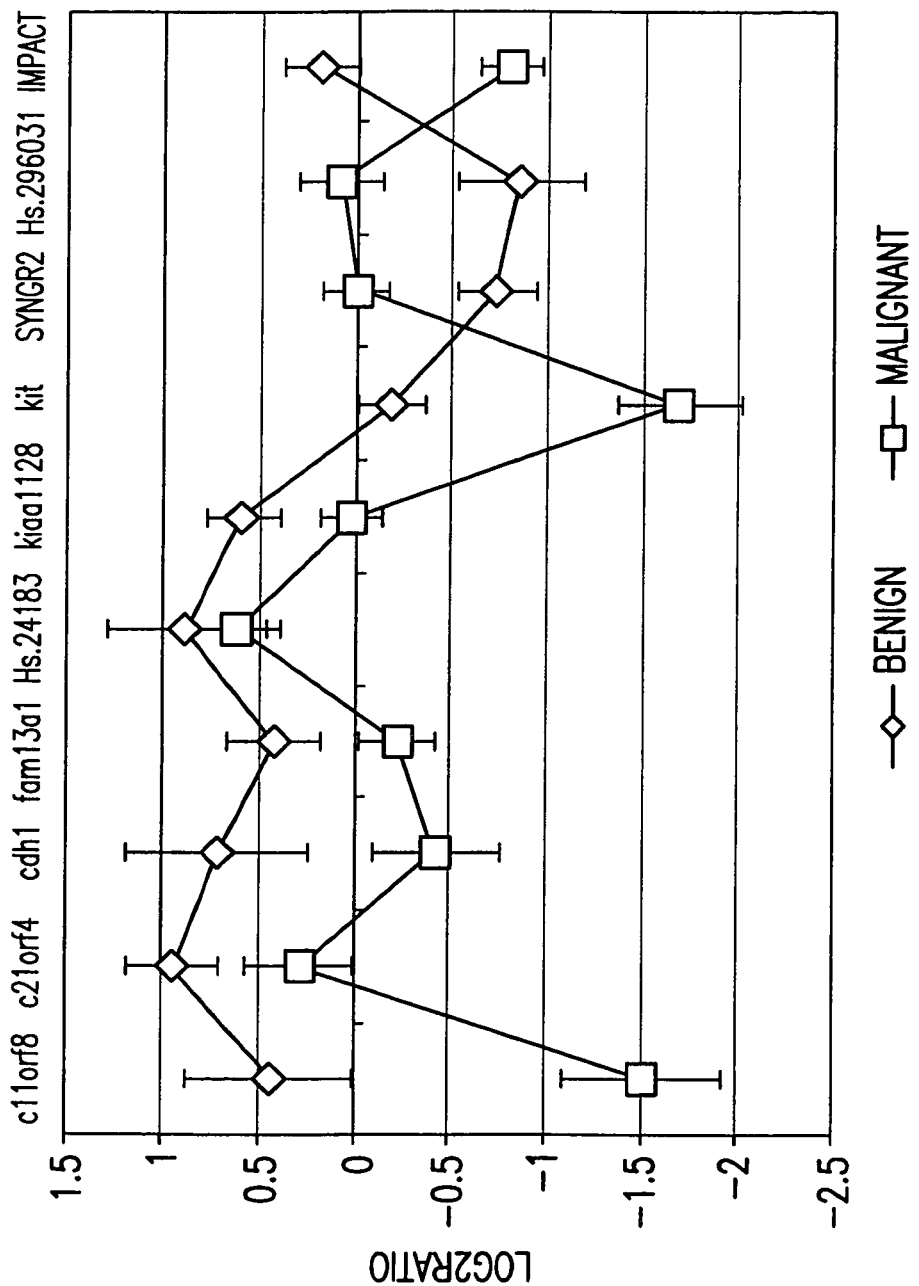
FIG. 7 shows the results of RT-PCR utilizing the 10 gene predictor model. The RT-PCR data using 10 genes demonstrate separation by group.

As described in Example 1 and FIG. 7, in a ten-gene panel, C21orf4 (DET1), Hs.145049 (DET2), KIT (DET4), C11orf8 (DET7), CDH1 (DET8), FAM13A1 (DET9), IMPACT (DET10), KIAA1128 (DET11) were upregulated in benign samples as compared to malignant samples (the expression of c21orf4, Hs.145049, KIT, FAM13A1, C11orf8, KIAA1128, IMPACT and CDH1 decreases during malignancy). Hs.296031 (DET3) and SYNGR2 (DET6) were upregulated in malignant samples as compared to benign samples (expression of Hs.296031 and SYNGR2 increases during malignancy)

Thus, provided is a method for classifying a thyroid lesion in a subject as a benign lesion comprising: a) measuring the expression of DET1, DET2, DET3, DET4, DET6, DET7, DET8, DET9, DET10 and DET11 in a test cell population, wherein at least one cell in said test cell population is capable of expressing DET1, DET2, DET3, DET4, DET6, DET7, DET8, DET9, DET10 and DET11; b) comparing the expression of the nucleic acid sequence(s) to the expression of the same nucleic acid sequences in a reference cell population comprising at least one cell from a thyroid lesion known to be a benign lesion; and c) identifying similarity of expression levels of DET1, DET2, DET3, DET4, DET6, DET7, DET8, DET9, DET10 and DET11 in the test cell population and reference cell population, thereby classifying the thyroid lesion in the subject as a benign thyroid lesion.

Thus, provided is a method for classifying a thyroid lesion in a subject as a benign lesion comprising: a) measuring the expression of DET1, DET2, DET3, DET4, DET5 and DET6 in a test cell population, wherein at least one cell in said test cell population is capable of expressing DET1, DET2, DET3, DET4, DET5 and DET6; b) comparing the expression of the nucleic acid sequence(s) to the expression of the same nucleic acid sequences in a reference cell population comprising at least one cell from a thyroid lesion known to be a benign lesion; and c) identifying similarity of expression levels of DET1, DET2, DET3, DET4, DET6, DET7, DET8, DET9, DET10 and DET11 in the test cell population and reference cell population, thereby classifying the thyroid lesion in the subject as a benign thyroid lesion.

Thus, provided is a method for classifying a thyroid lesion in a subject as a benign lesion comprising: a) measuring the expression of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 in a test cell population, wherein at least one cell in said test cell population is capable of expressing DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85; b) comparing the expression of the nucleic acid sequence(s) to the expression of the same nucleic acid sequences in a reference cell population comprising at least one cell from a thyroid lesion known to be a benign lesion; and c) identifying similarity of expression levels of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 in the test cell population and reference cell population, thereby classifying the thyroid lesion in the subject as a benign thyroid lesion.

Thus, provided is a method for classifying a thyroid lesion in a subject as a malignant lesion comprising: a) measuring the expression of DET1, DET2, DET3, DET4, DET6, DET7, DET8, DET9, DET10 and DET11 in a test cell population, wherein at least one cell in said test cell population is capable of expressing DET1, DET2, DET3, DET4, DET6, DET7, DET8, DET9, DET10 and DET11; b) comparing the expression of the nucleic acid sequence(s) to the expression of the same nucleic acid sequences in a reference cell population comprising at least one cell from a thyroid lesion known to be a malignant lesion; and c) identifying similarity of expression levels of DET1, DET2, DET3, DET4, DET6, DET7, DET8, DET9, DET10 and DET11 in the test cell population and reference cell population, thereby classifying the thyroid lesion in the subject as a malignant thyroid lesion.

Thus, provided is a method for classifying a thyroid lesion in a subject as a malignant lesion comprising: a) measuring the expression of DET1, DET2, DET3, DET4, DET5 and DET6 in a test cell population, wherein at least one cell in said test cell population is capable of expressing DET1, DET2, DET3, DET4, DET5 and DET6; b) comparing the expression of the nucleic acid sequence(s) to the expression of the same nucleic acid sequences in a reference cell population comprising at least one cell from a thyroid lesion known to be a malignant lesion; and c) identifying similarity of expression levels of DET1, DET2, DET3, DET4, DET6, DET7, DET8, DET9, DET10 and DET11 in the test cell population and reference cell population, thereby classifying the thyroid lesion in the subject as a malignant thyroid lesion.

Thus, provided is a method for classifying a thyroid lesion in a subject as a malignant lesion comprising: a) measuring the expression of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 in a test cell population, wherein at least one cell in said test cell population is capable of expressing DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85; b) comparing the expression of the nucleic acid sequence(s) to the expression of the same nucleic acid sequences in a reference cell population comprising at least one cell from a thyroid lesion known to be a malignant lesion; and c) identifying similarity of expression levels of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 in the test cell population and reference cell population, thereby classifying the thyroid lesion in the subject as a malignant thyroid lesion.

The present invention provides a method for one skilled in the art using the molecular biological and statistical methods described herein to quantify the gene expression levels of a particular DET gene in a number of tumor samples (reference cell populations) and get a statistical distribution of gene expression levels for that particular DET gene that are characteristic of a collection of benign or malignant tissues. Based on this information, a test cell population that is derived from a thyroid tumor of uncertain diagnosis can have its expression level for that particular DET gene characterized as statistically more likely belonging to either the benign or malignant distribution of gene expression levels by using standard statistical software, thereby designating that test cell population from a particular thyroid tumor as being either benign or malignant.

As disclosed herein, the nucleic acid sequences selected from the group consisting of C21orf4 (DET1) and Hs.145049 (DET2) are upregulated in malignant thyroid lesions consisting of cell populations from papillary thyroid carcinomas and follicular variant of papillary thyroid carcinomas, when compared to benign thyroid lesions consisting of cell populations from follicular adenomas and hyperplastic nodules. Thus, provided is a method to distinguish malignant thyroid lesions consisting of cell populations from papillary thyroid carcinomas and follicular variant of papillary thyroid carcinomas, from benign thyroid lesions consisting of cell populations from follicular adenomas and hyperplastic nodules.

As disclosed herein, the nucleic acid sequences selected from the group consisting of HMGA2 (DET12), KLK7 (DET13), MRC2 (DET14), LRRK2 (DET15), PLAG1 (DET16), CYP1B1 (DET17), DPP4 (DET18), FNDC4 (DET19), PHLDA2 (DET20), CCNA1 (DET21), CDH3 (DET22), CEACAM6 (DET23), QSCN6 (DET24), COL7A1 (DET25), MGC9712 (DET26), IL1RAP (DET27), LAMB3 (DET28), PRSS3 (DET29), LRP4 (DET30), SPOCK1 (DET31), PDE5A (DET32), FLJ37078 (DET33), FBN3 (DET34), DIRAS3 (DET35), PRSS1 (DET36), CAMK2N1 (DET37), SNIP (DET38), KCNJ2 (DET39), SFN (DET40), GALNT7 (DET41), TGFA (DET42), BAIAP3 (DET43), and KCNK15 (DET44) are upregulated in malignant thyroid lesions consisting of cell populations from papillary thyroid carcinomas, follicular variant of papillary thyroid carcinomas, follicular carcinomas, and Hurthle cell carcinomas, when compared to benign thyroid lesions consisting of cell populations from adenomatoid nodules, follicular adenomas, Hurthle cell adenomas, and lymphocytic thyroid nodules. Thus, provided is a method to distinguish malignant thyroid lesions consisting of cell populations from papillary thyroid carcinomas, follicular variant of papillary thyroid carcinomas, follicular carcinomas, and Hurthle cell carcinomas, from benign thyroid lesions consisting of cell populations from adenomatoid nodules, follicular adenomas, Hurthle cell adenomas, and lymphocytic thyroid nodules.

As disclosed herein, the nucleic acid sequences selected from the group consisting of KIT(DET4), LSM7(DET5), C11orf8(DET7), FAM13A1(DET9), IMPACT(DET10), KIAA1128(DET11), and CDH1(DET8), are downregulated in malignant thyroid lesions consisting of cell populations from papillary thyroid carcinomas and follicular variant of papillary thyroid carcinomas, when compared to benign thyroid lesions consisting of cell populations from follicular adenomas and hyperplastic nodules. Thus, provided is a method to distinguish malignant thyroid lesions consisting of cell populations from papillary thyroid carcinomas and follicular variant of papillary thyroid carcinomas, from benign thyroid lesions consisting of cell populations from follicular adenomas and hyperplastic nodules.

Also disclosed herein, the nucleic acid sequences selected from the group consisting of KIT(DET4), RAG2 (DET45), CLYBL (DET46), NEB (DET47), TNFRSF11B (DET48), GNAI1 (DET49), AGTR1 (DET50), HLF (DET51), SLC26A4 (DET52), MT1A (DET53), FABP4 (DET54), LRP1B (DET55), SLC4A4 (DET56), LOC646278 (DET57), MAN1C1 (DET58), KCNIP3 (DET59), DNAJB9 (DET60), UBR1 (DET61), HSD17B6 (DET62), SLC33A1 (DET63), CDH16 (DET64), TBC1D1 (DET65), SLC26A7 (DET66), C11orf74 (DET67), PLA2R1 (DET68), PTTG3 (DET69), EFEMP1 (DET70), ZMAT4 (DET71), STEAP3 (DET72), DIO1 (DET73), TPO (DET74), PTTG1 (DET75), LGI3 (DET76), TMEM38B (DET77), SLITRK4 (DET78), VBP1 (DET79), COL9A3 (DET80), IRS1 (DET81), STARD13 (DET82), LOC654085 (DET83), RPS3A (DET84), SPARCL1 (DET85) are downregulated in malignant thyroid lesions consisting of cell populations from papillary thyroid carcinomas, follicular variant of papillary thyroid carcinomas, follicular carcinomas, and Hurthle cell carcinomas, when compared to benign thyroid lesions consisting of cell populations from adenomatoid nodules, follicular adenomas, Hurthle cell adenomas, and lymphocytic thyroid nodules. Thus, provided is a method to distinguish malignant thyroid lesions consisting of cell populations from papillary thyroid carcinomas, follicular variant of papillary thyroid carcinomas, follicular carcinomas, and Hurthle cell carcinomas, from benign thyroid lesions consisting of cell populations from adenomatoid nodules, follicular adenomas, Hurthle cell adenomas, and lymphocytic thyroid nodules.

The disclosed methods of the present invention, including classifying, staging, and screening for a therapeutic, include an embodiment wherein the gene expression is not measured for only one of the DET genes selected from the group consisting of HMGA2, CYP1B1, DPP4, PHLDA2, LAMB3, LRP4, TGFA, RAG2, TNFRSF11B, SLC26A4, MT1A, FABP4, MAN1C1, HSD17B6 (RODH), PLA2R1, EFEMP1, D100, KIT, TPO, PTTG1, COL9A3, IRS1, and SPARCL1, or for only a combination of the DET genes selected from the group consisting of HMGA2, CYP1B1, DPP4, PHLDA2, LAMB3, LRP4, TGFA, RAG2, TNFRSF11B, SLC26A4, MT1A, FABP4, MAN1C1, HSD17B6 (RODH), PLA2R1, EFEMP1, D100, KIT, TPO, PTTG1, COL9A3, IRS1, and SPARCL1.

Diagnostic Methods

The diagnostic (e.g., staging and classification) methods provided herein are based on the comparison of an expression profile for a specific set of DET (one or more) in a test cell population to the expression profile for the same set of DET for a test cell population of known condition (e.g., normal thyroid, malignant thyroid tumor or benign thyroid tumor).

The present invention provides a method for classifying a thyroid lesion in a subject comprising: a) measuring the expression of one or more nucleic acid sequences selected from the group consisting of DET1, DET2, DET3, DET4, DET6, DET7, DET8, DET9, DET10 and DET11 in a test cell population, wherein at least one cell in said test cell population is capable of expressing one or more nucleic acid sequences selected from the group consisting of DET1, DET2, DET3, DET4, DET6, DET7, DET8, DET9, DET10 and DET11; b) comparing the expression of the nucleic acid sequence(s) to the expression of the nucleic acid sequence(s) in a reference cell population comprising at least one cell for which a thyroid lesion classification is known; and c) identifying a difference, if present, in expression levels of one or more nucleic acid sequences selected from the group consisting of DET1, DET2, DET3, DET4, DET6, DET7, DET8, DET9, DET10 and DET11, in the test cell population and reference cell population, thereby classifying the thyroid lesion in the subject.

The present invention also provides a method for classifying a thyroid lesion in a subject comprising: a) measuring the expression of one or more nucleic acid sequences selected from the group consisting of DET1, DET2, DET3, DET4, DET5 and DET6 in a test cell population, wherein at least one cell in said test cell population is capable of expressing one or more nucleic acid sequences selected from the group consisting of DET1, DET2, DET3, DET4, DET5 and DET6; b) comparing the expression of the nucleic acid sequence(s) to the expression of the nucleic acid sequence(s) in a reference cell population comprising at least one cell for which a thyroid lesion classification is known; and c) identifying a difference, if present, in expression levels of one or more nucleic acid sequences selected from the group consisting of DET1, DET2, DET3, DET4, DET5 and DET6, in the test cell population and reference cell population, thereby classifying the thyroid lesion in the subject.

The present invention also provides a method for classifying a thyroid lesion in a subject comprising: a) measuring the expression of one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 in a test cell population, wherein at least one cell in said test cell population is capable of expressing one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85; b) comparing the expression of the nucleic acid sequence(s) to the expression of the nucleic acid sequence(s) in a reference cell population comprising at least one cell for which a thyroid lesion classification is known; and c) identifying a difference, if present, in expression levels of one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85, in the test cell population and reference cell population, thereby classifying the thyroid lesion in the subject.

In the methods of the present invention, "classifying a thyroid lesion" is equivalent to diagnosing a subject with a type of thyroid lesion. These lesions can be benign or malignant. Examples of a benign lesion include, but are not limited to, follicular adenoma, hyperplastic nodule, papillary adenoma, thyroiditis nodule, multinodular goiter, adenomatoid nodules, Hürthle cell adenomas, and lymphocytic thyroiditis nodules. Examples of malignant lesions include, but are not limited to, papillary thyroid carcinoma, follicular variant of papillary thyroid carcinoma, follicular carcinoma, Hurthle cell tumor, anaplastic thyroid cancer, medullary thyroid cancer, thyroid lymphoma, poorly differentiated thyroid cancer and thyroid angiosarcoma.

In the methods of the present invention, measuring the expression levels of one or more nucleic acids sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 means that the expression of any combination of these sequences can be measured.

For example, the expression level of one, two, three, four, five, six, seven, eight, nine, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 or 85 sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 can be measured.

Also disclosed herein is a method of classifying a tumor as malignant or benign based on the statistical similarity of the expression levels found in the tumor cells of question of the nucleic acid sequences selected from the group consisting of C21orf4 (DET1), Hs.145049(DET2), HMGA2 (DET12), KLK7 (DET13), MRC2 (DET14), LRRK2 (DET15), PLAG1 (DET16), CYP1B1 (DET17), DPP4 (DET18), FNDC4 (DET19), PHLDA2 (DET20), CCNA1 (DET21), CDH3 (DET22), CEACAM6 (DET23), QSCN6 (DET24), COL7A1 (DET25), MGC9712 (DET26), IL1RAP (DET27), LAMB3 (DET28), PRSS3 (DET29), LRP4 (DET30), SPOCK1 (DET31), PDE5A (DET32), FLJ37078 (DET33), FBN3 (DET34), DIRAS3 (DET35), PRSS1 (DET36), CAMK2N1 (DET37), SNIP (DET38), KCNJ2 (DET39), SFN (DET40), GALNT7 (DET41), TGFA (DET42), BAIAP3 (DET43), and KCNK15 (DET44), that are upregulated in malignant thyroid lesions consisting of cell populations from papillary thyroid carcinomas and follicular variant of papillary thyroid carcinomas, when compared to benign thyroid lesions consisting of cell populations from follicular adenomas and hyperplastic nodules.

The present invention also provides a method for classifying a thyroid lesion as malignant or benign in a subject comprising: a) measuring the expression of one or more nucleic acid sequences selected from the group consisting of C21orf4 (DET1), Hs.145049(DET2), HMGA2 (DET12), KLK7 (DET13), MRC2 (DET14), LRRK2 (DET15), PLAG1 (DET16), CYP1B1 (DET17), DPP4 (DET18), FNDC4 (DET19), PHLDA2 (DET20), CCNA1 (DET21), CDH3 (DET22), CEACAM6 (DET23), QSCN6 (DET24), COL7A1 (DET25), MGC9712 (DET26), IL1RAP (DET27), LAMB3 (DET28), PRSS3 (DET29), LRP4 (DET30), SPOCK1 (DET31), PDE5A (DET32), FLJ37078 (DET33), FBN3 (DET34), DIRAS3 (DET35), PRSS1 (DET36), CAMK2N1 (DET37), SNIP (DET38), KCNJ2 (DET39), SFN (DET40), GALNT7 (DET41), TGFA (DET42), BAIAP3 (DET43), and KCNK15 (DET44), in a test cell population, wherein at least one cell in said test cell population is capable of expressing one or more nucleic acid sequences selected from the group consisting of C21orf4 (DET1), Hs.145049(DET2), HMGA2 (DET12), KLK7 (DET13), MRC2 (DET14), LRRK2 (DET15), PLAG1 (DET16), CYP1B1 (DET17), DPP4 (DET18), FNDC4 (DET19), PHLDA2 (DET20), CCNA1 (DET21), CDH3 (DET22), CEACAM6 (DET23), QSCN6 (DET24), COL7A1 (DET25), MGC9712 (DET26), IL1RAP (DET27), LAMB3 (DET28), PRSS3 (DET29), LRP4 (DET30), SPOCK1 (DET31), PDE5A (DET32), FLJ37078 (DET33), FBN3 (DET34), DIRAS3 (DET35), PRSS1 (DET36), CAMK2N1 (DET37), SNIP (DET38), KCNJ2 (DET39), SFN (DET40), GALNT7 (DET41), TGFA (DET42), BAIAP3 (DET43), and KCNK15 (DET44); b) comparing the expression of the nucleic acid sequence(s) to the expression of the nucleic acid sequence(s) in two reference cell populations comprising cells from malignant thyroid lesions, and cells from benign thyroid lesions; and c)

identifying a similarity, if present, in expression levels of one or more nucleic acid sequences selected from the group consisting of C21orf4 (DET1), Hs.145049(DET2), HMGA2 (DET12), KLK7 (DET13), MRC2 (DET14), LRRK2 (DET15), PLAG1 (DET16), CYP1B1 (DET17), DPP4 (DET18), FNDC4 (DET19), PHLDA2 (DET20), CCNA1 (DET21), CDH3 (DET22), CEACAM6 (DET23), QSCN6 (DET24), COL7A1 (DET25), MGC9712 (DET26), IL1RAP (DET27), LAMB3 (DET28), PRSS3 (DET29), LRP4 (DET30), SPOCK1 (DET31), PDE5A (DET32), FLJ37078 (DET33), FBN3 (DET34), DIRAS3 (DET35), PRSS1 (DET36), CAMK2N1 (DET37), SNIP (DET38), KCNJ2 (DET39), SFN (DET40), GALNT7 (DET41), TGFA (DET42), BAIAP3 (DET43), and KCNK15 (DET44), in the test cell population and reference cell populations, thereby classifying the thyroid lesion in the subject as malignant if one or more nucleic acid sequences consisting of C21orf4 (DET1), Hs.145049(DET2), HMGA2 (DET12), KLK7 (DET13), MRC2 (DET14), LRRK2 (DET15), PLAG1 (DET16), CYP1B1 (DET17), DPP4 (DET18), FNDC4 (DET19), PHLDA2 (DET20), CCNA1 (DET21), CDH3 (DET22), CEACAM6 (DET23), QSCN6 (DET24), COL7A1 (DET25), MGC9712 (DET26), IL1RAP (DET27), LAMB3 (DET28), PRSS3 (DET29), LRP4 (DET30), SPOCK1 (DET31), PDE5A (DET32), FLJ37078 (DET33), FBN3 (DET34), DIRAS3 (DET35), PRSS1 (DET36), CAMK2N1 (DET37), SNIP (DET38), KCNJ2 (DET39), SFN (DET40), GALNT7 (DET41), TGFA (DET42), BAIAP3 (DET43), and KCNK15 (DET44), are found to be overexpressed. For example, if any one of these DET genes, DET 1, DET2, and DET12-44, are used alone, it has been shown that they were all significantly differentially overexpressed in malignant vs. benign tumor types. In the methods of the invention the malignant cell populations can be from papillary thyroid carcinomas, follicular variant of papillary thyroid carcinomas, follicular carcinomas, and Hurthle cell carcinomas. In the methods of the invention the benign cell populations can be from follicular adenomas, hyperplastic nodules, adenomatoid nodules, Hurthle cell adenomas, and lymphocytic thyroid nodules.

Also disclosed herein, the method of classifying a tumor as malignant or benign based on the statistical similarity of the expression levels found in the tumor cells of question of the nucleic acid sequences selected from the group consisting of KIT(DET4), LSM7(DET5), C11orf8(DET7), FAM13A1 (DET9), IMPACT(DET10), KIAA1128(DET11), CDH1 (DET8), RAG2 (DET45), CLYBL (DET46), NEB (DET47), TNFRSF11B (DET48), GNAI1 (DET49), AGTR1 (DET50), HLF (DET51), SLC26A4 (DET52), MT1A (DET53), FABP4 (DET54), LRP1B (DET55), SLC4A4 (DET56), LOC646278 (DET57), MAN1C1 (DET58), KCNIP3 (DET59), DNAJB9 (DET60), UBR1 (DET61), HSD17B6 (DET62), SLC33A1 (DET63), CDH16 (DET64), TBC1D1 (DET65), SLC26A7 (DET66), C11orf74 (DET67), PLA2R1 (DET68), PTTG3 (DET69), EFEMP1 (DET70), ZMAT4 (DET71), STEAP3 (DET72), DIO1 (DET73), TPO (DET74), PTTG1 (DET75), LGI3 (DET76), TMEM38B (DET77), SLITRK4 (DET78), VBP1 (DET79), COL9A3 (DET80), IRS1 (DET81), STARD13 (DET82), LOC654085 (DET83), RPS3A (DET84), and SPARCL1 (DET85), that are downregulated in malignant thyroid lesions consisting of cell populations from papillary thyroid carcinomas and follicular variant of papillary thyroid carcinomas, when compared to benign thyroid lesions consisting of cell populations from follicular adenomas and hyperplastic nodules.

The present invention also provides a method for classifying a thyroid lesion as malignant or benign in a subject comprising: a) measuring the expression of one or more nucleic acid sequences selected from the group consisting of KIT (DET4), LSM7(DET5), C11orf8(DET7), FAM13A1 (DET9), IMPACT(DET10), KIAA1128(DET11), CDH1 (DET8), RAG2 (DET45), CLYBL (DET46), NEB (DET47), TNFRSF11B (DET48), GNAI1 (DET49), AGTR1 (DET50), HLF (DET51), SLC26A4 (DET52), MT1A (DET53), FABP4 (DET54), LRP1B (DET55), SLC4A4 (DET56), LOC646278 (DET57), MAN1C1 (DET58), KCNIP3 (DET59), DNAJB9 (DET60), UBR1 (DET61), HSD17B6 (DET62), SLC33A1 (DET63), CDH16 (DET64), TBC1D1 (DET65), SLC26A7 (DET66), C11orf74 (DET67), PLA2R1 (DET68), PTTG3 (DET69), EFEMP1 (DET70), ZMAT4 (DET71), STEAP3 (DET72), DIO1 (DET73), TPO (DET74), PTTG1 (DET75), LGI3 (DET76), TMEM38B (DET77), SLITRK4 (DET78), VBP1 (DET79), COL9A3 (DET80), IRS1 (DET81), STARD13 (DET82), LOC654085 (DET83), RPS3A (DET84), and SPARCL1 (DET85), in a test cell population, wherein at least one cell in said test cell population is capable of expressing one or more nucleic acid sequences selected from the group consisting of KIT(DET4), LSM7(DET5), C11orf8(DET7), FAM13A1(DET9), IMPACT(DET10), KIAA1128(DET11), CDH1(DET8), RAG2 (DET45), CLYBL (DET46), NEB (DET47), TNFRSF11B (DET48), GNAI1 (DET49), AGTR1 (DET50), HLF (DET51), SLC26A4 (DET52), MT1A (DET53), FABP4 (DET54), LRP1B (DET55), SLC4A4 (DET56), LOC646278 (DET57), MAN1C1 (DET58), KCNIP3 (DET59), DNAJB9 (DET60), UBR1 (DET61), HSD17B6 (DET62), SLC33A1 (DET63), CDH16 (DET64), TBC1D1 (DET65), SLC26A7 (DET66), C11orf74 (DET67), PLA2R1 (DET68), PTTG3 (DET69), EFEMP1 (DET70), ZMAT4 (DET71), STEAP3 (DET72), DIO1 (DET73), TPO (DET74), PTTG1 (DET75), LGI3 (DET76), TMEM38B (DET77), SLITRK4 (DET78), VBP1 (DET79), COL9A3 (DET80), IRS1 (DET81), STARD13 (DET82), LOC654085 (DET83), RPS3A (DET84), and SPARCL1 (DET85); b) comparing the expression of the nucleic acid sequence(s) to the expression of the nucleic acid sequence(s) in two reference cell populations comprising cells from malignant thyroid lesions, and cells from benign thyroid lesions; and c) identifying a similarity, if present, in expression levels of one or more nucleic acid sequences selected from the group consisting of KIT(DET4), LSM7(DET5), C11orf8(DET7), FAM13A1(DET9), IMPACT(DET10), KIAA1128(DET11), CDH1(DET8), RAG2 (DET45), CLYBL (DET46), NEB (DET47), TNFRSF11B (DET48), GNAI1 (DET49), AGTR1 (DET50), HLF (DET51), SLC26A4 (DET52), MT1A (DET53), FABP4 (DET54), LRP1B (DET55), SLC4A4 (DET56), LOC646278 (DET57), MAN1C1 (DET58), KCNIP3 (DET59), DNAJB9 (DET60), UBR1 (DET61), HSD17B6 (DET62), SLC33A1 (DET63), CDH16 (DET64), TBC1D1 (DET65), SLC26A7 (DET66), C11orf74 (DET67), PLA2R1 (DET68), PTTG3 (DET69), EFEMP1 (DET70), ZMAT4 (DET71), STEAP3 (DET72), DIO1 (DET73), TPO (DET74), PTTG1 (DET75), LGI3 (DET76), TMEM38B (DET77), SLITRK4 (DET78), VBP1 (DET79), COL9A3 (DET80), IRS1 (DET81), STARD13 (DET82), LOC654085 (DET83), RPS3A (DET84), and SPARCL1 (DET85), in the test cell population and reference cell populations, thereby classifying the thyroid lesion in the subject as malignant if one or more nucleic acid sequences consisting of KIT (DET4), LSM7(DET5), C11orf8(DET7), FAM13A1 (DET9), IMPACT(DET10), KIAA1128(DET11), CDH1 (DET8), RAG2 (DET45), CLYBL (DET46), NEB (DET47), TNFRSF11B (DET48), GNAI1 (DET49), AGTR1 (DET50), HLF (DET51), SLC26A4 (DET52), MT1A (DET53), FABP4 (DET54), LRP1B (DET55), SLC4A4 (DET56), LOC646278 (DET57), MAN1C1 (DET58), KCNIP3 (DET59), DNAJB9 (DET60), UBR1 (DET61), HSD17B6 (DET62), SLC33A1 (DET63), CDH16 (DET64), TBC1D1 (DET65), SLC26A7 (DET66), C11orf74 (DET67), PLA2R1 (DET68), PTTG3 (DET69), EFEMP1 (DET70), ZMAT4 (DET71), STEAP3 (DET72), DIO1 (DET73), TPO (DET74), PTTG1 (DET75), LGI3 (DET76), TMEM38B (DET77), SLITRK4 (DET78), VBP1 (DET79), COL9A3 (DET80), IRS1 (DET81), STARD13 (DET82), LOC654085 (DET83), RPS3A (DET84), and SPARCL1 (DET85), are found to be underexpressed. For example, if any one of these DET genes, DET4, DET5, DET7-11, and DET45-85, are used alone, it has been shown that they were all significantly differentially underexpressed in malignant vs. benign tumor types. In the methods of the invention the malignant cell populations can be from papillary thyroid carcinomas, follicular variant of papillary thyroid carcinomas, follicular carcinomas, and Hurthle cell carcinomas. In the methods of the invention the benign cell populations can be from follicular adenomas, hyperplastic nodules, adenomatoid nodules, Hurthle cell adenomas, and lymphocytic thyroid nodules.

As disclosed herein, the method for classifying a thyroid lesion in a subject as malignant or benign comprises receiving gene expression data of one or more nucleic acid sequences selected from the group consisting of the differentially expressed thyroid genes DET1, DET2, DET3, DET4, DET5, and DET6 in a test cell population, wherein at least one cell in said test cell population is capable of expressing one or more nucleic acid sequences selected from the group consisting of DET1, DET2, DET3, DET4, DET5, and DET6; and determining a class of tumor, wherein the determination is made by applying a statistical classifier or predictor model to the gene expression data; and outputting the class of tumor as malignant or benign based on the determination.

Figure 4:
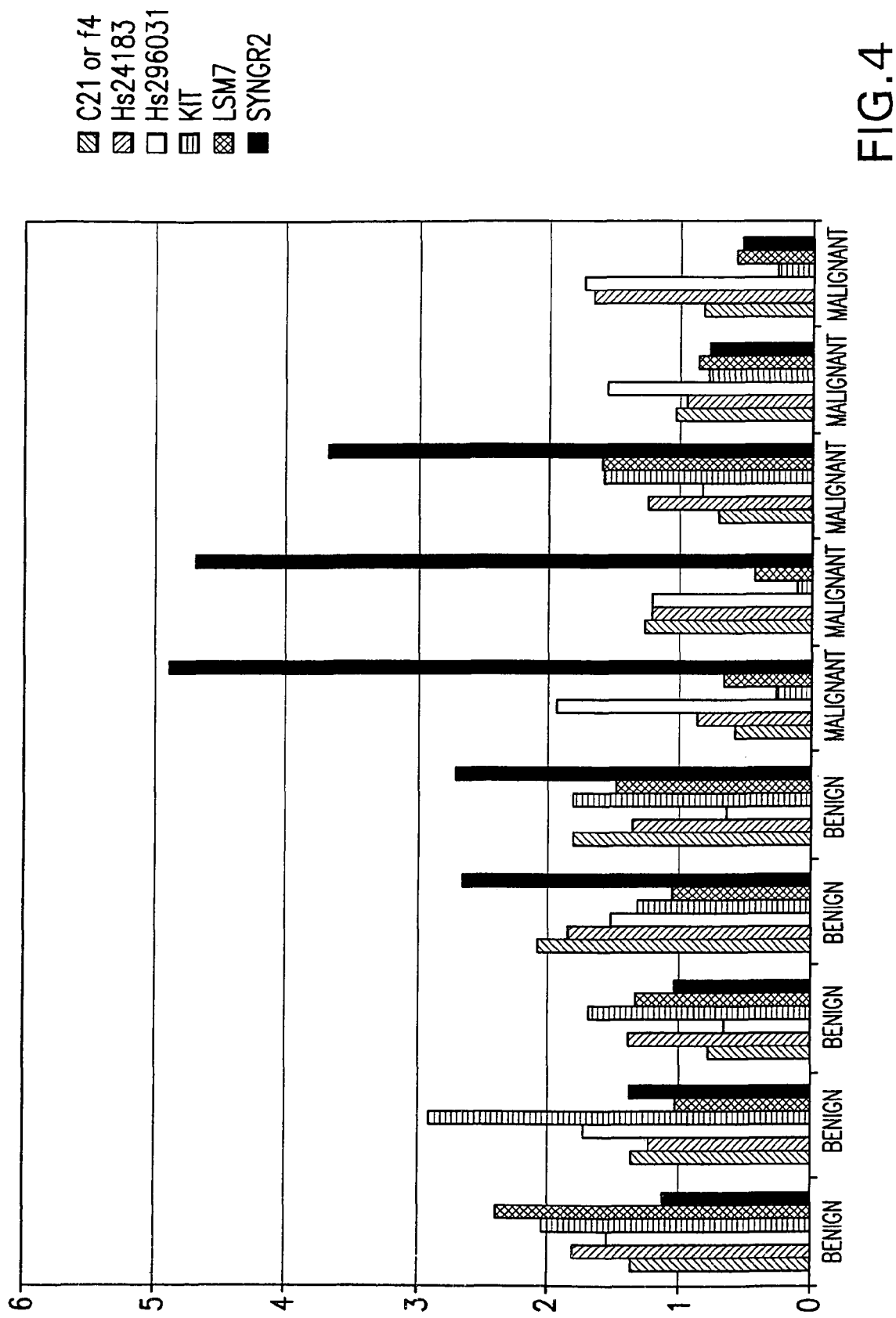
FIG. 4 is a graph showing gene expression profiles of ten unknown samples. On the basis of their profile the predictor model of this invention gave a correct diagnosis in 100% of the cases. The y axis represents the ratio between thyroid tumor mRNA expression level (Cy5 fluorescence intensity) and control thyroid tissue mRNA expression level (Cy3 fluorescence intensity).

For example, the specific DET1-6 gene expression patterns that are shown in FIG. 4 can be used as a comparator, such that if an unknown tumor sample matches these patterns, it can then be classified as malignant or benign. Thus, provided is a method of classifying, staging or identifying a therapeutic agent comprising the step of comparing the expression pattern of sample (e.g., thyroid tumor cell or tissue) from a subject with the patterns displayed in FIG. 4, thereby identifying the tumor as benign or malignant. A similar approach can be taken using other sets of genes to classify a thyroid tumor as benign versus malignant.

As disclosed herein, the method for classifying a thyroid lesion in a subject as malignant or benign comprises receiving gene expression data of one or more nucleic acid sequences selected from the group consisting of the differentially expressed thyroid genes DET1, DET2, DET3, DET4, DET6, DET7, DET8, DET9, DET10, DET11, in a test cell population, wherein at least one cell in said test cell population is capable of expressing one or more nucleic acid sequences selected from the group consisting of DET1, DET2, DET3, DET4, DET6, DET7, DET8, DET9, DET10, DET11; and determining a class of tumor, wherein the determination is made by applying a statistical classifier or predictor model to the gene expression data; and outputting the class of tumor as malignant or benign based on the determination.

As disclosed herein, the method for classifying a thyroid lesion in a subject as malignant or benign comprises receiving gene expression data of one or more nucleic acid sequences selected from the group consisting of the differentially expressed thyroid genes DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 in a test cell population, wherein at least one cell in said test cell population is capable of expressing one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85; and determining a class of tumor, wherein the determination is made by applying a statistical classifier or predictor model to the gene expression data; and outputting the class of tumor as malignant or benign based on the determination.

In the methods of the present invention, the classifier, predictor model, or diagnosis-predictor model can be a compound covariate predictor, a diagonal linear discriminant analysis, nearest-neighbor classification, or support vector machines with linear kernel. For example, with the nearest neighbor classifier or predictor model, data are provided that show 73% sensitivity, 82% specificity, and 78% predictive value for the prediction of malignancy.

In the methods of the present invention, the differentially expressed thyroid genes incorporated into the classifier, predictor model, or diagnosis-predictor model can be differentially expressed in malignant vs. benign thyroid tumors with a level of statistical significance signified with a P value of less than 0.05 using standard statistical analysis. More specifically, the P value can be less than 0.0001 to limit the number of false positives. In the methods of the present invention, standard statistical analysis can be an ANOVA test with Bonferroni correction, or a random-variance t test.

In the methods of the present invention, measuring the expression levels of one or more nucleic acids sequences selected from the group consisting of DET1, DET2, DET3, DET4, DET6, DET7, DET8, DET9, DET10 and DET11, means that the expression of any combination of these sequences can be measured. For example, the expression level of one, two, three, four, five, six, seven, eight, nine or ten sequences selected from the group consisting of DET1, DET2, DET3, DET4, DET6, DET7, DET8, DET9, DET10 and DET11 can be measured. Similarly, when measuring the expression levels of one or more nucleic acid sequences selected from the group consisting of DET1, DET2, DET3, DET4, DET5 and DET6, one of skill in the art can measure the expression level of one, two, three, four, five or six sequences selected from the group consisting of DET1, DET2, DET3, DET4, DET5 and DET6.

In the methods of the present invention, the invention includes providing a test population which includes at least once cell that is capable of expressing one or more of the sequences DET1-85. As utilized herein, "expression" refers to the transcription of a DET gene to yield a DET nucleic acid, such as a DET mRNA. The term "expression" also refers to the transcription and translation of a DET gene to yield the encoded protein, in particular a DET protein or a fragment thereof. Therefore, one of skill in the art can detect the expression of a DET gene by monitoring DET nucleic acid production and/or expression of the DET protein. As utilized herein, "upregulated" refers to an increase in expression and "downregulated" refers to a decrease in expression.

In the methods of the present invention, the reference cell population can be from normal thyroid tissue, cancerous thyroid tissue or any other type of thyroid tissue for which a classification is known. As used herein, "a cell of a normal subject" or "normal thyroid tissue" means a cell or tissue which is histologically normal and was obtained from a subject believed to be without malignancy and having no increased risk of developing a malignancy or was obtained from tissues adjacent to tissue known to be malignant and which is determined to be histologically normal (non-malignant) as determined by a pathologist. The reference cell population can be from any subject, including cells of the subject being tested obtained prior to developing the condition that lead to the testing. The normal reference cell population can be homogeneous for normal cells.

Using the sequence information provided herein and the sequences provided by the database entries, the expression of the DET sequences or fragments thereof can be detected, if present, and measured using techniques well known in the art. For example, sequences disclosed herein can be used to construct probes for detecting DET DNA and RNA sequences. The amount of a DET nucleic acid, for example, DET mRNA, in a cell can be determined by methods standard in the art for detecting or quantitating a nucleic acid in a cell, such as in situ hybridization, quantitative PCR, Northern blotting, ELISPOT, dot blotting, etc., as well as any other method now known or later developed for detecting or quantitating the amount of a nucleic acid in a cell.

The presence or amount of a DET protein in or produced by a cell can be determined by methods standard in the art, such as Western blotting, ELISA, ELISPOT, immunoprecipitation, immunofluorescence (e.g., FACS), immunohistochemistry, immunocytochemistry, etc., as well as any other method now known or later developed for detecting or quantitating protein in or produced by a cell.

As used throughout, "subject" means an individual. Preferably, the subject is a mammal such as a primate, and, more preferably, a human. The term "subject" includes domesticated animals, such as cats, dogs, etc., livestock (e.g., cattle, horses, pigs, sheep, goats, etc.), and laboratory animals (e.g., mouse, monkey, rabbit, rat, guinea pig, etc.).

The present invention also provides for detection of variants of the DET nucleic acids and polypeptides disclosed herein. In general, variants of nucleic acids and polypeptides herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent sequence similarity (also referred to herein as "homology") to the stated sequence or the native sequence. Those of skill in the art readily understand how to determine the homology of two polypeptides or nucleic acids. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.; the BLAST algorithm of Tatusova and Madden FEMS Microbiol. Lett. 174: 247-250 (1999) available from the National Center for Biotechnology Information or by inspection. Similarly, the present invention provides for the detection of DET proteins that are homologues of human DET proteins in other species. It would be readily apparent to one of skill in the art that the DET sequences set forth herein and in GenBank can be utilized in sequence comparisons to identify DET sequences in other species.

The sample of this invention, such as a test cell population or a reference cell population, can be from any organism and can be, but is not limited to, peripheral blood, urine, saliva, sputum, feces, bone marrow specimens, primary tumors, embedded tissue sections, frozen tissue sections, cell preparations, cytological preparations, exfoliate samples (e.g., sputum), fine needle aspirations, lung fluid, amnion cells, fresh tissue, dry tissue, and cultured cells or tissue. The sample can be from malignant tissue or non-malignant tissue. The sample can be thyroid cells or thyroid tissue. The sample can be unfixed or fixed according to standard protocols widely available in the art and can also be embedded in a suitable medium for preparation of the sample. For example, the sample can be embedded in paraffin or other suitable medium (e.g., epoxy or acrylamide) to facilitate preparation of the biological specimen for the detection methods of this invention. Furthermore, the sample can be embedded in any commercially available mounting medium, either aqueous or organic.

The sample can be on, supported by, or attached to, a substrate which facilitates detection. A substrate of the present invention can be, but is not limited to, a microscope slide, a culture dish, a culture flask, a culture plate, a culture chamber, ELISA plates, as well as any other substrate that can be used for containing or supporting biological samples for analysis according to the methods of the present invention. The substrate can be of any material suitable for the purposes of this invention, such as, for example, glass, plastic, polystyrene, mica and the like. The substrates of the present invention can be obtained from commercial sources or prepared according to standard procedures well known in the art.

Additionally, an antibody or fragment thereof, an antigenic fragment of a DET protein, or DET nucleic acid of the invention can be on, supported by, or attached to a substrate which facilitates detection. Such a substrate can include a chip, a microarray or a mobile solid support. Thus, provided by the invention are substrates including one or more of the antibodies or antibody fragments, antigenic fragments of DET proteins, or DET nucleic acids of the invention.

The nucleic acids of this invention can be detected with a probe capable of hybridizing to the nucleic acid of a cell or a sample. This probe can be a nucleic acid comprising the nucleotide sequence of a coding strand or its complementary strand or the nucleotide sequence of a sense strand or antisense strand, or a fragment thereof. The nucleic acid can comprise the nucleic acid of a DET gene or fragments thereof. Thus, the probe of this invention can be either DNA or RNA and can bind either DNA or RNA, or both, in the biological sample. The probe can be the coding or complementary strand of a complete DET gene or DET gene fragment.

The nucleic acids of the present invention, for example, DET1-DET85 nucleic acids and fragments thereof, can be utilized as probes or primers to detect DET nucleic acids.

Therefore, the present invention provides DET polynucleotide probes or primers that can be at least 15, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 250, 300, 350 or at least 400 nucleotides in length.

As used herein, the term "nucleic acid probe" refers to a nucleic acid fragment that selectively hybridizes under stringent conditions with a nucleic acid comprising a nucleic acid set forth in a DET sequence provided herein. This hybridization must be specific. The degree of complementarity between the hybridizing nucleic acid and the sequence to which it hybridizes should be at least enough to exclude hybridization with a nucleic acid encoding an unrelated protein.

Stringent conditions refers to the washing conditions used in a hybridization protocol. In general, the washing conditions should be a combination of temperature and salt concentration chosen so that the denaturation temperature is approximately 5-20° C. below the calculated $T_m$ of the nucleic acid hybrid under study. The temperature and salt conditions are readily determined empirically in preliminary experiments in which samples of reference DNA immobilized on filters are hybridized to the probe or protein coding nucleic acid of interest and then washed under conditions of different stringencies. The $T_m$ of such an oligonucleotide can be estimated by allowing 2° C. for each A or T nucleotide, and 4° C. for each G or C. For example, an 18 nucleotide probe of 50% G+C would, therefore, have an approximate $T_m$ of 54° C.

Stringent conditions are known to one of skill in the art. See, for example, Sambrook et al. (2001). An example of stringent wash conditions is 4×SSC at 65° C. Highly stringent wash conditions include, for example, 0.2×SSC at 65° C.

As mentioned above, the DET nucleic acids and fragments thereof can be utilized as primers to amplify a DET nucleic acid, such as a DET gene transcript, by standard amplification techniques. For example, expression of a DET gene transcript can be quantified by RT-PCR using RNA isolated from cells, as described in the Examples.

A variety of PCR techniques are familiar to those skilled in the art. For a review of PCR technology, see White (1997) and the publication entitled "PCR Methods and Applications" (1991, Cold Spring Harbor Laboratory Press), which is incorporated herein by reference in its entirety for amplification methods. In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202 and 4,965,188. Each of these publications is incorporated herein by reference in its entirety for PCR methods. One of skill in the art would know how to design and synthesize primers that amplify a DET sequence or a fragment thereof.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g., $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product. The amplification reaction can also include a dual fluorescent probe, as described in the Examples, which hybridizes to and detects the amplification product thus allowing real time quantitation of the amplification product.

Therefore, expression of the nucleic acid(s) of the present invention can be measured by amplifying the nucleic acid(s) and detecting the amplified nucleic acid with a fluorescent probe.

For example, DET1 can be amplified utilizing forward primer GCAATCCTCTTACCTCCGCTTT (SEQ ID NO: 7) and reverse primer GGAATCGGAGACAGAAGAGAGCTT (SEQ ID NO: 8). The nucleic acid amplified by these primers can be detected with a probe comprising the nucleic acid sequence CTGGGACCACAGATGTATCCTCCACTCC (SEQ ID NO: 9) linked to a fluorescent label. These primers are merely exemplary for the amplification of DET1 as one of skill in the art would know how to design primers, based on the DET1 nucleic acid sequences provided herein, such as SEQ ID NO: 40 and the nucleic acid sequences provided by the database entries, to amplify a DET1 nucleic acid. Similarly, the probe sequences provided herein are merely exemplary for the detection of a DET1 nucleic acid, as one of skill in the art would know how to design a probe, based on the DET1 nucleic acid sequences provided herein, such as SEQ ID NO: 40 and the nucleic acid sequences provided by the database entries, to detect a DET2 nucleic acid.

DET2 can be amplified utilizing forward primer GGCTGACTGGCAAAAAGTCTTG (SEQ ID NO: 1) and reverse primer TTGGTTCCCTTAAGTTCTCAGAGTTT (SEQ ID NO: 2). The nucleic acid amplified by these primers can be detected with a probe comprising the nucleic acid sequence TGGCCCTGTCACTCCCATGATGC (SEQ ID NO: 3) linked to a fluorescent label. These primers are merely exemplary for the amplification of DET2 as one of skill in the art would know how to design primers, based on the DET2 nucleic acid sequences provided herein, such as SEQ ID NO: 42 and the nucleic acid sequences provided by the database entries, to amplify a DET2 nucleic acid. Similarly, the probe sequences provided herein are merely exemplary for the detection of a DET2 nucleic acid, as one of skill in the art would know how to design a probe, based on the DET2 nucleic acid sequences provided herein, such as SEQ ID NO: 42 and the nucleic acid sequences provided by the database entries, to detect a DET2 nucleic acid.

DET3 can be amplified utilizing forward primer TGCCAAGGAGCTTTGTTTATAGAA (SEQ ID NO: 19) and reverse primer ATGACGGCATGTACCAACCA (SEQ ID NO: 20). The nucleic acid amplified by these primers can be detected with a probe comprising the nucleic acid sequence TTGGTCCCCTCAGTTCTATGCTGTTGTGT (SEQ ID NO: 21) linked to a fluorescent label. These primers are merely exemplary for the amplification of DET3 as one of skill in the art would know how to design primers, based on the DET3 nucleic acid sequences provided herein, such as SEQ ID NO: 44 and the nucleic acid sequences provided by the database entries, to amplify a DET3 nucleic acid. Similarly, the probe sequences provided herein are merely exemplary for the detection of a DET3 nucleic acid, as one of skill in the art would know how to design a probe, based on the DET3 nucleic acid sequences provided herein, such as SEQ ID NO: 44 and the nucleic acid sequences provided by the database entries, to detect a DET3 nucleic acid.

DET4 can be amplified utilizing forward primer GCACCTGCTGAAATGTATGACATAAT (SEQ ID NO: 22) and reverse primer TTTGCTAAGTTGGAGTAAATATGATTGG (SEQ ID NO: 23). The nucleic acid amplified by these primers can be detected with a probe comprising the nucleic acid sequence ATTGTTCAGCTAATTGAGAAGCAGATTTCAGAGAGC (SEQ ID NO: 24) linked to a fluorescent label. These primers are merely exemplary for the amplification of DET4 as one of skill in the art would know how to design primers, based on the DET4 nucleic acid sequences provided herein, such as SEQ ID NO: 45 and the nucleic acid sequences provided by the database entries, to amplify a DET4 nucleic acid. Similarly, the probe sequences provided herein are merely exemplary for the detection of a DET4 nucleic acid, as one of skill in the art would know how to design a probe, based on the DET4 nucleic acid sequences provided herein, such as SEQ ID NO: 45 and the nucleic acid sequences provided by the database entries, to detect a DET4 nucleic acid.

DET5 can be amplified utilizing forward primer GACGATCCGGGTAAAGTTCCA (SEQ ID NO: 34) and reverse primer AGGTTGAGGAGTGGGTCGAA (SEQ ID NO: 35) The nucleic acid amplified by these primers can be detected with a probe comprising the nucleic acid sequence AGGCCGCGAAGCCAGTGGAATC (SEQ ID NO: 36) linked to a fluorescent label. These primers are merely exemplary for the amplification of DET5 as one of skill in the art would know how to design primers, based on the DET5 nucleic acid sequences provided herein, such as SEQ ID NO: 47 and the nucleic acid sequences provided by the database entries, to amplify a DET5 nucleic acid. Similarly, the probe sequences provided herein are merely exemplary for the detection of a DET5 nucleic acid, as one of skill in the art would know how to design a probe, based on the DET5 nucleic acid sequences provided herein, such as SEQ ID NO: 47 and the nucleic acid sequences provided by the database entries, to detect a DET5 nucleic acid.

DET6 can be amplified utilizing forward primer GCTGGTGCTCATGGCACTT (SEQ ID NO: 31) and reverse primer CCCTCCCCAGGCTTCCTAA (SEQ ID NO: 32). The nucleic acid amplified by these primers can be detected with a probe comprising the nucleic acid sequence AAGGGCTTTGCCTGACAACACCCA (SEQ ID NO: 33) linked to a fluorescent label. These primers are merely exemplary for the amplification of DET6 as one of skill in the art would know how to design primers, based on the DET6 nucleic acid sequences provided herein, such as SEQ ID NO: 49 and the nucleic acid sequences provided by the database entries, to amplify a DET6 nucleic acid. Similarly, the probe sequences provided herein are merely exemplary for the detection of a DET6 nucleic acid, as one of skill in the art would know how to design a probe, based on the DET6 nucleic acid sequences provided herein, such as SEQ ID NO: 49 and the nucleic acid sequences provided by the database entries, to detect a DET6 nucleic acid.

DET7 can be amplified utilizing forward primer CCGGCCAAGCTCCAT (SEQ ID NO: 13) and reverse primer TTGTGTAACCGTCGGTCATGA (SEQ ID NO: 14). The nucleic acid amplified by these primers can be detected with a probe comprising the nucleic acid sequence TGTTTGGTGGAATCCATGAAGGTTATGGC (SEQ ID NO: 15) linked to a fluorescent label. These primers are merely exemplary for the amplification of DET7 as one of skill in the art would know how to design primers, based on the DET7 nucleic acid sequences provided herein, such as SEQ ID NO: 51 and the nucleic acid sequences provided by the database entries, to amplify a DET7 nucleic acid. Similarly, the probe sequences provided herein are merely exemplary for the detection of a DET7 nucleic acid, as one of skill in the art would know how to design a probe, based on the DET7 nucleic acid sequences provided herein, such as SEQ ID NO: 51 and the nucleic acid sequences provided by the database entries, to detect a DET7 nucleic acid.

DET8 can be amplified utilizing forward primer TGAGTGTCCCCCGGTATCTTC (SEQ ID NO: 28) and reverse primer CAGCCGCTTTCAGATTTTCAT (SEQ ID NO: 29). The nucleic acid amplified by these primers can be detected with a probe comprising the nucleic acid sequence CCTGCCAATCCCGATGAAATTGGAAAT (SEQ ID NO: 30) linked to a fluorescent label. These primers are merely exemplary for the amplification of DET8 as one of skill in the art would know how to design primers, based on the DET8 nucleic acid sequences provided herein, such as SEQ ID NO: 53 and the nucleic acid sequences provided by the database entries, to amplify a DET8 nucleic acid. Similarly, the probe sequences provided herein are merely exemplary for the detection of a DET8 nucleic acid, as one of skill in the art would know how to design a probe, based on the DET8 nucleic acid sequences provided herein, such as SEQ ID NO: 53 and the nucleic acid sequences provided by the database entries, to detect a DET8 nucleic acid.

DET9 can be amplified utilizing forward primer ATGGCAGTGCAGTCATCATCTT (SEQ ID NO: 10) and reverse primer GCATTCATACAGCTGCTTACCATCT (SEQ ID NO: 11). The nucleic acid amplified by these primers can be detected with a probe comprising the nucleic acid sequence TTTGGTCCCTGCCTAGGACCGGG (SEQ ID NO: 12) linked to a fluorescent label. These primers are merely exemplary for the amplification of DET9 as one of skill in the art would know how to design primers, based on the DET9 nucleic acid sequences provided herein, such as SEQ ID NO: 55 and the nucleic acid sequences provided by the database entries, to amplify a DET9 nucleic acid. Similarly, the probe sequences provided herein are merely exemplary for the detection of a DET9 nucleic acid, as one of skill in the art would know how to design a probe, based on the DET9 nucleic acid sequences provided herein, such as SEQ ID NO: 55 and the nucleic acid sequences provided by the database entries, to detect a DET9 nucleic acid.

DET10 can be amplified utilizing forward primer TGAAGAATGTCATGGTGGTAGTATCA (SEQ ID NO: 25) and reverse primer ATGACTCCTCAGGTGAATTTGTGTAG (SEQ ID NO: 26). The nucleic acid amplified by these primers can be detected with a probe comprising the nucleic acid sequence CTGGTATGGAGGGATTCTGCTAGGACCAG (SEQ ID NO: 27) linked to a fluorescent label. These primers are merely exemplary for the amplification of DET10 as one of skill in the art would know how to design primers, based on the DET10 nucleic acid sequences provided herein, such as SEQ ID NO: 57 and the nucleic acid sequences provided by the database entries, to amplify a DET10 nucleic acid. Similarly, the probe sequences provided herein are merely exemplary for the detection of a DET10 nucleic acid, as one of skill in the art would know how to design a probe, based on the DET10 nucleic acid sequences provided herein, such as SEQ ID NO: 57 and the nucleic acid sequences provided by the database entries, to detect a DET10 nucleic acid.

DET11 can be amplified utilizing forward primer GAGAGCGTGATCCCCCTACA (SEQ ID NO: 16) and reverse primer ACCAAGAGTGCACCTCAGTGTCT (SEQ ID NO: 17). The nucleic acid amplified by these primers can be detected with a probe comprising the nucleic acid sequence TCACTTCCAAATGTTCCTGTAGCATAAATGGTG (SEQ ID NO: 18) linked to a fluorescent label. These primers are merely exemplary for the amplification of DET11 as one of skill in the art would know how to design primers, based on the DET11 nucleic acid sequences provided herein, such as SEQ ID NO: 59 and the nucleic acid sequences provided by the database entries, to amplify a DET11 nucleic acid. Similarly, the probe sequences provided herein are merely exemplary for the detection of a DET11 nucleic acid, as one of skill in the art would know how to design a probe, based on the DET11 nucleic acid sequences provided herein, such as SEQ ID NO: 59 and the nucleic acid sequences provided by the database entries, to detect a DET11 nucleic acid.

The sample nucleic acid, e.g. amplified fragment, can be analyzed by one of a number of methods known in the art. The nucleic acid can be sequenced by dideoxy or other methods. Hybridization with the sequence can also be used to determine its presence, by Southern blots, dot blots, etc.

The DET nucleic acids of the invention can also be used in polynucleotide arrays. Polynucleotide arrays provide a high throughput technique that can assay a large number of polynucleotide sequences in a single sample. This technology can be used, for example, as a diagnostic tool to identify samples with differential expression of DET nucleic acids as compared to a reference sample.

To create arrays, single-stranded polynucleotide probes can be spotted onto a substrate in a two-dimensional matrix or array. Each single-stranded polynucleotide probe can comprise at least 6, 7, 8, 9, 10, 11, 12, 13, 14, 15, 16, 17, 18, 19, 20, 25, or 30 or more contiguous nucleotides selected from the nucleotide sequences of DET1-DET85. The substrate can be any substrate to which polynucleotide probes can be attached, including but not limited to glass, nitrocellulose, silicon, and nylon. Polynucleotide probes can be bound to the substrate by either covalent bonds or by non-specific interactions, such as hydrophobic interactions. Techniques for constructing arrays and methods of using these arrays are described in EP No. 0 799 897; PCT No. WO 97/29212; PCT No. WO 97/27317; EP No. 0 785 280; PCT No. WO 97/02357; U.S. Pat. Nos. 5,593,839; 5,578,832; EP No. 0 728 520; U.S. Pat. No. 5,599,695; EP No. 0 721 016; U.S. Pat. No. 5,556,752; PCT No. WO 95/22058; and U.S. Pat. No. 5,631,734 (each of which is incorporated herein by reference for its teaching of preparation of arrays). Commercially available polynucleotide arrays, such as Affymetrix GeneChip™, can also be used. Use of the GeneChip™ to detect gene expression is described, for example, in Lockhart et al., Nature Biotechnology 14:1675 (1996); Chee et al., Science 274:610 (1996); Hacia et al., Nature Genetics 14:441, 1996; and Kozal et al., Nature Medicine 2:753, 1996.

Tissue samples can be treated to form single-stranded polynucleotides, for example by heating or by chemical denaturation, as is known in the art. The single-stranded polynucleotides in the tissue sample can then be labeled and hybridized to the polynucleotide probes on the array. Detectable labels which can be used include but are not limited to radiolabels, biotinylated labels, fluorophors, and chemiluminescent labels. Double stranded polynucleotides, comprising the labeled sample polynucleotides bound to polynucleotide probes, can be detected once the unbound portion of the sample is washed away. Detection can be visual or with computer assistance.

The present invention also provides methods of detecting and measuring a DET protein or fragment thereof. An amino acid sequence for a C21orf4 (DET1) protein is set forth herein as SEQ ID NO: 41. An amino acid sequence for a Hs. 145049 (DET2) protein is set forth as SEQ ID NO: 43. An amino acid sequence for a KIT (DET4) protein is set forth herein as SEQ ID NO: 46. An amino acid sequence for a LSM7 (DET5) protein is set forth herein SEQ ID NO: 48. An amino acid sequence for a SYNGR2 (DET6) protein is set forth herein as SEQ IN NO: 50. An amino acid sequence for a C11orf8 (DET7) protein is provided herein as SEQ ID NO: 52. An amino acid sequence for a CDH1 (DET8) protein is set forth herein as SEQ ID NO: 54. An amino acid sequence for a FAM13A1(DET9) protein is set forth herein as SEQ ID NO: 56. An amino acid sequence for IMPACT(DET10) protein is provided herein as SEQ ID NO: 58. An amino acid sequence for KIAA1128(DET11) protein is set forth herein as SEQ ID NO: 60. Therefore, the present invention provides antibodies that bind to the DET protein sequences or fragments thereof set forth herein. The antibody utilized to detect a DET polypeptide, or fragment thereof, can be linked to a detectable label either directly or indirectly through use of a secondary and/or tertiary antibody; thus, bound antibody, fragment or molecular complex can be detected directly in an ELISA or similar assay.

The sample can be on, supported by, or attached to, a substrate which facilitates detection. A substrate of the present invention can be, but is not limited to, a microscope slide, a culture dish, a culture flask, a culture plate, a culture chamber, ELISA plates, as well as any other substrate that can be used for containing or supporting biological samples for analysis according to the methods of the present invention. The substrate can be of any material suitable for the purposes of this invention, such as, for example, glass, plastic, polystyrene, mica and the like. The substrates of the present invention can be obtained from commercial sources or prepared according to standard procedures well known in the art.

Conversely, an antibody or fragment thereof, an antigenic fragment of a DET protein can be on, supported by, or attached to a substrate which facilitates detection. Such a substrate can be a mobile solid support. Thus, provided by the invention are substrates including one or more of the antibodies or antibody fragments, or antigenic fragments of a DET polypeptide.

In the methods of the present invention, once the expression levels of one or more DET nucleic acids is measured, these expression levels are compared to the expression of the nucleic acid sequence(s) in a reference cell population comprising at least one cell for which a thyroid lesion classification is known. Once this comparison is performed, a difference in expression levels, if present, is identified by one of skill in the art.

A difference or alteration in expression of any DET nucleic acid measured in the test cell population (i.e., in one or more DET nucleic acids), as compared to the expression of the same DET nucleic acid(s) in the reference cell population, indicates that the test cell population is different from the reference cell population. By "difference" or "alteration" is meant that the expression of one or more DET nucleic acid sequences is either increased or decreased as compared to the expression levels of the reference cell population. If desired, but not necessary, relative expression levels within the test and reference cell populations can be normalized by reference to the expression level of a nucleic acid sequence that does not vary according to thyroid cancer stage in the subject. The absence of a difference or alteration in expression of any DET nucleic acid measured in the test cell population (i.e., in one or more DET nucleic acids), as compared to the expression of the same DET nucleic acid(s) in the reference cell population, indicates that the test cell population is similar to the reference cell population.

The comparison of a set of expression levels of one or more DET nucleic acids in a test cell population to the expression level of the same set of one or more DET nucleic acid(s) in the reference cell population provides the expression profile for that DET for the cell population. As an example, if the reference cell population is from normal thyroid tissue, a similar DET gene expression profile in the test cell population indicates that the test cell population is also normal whereas a different profile indicates that the test cell population is not normal. By "similar" is meant that an expression pattern does not have to be exactly like the expression pattern but similar enough such that one of skill in the art would know that the expression pattern is more closely associated with one type of tissue than with another type of tissue. In another example, if the reference cell population is from malignant thyroid tissue, a similar DET gene expression profile in the test cell population indicates that the test cell population is also malignant whereas a different profile indicates that the test cell population is not malignant. Similarly, if the reference cell population is from benign thyroid tissue (e.g., a benign thyroid lesion), a similar DET gene expression profile in the test cell population indicates that the test cell population is also benign whereas a different profile indicates that the test cell population is not benign.

Upon observing a difference between the test cell population and a normal reference cell population, one of skill in the art can classify the test cell population as benign or malignant by comparing the expression pattern to known expression patterns for benign and malignant cells. This comparison can be done by comparing the expression pattern of the test cell population to the expression pattern obtained from a plurality of reference cells used as a control while measuring expression levels in the test cell population. One of skill in the art can also compare the expression pattern of the test cell population with a database of expression patterns corresponding to normal, benign and malignant cells and subcategories thereof. For example, upon observing a difference between the test cell population and a reference cell population from normal thyroid tissue, one of skill in the art can compare the expression pattern of the test cell population with a database of expression patterns corresponding to normal, benign and malignant cells. One of skill in the art would then determine which expression pattern in the database is most similar to the expression pattern obtained for the test cell population and classify the test cell population as benign or malignant, as well as classify the test cell population as a type of benign or malignant lesion. For example, if the test cell population is classified as being from a benign lesion, this population can be further classified as being from a follicular adenoma, hyperplastic nodule, papillary adenoma, thyroiditis nodue, multimodal goiter or any other type of benign thyroid lesion. If the test cell population is classified as being from a malignant lesion, this population can be further classified as being from papillary thyroid carcinoma, follicular variant of papillary thyroid carcinoma, follicular carcinoma, Hurthle cell tumor, anaplastic thyroid cancer, medullary thyroid cancer, thyroid lymphoma, poorly differentiated thyroid cancer and thyroid angiosarcoma or any other type of malignant thyroid lesion. Therefore, utilizing the methods of the present invention, one of skill in the art can diagnose a benign or malignant thyroid lesion in a subject, as well as the type of benign or malignant lesion in the subject.

Staging of Thyroid Cancer

Once a subject has been diagnosed with a malignant lesion or thyroid tumor, the stage of thyroid malignancy can also be determined by the methods of the present invention. Staging of a thyroid malignancy or tumor can be useful in prescribing treatment as well as in determining a prognosis for the subject.

Therefore, also provided by the present invention is a method of identifying the stage of a thyroid tumor in a subject comprising: a) measuring the expression of one or more nucleic acid sequences selected from the group consisting of DET1, DET2, DET3, DET4, DET6, DET7, DET8, DET9, DET10 and DET11 in a test cell population, wherein at least one cell in said test cell population is capable of expressing one or more nucleic acid sequences selected from the group consisting of DET1, DET2, DET3, DET4, DET6, DET7, DET8, DET9, DET10 and DET11; b) comparing the expression of said nucleic acid sequences to the expression of the same nucleic acid sequence(s) in a reference cell population comprising at least one cell for which a thyroid tumor stage is known; and c) identifying a difference, if present, in expression levels of one or more nucleic acid sequences selected from the group consisting of DET1, DET2, DET3, DET4, DET6, DET7, DET8, DET9, DET10 and DET11, in the test cell population and reference cell population, thereby identifying the stage of the thyroid tumor in the subject.

Also provided by the present invention is a method of identifying the stage of a thyroid tumor in a subject comprising: a) measuring the expression of one or more nucleic acid sequences selected from the group consisting of DET1, DET2, DET3, DET4, DET5 and DET6 in a test cell population, wherein at least one cell in said test cell population is capable of expressing one or more nucleic acid sequences selected from the group consisting of DET1, DET2, DET3, DET4, DET5 and DET6; b) comparing the expression of said nucleic acid sequences to the expression of the same nucleic acid sequence(s) in a reference cell population comprising at least one cell for which a thyroid tumor stage is known; and c) identifying a difference, if present, in expression levels of one or more nucleic acid sequences selected from the group consisting of DET1, DET2, DET3, DET4, DET5 and DET6, in the test cell population and reference cell population, thereby identifying the stage of the thyroid tumor in the subject.

Also provided by the present invention is a method of identifying the stage of a thyroid tumor in a subject comprising: a) measuring the expression of one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 in a test cell population, wherein at least one cell in said test cell population is capable of expressing one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85; b) comparing the expression of said nucleic acid sequences to the expression of the same nucleic acid sequence(s) in a reference cell population comprising at least one cell for which a thyroid tumor stage is known; and c) identifying a difference, if present, in expression levels of one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85, in the test cell population and reference cell population, thereby identifying the stage of the thyroid tumor in the subject.

As disclosed herein, the method for identifying the stage of a thyroid tumor in a subject comprises receiving gene expression data of one or more nucleic acid sequences selected from the group consisting of the differentially expressed thyroid genes DET1, DET2, DET3, DET4, DET5, and DET6 in a test cell population, wherein at least one cell in said test cell population is capable of expressing one or more nucleic acid sequences selected from the group consisting of DET1, DET2, DET3, DET4, DET5, and DET6; and determining the stage of the thyroid tumor, wherein the determination is made by applying a statistical classifier or predictor model to the gene expression data; and outputting the stage of the thyroid tumor based on the determination.

As disclosed herein, the method for identifying the stage of a thyroid tumor in a subject comprises receiving gene expression data of one or more nucleic acid sequences selected from the group consisting of the differentially expressed thyroid genes DET1, DET2, DET3, DET4, DET6, DET7, DET8, DET9, DET10, DET11, in a test cell population, wherein at least one cell in said test cell population is capable of expressing one or more nucleic acid sequences selected from the group consisting of DET1, DET2, DET3, DET4, DET6, DET7, DET8, DET9, DET10, DET11; and determining the stage of the thyroid tumor, wherein the determination is made by applying a statistical classifier or predictor model to the gene expression data; and outputting the stage of the thyroid tumor based on the determination.

As disclosed herein, the method for identifying the stage of a thyroid tumor in a subject comprises receiving gene expression data of one or more nucleic acid sequences selected from the group consisting of the differentially expressed thyroid genes DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 in a test cell population, wherein at least one cell in said test cell population is capable of expressing one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85; and determining the stage of the thyroid tumor, wherein the determination is made by applying a statistical classifier or predictor model to the gene expression data; and outputting the stage of the thyroid tumor based on the determination.

In the methods of the present invention, the classifier, predictor model, or diagnosis-predictor model can be a compound covariate predictor, a diagonal linear discriminant analysis, nearest-neighbor classification, or support vector machines with linear kernel.

In the methods of the present invention, the differentially expressed thyroid genes incorporated into the classifier, predictor model, or diagnosis-predictor model can be differentially expressed in malignant vs. benign thyroid tumors with a level of statistical significance signified with a P value of less than 0.05 using standard statistical analysis. More specifically, the P value can be less than 0.0001 to limit the number of false positives. In the methods of the present invention, standard statistical analysis can be an ANOVA test with Bonferroni correction, or a random-variance t test.

Also provided by the present invention is a method of determining a prognosis for subject comprising: a) measuring the expression of one or more nucleic acid sequences selected from the group consisting of DET1, DET2, DET3, DET4, DET6, DET7, DET8, DET9, DET10 and DET11 in a test cell population, wherein at least one cell in said test cell population is capable of expressing one or more nucleic acid sequences selected from the group consisting of DET1, DET2, DET3, DET4, DET6, DET7, DET8, DET9, DET10 and DET11; b) comparing the expression of said nucleic acid sequences to the expression of the same nucleic acid sequence(s) in a reference cell population comprising at least one cell for which a thyroid tumor stage is known; and c) identifying a difference, if present, in expression levels of one or more nucleic acid sequences selected from the group consisting of DET1, DET2, DET3, DET4, DET6, DET7, DET8, DET9, DET10 and DET11, in the test cell population and reference cell population, thereby determining the prognosis for the subject.

Also provided by the present invention is a method of determining the prognosis for a subject comprising: a) measuring the expression of one or more nucleic acid sequences selected from the group consisting of DET1, DET2, DET3, DET4, DET5 and DET6 in a test cell population, wherein at least one cell in said test cell population is capable of expressing one or more nucleic acid sequences selected from the group consisting of DET1, DET2, DET3, DET4, DET5 and DET6; b) comparing the expression of said nucleic acid sequences to the expression of the same nucleic acid sequence(s) in a reference cell population comprising at least one cell for which a thyroid tumor stage is known; and c) identifying a difference, if present, in expression levels of one or more nucleic acid sequences selected from the group consisting of DET1, DET2, DET3, DET4, DET5 and DET6, in the test cell population and reference cell population, thereby determining the prognosis for the subject.

Also provided by the present invention is a method of determining the prognosis for a subject comprising: a) measuring the expression of one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 in a test cell population, wherein at least one cell in said test cell population is capable of expressing one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85; b) comparing the expression of said nucleic acid sequences to the expression of the same nucleic acid sequence(s) in a reference cell population comprising at least one cell for which a thyroid tumor stage is known; and c) identifying a difference, if present, in expression levels of one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85, in the test cell population and reference cell population, thereby determining the prognosis for the subject.

As disclosed herein, the method for determining the prognosis for a subject comprises receiving gene expression data of one or more nucleic acid sequences selected from the group consisting of the differentially expressed thyroid genes DET1, DET2, DET3, DET4, DET5, and DET6 in a test cell population, wherein at least one cell in said test cell population is capable of expressing one or more nucleic acid sequences selected from the group consisting of DET1, DET2, DET3, DET4, DET5, and DET6; and determining the prognosis for a subject, wherein the determination is made by applying a statistical classifier or predictor model to the gene expression data; and outputting the prognosis for the subject based on the determination.

As disclosed herein, the method for determining the prognosis for a subject comprises receiving gene expression data of one or more nucleic acid sequences selected from the group consisting of the differentially expressed thyroid genes DET1, DET2, DET3, DET4, DET6, DET7, DET8, DET9, DET10, DET11, in a test cell population, wherein at least one cell in said test cell population is capable of expressing one or more nucleic acid sequences selected from the group consisting of DET1, DET2, DET3, DET4, DET6, DET7, DET8, DET9, DET10, DET11; and determining the prognosis for a subject, wherein the determination is made by applying a statistical classifier or predictor model to the gene expression data; and outputting the prognosis for the subject based on the determination.

As disclosed herein, the method for determining the prognosis for a subject comprises receiving gene expression data of one or more nucleic acid sequences selected from the group consisting of the differentially expressed thyroid genes DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 in a test cell population, wherein at least one cell in said test cell population is capable of expressing one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85; and determining the prognosis for a subject, wherein the determination is made by applying a statistical classifier or predictor model to the gene expression data; and outputting the prognosis for the subject based on the determination.

In the methods of the present invention, the classifier, predictor model, or diagnosis-predictor model can be a compound covariate predictor, a diagonal linear discriminant analysis, nearest-neighbor classification, or support vector machines with linear kernel.

In the methods of the present invention, the differentially expressed thyroid genes incorporated into the classifier, predictor model, or diagnosis-predictor model can be differentially expressed in malignant vs. benign thyroid tumors with a level of statistical significance signified with a P value of less than 0.05 using standard statistical analysis. More specifically, the P value can be less than 0.0001 to limit the number of false positives. In the methods of the present invention, standard statistical analysis can be an ANOVA test with Bonferroni correction, or a random-variance t test.

In staging a thyroid tumor, once the expression levels of one or more DET nucleic acids is measured, these expression levels are compared to the expression of the same nucleic acid sequence(s) in a reference cell population comprising at least one cell for which a stage of thyroid tumor is known. Once this comparison is performed, a difference in expression levels, if present, is identified by one of skill in the art.

A difference or alteration in expression of one or more DET nucleic acids in the test cell population, as compared to the reference cell population, indicates that the test cell population is at a different stage than the stage of the reference cell population. By "difference" or "alteration" is meant that the expression of one or more DET nucleic acid sequences is either increased or decreased as compared to the expression levels of the reference cell population. If desired, but not necessary, relative expression levels within the test and reference cell populations can be normalized by reference to the expression level of a nucleic acid sequence that does not vary according to thyroid cancer stage in the subject. The absence of a difference or alteration in expression of one or more DET nucleic acids in the test cell population, as compared to the expression of the same one or more DET nucleic acid(s) in the reference cell population, indicates that the test cell population is at the same stage as that of the reference cell population. As an example, if the reference cell population is from an early stage thyroid tumor, a similar DET gene expression profile in the test cell population indicates that the test cell population is also from an early stage thyroid tumor whereas a different profile indicates that the test cell population is not from an early stage thyroid tumor. By "similar" is meant that an expression pattern (expression profile) does not have to be exactly like another expression pattern but similar enough such that one of skill in the art would know that the expression pattern is more closely associated with one stage than with another stage.

In order to establish a database of stages of thyroid cancer, one skilled in the art can measure DET nucleic acid levels and/or DET polypeptide levels in numerous subjects in order to establish expression patterns that correspond to clinically defined stages such as, for example, 1) normal, 2) at risk of developing thyroid cancer, 3) pre-cancerous or 4) cancerous as well as other substages defined within each of these stages, e.g., stage I papillary, stage II papillary, stage III papillary, stage IV papillary, stage I follicular, stage II follicular, stage III follicular, stage IV follicular, stage I medullary, stage II medullary, stage III medullary, or stage IV medullary thyroid cancer. These stages are not intended to be limiting as one of skill in the art may define other stages depending on the type of sample, type of cancer, age of the subject and other factors. This database can then be used to compare an expression pattern from a test sample and make clinical decisions. Upon correlation of a DET expression pattern with a particular stage of thyroid cancer, the skilled practitioner can administer a therapy suited for the treatment of cancer. The present invention also allows the skilled artisan to correlate a DET expression pattern with a type of thyroid lesion and correlate the expression pattern with a particular stage of thyroid cancer. Thus, the present methods can comprise a step of correlating a DET expression pattern with the status of a thyroid tumor as, for example, benign or malignant or a certain stage of malignancy. The subjects of this invention undergoing anti-cancer therapy can include subjects undergoing surgery, chemotherapy, radiotherapy, immunotherapy or any combination thereof. Examples of chemotherapeutic agents include cisplatin, 5-fluorouracil and S-1. Immunotherapeutics methods include administration of interleukin-2 and interferon-$\alpha$.

In determining the prognosis for a subject, once the expression levels of one or more DET nucleic acids is measured, these expression levels are compared to the expression of the same nucleic acid sequence(s) in a reference cell population comprising at least one cell for which a prognosis is known. Once this comparison is performed, a difference in expression levels, if present, is identified by one of skill in the art. Thus, the present method can comprise a step of correlating a DET expression pattern with the prognosis of a subject having a thyroid tumor.

One skilled in the art can measure DET nucleic acid levels and/or DET polypeptide levels in order to determine a prognosis for a subject. One of skill in the art can measure DET nucleic acid levels and/or DET polypeptide levels in numerous subjects with varying prognoses in order to establish reference expression patterns that correspond to prognoses for subjects. As utilized herein, "prognosis" means a prediction of probable development and/or outcome of a disease. These reference expression patterns or a database of reference expression patterns can then be used to compare an expression pattern from a test sample and determine what the prognosis for a subject is. These expression patterns can also be used to compare an expression pattern from a test sample from a subject and determine whether or not a subject can recover from the disease. Upon correlation of a DET expression pattern with a particular prognosis, the skilled practitioner can then determine if a therapy suited for the treatment of cancer is applicable.

The present invention provides a computer system comprising a) a database including records comprising a plurality of reference DET gene expression profiles or patterns for benign, malignant and normal tissue samples and associated diagnosis and therapy data; and b) a user interface capable of receiving a selection of one or more test gene expression profiles for use in determining matches between the test expression profiles and the reference DET gene expression profiles and displaying the records associated with matching expression profiles. The database can also include DET gene expression profiles for subclasses of benign tissue samples such as follicular adenoma, hyperplastic nodule, papillary adenoma, thyroiditis nodule and multinodular goiter. The database can also include DET gene expression profiles for subclasses of malignant tissue samples such as papillary thyroid carcinoma, follicular variant of papillary thyroid carcinoma, follicular carcinoma, Hurthle cell tumor, anaplastic thyroid cancer, medullary thyroid cancer, thyroid lymphoma, poorly differentiated thyroid cancer and thyroid angiosarcoma. The database can also include DET gene expression profiles for stages of thyroid cancer as well as DET gene expression profiles that correspond to prognoses for subjects.

It will be appreciated by those skilled in the art that the DET gene expression profiles provided herein as well as the DET expression profiles identified from samples and subjects can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate a list of DET gene expression profiles comprising one or more of the DET expression profiles of the invention. Another aspect of the present invention is a computer readable medium having recorded thereon at least 2, 5, 10, 15, 20, 25, 30, 50, 100, 200, 250, 300, 400, 500, 1000, 2000, 3000, 4000 or 5000 expression profiles of the invention or expression profiles identified from subjects.

Computer readable media include magnetically readable media, optically readable media, electronically readable media and magnetic/optical media. For example, the computer readable media may be a hard disc, a floppy disc, a magnetic tape, CD-ROM, DVD, RAM, or ROM as well as other types of other media known to those skilled in the art.

Embodiments of the present invention include systems, particularly computer systems which contain the DET gene expression information described herein. As used herein, "a computer system" refers to the hardware components, software components, and data storage components used to store and/or analyze the DET gene expression profiles of the present invention or other DET gene expression profiles. The computer system preferably includes the computer readable media described above, and a processor for accessing and manipulating the DET gene expression data.

Preferably, the computer is a general purpose system that comprises a central processing unit (CPU), one or more data storage components for storing data, and one or more data retrieving devices for retrieving the data stored on the data storage components. A skilled artisan can readily appreciate that any one of the currently available computer systems are suitable.

In one particular embodiment, the computer system includes a processor connected to a bus which is connected to a main memory, preferably implemented as RAM, and one or more data storage devices, such as a hard drive and/or other computer readable media having data recorded thereon. In some embodiments, the computer system further includes one or more data retrieving devices for reading the data stored on the data storage components. The data retrieving device may represent, for example, a floppy disk drive, a compact disk drive, a magnetic tape drive, a hard disk drive, a CD-ROM drive, a DVD drive, etc. In some embodiments, the data storage component is a removable computer readable medium such as a floppy disk, a compact disk, a magnetic tape, etc. containing control logic and/or data recorded thereon. The computer system may advantageously include or be programmed by appropriate software for reading the control logic and/or the data from the data storage component once inserted in the data retrieving device. Software for accessing and processing the expression profiles of the invention (such as search tools, compare tools, modeling tools, etc.) may reside in main memory during execution.

In some embodiments, the computer system may further comprise a program for comparing expression profiles stored on a computer readable medium to another test expression profile on a computer readable medium. An "expression profile comparer" refers to one or more programs which are implemented on the computer system to compare an expression profile with other expression profiles.

Accordingly, one aspect of the present invention is a computer system comprising a processor, a data storage device having stored thereon a DET gene expression profile of the invention, a data storage device having retrievably stored thereon reference DET gene expression profiles to be compared with test or sample sequences and an expression profile comparer for conducting the comparison. The expression profile comparer may indicate a similarity between the expression profiles compared or identify a difference between the two expression profiles.

Alternatively, the computer program may be a computer program which compares a test expression profile(s) from a subject or a plurality of subjects to a reference expression profile (s) in order to determine whether the test expression profile(s) differs from or is the same as a reference expression profile.

This invention also provides for a computer program that correlates DET gene expression profiles with a type of cancer and/or a stage of cancer and/or a prognosis. The computer program can optionally include treatment options or drug indications for subjects with DET gene expression profiles associated with a type of cancer and/or stage of cancer.

Screening Methods

Further provided by the present invention is a method of identifying an agent for treating a thyroid tumor, the method comprising: a) contacting a population of thyroid tumor cells from a subject for which a tumor stage is known, wherein at least one cell in said population is capable of expressing one or more nucleic acid sequences selected from the group consisting of DET1, DET2, DET3, DET4, DET6, DET7, DET8, DET9, DET10 and DET11, with a test agent; b) measuring the expression of one or more nucleic acid sequences selected from the group consisting of DET1, DET2, DET3, DET4, DET6, DET7, DET8, DET9, DET10 and DET11 in the cell population; c) comparing the expression of the nucleic acid sequence(s) to the expression of the same nucleic acid sequence(s) in a reference cell population comprising at least one cell for which a thyroid tumor stage is known; and d) identifying a difference, if present, in expression levels of one or more nucleic acid sequences selected from the group consisting of DET1, DET2, DET3, DET4, DET6, DET7, DET8, DET9, DET10 and DET11, in the test cell population and reference cell population, such that if there is a difference corresponding to an improvement, a therapeutic agent for treating thyroid tumor has been identified.

Further provided by the present invention is a method of identifying an agent for treating a thyroid tumor, the method comprising: a) contacting a population of thyroid tumor cells from a subject for which a tumor stage is known, wherein at least one cell in said test population is capable of expressing one or more nucleic acid sequences selected from the group consisting of DET1, DET2, DET3, DET4, DET5 and DET6, with a test agent; b) measuring the expression of one or more nucleic acid sequences selected from the group consisting of DET1, DET2, DET3, DET4, DET5 and DET6 in the cell population; c) comparing the expression of the nucleic acid sequence(s) to the expression of the same nucleic acid sequence(s) in a reference cell population comprising at least one cell for which a thyroid tumor stage is known; and d) identifying a difference, if present, in expression levels of one or more nucleic acid sequences selected from the group consisting of DET1, DET2, DET3, DET4, DET5 and DET6, in the cell population and reference cell population, such that if there is a difference corresponding to an improvement, a therapeutic agent for treating thyroid tumor has been identified.

Further provided by the present invention is a method of identifying an agent for treating a thyroid tumor, the method comprising: a) contacting with a test agent a population of thyroid tumor cells from a subject for which a tumor stage is known, wherein at least one cell in said test population is capable of expressing one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85; b) measuring the expression of one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 in the cell population; c) comparing the expression of the nucleic acid sequence(s) to the expression of the same nucleic acid sequence(s) in a reference cell population comprising at least one cell for which a thyroid tumor stage is known; and d) identifying a difference, if present, in expression levels of one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85, in the cell population and reference cell population, such that if there is a difference corresponding to an improvement, a therapeutic agent for treating a thyroid tumor has been identified.

As disclosed herein, the method of identifying an agent for treating a thyroid tumor comprises receiving gene expression data after contacting with a test agent a population of thyroid tumor cells from a subject for which a tumor stage is known, wherein at least one cell in said test population is capable of expressing one or more nucleic acid sequences selected from the group consisting of differentially expressed thyroid genes DET1, DET2, DET3, DET4, DET5, and DET6; and measuring the expression of one or more nucleic acid sequences selected from the group consisting of DET1, DET2, DET3, DET4, DET5 and DET6 in the cell population; and determining the identity of the agent to treat the thyroid tumor, wherein the determination is made by applying a statistical classifier or predictor model to the gene expression data; and outputting the identity of an agent to treat the thyroid tumor based on the determination.

As disclosed herein, the method of identifying an agent for treating a thyroid tumor comprises receiving gene expression data after contacting with a test agent a population of thyroid tumor cells from a subject for which a tumor stage is known, wherein at least one cell in said test population is capable of expressing one or more nucleic acid sequences selected from the group consisting of differentially expressed thyroid genes DET1, DET2, DET3, DET4, DET6, DET7, DET8, DET9, DET10, DET11; and measuring the expression of one or more nucleic acid sequences consisting of DET1, DET2, DET3, DET4, DET6, DET7, DET8, DET9, DET10, DET11 in the cell population; and determining the identity of the agent to treat the thyroid tumor, wherein the determination is made by applying a statistical classifier or predictor model to the gene expression data; and outputting the identity of an agent to treat the thyroid tumor based on the determination.

As disclosed herein, the method of identifying an agent for treating a thyroid tumor comprises receiving gene expression data after contacting with a test agent a population of thyroid tumor cells from a subject for which a tumor stage is known, wherein at least one cell in said test population is capable of expressing one or more nucleic acid sequences selected from the group consisting of differentially expressed thyroid genes DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85; and measuring the expression of one or more nucleic acid sequences selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 in the cell population; and determining the identity of the agent to treat the thyroid tumor, wherein the determination is made by applying a statistical classifier or predictor model to the gene expression data; and outputting the identity of an agent to treat the thyroid tumor based on the determination.

In the methods of the present invention, the classifier, predictor model, or diagnosis-predictor model can be a compound covariate predictor, a diagonal linear discriminant analysis, nearest-neighbor classification, or support vector machines with linear kernel.

In the methods of the present invention, the differentially expressed thyroid genes incorporated into the classifier, predictor model, or diagnosis-predictor model can be differentially expressed in malignant vs. benign thyroid tumors with a level of statistical significance signified with a P value of less than 0.05 using standard statistical analysis. More specifically, the P value can be less than 0.0001 to limit the number of false positives. In the methods of the present invention, standard statistical analysis can be an ANOVA test with Bonferroni correction, or a random-variance t test.

The test agents used in the methods described herein can be made by methods standard in the art and include, but are not limited to, chemicals, small molecules, antisense molecules, siRNAs, drugs, antibodies, peptides and secreted proteins.

By "improvement" is meant that the treatment leads to a shift in a thyroid tumor stage to a less advanced stage. As mentioned above, the expression pattern obtained for the test cell population can be compared to expression patterns in a database before and after contacting the test cell population with a test agent to determine the stage of the test cell population before and after treatment.

The reference cell population can be from normal thyroid tissue. For example, if the cell population from the subject is from an early stage thyroid tumor, and after treatment, the expression pattern of the cell population when compared to the reference cell population from normal thyroid tissue, is similar to that of the reference cell population, the agent is effective in treating a thyroid tumor. By "similar" is meant that the expression pattern does not have to be exactly like the expression pattern from normal thyroid tissue but similar enough such that one of skill in the art would know that the treatment leads to expression patterns more closely associated with normal thyroid tissue. As an another example, if both the cell population from the subject and the reference cell population are from an early stage thyroid tumor, and after treatment, the expression pattern of the cell population is similar to the reference cell population, the agent is not effective in treating a thyroid tumor. By "similar" is meant that the expression pattern does not have to be exactly like the expression pattern from the early stage thyroid tumor cell population but similar enough such that one of skill in the art would know that the treatment does not lead to an expression pattern corresponding to a less advanced thyroid tumor stage. As another example, if both the cell population from the subject and the reference cell population are from an early stage thyroid tumor, and after treatment, the expression pattern of the cell population is different from the reference cell population, and correlates with a less advanced thyroid tumor stage, the agent is effective in treating a thyroid tumor. These examples are not intended to be limiting with regard to the types of thyroid tumor populations that can be contacted with an agent, the types of agents that can be utilized, the type of reference cell population that can be utilized or the effects observed as there are numerous variations known to one of skill in the art for performing these methods.

Also disclosed herein, the method of identifying an agent for treating a thyroid tumor by screening tumor cells for agents that preferentially decrease the expression of the nucleic acid sequences found in the malignant vs. the benign tumor cells, wherein those nucleic acid sequences are selected from the group consisting of C21orf4 (DET1) and Hs.145049(DET2) that are upregulated in malignant thyroid lesions consisting of cell populations from papillary thyroid carcinomas and follicular variant of papillary thyroid carcinomas, when compared to benign thyroid lesions consisting of cell populations from follicular adenomas and hyperplastic nodules.

Also disclosed herein, the method of identifying an agent for treating a thyroid tumor by screening tumor cells for agents that preferentially decrease the expression of the nucleic acid sequences found in the malignant vs. the benign tumor cells, wherein those nucleic acid sequences are selected from the group consisting of HMGA2 (DET12), KLK7 (DET13), MRC2 (DET14), LRRK2 (DET15), PLAG1 (DET16), CYP1B1 (DET17), DPP4 (DET18), FNDC4 (DET19), PHLDA2 (DET20), CCNA1 (DET21), CDH3 (DET22), CEACAM6 (DET23), QSCN6 (DET24), COL7A1 (DET25), MGC9712 (DET26), IL1RAP (DET27), LAMB3 (DET28), PRSS3 (DET29), LRP4 (DET30), SPOCK1 (DET31), PDE5A (DET32), FLJ37078 (DET33), FBN3 (DET34), DIRAS3 (DET35), PRSS1 (DET36), CAMK2N1 (DET37), SNIP (DET38), KCNJ2 (DET39), SFN (DET40), GALNT7 (DET41), TGFA (DET42), BAIAP3 (DET43), and KCNK15 (DET44), that are upregulated in malignant thyroid lesions consisting of cell populations from papillary thyroid carcinomas, follicular variant of papillary thyroid carcinomas, follicular carcinomas, and Hurthle cell carcinomas, when compared to benign thyroid lesions consisting of cell populations from adenomatoid nodules, follicular adenomas, Hurthle cell adenomas, and lymphocytic thyroid nodules.

The present invention also provides a method for identifying an agent for treating a thyroid tumor, the method comprising: a) contacting with a test agent a population of thyroid tumor cells from a subject for which a tumor classification is known, wherein at least one cell in said test population is capable of expressing one or more nucleic acid sequences selected from the group consisting of C21orf4 (DET1), Hs.145049(DET2), HMGA2 (DET12), KLK7 (DET13), MRC2 (DET14), LRRK2 (DET15), PLAG1 (DET16), CYP1B1 (DET17), DPP4 (DET18), FNDC4 (DET19), PHLDA2 (DET20), CCNA1 (DET21), CDH3 (DET22), CEACAM6 (DET23), QSCN6 (DET24), COL7A1 (DET25), MGC9712 (DET26), IL1RAP (DET27), LAMB3 (DET28), PRSS3 (DET29), LRP4 (DET30), SPOCK1 (DET31), PDE5A (DET32), FLJ37078 (DET33), FBN3 (DET34), DIRAS3 (DET35), PRSS1 (DET36), CAMK2N1 (DET37), SNIP (DET38), KCNJ2 (DET39), SFN (DET40), GALNT7 (DET41), TGFA (DET42), BAIAP3 (DET43), and KCNK15 (DET44); b) measuring the expression of one or more nucleic acid sequences selected from the group consisting of C21orf4 (DET1), Hs.145049(DET2), HMGA2 (DET12), KLK7 (DET13), MRC2 (DET14), LRRK2 (DET15), PLAG1 (DET16), CYP1B1 (DET17), DPP4 (DET18), FNDC4 (DET19), PHLDA2 (DET20), CCNA1 (DET21), CDH3 (DET22), CEACAM6 (DET23), QSCN6 (DET24), COL7A1 (DET25), MGC9712 (DET26), IL1RAP (DET27), LAMB3 (DET28), PRSS3 (DET29), LRP4 (DET30), SPOCK1 (DET31), PDE5A (DET32), FLJ37078 (DET33), FBN3 (DET34), DIRAS3 (DET35), PRSS1 (DET36), CAMK2N1 (DET37), SNIP (DET38), KCNJ2 (DET39), SFN (DET40), GALNT7 (DET41), TGFA (DET42), BAIAP3 (DET43), and KCNK15 (DET44) in the cell population; c) comparing the expression of the nucleic acid sequence(s) to the expression of the same nucleic acid sequence(s) in a reference cell population comprising at least one cell for which a thyroid tumor classification is known; and d) identifying a difference, if present, in expression levels of one or more nucleic acid sequences selected from the group consisting of C21orf4 (DET1), Hs.145049(DET2), HMGA2 (DET12), KLK7 (DET13), MRC2 (DET14), LRRK2 (DET15), PLAG1 (DET16), CYP1B1 (DET17), DPP4 (DET18), FNDC4 (DET19), PHLDA2 (DET20), CCNA1 (DET21), CDH3 (DET22), CEACAM6 (DET23), QSCN6 (DET24), COL7A1 (DET25), MGC9712 (DET26), IL1RAP (DET27), LAMB3 (DET28), PRSS3 (DET29), LRP4 (DET30), SPOCK1 (DET31), PDE5A (DET32), FLJ37078 (DET33), FBN3 (DET34), DIRAS3 (DET35), PRSS1 (DET36), CAMK2N1 (DET37), SNIP (DET38), KCNJ2 (DET39), SFN (DET40), GALNT7 (DET41), TGFA (DET42), BAIAP3 (DET43), and KCNK15 (DET44) in the cell population and reference cell population, such that if there is a downregulation corresponding to an improvement, then a therapeutic agent for treating a thyroid tumor has been identified. For example, if any one of these DET genes, DET 1, DET2, and DET12-44, are used alone, it has been shown that they were all significantly differentially overexpressed in malignant vs. benign tumor types. In the methods of the invention the malignant cell populations can be from papillary thyroid carcinomas, follicular variant of papillary thyroid carcinomas, follicular carcinomas, and Hurthle cell carcinomas. In the methods of the invention the benign cell populations can be from follicular adenomas, hyperplastic nodules, adenomatoid nodules, Hurthle cell adenomas, and lymphocytic thyroid nodules.

Also disclosed herein, the method of identifying an agent for treating a thyroid tumor by screening tumor cells for agents that preferentially increase the expression of the nucleic acid sequences found in the malignant vs. the benign tumor cells, wherein those nucleic acid sequences are selected from the group consisting of KIT(DET4), LSM7 (DET5), C11orf8(DET7), FAM13A1(DET9), IMPACT (DET10), KIAA1128(DET11), and CDH1(DET8), that are downregulated in malignant thyroid lesions consisting of cell populations from papillary thyroid carcinomas and follicular variant of papillary thyroid carcinomas, when compared to benign thyroid lesions consisting of cell populations from follicular adenomas and hyperplastic nodules.

Also disclosed herein, the method of identifying an agent for treating a thyroid tumor by screening tumor cells for agents that preferentially increase the expression of the nucleic acid sequences found in the malignant vs. the benign tumor cells, wherein those nucleic acid sequences are selected from the group consisting of KIT(DET4), RAG2 (DET45), CLYBL (DET46), NEB (DET47), TNFRSF11B (DET48), GNAI1 (DET49), AGTR1 (DET50), HLF (DET51), SLC26A4 (DET52), MT1A (DET53), FABP4 (DET54), LRP1B (DET55), SLC4A4 (DET56), LOC646278 (DET57), MAN1C1 (DET58), KCNIP3 (DET59), DNAJB9 (DET60), UBR1 (DET61), HSD17B6 (DET62), SLC33A1 (DET63), CDH16 (DET64), TBC1D1 (DET65), SLC26A7 (DET66), C11orf74 (DET67), PLA2R1 (DET68), PTTG3 (DET69), EFEMP1 (DET70), ZMAT4 (DET71), STEAP3 (DET72), DIO1 (DET73), TPO (DET74), PTTG1 (DET75), LGI3 (DET76), TMEM38B (DET77), SLITRK4 (DET78), VBP1 (DET79), COL9A3 (DET80), IRS1 (DET81), STARD13 (DET82), LOC654085 (DET83), RPS3A (DET84), and SPARCL1 (DET85), that are downregulated in malignant thyroid lesions consisting of cell populations from papillary thyroid carcinomas and follicular variant of papillary thyroid carcinomas, follicular variant of papillary thyroid carcinomas, follicular carcinomas, and Hurthle cell carcinomas, when compared to benign thyroid lesions consisting of cell populations from adenomatoid nodules, follicular adenomas, Hurthle cell adenomas, and lymphocytic thyroid nodules.

The present invention also provides a method for identifying an agent for treating a thyroid tumor, the method comprising: a) contacting with a test agent a population of thyroid tumor cells from a subject for which a tumor classification is known, wherein at least one cell in said test population is capable of expressing one or more nucleic acid sequences selected from the group consisting of KIT(DET4), LSM7 (DET5), C11orf8(DET7), FAM13A1(DET9), IMPACT (DET10), KIAA1128(DET11), CDH1(DET8), RAG2 (DET45), CLYBL (DET46), NEB (DET47), TNFRSF11B (DET48), GNAI1 (DET49), AGTR1 (DET50), HLF (DET51), SLC26A4 (DET52), MT1A (DET53), FABP4 (DET54), LRP1B (DET55), SLC4A4 (DET56), LOC646278 (DET57), MAN1C1 (DET58), KCNIP3 (DET59), DNAJB9 (DET60), UBR1 (DET61), HSD17B6 (DET62), SLC33A1 (DET63), CDH16 (DET64), TBC1D1 (DET65), SLC26A7 (DET66), C11orf74 (DET67), PLA2R1 (DET68), PTTG3 (DET69), EFEMP1 (DET70), ZMAT4 (DET71), STEAP3 (DET72), DIO1 (DET73), TPO (DET74), PTTG1 (DET75), LGI3 (DET76), TMEM38B (DET77), SLITRK4 (DET78), VBP1 (DET79), COL9A3 (DET80), IRS1 (DET81), STARD13 (DET82), LOC654085 (DET83), RPS3A (DET84), and SPARCL1 (DET85); b) measuring the expression of one or more nucleic acid sequences selected from the group consisting of KIT(DET4), LSM7(DET5), C11orf8 (DET7), FAM13A1(DET9), IMPACT(DET10), KIAA1128 (DET11), CDH1(DET8), RAG2 (DET45), CLYBL (DET46), NEB (DET47), TNFRSF11B (DET48), GNAI1 (DET49), AGTR1 (DET50), HLF (DET51), SLC26A4 (DET52), MT1A (DET53), FABP4 (DET54), LRP1B (DET55), SLC4A4 (DET56), LOC646278 (DET57), MAN1C1 (DET58), KCNIP3 (DET59), DNAJB9 (DET60), UBR1 (DET61), HSD17B6 (DET62), SLC33A1 (DET63), CDH16 (DET64), TBC1D1 (DET65), SLC26A7 (DET66), C11orf74 (DET67), PLA2R1 (DET68), PTTG3 (DET69), EFEMP1 (DET70), ZMAT4 (DET71), STEAP3 (DET72), DIO1 (DET73), TPO (DET74), PTTG1 (DET75), LGI3 (DET76), TMEM38B (DET77), SLITRK4 (DET78), VBP1 (DET79), COL9A3 (DET80), IRS1 (DET81), STARD13 (DET82), LOC654085 (DET83), RPS3A (DET84), and SPARCL1 (DET85) in the cell population; c) comparing the expression of the nucleic acid sequence(s) to the expression of the same nucleic acid sequence(s) in a reference cell population comprising at least one cell for which a thyroid tumor classification is known; and d) identifying a difference, if present, in expression levels of one or more nucleic acid sequences selected from the group consisting of KIT(DET4), LSM7(DET5), C11orf8(DET7), FAM13A1(DET9), IMPACT(DET10), KIAA1128(DET11), CDH1(DET8), RAG2 (DET45), CLYBL (DET46), NEB (DET47), TNFRSF11B (DET48), GNAI1 (DET49), AGTR1 (DET50), HLF (DET51), SLC26A4 (DET52), MT1A (DET53), FABP4 (DET54), LRP1B (DET55), SLC4A4 (DET56), LOC646278 (DET57), MAN1C1 (DET58), KCNIP3 (DET59), DNAJB9 (DET60), UBR1 (DET61), HSD17B6 (DET62), SLC33A1 (DET63), CDH16 (DET64), TBC1D1 (DET65), SLC26A7 (DET66), C11orf74 (DET67), PLA2R1 (DET68), PTTG3 (DET69), EFEMP1 (DET70), ZMAT4 (DET71), STEAP3 (DET72), DIO1 (DET73), TPO (DET74), PTTG1 (DET75), LGI3 (DET76), TMEM38B (DET77), SLITRK4 (DET78), VBP1 (DET79), COL9A3 (DET80), IRS1 (DET81), STARD13 (DET82), LOC654085 (DET83), RPS3A (DET84), and SPARCL1 (DET85) in the cell population and reference cell population, such that if there is an upregulation corresponding to an improvement, then a therapeutic agent for treating a thyroid tumor has been identified. For example, if any one of these DET genes, DET4, DET5, DET7-11, and DET45-85, are used alone, it has been shown that they were all significantly differentially underexpressed in malignant vs. benign tumor types. In the methods of the invention the malignant cell populations can be from papillary thyroid carcinomas, follicular variant of papillary thyroid carcinomas, follicular carcinomas, and Hurthle cell carcinomas. In the methods of the invention the benign cell populations can be from follicular adenomas, hyperplastic nodules, adenomatoid nodules, Hurthle cell adenomas, and lymphocytic thyroid nodules.

Treatment Methods

Also provided by the present invention is a method of treating malignant thyroid lesions or thyroid cancer in a subject suffering from or at risk of developing thyroid cancer comprising administering to the subject an agent that modulates the expression of one or more DET sequences. By "at risk for developing" is meant that the subject's prognosis is less favorable and that the subject has an increased likelihood of developing thyroid cancer. Administration of the agent can be prophylactic or therapeutic.

By "modulation" is meant that the expression of one or more DET sequences can be increased or decreased.

For example, KIT(DET4), LSM7(DET5), C11orf8 (DET7), FAM13A1(DET9), IMPACT(DET10), KIAA1128

(DET11), CDH1(DET8), RAG2 (DET45), CLYBL (DET46), NEB (DET47), TNFRSF11B (DET48), GNAI1 (DET49), AGTR1 (DET50), HLF (DET51), SLC26A4 (DET52), MT1A (DET53), FABP4 (DET54), LRP1B (DET55), SLC4A4 (DET56), LOC646278 (DET57), MAN1C1 (DET58), KCNIP3 (DET59), DNAJB9 (DET60), UBR1 (DET61), HSD17B6 (DET62), SLC33A1 (DET63), CDH16 (DET64), TBC1D1 (DET65), SLC26A7 (DET66), C11orf74 (DET67), PLA2R1 (DET68), PTTG3 (DET69), EFEMP1 (DET70), ZMAT4 (DET71), STEAP3 (DET72), DIO1 (DET73), TPO (DET74), PTTG1 (DET75), LGI3 (DET76), TMEM38B (DET77), SLITRK4 (DET78), VBP1 (DET79), COL9A3 (DET80), IRS1 (DET81), STARD13 (DET82), LOC654085 (DET83), RPS3A (DET84), SPARCL1 (DET85) were all downregulated or underexpressed in malignant thyroid lesions as compared to benign thyroid tissue. Therefore, a subject can be treated with an effective amount of an agent that increases the amount of the downregulated or underexpressed nucleic acids in the subject. Administration can be systemic or local, e.g. in the immediate vicinity of the subject's cancerous cells. This agent can be for example, the protein product of a downregulated or underexpressed DET gene or a biologically active fragment thereof, a nucleic acid encoding a downregulated or underexpressed DET gene and having expression control sequences permitting expression in the thyroid cancer cells or an agent which increases the endogenous level of expression of the gene.

With regard to genes that are upregulated or overexpressed in malignant as compared to benign thyroid tissue, C21orf4 (DET1), Hs.145049(DET2), HMGA2 (DET12), KLK7 (DET13), MRC2 (DET14), LRRK2 (DET15), PLAG1 (DET16), CYP1B1 (DET17), DPP4 (DET18), FNDC4 (DET19), PHLDA2 (DET20), CCNA1 (DET21), CDH3 (DET22), CEACAM6 (DET23), QSCN6 (DET24), COL7A1 (DET25), MGC9712 (DET26), IL1RAP (DET27), LAMB3 (DET28), PRSS3 (DET29), LRP4 (DET30), SPOCK1 (DET31), PDE5A (DET32), FLJ37078 (DET33), FBN3 (DET34), DIRAS3 (DET35), PRSS1 (DET36), CAMK2N1 (DET37), SNIP (DET38), KCNJ2 (DET39), SFN (DET40), GALNT7 (DET41), TGFA (DET42), BAIAP3 (DET43), and KCNK15 (DET44) were upregulated or overexpressed in malignant thyroid lesions as compared to benign thyroid tissue. Therefore, a subject can be treated with an effective amount of an agent that decreases the amount of the upregulated or overexpressed nucleic acids in the subject. Administration can be systemic or local, e.g. in the immediate vicinity of the subject's cancerous cells. The agent can be, for example, a nucleic acid that inhibits or antagonizes the expression of the overexpressed DET gene, such as an antisense nucleic acid or an siRNA. The agent can also be an antibody that binds to a DET protein that is overexpressed.

In the treatment methods of the present invention, the subject can be treated with one or more agents which decrease the expression of overexpressed DET sequences alone or in combination with one or more agents which increase the expression of DET sequences that are downregulated or underexpressed in thyroid cancer. The subject can also be treated with one or more agents which increase the expression of DET sequences that are downregulated or underexpressed in thyroid cancer alone, or in combination with one or more agents which decrease the expression of overexpressed DET sequences.

These treatment methods can be combined with other anticancer treatments such as surgery, chemotherapy, radiotherapy, immunotherapy or any combination thereof. Immunotherapeutics methods include administration of interleukin-2 and interferon-α.

The following are lists of anti-cancer (anti-neoplastic) drugs that can be used in conjunction with the presently disclosed methods. Antineoplastic: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil (e.g., 5-fluorouracil); Fluorocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-neoplastic compounds include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; atrsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocannycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance genie inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfmosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Identification of Differentially Expressed Thyroid Genes

The present invention also provides a method of identifying differentially expressed genes and/or expression patterns for such genes in other types of benign and malignant lesions. As set forth in the Examples, one of skill in the art can utilize gene expression profiling and supervised machine learning algorithms to construct a molecular classification scheme for other types of thyroid tumors. These include any type of benign lesion such as papillary adenoma, multinodular goiter or thyroiditis nodule, and any type of malignant lesion, such as papillary thyroid carcinoma, follicular carcinoma, Hurthle cell tumor, anaplastic thyroid cancer, medullary thyroid cancer, thyroid lymphoma, poorly differentiated thyroid cancer and thyroid angiosarcoma. Those genes and expression patterns identified via these methods can be utilized in the methods of the present invention to diagnose, stage and treat cancer.

Kits

The present invention also provides a kit comprising one or more reagents for detecting one or more nucleic acid sequences selected from the group consisting of DET1-DET85. In various embodiments the expression of one or more of the sequences represented by DET1-DET85 are measured. The kit can identify the DET nucleic acids by having homologous nucleic acid sequences, such as oligonucleotide sequences, complimentary to a portion of the recited nucleic acids, or antibodies to proteins encoded by the DET nucleic acids. The kit can also include amplification primers for performing RT-PCR, such as those set forth in Table 4 and probes, such as those set forth in Table 4, that can be fluorescently labeled for detecting amplification products in, for example, a Taqman assay. The kits of the present invention can optionally include buffers, enzymes, detectable labels and other reagents for the detecting expression of DET sequences described herein.

For example, a kit comprising one or more reagents for detecting the expression of one or more nucleic acid(s) selected from the group consisting of DET1, DET2, DET3, DET4, DET5, and DET6. The kit can contain amplification primers for DET1, DET2, DET3, DET4, DET5 and DET6; and probes for detecting DET1, DET2, DET3, DET4, DET5 and DET6 amplification products. The kit can also contain an antibody or antibodies that detect one or more of the DET proteins encoded by one or more of the nucleic acid sequences consisting of DET1, DET2, DET3, DET4, DET5 and DET6.

A further example is a kit comprising one or more reagents for detecting the expression of one or more nucleic acid(s) selected from the group consisting of DET1, DET2, DET3, DET4, DET6, DET7, DET8, DET9, DET10 and DET11. The kit can contain amplification primers for DET1, DET2, DET3, DET4, DET6, DET7, DET8, DET9, DET10 and DET11; and probes for detecting DET1, DET2, DET3, DET4, DET6, DET7, DET8, DET9, DET10 and DET11 amplification products. The kit can also contain an antibody or antibodies that detect one or more of the DET proteins encoded by one or more of the nucleic acid sequences consisting of DET1, DET2, DET3, DET4, DET6, DET7, DET8, DET9, DET10 and DET11.

A further example is a kit comprising one or more reagents for detecting the expression of one or more nucleic acid(s) selected from the group consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85. The kit can contain amplification primers for DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85; and probes for detecting DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85 amplification products. The kit can also contain an antibody or antibodies that detect one or more of the DET proteins encoded by one or more of the nucleic acid sequences consisting of DET1, DET2, DET3, DET4, DET5, DET6, DET7, DET8, DET9, DET10, DET11, DET12, DET13, DET14, DET15, DET16, DET17, DET18, DET19, DET20, DET21, DET22, DET23, DET24, DET25, DET26, DET27, DET28, DET29, DET30, DET31, DET32, DET33, DET34, DET35, DET36, DET37, DET38, DET39, DET40, DET41, DET42, DET43, DET44, DET45, DET46, DET47, DET48, DET49, DET50, DET51, DET52, DET53, DET54, DET55, DET56, DET57, DET58, DET59, DET60, DET61, DET62, DET63, DET64, DET65, DET66, DET67, DET68, DET69, DET70, DET71, DET72, DET73, DET74, DET75, DET76, DET77, DET78, DET79, DET80, DET81, DET82, DET83, DET84, and DET85.

The following examples are put forth so as to provide those of ordinary skill in the art with a complete disclosure and description of how the antibodies, polypeptides, nucleic acids, compositions, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for.

EXAMPLES

DNA microarrays allow quick and complete evaluation of a cell's transcriptional activity. Expression genomics is very powerful in that it can generate expression data for a large number of genes simultaneously across multiple samples. In cancer research, an intriguing application of expression arrays includes assessing the molecular components of the neoplastic process and in cancer classification (1). Classification of human cancers into distinct groups based on their molecular profile rather than their histological appearance can be more relevant to specific cancer diagnoses and cancer treatment regimes. Several attempts to formulate a consensus about classification and treatment of thyroid carcinoma based on standard histopathologic analysis have resulted in published guidelines for diagnosis and initial disease management (2). In the past few decades no improvement has been made in the differential diagnosis of thyroid tumors by fine needle aspiration biopsy (FNA), specifically suspicious or indeterminate thyroid lesions, suggesting that a new approach to this should be explored.

There is a compelling need to develop more accurate initial diagnostic tests for evaluating a thyroid nodule. Recent studies suggest that gene expression data from cDNA microarray analysis holds promise for improving tumor classification and for predicting response to therapy among cancer patients (17) (18) (19). No clear consensus exists regarding which computational tool is optimal for the analysis of large gene expression profiling datasets, especially when they are used to predict outcome (20).

This invention describes the use of gene expression profiling and supervised machine learning algorithms to construct a molecular classification scheme for thyroid tumors (22). The gene expression signatures provided herein include new tumor related genes whose encoded proteins can be useful for improving the diagnosis of thyroid tumors.

Example 1

DET1-DET11

In this study a gene expression approach was developed to diagnose benign vs malignant thyroid lesions in 73 patients with thyroid tumors. A 10 gene and 6 gene model were developed to be able to differentiate benign vs. malignant thyroid tumors. These results provide a molecular classification system for thyroid tumors and this in turn provides a more accurate diagnostic tool for the clinician managing patients with suspicious thyroid lesions.

Tissue Samples

Thyroid tissues collected under John Hopkins University Hospital Institutional Review Board-approved protocols were snap-frozen in liquid nitrogen and stored at −80° C. until use. The specimens were chosen based on their tumor type: papillary thyroid carcinoma (PTC n=17), follicular variant of PTC (FVPTC n=15), follicular adenoma (FA n=16) and hyperplastic nodule (HN n=15). All diagnoses were made by the Surgical Pathology Department at Johns Hopkins.

Tissue Processing and Isolation of RNA

Frozen sections of 100-300 mg of tissue were collected in test tubes containing 1 ml of Trizol. Samples were transferred to FastRNA tubes containing mini beads and homogenized in a FastPrep beater (Bio101Savant, Carlsbad, Calif.) for 1.5 min at speed 6. The lysate was transferred to a new tube and total RNA was extracted according to the Trizol protocol (Molecular Research Center, Inc. Cincinnati, Ohio). Approximately 12 ug of total RNA was obtained from each tumor sample. The total RNA was then subjected to two rounds of amplification following the modified Eberwine method (23) (24) resulting in approximately 42 µg of messenger RNA (mRNA). The quality of the extracted RNA was tested by spectrophotometry and by evaluations on minichips (BioAnalyzer, Agilent Tecnologies, Palo Alto, Calif.).

Microarray Analysis

Hybridization was performed on 10 k human cDNA microarrays, Hs-UniGem2, produced by the NCI/NIH (ATC, Gaithersburg, Md.). Comparisons were made for each tumor with the same control which consisted of amplified RNA extracted from normal thyroid tissue and provided by Ambion Inc (Austin, Tex.). Fluorescent marker dyes (Cy5 and Cy3) were used to label the test and control samples, respectively. The respective dyes and samples were also switched in order to test for any labeling bias. The mixture of the two populations of RNA species was then hybridized to the same microarray and incubated for 16 hr at 42° C. cDNA microarrays were then washed and scanned using the GenePix® 4000B (Axon Instruments Inc., CA) and images were analyzed with GenePix software version 3.0. For each sample a file containing the image of the array and an Excel file containing the expression ratio values for each gene was uploaded onto the MadbArray web-site (National Center for Biotechnology Information/NIH) http://nciarray.nci.nih.gov for further analysis. To accurately compare measurements from different experiments, the data were normalized and the ratio (Signal Cy5/Signal Cy3) was calculated so that the median (Ratio) was 1.0.

Immunohistochemistry

Figure 6:
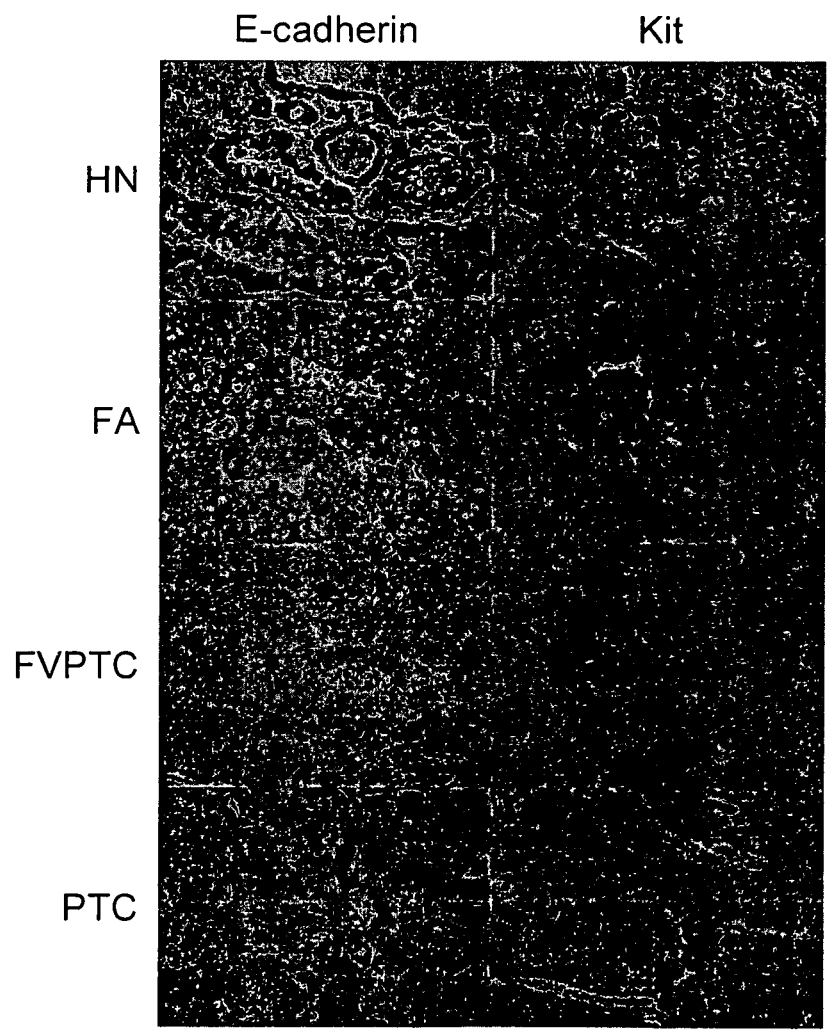
FIG. 6 shows immunohistochemical results for expression of KIT and CDH1 in malignant and benign thyroid lesions. These results correlate with the expression data obtained via microarray and RT-PCR.

Immunohistochemistry studies utilizing antibodies to two gene products in the predictor models have also been performed and these data correlate with the expression data. Taqman analysis was performed for CHD1 and KIT. Both KIT and CDH1 expression decreased in malignancy, which correlates with the microarray data. As shown in FIG. 6, immunohistochemical results show that both KIT and CDH1 expression decrease in malignancy which correlates with the expression results obtained via microarray and Taqman analysis.

Statistical Analysis

Data from the 73 thyroid tumors were used to build a benign (FA and HN) vs. malignant (PTC and FVPTC) expression ratio-based model, capable of predicting the diagnosis (benign vs malignant) of each sample. After normalization, a file containing the gene expression ratio values from all 73 samples was imported into a statistical analysis software package (Partek Inc., MO). Samples were divided in two sets: one set (63 samples) was used to train the diagnosis predictor model and a second set (10) was used as a validation set to test the model. These 10 samples were not previously used to do any other analysis. As a first step, the data from the 63 samples were subjected to Principal Component Analysis (PCA) to perform an exploratory analysis and to view the overall trend of the data. PCA is an exploratory technique that describes the structure of high dimensional data by reducing its dimensionality. It is a linear transformation that converts n original variables (gene expression ratio values) into n new variables or principal components (PC) which have three important properties: they 1) are ordered by the amount of variance explained; 2) are uncorrelated and; 3) they explain all variation in the data. The new observations (each array) are represented by points in a three dimensional space. The distance between any pair of points is related to the similarity between the two observations in high dimensional space. Observations that are near each other are similar for a large number of variables and conversely, the ones that are far apart are different for a large number of variables.

An Anova test with Bonferroni correction was then used to identify genes that were statistically different between the two groups. The resulting significant genes were used to build a diagnosis-predictor model. Variable (gene) selection analysis with cross-validation was performed different times, each time testing a different number of gene combinations. For cross-validation the "leave-one-out" method was used to estimate the accuracy of the output class prediction rule: the whole dataset was divided into different parts and each part was individually removed from the data set. The remaining data set was used to train a class prediction rule; and the resulting rule was applied to predict the class of the "held-out" sample.

Figure 2:
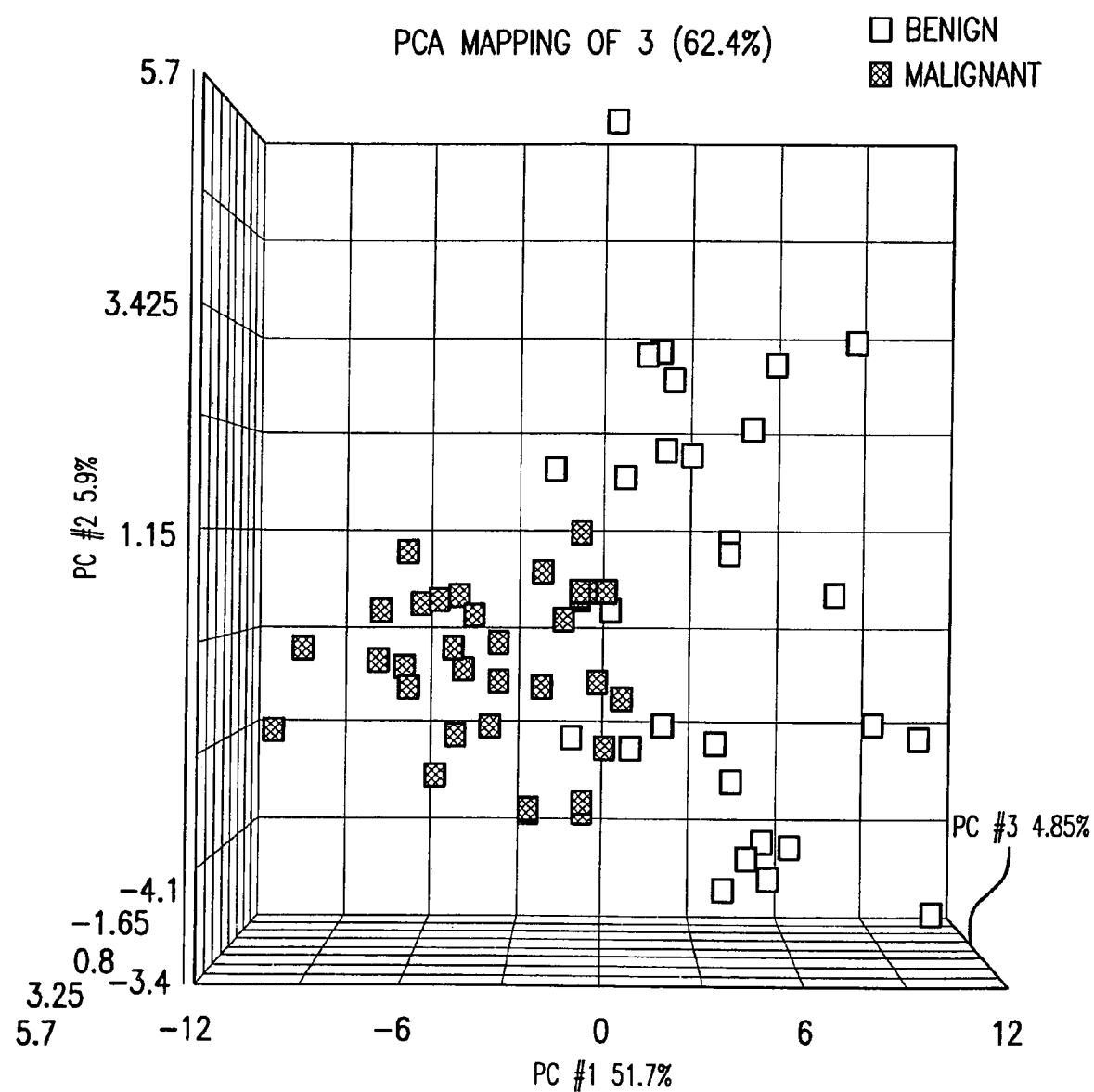
FIG. 2 shows PCA organization in a three-dimensional space of all samples divided into two groups: benign (HN-FA) and malignant (FVPTC-PTC). Each dot represents how that sample is localized in space on the basis of its gene expression profile. The distance between any pair of points is related to the similarity between the two observations in high dimensional space.

Anova test with Bonferroni correction was used on 9100 genes to identify ones that were statistically different among the 4 groups. PCA analysis of the 63 samples (FIG. 1) using the statistically significant genes showed a clear organization of the samples based on diagnosis. The same analysis (Anova test with Bonferroni correction) was performed on the dataset organized, this time, in benign (HN-FA) and malignant (PTC-FVPTC). For this analysis, 47 genes were found to be significantly different between the benign and the malignant group (Table 1). PCA analysis also separated the data clearly into two groups (FIG. 2).

For the purpose of this invention, attention was focused on the analysis of the dataset separating benign from malignant. These 47 genes were used to build a diagnostic predictor model. Variable (gene) selection analysis with cross validation was performed with a different number of gene combinations. After cross-validation the model was 87.1% accurate in predicting benign versus malignant with an error rate of 12.9% (Table 2). This suggested that it was possible to use the data to create a diagnostic predictor model.

The most accurate results were obtained with a combination of 6 to 10 genes. This combination of genes constituted a predictor model and a validation set of 10 additional thyroid samples was used to confirm the accuracy of this model (Table 3). The pathologic diagnosis for each sample was kept blinded to researchers at the time of the analysis. When the blind was broken, it was found that 9 of the samples were diagnosed in concordance with the pathologic diagnosis by our model. One sample that was originally diagnosed as a benign tumor by standard histologic criteria, was diagnosed as malignant by our model. This sample was re-reviewed by the Pathology Department at The Johns Hopkins Hospital and was subsequently found to be a neoplasm of uncertain malignant potential. The diagnosis was changed by pathology after review for clinical reasons, not because of the gene profiling. What is so extraordinary about this is that this was not discovered until the genotyping suggested that the lesion might be malignant and the pathology report examined a second time. By that time the report had been amended and it suggested that the tumor had undetermined malignant potential. Regarding the other tumors, all were examined a second time before array analysis to be certain that the tissue was representative and consistent with the pathology report. Therefore, this model was correct in assigning the diagnosis in all 10 cases.

Figure 3A:
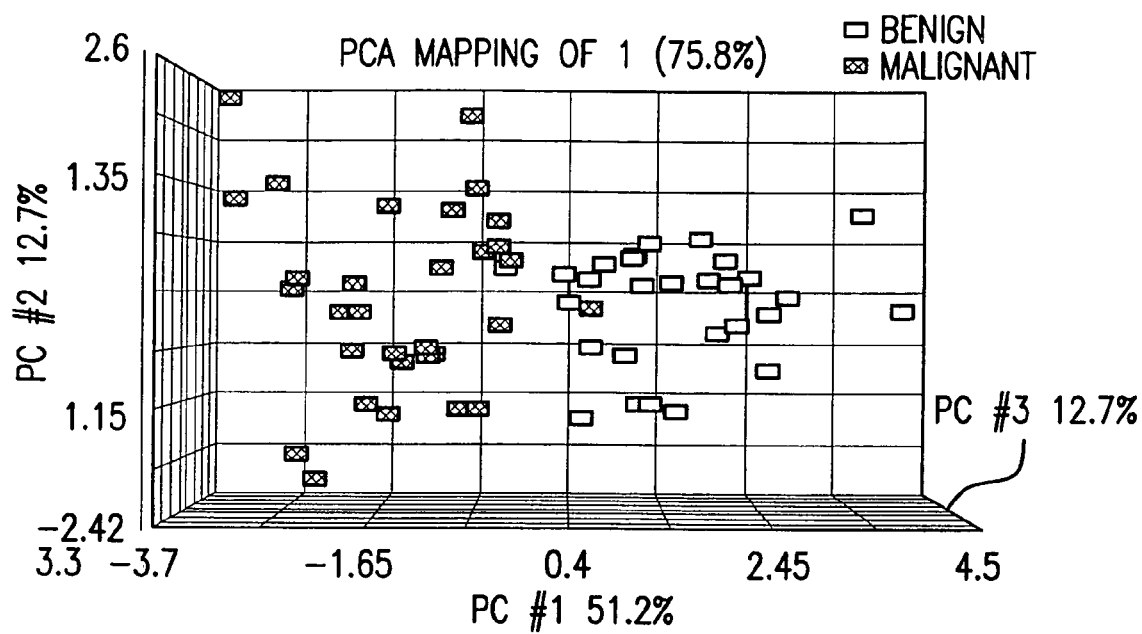
FIG. 3 shows PCA organization in a three-dimensional space of all samples with (A) and without the unknowns (B) based on the gene expressions values of the six most informative genes. It is clear there is a separation of the two groups and that it is possible to predict visually the diagnosis of each unknown. The pathological diagnoses of the unknowns are marked respectively with a+ and a* for the benign and the malignant tumor. The red+ sign indicates an unknown sample for which pathological diagnosis and predicted diagnosis were discordant. Based on the present six gene diagnostic predictor model, this lesion was placed in the malignant group. Upon re-review by the pathologist, this sample was reclassified from benign to a neoplasm of uncertain malignant potential.
Figure 3B:
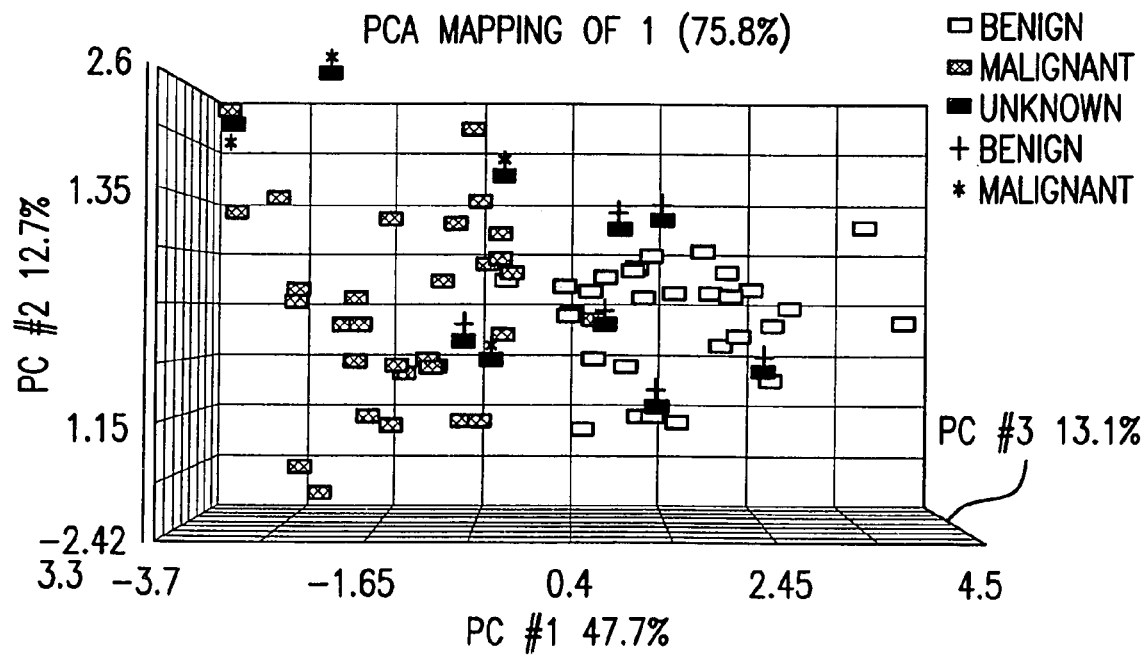

PCA analysis using only the six most informative genes was conducted on all the samples with and without the 10 unknown samples (FIG. 3A-B). It is clear from the PCA organization that the six genes strongly distinguish benign from malignant. In addition, these same genes can be used for diagnosis with respect to the four subcategories of thyroid lesion. Between the two-predictor models 11 genes are informative.

The identification of markers that can determine a specific type of tumor, predict patient outcome or the tumor response to specific therapies is currently a major focus of cancer research. This invention provides the use of gene expression profiling to build a predictor model able to distinguish a benign thyroid tumor from a malignant one. Such a model, when applied to FNA cytology, could greatly impact the clinical management of patients with suspicious thyroid lesions. To build the predictor model four types of thyroid lesions, papillary thyroid carcinoma (PTC), follicular variant of papillary thyroid carcinoma (FVPTC), follicular adenoma (FA) and hyperplastic nodules (HN) were used. Taken together, these represent the majority of thyroid lesions that often present as "suspicious". The choice of the appropriate control for comparative array experiments is often the subject of much discussion. In this case, in order to construct a predictive diagnostic algorithm based on a training set of samples, it was necessary to have a "common" reference standard to which all individual samples are compared. In this way, differences between each, and in fact all, samples could be analyzed. Had each tumor been compared to the adjacent normal thyroid tissue from the same patient, it would only be possible to comment on gene changes within each patient. A source of RNA from normal thyroid tissue was chosen since the source was replenishable and could be used for all of our future experiments once the diagnostic predictor algorithm was validated.

The mRNA extracted from each sample was amplified. It was found that the quality of the arrays and the data derived from them is superior when mRNA has been amplified from total RNA. Of note, all samples and all reference controls were amplified in the same fashion. Analysis of the overall gene expression profiles revealed that the benign lesions (FA, HN) could be distinguished from the malignant lesions (PTC, FVPTC). Furthermore, although not statistically significant, the 4 tumor sub-types appeared to have different gene profiles. The use of a powerful statistical analysis program (Partek) helped discover a group of 11 genes that were informative enough to create a predictor model. Two combinations were created out of these 11 genes, a combination of six genes and a combination of 10 genes. PCA analysis of the six most informative genes resulted in a nearly perfect distinction between the two groups (FIG. 3A-B). In general, PCA analysis describes similarities between samples and is not a commonly employed tool for predicting diagnosis. However, in this study the distinction was so powerful that it was possible to visually make a correct diagnosis for each of the 10 unknown samples (FIG. 3A-B). The predictor model determines the kind of tumor with a specific probability value diagnosis of all 10 unknown samples was correctly predicted, with a more accurate prediction using the six-gene combination (Table 3, see probabilities). It is clear from the graph in FIG. 4 how the combination of gene expression values gives a distinctly different profile between the benign and malignant lesions. However, within each tumor group there are differences among the profiles of the five samples tested. This could be explained by the fact that each tumor, even if of the same type, could be at a different stage of progression.

Of the 11 genes that were informative for the diagnosis, five genes are known genes and for the other six genes no functional studies are yet available. The genes that were identified are the ones that the model has determined best group the known samples into their correct diagnosis. Those genes identified are the ones that consistently grouped the samples into the categories and subcategories described herein. This type of pattern assignment is based on the analysis of thousands of genes and the recognition by the computer software that certain patterns are associated repeatedly with certain diagnostic groups. This type of analysis derives it power (and significance) by the number of genes that are analyzed, rather than the degree of up or down regulation of any particular gene. With respect to the specific genes identified, the computer is not biased by the knowledge of previously identified genes associated with thyroid cancer. The genes it identifies are those that best differentiate the varied diagnoses of the known samples. This occurs during the "training" phase of establishing the algorithm. Once the computer is trained with data from comparisons of RNA from known diagnoses to a standard reference, unknowns can be tested and fit to the diagnostic groups predicted during the training. For the purposes of such an approach, individual genes are less important. A specific gene which is found in a univariate study to be associated with thyroid cancer, may not turn out to be the best multivariate predictor of a diagnosis in an analysis such as the one presented here.

TaqMan Assay Utilizing 6 Gene Predictor Model and 10 Gene Predictor Model

Utilizing the information obtained for these differentially expressed genes TaqMan Real Time PCR analysis for the group of 6 genes and the group of 10 genes that are diagnostic for benign versus malignant thyroid lesions from total RNA extracted from thyroid tissue as well as RNA from control normal thyroids was performed. TaqMan Real Time PCR analysis was also performed for the group of 10 genes that are diagnostic for benign versus malignant thyroid lesions.

Thyroid samples were collected under Johns Hopkins University Hospital Institutional Review Board-approved protocols. The samples were snap-frozen in liquid nitrogen and stored at −80° C. until use. The specimens were chosen based on their tumor type: papillary thyroid cancer (PTC); follicular variant of papillary thyroid cancer (FVPTC); follicular adenoma (FA); and hyperplastic nodule (HN). All diagnoses were made using standard clinical criteria by the Surgical Pathology Department at Johns Hopkins University Hospital.

Tissue Processing and Isolation of RNA

Frozen sections of 100-300 mg of tissue were collected in test tubes containing 1 ml of Trizol. Samples were transferred to FastRNA™ tubes containing mini beads and homogenized in a FastPrep beater (Bio101Savant™, Carlsbad, Calif.) for 1.5 min at speed 6. The lysate was transferred to a new tube and total RNA was extracted according to the Trizol protocol in a final volume of 40 µl Rnase-free water (Molecular Research Center, Inc., Cincinnati, Ohio). The quality of the extracted RNA was tested by spectrophotometry and by evaluation on minichips (BioAnalyzer; Agilent Technologies, Palo Alto, Calif.). Minimal criteria for a successful total RNA run were the presence of two ribosomal peaks and one marker peak. Normal human thyroid RNA (Clontech, BD Biosciences) served as a reference control. The total RNA extracted from tissue samples and normal thyroid was then used as the template for one round of reverse transcription to generate cDNA. Eight microliters of purified total RNA (containing up to 3 µg of total RNA) was added to a mix containing 3 µg/1 µl of random hexamer primers, 4 µl of 1× reverse transcription buffer, 2 µl of DTT, 2 µl of dNTPs, 1 µl of Rnase inhibitor, and 2 µl of SuperScript II reverse transcriptase (200 U/µl) in a 20 µl reaction volume (all purchased from Invitrogen, Carlsbad, Calif.). Reverse transcription was performed according to the SuperScript First-Strand Synthesis System instructions (Invitrogen, Carlsbad, Calif.). Following the reverse transcription reaction, the SuperScript II enzyme was heat inactivated, and degradation of the original template RNA was performed using 2U/1 µl of RNAse H (Invitrogen, Carlsbad, Calif.) for 20 minutes at 37° C. The final volume of the mixture was brought to 500 µl using Rnase free water and stored at −20° C. until use.

Quantitative Real-Time PCR

For the quantitative analysis of mRNA expression, ABI Prism 7500 Sequence Detection System (Applied Biosystems) was used and the data analyzed using the Applied Biosystems 7500 System SDS Software Version 1.2.2. Primers and probes for the genes of interest and for G3PDH were designed using the Primer Express software (version 2.0; Applied Biosystems). Each primer was designed to produce an approximately 70-150 by amplicon. Primer and probe sequences that can be utilized in the 6 gene predictor model and the 10 gene predictor model are listed in Table 4. Table 4 lists the forward and reverse primer for each gene as well as the fluorescent probe sequence that was dual labeled. Table 4 also provides the GenBank Accession No. corresponding to each gene and the location of the primer and probe sequences within the full-length nucleotide sequences provided under the GenBank Accession Nos. Table 4 also provides the InCytePD clone number for each gene (if available), a Unigene identification number for each gene (if available), the chromosomal location for each gene, and additional information about the primers and probes. The primer and probe sequences set forth in Table 4 are examples of the primers and probes that can be utilized to amplify and detect DET1-11. These examples should not be limiting as one of skill in the art would know that other primer sequences for DET1-DET11 including primers comprising the sequences set forth in Table 4 and fragments thereof can be utilized to amplify DET1-DET11. Similarly, other probes which specifically detect DET1-DET11 can be utilized such as probes that comprise the probe sequences set forth in Table 4 and fragments thereof.

Primers and probes were synthesized by Sigma (sequences shown in Table 4; Sigma, The Woodlands, Tex.). Probes were labeled at the 5' end with the reporter dye FAM (emission wavelength, 518 nm) and at the 3' end with the quencher dye TAMRA (emission wavelength, 582 nm). Standards were created for the six genes using gel-extracted PCR products (Qiagen, Valencia, Calif.). The G3PDH standard was created using a plasmid construct containing the relevant G3PDH sequence (kind gift of Dr. Tetsuya Moriuchi, Osaka University[12]). For PCR, 12.5 µl TaqMan Universal PCR Master Mix, 0.5 µl per well each of 0.5 µM forward and reverse primers, and 0.5 µl per well of 10 µM dual labelled fluorescent probe were combined and adjusted to a total volume of 20 µl with Rnase-free water. Finally, 5 µl cDNA per well was added to a total reaction volume of 25 µl. The PCR reaction was performed for 40 cycles of a two-step program: denaturation at 95° C. for 15 seconds, annealing and extension at 60° C. for 1 minute. The fluorescence was read at the completion of the 60° C. step. For each experiment, a no-template reaction was included as a negative control. Each cDNA sample was tested in triplicate, and the mean values were calculated. Triplicate values varied by no more than 10% from the mean. We used the standard curve absolute quantification technique to quantify copy number. A standard curve was generated using a ten-fold dilution series of four different known concentrations of the standards. The number of PCR cycles required for the threshold detection of the fluorescence signal (cycle threshold or Ct) was determined for each sample. Ct values of the standard samples were determined and plotted against the log amount of standard. Ct values of the unknown samples were then compared with the standard curve to determine the amount of target in the unknown sample. Standard curves from each experiment were compared to insure accurate, precise and reproducible results. Each plate contained duplicate copies of serial dilutions of known standards and G3PDH, triplicate copies of cDNA from each sample and normal thyroid cDNA for amplification of G3PDH and the gene of interest.

Statistical Analysis

Data from 41 of the thyroid tumors were used to build a benign (FA, n=15; HN, n=10) versus malignant (PTC, n=9; FVPTC, n=7) expression ratio-based model, capable of predicting the diagnosis (benign versus malignant) of each sample. Ten additional samples were provided as blinded specimens, processed as described above and used as a validation set to test the model. These ten samples were not previously used to do any other analysis. Expression values of all six genes in all samples and normal thyroid were standardized to the expression of G3PDH, a common housekeeping gene chosen to serve as a reference control. The ratio of the expression values for each gene in each sample was then compared to the ratio in normal thyroid, and converted to log 2 to generate a gene expression ratio value for all 41 samples. A file containing the gene expression ratio values from all 51 samples (41 known, 10 unknown) was imported into a statistical analysis software package (Partek, Inc., St. Charles, Mo.).

As a first step, the data from the 41 samples were subjected to principal component analysis (PCA) to provide a three-dimensional visualization of the data. All six genes were used to build a diagnosis-predictor model called a class prediction rule. This resulting rule was applied to predict the class of the ten samples in the validation set. The same analysis was then performed on a second set of data from 47 of the thyroid tumors to build a benign (FA, n=15; HN, n=11) versus malignant (PTC, n=9; FVPTC, n=12) expression ratio-based model. Ten additional unstudied samples were provided as blinded specimens for this second training set.

Principal Component Analysis (PCA) of the 41 samples using the gene expression values for all six genes showed a clear organization of the samples based on diagnosis. PCA was then conducted on all of the 41 samples with the 10 unknown samples. This combination of genes constituted a first predictor model and the validation set of 10 additional thyroid samples was used to confirm the accuracy of the model. The pathological diagnosis for each sample was kept blinded until after the analysis was completed. When the blind was broken, it was found that 8 of the 10 unknown samples were diagnosed by this model in concordance with the pathological diagnosis determined by standard pathologic criteria. One sample that was originally diagnosed as a benign follicular adenoma by standard histological criteria was diagnosed as malignant by the six gene predictor model set forth herein; one sample that was originally diagnosed as a papillary thyroid carcinoma by standard histological criteria was diagnosed as benign by the six gene predictor model set forth herein.

Further to the analysis above, the G3PDH standard was redesigned and processing of all tissue for total RNA extraction was standardized. Following these two modifications, Principal Component Analysis (PCA) was performed on the second training set of 47 samples and on ten new unknown samples using the gene expression values for all six genes. Again, PCA demonstrated a clear organization of the samples based on diagnosis. The pathological diagnosis for these ten new unknowns was also kept blinded until after the analysis. When the blind was broken, it was found that 9 of the samples were diagnosed in concordance with the pathological diagnosis by the six gene predictor model set forth herein. One sample that was diagnosed as a benign hyperplastic nodule by standard histological criteria was diagnosed as malignant by our model.

Figure 5:
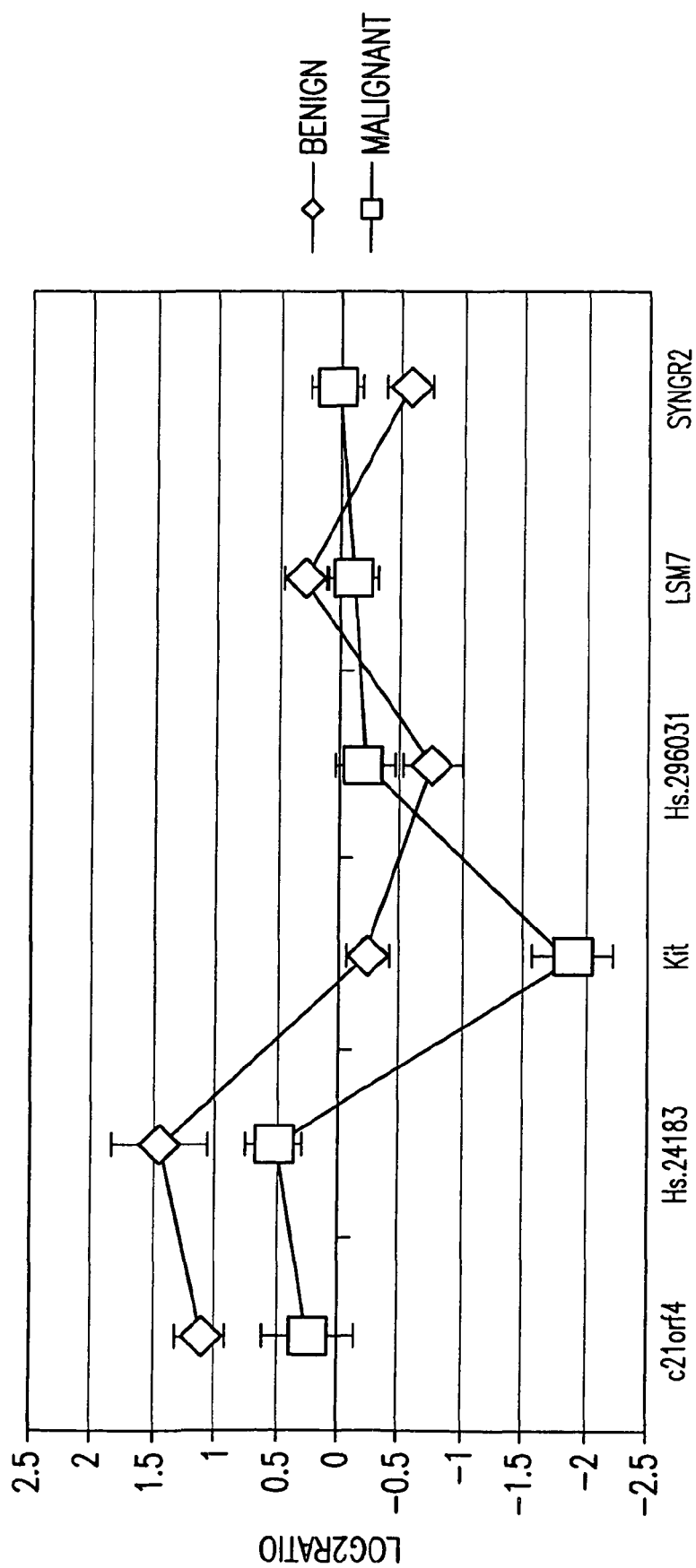
FIG. 5 shows the results of RT-PCR utilizing the 6 gene predictor model. The RT-PCR data using 6 genes across 42 patient samples demonstrates separation by group.

The results of the Taqman assays correlated with the microarray data. As shown in FIG. 5, the Taqman data utilizing the 6 gene model (DET1, DET2, DET3, DET4, DET5, DET6) demonstrate the ability to classify a thyroid sample as benign or malignant. Similar to results obtained via microarray, c21orf4, Hs.145049, KIT and LSM-7 were upregulated in benign samples as compared to malignant samples. In other words, the expression of c21orf4, Hs.145049, KIT and LSM7 decreases during malignancy. Hs.296031 and SYNGR2 were upregulated in malignant samples as compared to benign samples. In other words, expression of Hs.296031 and SYNGR2 increases during malignancy. The same analysis was performed with the 10 gene model utilizing the primers and probes set forth in Table 4 for DET 1, DET2, DET3, DET4, DET6, DET7, DET8, DET9, DET10 and DET11. As shown in FIG. 7, similar to results obtained via microarray, c21orf4, Hs.145049 (Hs. 24183), KIT, FAM13A1, C11orf8, KIAA1128, IMPACT and CDH1 were upregulated in benign samples as compared to malignant samples. In other words, the expression of c21orf4, Hs.145049, KIT, FAM13A1, C11orf8, KIAA1128, IMPACT and CDH1 decreases during malignancy. Hs.296031 and SYNGR2 were upregulated in malignant samples as compared to benign samples. In other words, expression of Hs.296031 and SYNGR2 increases during malignancy. Therefore, it is clear that this pattern of differences between malignant and benign samples can be utilized to classify thyroid lesions utilizing the 6 gene model and the 10 gene model. In addition to classification, the Real Time PCR Taqman assay can also be used for staging thyroid cancer and in identifying agents that treat thyroid tumors.

Analysis of the 6 gene expression and the 10 gene expression profiles revealed that the benign lesions could be distinguished from the malignant lesions, and that this profile could be used to diagnose unknown samples against the current "gold standard" of pathologic criteria with a high degree of accuracy. Of the six genes in the six gene model, downregulation of KIT was seen in tissue of both benign and malignant thyroid lesions when compared to normal control. The magnitude of this downregulation was much greater in malignant thyroid tissue. Kit is a well-known protooncogene.

As to the other five genes in the six gene model, for three of these no functional studies are yet available. Of the remaining two genes, SYNGR2 has been characterized as an integral vesicle membrane protein. LSM7 likewise has been described in the family of Sm-like proteins, possibly involved in pre-mRNA splicing. The interaction of LSM7 with the TACC1 complex may participate in breast cancer oncogenesis. However, the role of LSM7 in thyroid oncogenesis has not yet been explored.

The six gene model determined the accurate diagnosis of 17 out of 20 unknown samples tested. Accuracy was based on a comparison to the "gold standard" pathologic diagnosis as determined by clinical pathologists. Therefore, this strategy demonstrates the power of genomic analysis as a technique for studying the underlying pathways responsible for the pathophysiology of neuroendocrine tumors. Further evaluation and linkage of clinical data to molecular profiling allows for a better understanding of tumor pathogenesis, or even normal thyroid function and development. In addition, the use of qRT-PCR can lead to incorporation of this model and/or the 10 gene model into preoperative decision making for patients with thyroid nodules.

The present invention is a clear example of how gene-expression profiling can provide highly useful diagnostic information. It is likely that gene expression profiling will be used in the future for clinical decision-making. For this purpose adequate reporting of DNA-microarray data to clinicians will be necessary. Gene-expression profiles may be more reproducible and clinically applicable than well-established but highly subjective techniques, such as histopathology. The small number of genes for which RNA expression levels are diagnostically and prognostically relevant could lead to a robust, affordable, commercially available testing system. To this end, the present invention provides a useful method for classifying thyroid nodules as benign or malignant and therefore helps facilitate appropriate, and eliminate unnecessary, operations in patients with suspicious thyroid tumors.

Example 2

DET4 and DET12-DET85

Although fine-needle aspiration biopsy (FNA) is the most useful diagnostic tool in evaluating a thyroid nodule, preoperative diagnosis of thyroid nodules is frequently imprecise, with up to 30% of FNA cytology samples reported as 'suspicious' or 'indeterminate'. Therefore, other adjuncts, such as molecular-based diagnostic approaches are needed in the preoperative distinction of these lesions. In an attempt to identify diagnostic markers for the preoperative distinction of these lesions, microarray analysis was used to study the 8 different thyroid tumor subtypes that can present a diagnostic challenge to the clinician.

The present microaray-based analysis of 94 thyroid tumors identified 75 genes that are differentially expressed between benign and malignant tumor subtypes. Of these, 33 were over-expressed, and 42 under-expressed, in malignant compared to benign thyroid tumors. Statistical analysis of these genes, using Nearest Neighbor classification showed a 73% sensitivity and 82% specificity in predicting malignancy. Real-time RT-PCR validation for 12 of these genes was confirmatory. Tissue validation by Western blot and immunohistochemical analyses of one of the genes, HMGA2, further validated the microarray and real-time RT-PCR data. These 12 genes are useful in the development of a panel of markers to differentiate benign from malignant tumors and thus serve as an important step in solving the clinical problem associated with suspicious thyroid lesions.

Tumor Specimens

A total of 125 thyroid tumor samples were collected from patients who underwent thyroidectomy at Johns Hopkins Medical Institutions (Baltimore, Md.) between 2000 and 2005. All samples were collected with Institutional Review Board approval. Following surgical excision, samples were snap frozen in liquid nitrogen and stored at −80° C. until use. The specimens included 70 benign tumors (20 adenomatoid nodules, 20 follicular adenomas, 17 Hürthle cell adenomas, 13 lymphocytic thyroiditis nodules) and 55 malignant tumors (19 papillary thyroid carcinomas, 16 follicular variant of papillary thyroid carcinomas, 14 follicular carcinomas, and 6 Hürthle cell carcinomas). Each sample was obtained form the center of the tumor.

RNA Isolation

Fresh frozen sections were reviewed by a pathologist to verify the presence of tumor prior to tissue processing and RNA extraction. Total RNA was isolated from 50-75 mg of each tumor using TRIzol reagent (Invitrogen) and purified with the RNeasy Kit (Qiagen). The quantity and the integrity of extracted RNA was determined by ND-1000 Spectrometer (Nanodrop Technologies) and Bioanalyzer Nano Labchips (Agilent Technologies), respectively. RNA that included 56 pooled normal thyroid specimens was used as control (Clontech).

cRNA Synthesis, Labeling and Microarray Hybridization

One microgram of total RNA from each sample was subjected to single round amplification using Aminoallyl MessageAmp™ II aRNA Amplification Kit (Ambion Inc). After amplification, 5 µg of aminoallyl RNA (aaRNA) was labeled using a Cy-dye coupling method according to the manufacturer's instructions. Both Cy5-labeled tumor cRNA and Cy3-labeled control cRNA were hybridized to a 34K-human-oligonucleotide array produced by the National Cancer Institute (NCI) microarray facility (http://arraytracker.nci.nih.gov/). Microarray hybridization, washing and scanning (GenePix 4000B) were performed as described in NCI protocol (http://arraytracker.nci.nih.gov/nciarrays.manual.october.2006.pdf). In order to test for labeling bias, 10 representative tumor samples were used in dye swap experiments. Dye swap experiments were performed with Cy5-labeled control cRNA and Cy3-labeled tumor cRNA.

Bioinformatics and Statistical Analysis.

After image analysis using GenePix Pro 5.0, raw data from all 125 arrays were arranged in mAdb (http://nciarray.nci.nih.gov/) and then exported for further analysis with BRB ArrayTools (25).

For each array, global normalization was performed to median the center of the log-ratios in order to adjust for differences in labeling intensities of the Cy3 and Cy5 dyes. Genes exhibiting minimal variation across the set of arrays from different tumor subtypes were excluded and only genes exhibiting expression differences of at least 1.5 fold from the median in at least 20% of the arrays were retained for analysis.

Class Comparison

Genes that were differentially expressed between malignant and benign thyroid tumors were identified using a random-variance t-test (26). In order to limit the number of false positives, genes were included only if their p value was less than 0.001. We also performed a global test of whether the expression profiles differed between benign and malignant by permuting (1000 times) the labels of which array corresponded to which category. For each permutation, the p values were re-computed and the number of significant genes ($p \leq 001$) was noted. The proportion of permutations that resulted in at least as many genes as with the actual data was the significance level of the global test.

Class Prediction

We developed models that utilized gene expression profiles to predict class of tumors (benign vs. malignant). The models were based on several classification methods: Compound Covariate Predictor (27), Diagonal Linear Discriminant Analysis (28), Nearest Neighbor Classification (28), and Support Vector Machines with linear kernel (29). Genes that were differentially expressed ($p \leq 0.001$) were then incorporated into these models (26). We estimated the prediction error for each model using leave-one-out cross-validation (LOOCV). For each LOOCV set, the entire model was recreated, including the gene selection process. We also evaluated whether the cross-validated error rate for any given model was significantly less than what one would expect from random prediction. Class labels were randomly permuted and the entire LOOCV process was repeated 1,000 times. The significance level was the proportion of the random permutations that gave a cross-validated error rate no greater than the rate obtained with the real data.

Real Time RT-PCR.

To validate the genes found to be significantly differentially expressed, real time RT-PCR was performed on a subset of 76 tumors that were available from the original array analysis as well as on a new set of 31 tumors. cDNA was synthesized in a 50 µl reverse transcription reaction mixture that contained 3 µg total RNA from each tumor. After optimization for each primer pair, real-time PCR assays were performed on iQTM5 real-time PCR detection system (Bio-Rad Laboratories, Inc.) according to the manufacturer's recommendations. Briefly, 1 µl of cDNA was used in a 25 µl reaction mixture that contained an optimal concentration (150-250 nM) of primers and SYBR-Green Supermix. The thermal profile for PCR consisted of Taq-polymerase activation at 95° C. for 3 minutes, followed by 40 cycles of PCR at 95° C. for 20 seconds (denaturation), 55° C. for 30 seconds (annealing), and 72° C. for 60 seconds (extension). An average Ct (threshold cycle) from duplicate assays was used for further calculation, and GAPDH-normalized gene expression was determined using the relative quantification method as formulated below. Results were expressed as the median of 3-4 independent measurements.

Relative expression levels normalized to GAPDH=$2^{-(\text{Gene of interest Ct}-\text{GAPDH Ct})} \times 100$ Western Blot Analysis Total cellular proteins were extracted from thyroid tumors and their matching normal thyroid tissues. Tissues (20-25 mg) were ground and lysed in 250 μl ice-cold M-PER lysis buffer (Pierce) supplemented with a protease inhibitor cocktail for 60 min at 4° C. Supernatants were collected after centrifugation at 11,600×g at 4° C. and protein concentration was measured. Protein samples, loaded at 40 μg per lane were separated by 10% SDS-PAGE gels as described elsewhere. After transfer to a polyvinylidene diflouride membrane, both transfer efficiency and protein loads were checked by Ponceau S solution (Sigma). Specific proteins were probed with anti-HMGA2 antibody (sc-23684 Santa Cruz Biotechnology, Inc).

Tissue Array (TMA)

A total of 87 formalin-fixed, paraffin-embedded thyroid specimens from 87 different individuals were selected from the surgical pathology archives of the Johns Hopkins Hospital, including classic papillary thyroid carcinoma (n=20), follicular variant of papillary thyroid carcinoma (n=9), follicular carcinoma (n=14), lymphocytic thyroiditis nodules (n=1 1), follicular adenoma (n=14) and normal thyroid adjacent to tumor (n=19). These cases were different than those used for the gene expression analysis. Each case was reviewed by a pathologist (DPC) to confirm the diagnosis and select appropriate areas for inclusion in the tissue array. For follicular variant of papillary thyroid carcinoma, cores from areas within the tumor displaying florid nuclear features of papillary thyroid carcinoma and follicular architecture were chosen for the TMA. Tissue cores (0.6 mm diameter) from selected areas were obtained using a manual Tissue Puncher/Arrayer (Beecher Instruments, Silver Spring, Md.) and a high-density tissue array was generated as previously described (30). In addition to thyroid tumors, each TMA block had nine cylinders from non-thyroid control tissues. Five-micron sections were cut, and one H&E-stained slide was examined to verify the presence of diagnostic cells.

Immunohistochemistry

H & E staining and immunohistochemistry were done on 4-5 μm serial sections of formalin-fixed paraffin-embedded tissue. Briefly, sections were deparaffinized in xylene and rehydrated through a series of alcohol gradients. Antigen retrieval was achieved by heating in citrate buffer at pH 6.0. Endogenous peroxidase activity was quenched in 3% hydrogen peroxide and nonspecific binding of secondary antibody blocked by incubation with normal horse serum. Individual sections were incubated with anti-HMGA2 goat polyclonal antibodies overnight at 4° C. Conditions omitting primary antibody were used as negative controls. A streptavidin-biotin peroxidase detection system was used in accordance with the manufacturer's instructions and then developed using 3,3'-diaminobenzidine (Vector Laboratories, Inc). Sections were counterstained with hematoxylin and eosin. Formalin-fixed paraffin-embedded cellblock sections of lung cancer cell line, H1299 (ATCC) were used as positive controls.

Results

Microarray and Statistical Analysis

Ninety-four unique thyroid samples representing the 8 different thyroid tumor subtypes were used for microarray analysis. The specimens included: 50 benign tumors (13 adenomatoid nodules, 13 follicular adenomas, 13Hürthle cell adenomas and 11 lymphocytic thyroiditis nodules) and 44 malignant tumors (13 papillary thyroid carcinomas, 13 follicular variant of papillary thyroid carcinomas, 13 follicular carcinomas, and 5 μHürthle cell carcinomas). Several of these tumors were used more than once for the analysis, resulting in 128 arrays (Table 5).

Figure 12A:
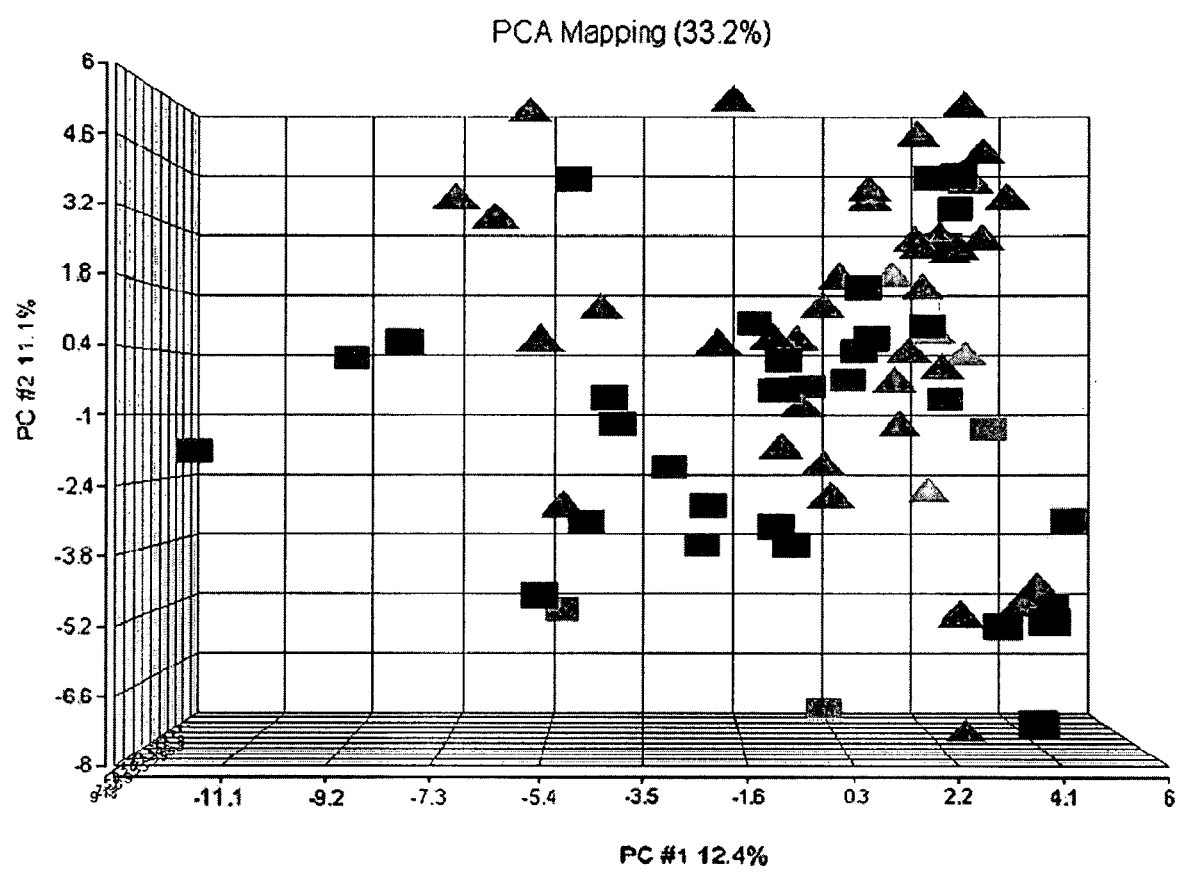
FIG. 12 shows Principal component analysis (PCA) using 94 thyroid tumor samples. A, expression values from all 15,745 genes. B, expression values from the most variable 1000 genes. C, expression values from the best 75 differentially expressed genes. Benign (triangle) and malignant (square) thyroid tumor samples are localized in three-dimensional space on the basis of their gene expression profile. The distance between any 2 points is related to the similarity between the two observations in high dimensional space.
Figure 12B:
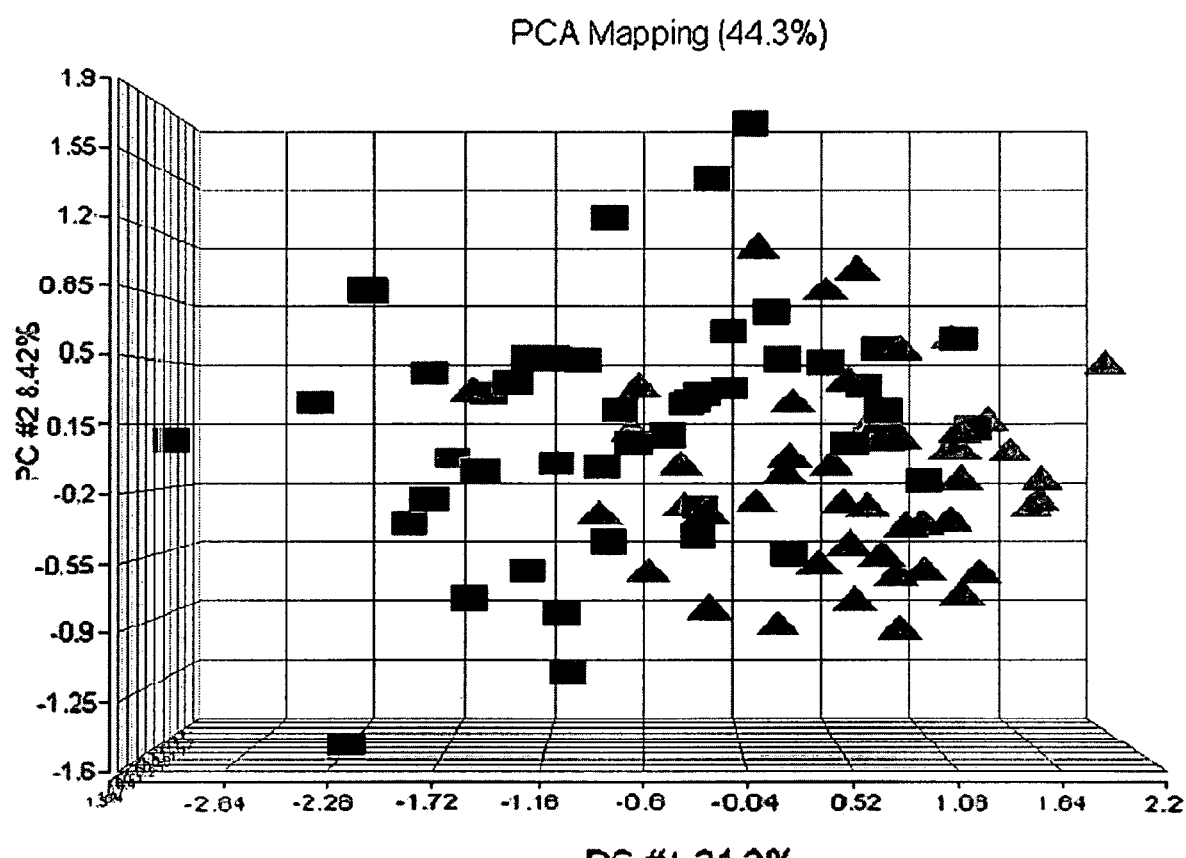
Figure 12C:
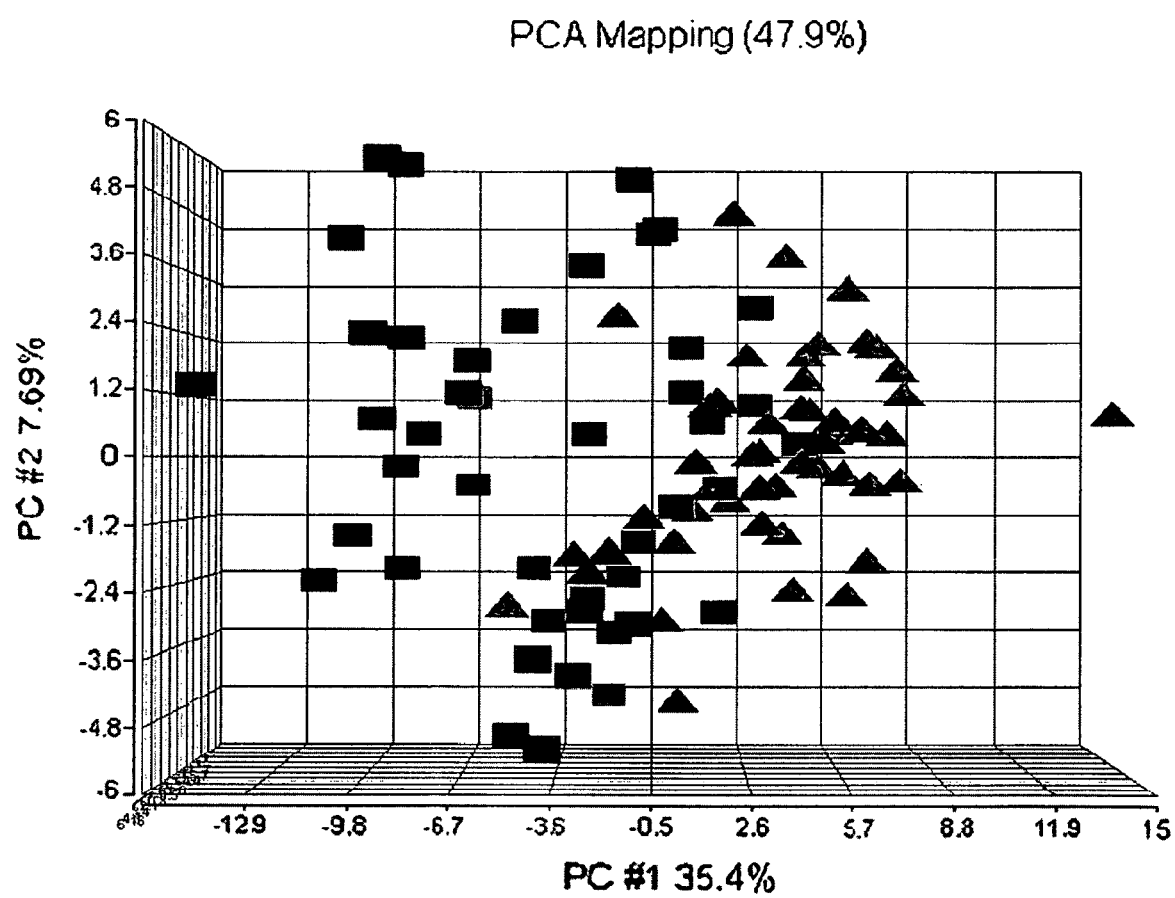

After the expression data from replicate samples were averaged, 15,745 genes met criteria for inclusion in the analysis by BRB ArrayTools. By using a random-variance t-test, the class comparison (benign vs. malignant) analysis identified 75 genes that were significantly (p≤0.001) differentially expressed between malignant and benign tumor types. Of these 75 differentially expressed genes, 33 were over-expressed (Table 6) and 42 were under-expressed (Table 7) in malignant thyroid tumors compared to benign. Principal component analysis of the 94 samples using these 75 genes showed a clear organization of the samples based on diagnosis (FIG. 12).

We further developed additional models utilizing gene expression data to predict and cross-validate the samples. In addition to this, we evaluated whether the estimated error-rate (cross-validated) for each model was significantly less than one would expect from random prediction. Statistical analysis using 1-Nearest Neighbor classification provided the best results and showed a 73% sensitivity, 82% specificity and 78% positive predictive value for the prediction of malignancy (Table 8).

RT-PCR Analysis

Figure 8:
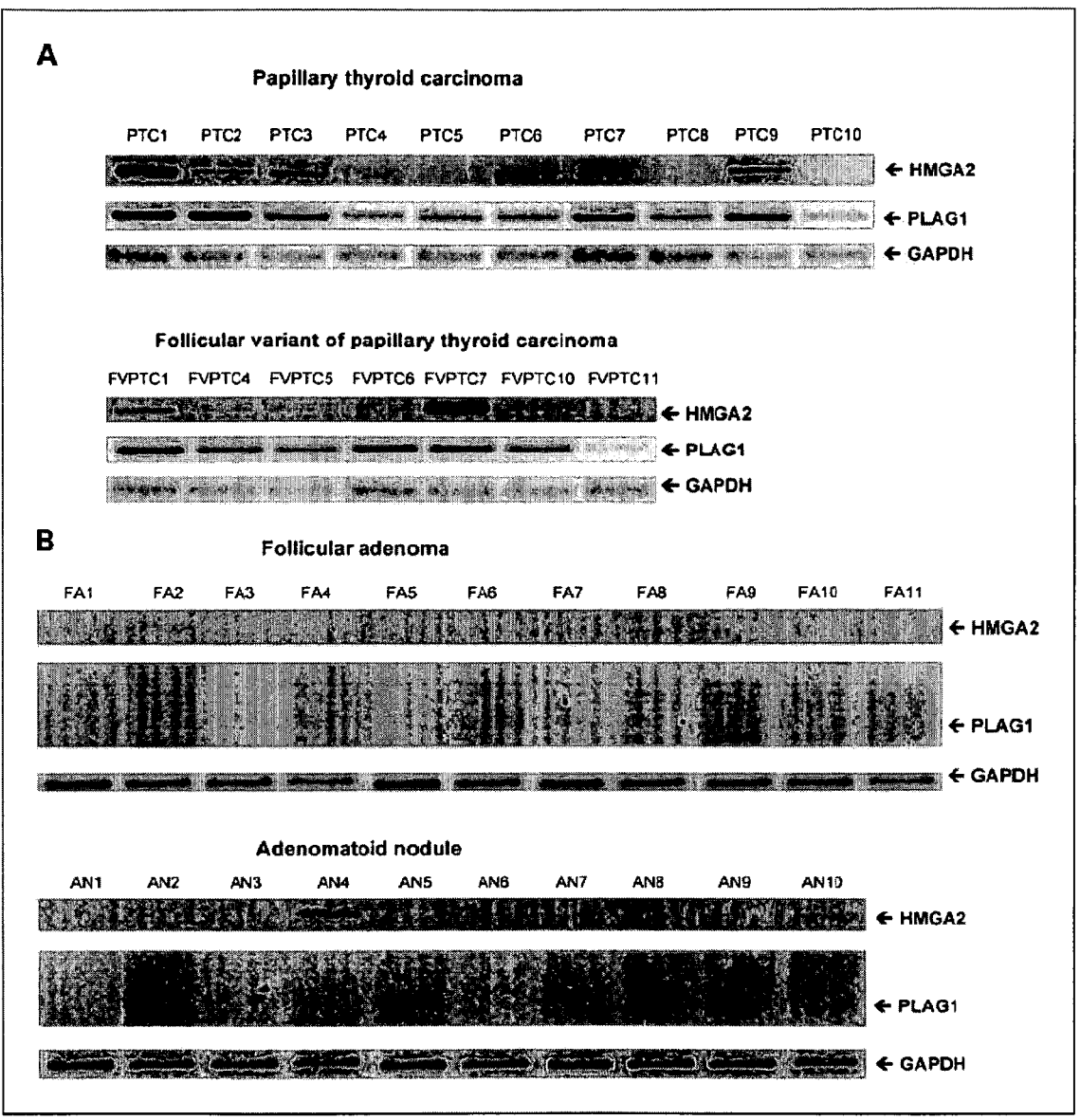
FIG. 8 shows RT-PCR analysis of HMGA2 and PLAG1 in thyroid tumors. The mRNA expression of both HMGA2 and PLAG1 in malignant [A; papillary thyroid carcinoma (PTC; n=10) & follicular variant of papillary thyroid carcinoma (FVPTC; n=7)] and benign [B; follicular adenoma (FA; n=11) & adenomatoid nodule (AN; n=10)] was determined by RT-PCR. GAPDH expression after 22 PCR-cycles and 35 PCR-cycles served as a loading control for malignant and benign tumors respectively. Note: With the exception of one adenomatoid nodule (AN4) the benign tumors exhibited no detectable levels of HMGA2 or PLAG1. Only smear was found after extending PCR-cycles to 40.

In order to validate the authenticity of the microarray data, RT-PCR analysis of two genes [high mobility group AT-hook 2 (HMGA2) and pleomorphic adenoma gene 1 (PLAG1)] was first performed using 11 follicular adenomas, 10 adenomatoid nodules, 10 papillary thyroid carcinomas and 7 follicular variant of papillary thyroid carcinomas (FIG. 8). These representative tumor samples were also used in the microarray analysis. As shown in FIG. 8A, the expression levels of both HMGA2 and PLAG1 were found to be very high in most of the malignant tumors (papillary and follicular variant of papillary thyroid carcinoma). In contrast, all benign tumors (follicular adenomas and adenomatoid nodules) exhibited no detectable levels of either HMGA2 or PLAG1 even after extending the PCR cycles to 40, with the exception of one of the benign tumors (adenomatoid nodule; AN4) that showed appreciable levels of HMGA2 expression (FIG. 8B).

Figure 9:
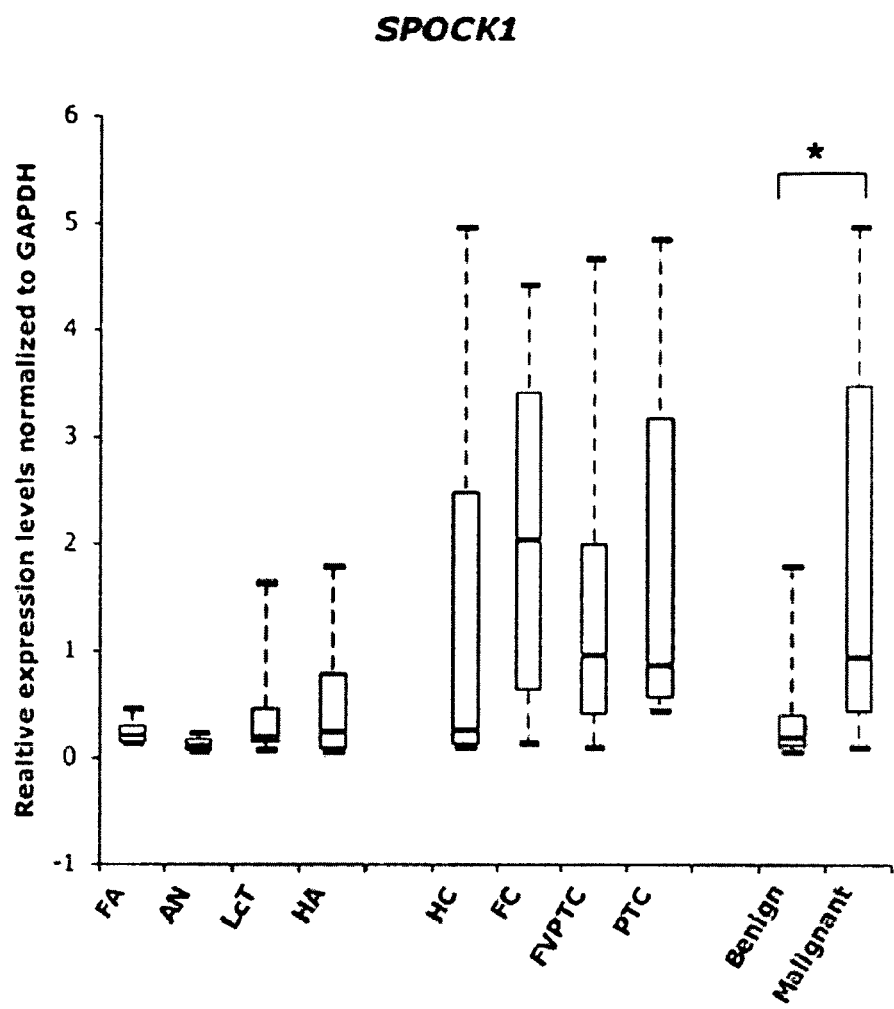
FIG. 9 shows Real-time RT-PCR validation of 6 genes (SPOCK1, CEACAM6, PRSS3, PDE5A, LRRK2 and TPO5) using 76 tumors from the original set of microarray samples. Relative gene expression levels normalized to GAPDH in 41 benign [follicular adenomas (FA; n=11), adenomatoid nodules (AN; n=10), lymphocytic thyroiditis nodules (LcT; n=10) & Hürthle cell adenomas (HA; n=10)] and 35 malignant [Hürthle cell carcinomas (HC; n=5), follicular carcinomas (FC; n=10), follicular variant of papillary thyroid carcinomas (FVPTC; n=10) & 10 papillary thyroid carcinomas (PTC; n=10)] tumors were determined using gene-specific primers as described in Materials and Methods. The upper and lower limits of each box represent 'third' and 'first' quartiles, respectively; Red lines represent medians; whiskers represent extreme measurements; *, P<0.001 by two-tailed t test between benign and malignant tumor-types. Note. As expected from the microarray analysis, SPOCK1, CEACAM6, PRSS3 & LRRK2 are overexpressed, and TPO5 is underexpressed in malignant tumors compared to benign.

Real-time RT-PCR analysis of 6 genes [sparc/osteonectin CWCV and kazal-like domain proteoglycan (SPOCK1), carcinoembryonic antigen-related cell adhesion molecule 6 (CEACAM6), protease serine 3 (PRSS3/mesotrypsin), phosphodiesterase 5A (PDE5A), leucine-rich repeat kinase 2 (LRRK2) and thyroid peroxidase (TPO5)] was also performed using RNA from 76 of the original tumor set used in the microarray analysis. The expected differential expression was confirmed in 5 out of 6 genes (FIG. 2). SPOCK1, CEACAM6, PRSS3 and LRRK2 were overexpressed in malignant compared to the benign tumor subtypes (Table 7 and FIG. 9). TPO5 was underexpressed in the majority of the malignant subtypes (Table 6 and FIG. 9). While we did not see any significant difference between benign vs. malignant tumors, the papillary thyroid cancers exhibited elevated levels of PDE5A compared to all other subtypes (FIG. 9).

In addition to the original set of tumor samples, a new set of 31 thyroid tumors was also used for validation by real-time RT-PCR. The new set of samples had not been used for the microarray analysis and was used to validate the following 6 genes: dipeptidyl-peptidase 4 (DPP4), cadherin 3 type1

Figure 10:
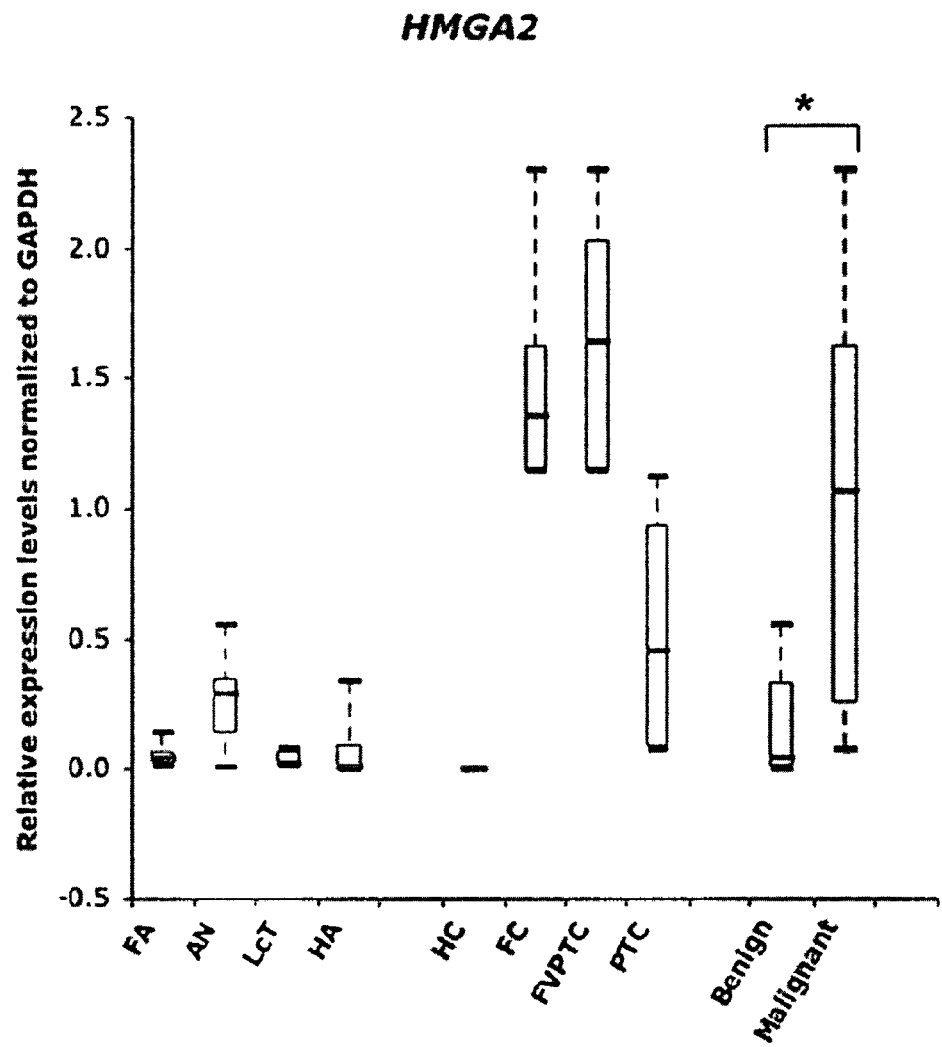
FIG. 10 shows Real-time RT-PCR validation of 6 genes (HMGA2, PLAG1, DPP4, CDH3, RAG2 and AGTR1) using 31 new thyroid tumors. Relative expression levels normalized to GAPDH in 20 benign [follicular adenomas (FA; n=7), adenomatoid nodules (AN; n=7), lymphocytic thyroiditis nodules (LcT; n=2) & Hürthle cell adenomas (HA; n=4)] and 11 malignant [Hürthle cell carcinomas (HC; n=1), follicular carcinomas (FC; n=3), follicular variant of papillary thyroid carcinomas (FVPTC; n=3) & 10 papillary thyroid carcinomas (PTC; n=4)] tumors were determined using gene-specific primers. The upper and lower limits of each box represent 'third' and 'first' quartiles, respectively; Red lines represent medians; whiskers represent extreme measurements; *, P<0.001 by two-tailed t test between benign and malignant tumor-types. Note: As expected from the microarray analysis, HMGA2, PLAG1 and CDH3 are overexpressed, while both RAG2 and AGTR1 are underexpressed in malignant tumors compared to benign.

(CDH3), recombination activating gene2 (RAG2), angiotensin II receptor type1 (AGTR1), HMGA2 and PLAG1. Again, all 6 genes that we analyzed were found to be differentially expressed in benign vs. malignant, as expected by the microarray analysis (FIG. 10). Very high expression levels of CDH3, HMGA2, and PLAG1 were observed in all of the malignant subtypes compared to the benign tumors. Indeed, the expression levels of HMGA2 and PLAG1 were quantified this time using a new set of thyroid tumors, and both genes were overexpressed in the majority of malignant compared to benign subtypes. Low expression levels of RAG2 and AGTR1 were documented in all malignant tumors (Table 7 and FIG. 10). With the exception of lymphocytic thyroiditis nodules that exhibited very high expression levels of DPP4, the other three benign subtypes (follicular adenomas, adenomatoid nodules and Hürthle cell adenomas) exhibited very low expression levels compared to malignant tumors (FIG. 10).

Validation by Western Blot and Immunohistochemistry Analysis

Figure 11A:
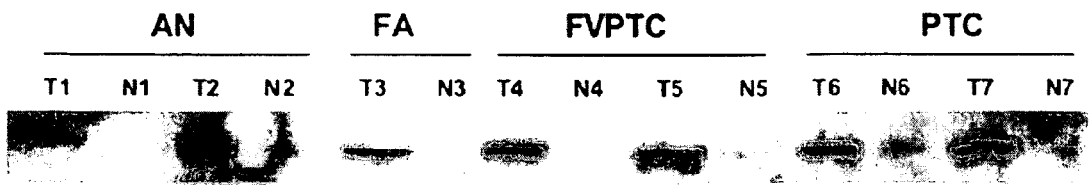
FIG. 11A shows HMGA2 expression in thyroid. Western blot analysis of HMGA2 protein expression in thyroid tumors (T1-T7) and in adjacent normal thyroid tissues (N-1-N7). The anti-HMGA2 goat polyclonal antibody recognized HMGA2 expression specifically in thyroid tumors but not in adjacent normal thyroid tissue. High protein expression of HMGA2 is detected in malignant tumors (T4, T5, T6, T7) compared to benign tumors (T1, T2, T3).
Figure 11B:
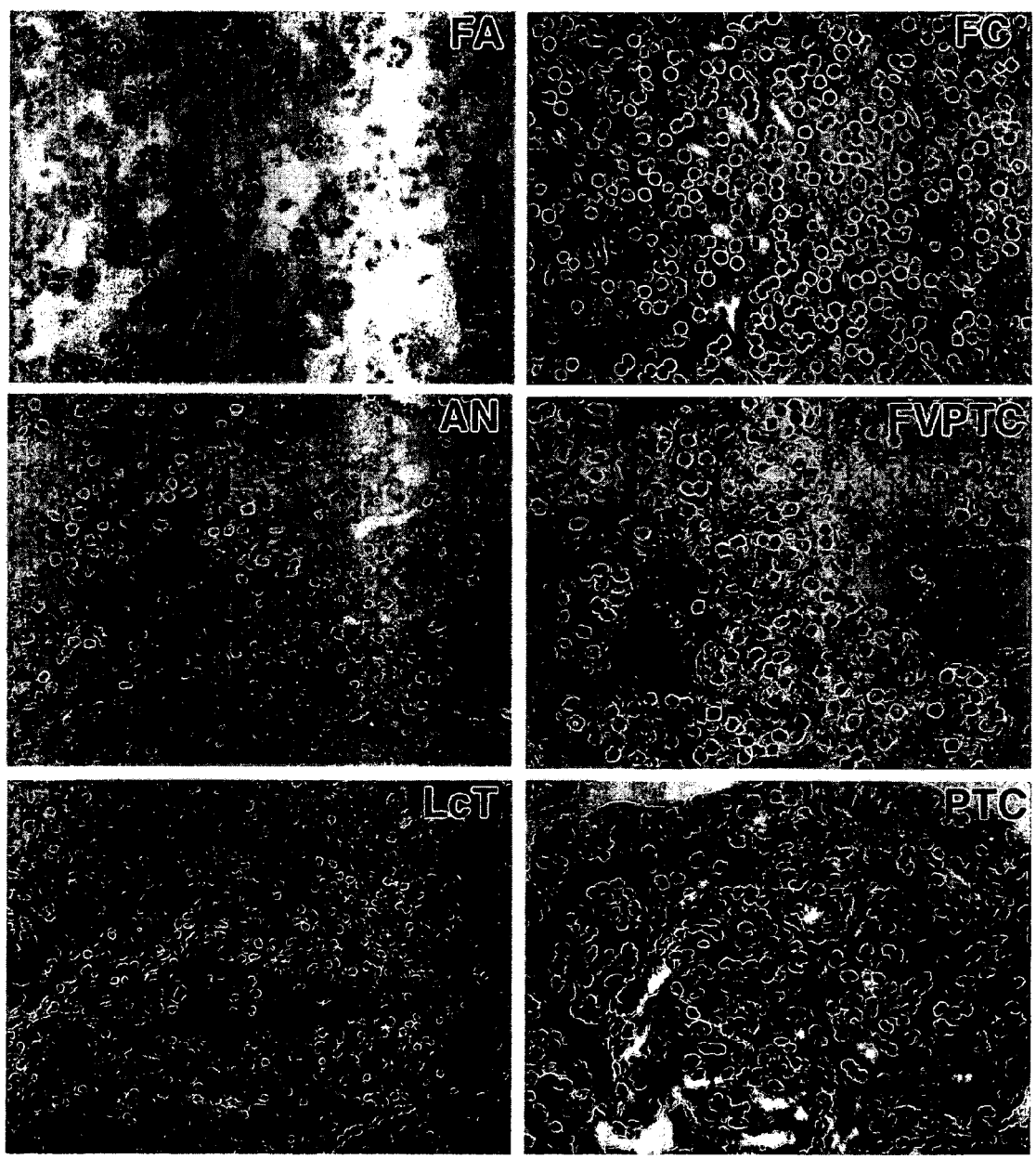
FIG. 11B shows immunohistochemistry of HMGA2 in thyroid tumors. Positive HMGA2 immunosignals were detected in the nuclei of all tumor cells and specifically in 70-90% of malignant tumor cells (FVPTC; follicular variant papillary thyroid carcinomas and PTC; papillary thyroid carcinomas) compared to only 20-30% of benign tumor cells (AN; adenomatoid nodules and FA; follicular adenoma). No detectable expression was seen in the adjacent normal thyroid tissue. Magnifications: ×400

Overexpression of HMGA2 in malignant tumors compared to benign subtypes was further confirmed by Western blot analysis and immunohistochemistry. As assessed by both Western blot analysis and immunohistochemistry, HMGA2 was expressed only in tumors but not in normal thyroid (FIG. 11). Western blot analysis revealed overall less protein expression in benign compared to malignant tumors (FIG. 11A). Based on immunohistochemistry, HMGA2 expression was observed in three patterns [classification]: (i) high expression (moderate to intense nuclear staining within >66% of tumor cells, (ii) moderate expression (moderate to intense nuclear staining within 33-66% of tumor cells, (iii) low expression (low to moderate nuclear expression in <33% of cells) and (iv) negative (no nuclear expression). As shown in Table 9, HMGA2 expression was positive in most of the malignant tumors including papillary thyroid carcinomas (26 of 30; 87%), follicular variant of papillary thyroid carcinomas (13 of 16; 81%) and follicular carcinomas (11 of 14; 79%). In contrast, most of the benign tumors were negative for HMGA2 expression, including follicular adenomas (22 of 25; 88%), adenomatoid nodules (8 of 10; 80%), and normal thyroid (17 of 19; 89%). Low levels of HMGA2 expression were detected in 6 of 11 (55%) lymphocytic thyroiditis nodules. Representative HMGA2 immunostaining of six thyroid tumors is shown in FIG. 4B. Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

BIBLIOGRAPHY

1. Miller, L. D., Long, P. M., Wong, L., Mukherjee, S., McShane, L. M., and Liu, E. T. Optimal gene expression analysis by microarrays. Cancer Cell, 2: 353-361, 2002.
2. Sherman, S. I. Thyroid carcinoma. Lancet, 361: 501-511, 2003.
3. Schulze, A. and Downward, J. Navigating gene expression using microarrays—a technology review. Nat Cell Biol, 3: E190-195, 2001.
4. Raychaudhuri, S., Sutphin, P. D., Chang, J. T., and Altman, R. B. Basic microarray analysis: grouping and feature reduction. Trends Biotechnol, 19: 189-193, 2001.
5. Van't Veer, L. J. and De Jong, D. The microarray way to tailored cancer treatment. Nature Medicine, 8: 13, 2002.
6. Gordon, G. J., Jensen, R. V., Hsiao, L. L., Gullans, S. R., Blumenstock, J. E., Richards, W. G., Jaklitsch, M. T., Sugarbaker, D. J., and Bueno, R. Using gene expression ratios to predict outcome among patients with mesothelioma. J Natl Cancer Inst, 95: 598-605, 2003.
7. West, M., Blanchette, C., Dressman, H., Huang, E., Ishida, S., Spang, R., Zuzan, H., Olson, J. A., Jr., Marks, J. R., and Nevins, J. R. Predicting the clinical status of human breast cancer by using gene expression profiles. Proc Natl Acad Sci USA, 98: 11462-11467, 2001.
8. Mazzaferri, E. L. Management of a solitary thyroid nodule. N. Engl. J. Med., 328: 553-559, 1993.
9. Mazzaferri E L and S M, J. Long term impact of initial surgical and medical therapy on paillary and follicular thyroid cancer. Am J Pathol, 97: 418-428, 1994.
10. Goellner, J. R. Problems and pitfalls in thyroid cytology. Monogr Pathol 75-93, 1997.
11. Hamberger, B., et al Fine-needle aspiration biopsy of thyroid nodules. Impact on thyroid practice and cost of care. Am J Med, 73: 381-334, 1982.
12. Suen, K. C. How does one separate cellular follicular lesions of the thyroid by fine-needle aspiration biopsy? Diagn Cytopathol, 4: 78-81, 1988.
13. Goellner, J. R., et al., Fine needle aspiration cytology of the thyroid, 1980 to 1986. Acta Cytol, 31: 587-590, 1987.
14. Caraway, N. P., Sneige, N., and Samaan, N. A. Diagnostic pitfalls in thyroid fine-needle aspiration: a review of 394 cases. Diagn Cytopathol, 9: 345-350, 1993.
15. Ravetto, C., Colombo, L., and Dottorini, M. E. Usefulness of fine-needle aspiration in the diagnosis of thyroid carcinoma: a retrospective study in 37,895 patients. Cancer, 90: 357-363, 2000.
16. Gharib, H., Goellner, J. R., Zinsmeister, A. R., Grant, C. S., and Van Heerden, J. A. Fine-needle aspiration biopsy of the thyroid. The problem of suspicious cytologic findings. Ann Intern Med, 101: 25-28, 1984.
17. Staudt, L. M. Gene expression profiling of lymphoid malignancies. Arum Rev Med, 53: 303-318, 2002.
18. van de Vijver, M. J., He, Y. D., van't Veer, L. J., Dai, H., Hart, A. A., Voskuil, D. W., Schreiber, G. J., Peterse, J. L., Roberts, C., Marton, M. J., Parrish, M., Atsma, D., Witteveen, A., Glas, A., Delahaye, L., van der Velde, T., Bartelink, H., Rodenhuis, S., Rutgers, E. T., Friend, S. H., and Bernards, R. A gene-expression signature as a predictor of survival in breast cancer. N Engl J Med, 347: 1999-2009, 2002.
19. Sauter, G. and Simon, R. Predictive molecular pathology. N Engl J Med, 347: 1995-1996, 2002.
20. Simon, R., Radmacher, M. D., Dobbin, K., and McShane, L. M. Pitfalls in the use of DNA microarray data for diagnostic and prognostic classification. J Natl Cancer Inst, 95: 14-18, 2003.
21. Barden, C. B., Shister, K. W., Zhu, B., Guiter, G., Greenblatt, D. Y., M. A., Z., and Fahey, T. J. I. Classification of follicular thyroid tumors by molecular signature: results of gene profiling. Clinical Cancer Reserach, 9: 1792-1800, 2003.

22. Golub, T. R., Slonim, D. K., Tamayo, P., Huard, C., Gaasenbeek, M., Mesirov, J. P., Coller, H., Loh, M. L., Downing, J. R., Caligiuri, M. A., Bloomfield, C. D., and Lander, E. S. Molecular classification of cancer: class discovery and class prediction by gene expression monitoring. Science, 286: 531-537, 1999.
23. Eberwine, J. Amplification of mRNA populations using aRNA generated from immobilized oligo(dT)-T7 primed cDNA. Biotechniques, 20: 584-591, 1996.
24. Wang, E., Miller, L. D., Ohnmacht, G. A., Liu, E. T., and Marincola, F. M. High-fidelity mRNA amplification for gene profiling. Nat Biotechnol, 18: 457-459, 2000.25. Simon R, Lam A, Li M, Ngan M, Menenzes S, Zhao Y. Analysis of Gene Expression Data Using BRB-Array Tools. Cancer Informatics 2007, 2: 11-7.
26. Wright G W, Simon R M. A random variance model for detection of differential gene expression in small microarray experiments. Bioinformatics 2003, 19: 2448-55.
27. Radmacher M D, McShane L M, Simon R. A paradigm for class prediction using gene expression profiles. J Comput Biol 2002, 9: 505-11.
28. Dudoit S, Fridlyand F, Speed T P. Comparison of discrimination methods for classification of tumors using DNA microarrays. Journal of the American Statistical Association 2002, 97: 77-87.
29. Ramaswamy S, Tamayo P, Rifkin R, et al. Multiclass cancer diagnosis using tumor gene expression signatures. Proc Natl Acad Sci USA 2001, 98: 15 149-54.
30. Fedor H L, De Marzo A M. Practical methods for tissue microarray construction. Methods Mol Med 2005, 103: 89-101

TABLE 1

Two tail Anova analysis with Bonferroni correction resulted in 47 genes significantly different (p = < 0.05) between the malignant and the benign group. The genes are listed from the most to the least significant. In bold are all the genes that combined together created the best predictor model.

| Gene | Bonferroni p-value | Mean (benign) | S.D.+/− | Mean (malignant) | S.D.+/− |
|---|---|---|---|---|---|
| C21orf4 | <0.0001 | 1.54 | 0.36 | 0.92 | 0.36 |
| KIT | <0.0001 | 1.20 | 0.66 | 0.38 | 0.32 |
| FLJ20477 | <0.0001 | 1.16 | 0.28 | 0.76 | 0.22 |
| MGC4276 | 0.0001 | 1.02 | 0.37 | 0.54 | 0.22 |
| KIAA0062 | 0.001 | 1.03 | 0.51 | 0.46 | 0.25 |
| CDH1 | 0.001 | 1.51 | 0.46 | 0.87 | 0.45 |
| LSM7 | 0.001 | 1.28 | 0.53 | 0.69 | 0.27 |
| ACYP1 | <0.01 | 2.11 | 0.91 | 1.09 | 0.51 |
| SYNGR2 | <0.01 | 0.75 | 0.41 | 1.87 | 1.05 |
| XPA | <0.01 | 2.29 | 0.84 | 1.31 | 0.58 |
| AD-017 | <0.01 | 1.57 | 0.63 | 0.84 | 0.44 |
| DP1 | <0.01 | 1.59 | 0.69 | 0.84 | 0.39 |
| IDI1 | <0.01 | 1.37 | 0.61 | 0.74 | 0.29 |
| RODH | <0.01 | 1.36 | 0.93 | 0.45 | 0.36 |
| ID4 | <0.01 | 1.10 | 0.56 | 0.48 | 0.37 |
| Hs.24183 | <0.01 | 2.05 | 0.70 | 1.30 | 0.42 |
| HTCD37 | <0.01 | 1.22 | 0.37 | 0.78 | 0.30 |
| DUSP5 | <0.01 | 0.97 | 0.60 | 3.93 | 3.15 |
| Hs.87327 | <0.01 | 1.54 | 0.53 | 1.01 | 0.26 |
| CRNKL1 | 0.01 | 1.33 | 0.49 | 0.79 | 0.34 |
| LOC54499 | 0.01 | 1.33 | 0.50 | 0.83 | 0.26 |
| RAP140 | 0.01 | 1.60 | 0.58 | 1.00 | 0.35 |
| MAPK4 | 0.01 | 0.66 | 0.38 | 0.30 | 0.16 |
| Hs.296031 | 0.01 | 1.13 | 0.63 | 2.28 | 1.12 |
| ATP6V1D | 0.01 | 1.71 | 0.75 | 0.94 | 0.46 |
| TXNL | 0.01 | 1.19 | 0.66 | 0.57 | 0.28 |
| FAM13A1 | 0.02 | 1.35 | 0.60 | 0.71 | 0.43 |
| GUK1 | 0.02 | 0.87 | 0.43 | 1.56 | 0.66 |
| Hs.383203 | 0.02 | 1.55 | 0.57 | 0.91 | 0.45 |
| C11orf8 | 0.02 | 0.81 | 0.43 | 0.36 | 0.30 |
| DENR | 0.02 | 1.54 | 0.42 | 1.02 | 0.42 |
| PRDX1 | 0.02 | 1.36 | 0.40 | 0.84 | 0.44 |
| FLJ20534 | 0.02 | 1.94 | 0.92 | 1.08 | 0.40 |
| DIO2 | 0.02 | 1.95 | 1.37 | 0.70 | 0.52 |
| C21orf51 | 0.02 | 1.01 | 0.40 | 0.63 | 0.22 |
| KIAA1128 | 0.03 | 1.76 | 0.87 | 0.90 | 0.52 |
| IMPACT | 0.03 | 1.32 | 0.48 | 0.86 | 0.27 |
| KIAA0089 | 0.03 | 1.43 | 0.63 | 0.76 | 0.49 |
| HSD17B4 | 0.03 | 1.45 | 0.57 | 0.88 | 0.36 |
| MAP4K5 | 0.04 | 1.59 | 0.61 | 0.97 | 0.44 |
| ELF3 | 0.04 | 0.82 | 0.24 | 1.45 | 0.72 |
| ALDH7A1 | 0.04 | 1.61 | 0.52 | 0.96 | 0.58 |
| BET1 | 0.04 | 1.38 | 0.55 | 0.82 | 0.39 |
| GTF2H2 | 0.04 | 1.80 | 0.54 | 1.23 | 0.44 |
| DC6 | 0.04 | 1.19 | 0.34 | 0.81 | 0.29 |
| CDH1 | 0.04 | 1.31 | 0.49 | 0.82 | 0.34 |

TABLE 2

Results of the cross validation analysis using the "leave-one out" method (see materials and methods). The predictor model was able to correctly predict 87% of the diagnoses. The outcome is called a confusion matrix.

|  | # per-Class | # Correct | # Error | % Correct | % Error |
|---|---|---|---|---|---|
| Benign | 31 | 27 | 4 | 87.1 | 12.9 |
| Malignant | 32 | 28 | 4 | 87.5 | 12.5 |
| Total | 63 | 55 | 8 | 87.3 | 12.7 |
| Normalized |  |  |  | 87.3 | 12.7 |

TABLE 3

31 benign tumors
32 malignant tumors — DIAGNOSIS PREDICTOR MODEL
10 gene diagnosis predictor model — cross validation of 87%

| C11orf8 | C21orf4 | CDH1 | FAM13A1 | Hs.24183 | Hs.286031 | IMPACT | KIAA1128 | KIT | SYNGR2 | % benign prob. | % malignant prob. | Predicted Diagnosis | Pathologic Diagnosis |
|---|---|---|---|---|---|---|---|---|---|---|---|---|---|
| 0.4561 | 1.35 | 1.53 | 0.76 | 1.81 | 1.55 | 1.02 | 1.21 | 2.03 | 1.12 | 0.99 | 0.01 | benign | FA |
| 0.4988 | 0.82 | 0.83 | 0.45 | 1.67 | 1.74 | 0.98 | 1.27 | 0.27 | 0.54 | 0.02 | 0.98 | malignant | FVPTC |
| 1.1311 | 0.78 | 2.13 | 1.13 | 1.39 | 0.65 | 1.35 | 1.19 | 1.70 | 1.04 | 0.91 | 0.09 | benign | HN |
| 0.5143 | 1.05 | 0.62 | 0.85 | 0.985 | 1.56 | 1.16 | 0.86 | 0.80 | 0.79 | 0.43 | 0.57 | malignant | PTC |
| 0.3786 | 2.07 | 0.64 | 1.44 | 1.84 | 1.51 | 0.48 | 1.14 | 1.32 | 2.65 | 0.94 | 0.06 | benign | FA |
| 0.7376 | 1.81 | 0.85 | 1.85 | 1.34 | 0.65 | 0.91 | 1.56 | 1.83 | 2.70 | 1.00 | 0.00 | benign | FA |
| 0.1206 | 0.57 | 0.50 | 0.55 | 0.86 | 1.94 | 0.64 | 0.99 | 0.25 | 4.66 | 0.00 | 1.00 | malignant | PTC |
| 0.026 | 1.27 | 0.46 | 0.59 | 1.22 | 1.19 | 0.91 | 0.56 | 0.11 | 4.69 | 0.00 | 1.00 | malignant | PTC |
| 0.1097 | 0.70 | 2.17 | 1.01 | 1.24 | 0.82 | 0.95 | 0.93 | 1.59 | 3.69 | 0.05 | 0.95 | malignant | HN |
| 1.0368 | 1.37 | 1.24 | 1.50 | 1.23 | 1.74 | 0.94 | 1.82 | 2.92 | 1.38 | 1.00 | 0.00 | benign | HN |

6 gene diagnosis predictor model — cross validation of 87%

| C21orf4 | Hs.24183 | Hs.296031 | KIT | LSM7 | SYNGR2 | % benign prob. | % malignant prob. | Predicted Diagnosis | Pathologic Diagnosis |
|---|---|---|---|---|---|---|---|---|---|
| 1.3518 | 1.81 | 1.55 | 2.03 | 2.40 | 1.12 | 1.00 | 0.00 | benign | FA |
| 0.819 | 1.67 | 1.74 | 0.27 | 0.56 | 0.54 | 0.15 | 0.85 | malignant | FVPTC |
| 0.7822 | 1.39 | 0.65 | 1.70 | 1.33 | 1.04 | 0.94 | 0.06 | benign | HN |
| 1.0457 | 0.95 | 1.56 | 0.80 | 0.85 | 0.79 | 0.33 | 0.67 | malignant | PTC |
| 2.0723 | 1.84 | 1.51 | 1.32 | 1.05 | 2.65 | 0.86 | 0.14 | benign | FA |
| 1.8053 | 1.34 | 0.65 | 1.63 | 1.47 | 2.70 | 0.96 | 0.04 | benign | FA |
| 0.5666 | 0.86 | 1.94 | 0.25 | 0.66 | 4.88 | 0.00 | 1.00 | malignant | PTC |
| 1.2698 | 1.22 | 1.19 | 0.11 | 0.43 | 4.69 | 0.00 | 1.00 | malignant | PTC |
| 0.698 | 1.24 | 0.82 | 1.59 | 1.60 | 3.69 | 0.10 | 0.90 | malignant | HN |
| 1.3677 | 1.23 | 1.74 | 2.92 | 1.04 | 1.36 | 0.99 | 0.01 | benign | HN |

In this table the two predictor model of 10 and 6 genes is shown with their gene expression values, the predicted diagnosis, the percentage probability of the diagnosis being correct and the pathologic diagnosis.
FA = follicular adenoma, HN = hyperplastic nodules, FVPTC = follicular variant papillary thyroid carcinoma and PTC = papillary thyroid carcinoma.
The square indicates the unknown sample for which there was discordance between the predicted and the pathologic diagnosis.
The percentage diagnosis probability for both 6 and 10 gene combinations strongly suggested that this was a malignant sample. The sample was re-reviewed by the pathologist and the pathologic diagnosis was in-fact changed to a neoplasm with uncertain malignant potential.

TABLE 4

Primers and probes for select DET genes.
Thyroid Primer/Probes

| Oligo Name | | Length | Sequence(5'-3') | Tm |
|---|---|---|---|---|
| Hs.24183-Forward | SEQ ID NO: 1 | 22 | ggctgactggcaaaaagtcttg | |
| Hs.24183-Reverse | SEQ ID NO: 2 | 26 | ttggttcccttaagttctcagagttt | |
| Hs.24183-Probe | SEQ ID NO: 3 | 23 | (6Fam)TggCCCTgTCACTCCCATgATgC(Tamra) | |
| thyroglobulin-forward | SEQ ID NO: 4 | 18 | aagggctcgcatgcaaag | 59 |

TABLE 4-continued

Primers and probes for select DET genes.
Thyroid Primer/Probes

| | | | | |
|---|---|---|---|---|
| thyroglobulin-reverse | SEQ ID NO: 5 | 25 | cacagtagcactctgagttgaagca | 60 |
| thyroglobulin-probe | SEQ ID NO 6 | 33 | (6Fam)TTTgTCCCTgCTTgTACTAgTgAgg(Tamra) | 69 |
| c21orf4-forward | SEQ ID NO: 7 | 22 | gcaatcctcttacctccgcttt | |
| c21orf4-reverse | SEQ ID NO: 8 | 25 | ggaatcggagacagaagagagctt | |
| c21orf4-Probe | SEQ ID NO: 9 | 28 | (6Fam)CTgggACCACAgATgTATCCTCCACTCC(Tamra) | |
| fam13a1-forward | SEQ ID NO: 10 | 22 | atggcagtgcagtcatcatctt | |
| fam13a1-reverse | SEQ ID NO: 11 | 25 | gcattcatacagctgcttaccatct | |
| fam13a1-Probe | SEQ ID NO: 12 | 23 | (6Fam)TTTggTCCCTgCCTAggACCggg(Tamra) | |
| c11orf8-forward | SEQ ID NO: 13 | 16 | ccggcccaagctccat | |
| c11orf8-reverse | SEQ ID NO: 14 | 21 | ttgtgtaaccgtcggtcatga | |
| c11orf8-Probe | SEQ ID NO: 15 | 29 | (6Fam)TgTTTggTggAATCCATgAAggTTATggC(Tamra) | |
| kiaa1128-forward | SEQ ID NO: 16 | 20 | gagagcgtgatccccctaca | |
| kiaa1128-reverse | SEQ ID NO: 17 | 23 | accaagagtgcacctcagtgtct | |
| kiaa1128-probe | SEQ ID NO: 18 | 33 | (6Fam)TCACTTCCAAATgTTCCTgTAgCATAAATggTg(Tamra) | |
| Hs.296031-forward | SEQ ID NO: 19 | 24 | tgccaaggagctttgtttatagaa | |
| Hs.296031-reverse | SEQ ID NO: 20 | 20 | atgacggcatgtaccaacca | |
| Hs.296031-probe | SEQ ID NO: 21 | 29 | (6Fam)TTggTCCCCTCAgTTCTATgCTgTTgTgT(Tamra) | |
| kit-forward | SEQ ID NO: 22 | 26 | gcacctgctgaaatgtatgacataat | |
| kit-reverse | SEQ ID NO: 23 | 28 | tttgctaagttggagtaaatatgattgg | |
| kit-probe | SEQ ID NO: 24 | 36 | (6Fam)ATTgTTCAgCTAATTgAgAAgCAgATTTCAgAgAgC(Tamra) | |
| impact-forward | SEQ ID NO: 25 | 26 | tgaagaatgtcatggtggtagtatca | |
| impact-reverse | SEQ ID NO: 26 | 26 | atgactcctcaggtgaatttgtgtag | |
| impact-probe | SEQ ID NO: 27 | 29 | (6Fam)CTggTATggAgggATTCTgCTAggACCAg(Tamra) | |
| cdh1-forward | SEQ ID NO: 28 | 21 | tgagtgtcccccggtatcttc | |
| cdh1-reverse | SEQ ID NO: 29 | 21 | cagccgctttcagattttcat | |
| cdh1-probe | SEQ ID NO: 30 | 27 | (6Fam)CCTgCCAATCCCgAT9AAATTggAAAT(Tamra) | |
| syngr2-forward | SEQ ID NO: 31 | 19 | gctggtgctcatggcactt | |
| syngr2-reverse | SEQ ID NO: 32 | 19 | ccctccccaggcttcctaa | |
| syngr2-probe | SEQ ID NO: 33 | 24 | (6Fam)aagggctttgcctgacaacaccca(Tamra) | |
| lsm7-forward | SEQ ID NO: 34 | 21 | gacgatccaggtaaagttcca | |
| lsm7-reverse | SEQ ID NO: 35 | 20 | aggttgaggagtgggtcgaa | |
| lsm7-probe | SEQ ID NO: 36 | 22 | (6Fam)aggccgcgaagccagtggaatc(Tamra) | |
| G3PDH-Forward | SEQ ID NO: 37 | 22 | TCACCAGGGCTGCTTTTAACTC | |
| G3PDH-Reverse | SEQ ID NO: 38 | 26 | GGAATCATATTGGAACATGTAAACCA | |
| G3PDH-probe | SEQ ID NO: 39 | 27 | FAM-TTGCCATCAATGACCCCTTCATTGACC-TAMRA | |
| normal thyroid sample | | | Clontec Lot 63100284 | |

TABLE 4-continued

Primers and probes for select DET genes.
Thyroid Primer/Probes

| Oligo Name | Residues | InCytePD Clone | ret = retired Unigene |
|---|---|---|---|
| Hs.24183-Forward | 2436-2457 | 2123020 | Hs24183 |
| Hs.24183-Reverse | 2530-2505 | 2123020 | Hs24183 |
| Hs.24183-Probe | 2462-2484 | 2123020 | Hs24183 |
| thyroglobulin-forward | 2036-2053 | | |
| thyroglobulin-reverse | 2157-2133 | | |
| thyroglobulin-probe | 2088-2120 | | |
| c21orf4-forward | 2622-2643 | 1710736 | (Hs284142-ret)Hs433668 |
| c21orf4-reverse | 2743-2712 | 1710736 | (Hs284142-ret)Hs433668 |
| c21orf4-Probe | 2652-2679 | 1710736 | (Hs284142-ret)Hs433668 |
| fam13a1-forward | 2931-2952 | 1458366 | (Hs177644-removed)Hs.442818 |
| fam13a1-reverse | 3058-3034 | 1458366 | (Hs177644-removed)Hs.442818 |
| fam13a1-Probe | 2992-3014 | 1458366 | (Hs177644-removed)Hs.442818 |
| c11orf8-forward | 849-864 | 4117578 | (Hs46638-ret) Hs.432000 |
| c11orf8-reverse | 916-896 | 4117578 | (Hs46638-ret) Hs.432000 |
| c11orf8-Probe | 866-894 | 4117578 | (Hs46638-ret) Hs.432000 |
| kiaa1128-forward | 5980-5999 | 1428225 | Hs81897 |
| kiaa1128-reverse | 6063-6041 | 1428225 | Hs81897 |
| kiaa1128-probe | 6004-6036 | 1428225 | Hs81897 |
| Hs.296031-forward | 4271-4294 | 29557644 | Hs296031 |
| Hs.296031-reverse | 4353-4334 | 29557644 | Hs296031 |
| Hs.296031-probe | 4301-4329 | 29557644 | Hs296031 |
| kit-forward | 2704-2729 | 2358031/1672225 | Hs81665 |
| kit-reverse | 2843-2816 | 2358031/1672225 | Hs81665 |
| kit-probe | 2779-2814 | 2358031/1672225 | Hs81665 |
| impact-forward | 809-834 | 973364 | Hs284245 |
| impact-reverse | 943-918 | 973364 | H284245 |
| impact-probe | 837-865 | 973364 | Hs284245 |
| cdh1-forward | 2499-2519 | 2793857/1858050/1208946 | HS194657 |
| cdh1-reverse | 2579-2559 | 2793857/1858050/1208946 | HS194657 |
| cdh1-probe | 2525-2551 | 2793857/1858050/1208946 | HS194657 |
| syngr2-forward | 1255-1273 | 983008 | (Hs5097-ret) Hs.433753 |
| syngr2-reverse | 1374-1356 | 983008 | (Hs5097-ret) Hs.433753 |
| syngr2-probe | 1303-1326 | 983008 | (Hs5097-ret) Hs.433753 |
| lsm7-forward | 72-92 | 1911913/2060560 | (Hs70830-ret)Hs.512610 |
| lsm7-reverse | 146-127 | 1911913/2060560 | (Hs70830-ret)Hs.512610 |
| lsm7-probe | 96-117 | 1911913/2060560 | (Hs70830-ret)Hs.512610 |
| G3PDH-Forward | 128-149 | | |

TABLE 4-continued

Primers and probes for select DET genes.
Thyroid Primer/Probes

| | | |
|---|---|---|
| G3PDH-Reverse | 228-203 | |
| G3PDH-probe | 167-193 | |
| normal thyroid sample | pooled 65 autopsy patients | 650-424-8222 |

| Oligo Name | CM Paper GenBank/RefSeq | TAQman GenBank/RefSeq |
|---|---|---|
| Hs.24183-Forward | NP060265 | AL832414.1 |
| Hs.24183-Reverse | NP060265 | AL832414.1 |
| Hs.24183-Probe | NP060265 | AL832414.1 |
| thyroglobulin-forward | NM_003235 | NM_003235 |
| thyroglobulin-reverse | NM_003235 | NM_003235 |
| thyroglobulin-probe | NM_003235 | NM_003235 |
| c21orf4-forward | AP001717 | NM_006134.4 |
| c21orf4-reverse | AP001717 | NM_006134.4 |
| c21orf4-Probe | AP001717 | NM_006134.4 |
| fam13a1-forward | (NM014883)fromAB020721 | (NM014883)fromAB020721 |
| fam13a1-reverse | (NM014883)fromAB020721 | (NM014883)fromAB020721 |
| fam13a1-Probe | (NM014883)fromAB020721 | (NM014883)fromAB020721 |
| c11orf8-forward | NM001584 | NM001584 |
| c11orf8-reverse | NM001584 | NM001584 |
| c11orf8-Probe | NM001584 | NM001584 |
| kiaa1128-forward | AB032914.1-this is actually AB032954.1 | AB032954.1 |
| kiaa1128-reverse | AB032914.1-this is actually AB032954.1 | AB032954.1 |
| kiaa1128-probe | AB032914.1-this is actually AB032954.1 | AB032954.1 |
| Hs.296031-forward | BC38512.1 | BC38512.1 |
| Hs.296031-reverse | BC38512.1 | BC38512.1 |
| Hs.296031-probe | BC38512.1 | BC38512.1 |
| kit-forward | XO6182.1 | XO6182.1 |
| kit-reverse | XO6182.1 | XO6182.1 |
| kit-probe | XO6182.1 | XO6182.1 |
| impact-forward | NM018439 | NM018439 |
| impact-reverse | NM018439 | NM018439 |
| impact-probe | NM018439 | NM018439 |
| cdh1-forward | NM004360 | NM004360 |
| cdh1-reverse | NM004360 | NM004360 |
| cdh1-probe | NM004360 | NM004360 |
| syngr2-forward | NM004710.2 | NM004710.2 |
| syngr2-reverse | NM004710.2 | NM004710.2 |
| syngr2-probe | NM004710.2 | NM004710.2 |
| lsm7-forward | NM0161991.1 | NM0161991.1 |

TABLE 4-continued

Primers and probes for select DET genes.
Thyroid Primer/Probes

| | | |
|---|---|---|
| lsm7-reverse | NM0161991.1 | NM0161991.1 |
| lsm7-probe | NM0161991.1 | NM0161991.1 |
| G3PDH-Forward | | NM_002046 |
| G3PDH-Reverse | | NM_002046 |
| G3PDH-probe | | NM_002046 | normal thyroid sample

| Oligo Name | Chromosome | Primer/Probe Details |
|---|---|---|
| Hs.24183-Forward | ?1 | used later part of sequence |
| Hs.24183-Reverse | | |
| Hs.24183-Probe | | |
| thyroglobulin-forward | | used within Exon 9 |
| thyroglobulin-reverse | | |
| thyroglobulin-probe | | |
| c21orf4-forward | 21q22.11 | spans Exon 7-8 |
| c21orf4-reverse | | |
| c21orf4-Probe | | |
| fam13a1-forward | 4q22.1 | used later part of seq-exon 19 |
| fam13a1-reverse | | |
| fam13a1-Probe | | |
| c11orf8-forward | 11p13 | spans Exon 5-6 |
| c11orf8-reverse | | |
| c11orf8-Probe | | |
| kiaa1128-forward | 10q23.2 | used later part of sequence |
| kiaa1128-reverse | | |
| kiaa1128-probe | | |
| Hs.296031-forward | X | used later part of sequence |
| Hs.296031-reverse | | |
| Hs.296031-probe | | |
| kit-forward | 4q11-q12 | spans Exon 19-20 |
| kit-reverse | | |
| kit-probe | | |
| impact-forward | 18q11.2-q12.1 | spans Exon 10-11 |
| impact-reverse | | |
| impact-probe | | |
| cdh1-forward | 16q22.1 | spans Exon 15-16 |
| cdh1-reverse | | |
| cdh1-probe | | |
| syngr2-forward | 17q25.3 | used later sequence |
| syngr2-reverse | | |

TABLE 4-continued

Primers and probes for select DET genes.
Thyroid Primer/Probes

| | | | |
|---|---|---|---|
| syngr2-probe | | | |
| lsm7-forward | | 19p13.3 | used later sequence |
| lsm7-reverse | | | |
| lsm7-probe | | | |
| G3PDH-Forward | | | from Takahashi paper |
| G3PDH-Reverse | | | |
| G3PDH-probe | | | |
| normal thyroid sample | | | |

TABLE 5

Schematic of microarray analysis of benign and malignant thyroid tumors.

| Benign subtypes | | | | Malignant subtypes | | | |
|---|---|---|---|---|---|---|---|
| FA | AN | LcT | HA | HC | FC | PTC | FVPTC |
| FA 1 | AN 1 | LcT 1* | HA 1* | HC 1* | FC 1 | PTC 1* | FVPTC 1 |
| FA 2 | AN 2 | LcT 2 | HA 2 | HC 2* | FC 2 | PTC 2 | FVPTC 2 |
| FA 3 | AN 3 | LcT 3 | HA 3 | HC 3* | FC 3 | PTC 3 | FVPTC 3 |
| FA 4 | AN 4 | LcT 4 | HA 4 | HC 4* | FC 4 | PTC 4 | FVPTC 4 |
| FA 5 | AN 5 | LcT 5 | HA 5 | HC 5* | FC 5 | PTC 5 | FVPTC 5 |
| FA 6 | AN 6 | LcT 6 | HA 6 | HC 1* | FC 6 | PTC 6 | FVPTC 6 |
| FA 7 | AN 7 | LcT 7 | HA 7 | HC 2* | FC 7 | PTC 7 | FVPTC 7 |
| FA 8* | AN 8* | LcT 8* | HA 8* | HC 3* | FC 8* | PTC 8* | FVPTC 8 |
| FA 9* | AN 9* | LcT 9* | HA 9* | HC 4* | FC 9* | PTC 9* | FVPTC 9* |
| FA 10 | AN 10* | LcT 10* | HA 10 | HC 5* | FC 10* | PTC 10 | FVPTC 10* |
| FA 11* | AN 11 | LcT 11* | HA 11 | HC 1* | FC 11 | PTC 11 | FVPTC 11* |
| FA 8* | AN 8* | LcT 8* | HA 8* | HC 1* | FC 12 | PTC 8* | FVPTC 11* |
| FA 9* | AN 9* | LcT 9* | HA 9* | HC 1* | FC 9* | PTC 9* | FVPTC 9* |
| FA 12 | AN 10* | LcT 10* | HA 1* | HC 1* | FC 10* | PTC 1* | FVPTC 10* |
| FA 11* | AN 12 | LcT 11* | HA 12 | HC 1* | FC 13 | PTC 12 | FVPTC 12 |
| FA 13 | AN 13 | LcT 1* | HA 13 | HC 1* | FC 8* | PTC 13 | FVPTC 13 |

Microarray analysis was performed using 50 benign tumors [13 follicular adenomas (FA), 13 adenomatoid nodules (AN), 11 lymphocytic thyroiditis (LcT) and 13 Hürthle cell adenomas (HA)] and 44 malignant tumors [5 Hürthle cell carcinomas (HC), 13 follicular carcinomas (FC), 13 papillary thyroid carcinomas (PTC) and 13 follicular variant of papillary thyroid carcinomas (FVPTC)]. To minimize experimental variation all 8 tumor subtypes in each row were arrayed simultaneously
*Some tumor samples were used more than once and were considered as technical replicates during data analysis.

TABLE 6

Genes overexpressed in malignant thyroid tumors identified by microarray analysis.

| Description | UG cluster | Gene symbol* | Parametric P value | Ratio† M/B |
|---|---|---|---|---|
| High mobility group AT-hook 2, transcript variant 1‡ | Hs.505924 | HMGA2 | 0.0001597 | 2.6 |
| Kallikrein 7 (chymotryptic, stratum corneum), transcript variant 1 | Hs.151254 | KLK7 | 0.0002012 | 2.5 |
| Mannose receptor, C type 2 | Hs.7835 | MRC2 | <1e−07 | 2.5 |
| Leucine-rich repeat kinase 2‡ | Hs.187636 | LRRK2 | 3.46e−05 | 2.2 |
| Pleiomorphic adenoma gene 1‡ | Hs.14968 | PLAG1 | 0.0002047 | 2.2 |
| Cytochrome P450, family 1, subfamily B, polypeptide 1 | Hs.154654 | CYP1B1 | 0.0003485 | 2.0 |
| Dipeptidyl-peptidase 4 (CD26,‡ adenosine deaminase complexing protein 2) | Hs.368912 | DPP4 | 0.0006842 | 1.9 |
| Fibronectin type III domain containing 4 | Hs.27836 | FNDC4 | 3.30e−05 | 1.9 |
| Pleckstrin homology-like domain, family A, member 2 | Hs.154036 | PHLDA2 | 6.00e−07 | 1.9 |
| Cyclin A1 | Hs.417050 | CCNA1 | 8.08e−05 | 1.8 |
| Cadherin 3, type 1, P-cadherin (placental)‡ | Hs.554598 | CDH3 | 1.10e−06 | 1.8 |
| Carcinoembryonic antigen-related cell adhesion molecule 6 (nonspecific cross-reacting antigen) | Hs.466814 | CEACAM6 | 0.0001172 | 1.8 |
| Quiescin Q6 | Hs.518374 | QSCN6 | <1e−07 | 1.7 |
| Collagen, type VII, α 1 (epidermolysis bullosa, dystrophic, dominant and recessive) | Hs.476218 | COL7A1 | 3.24e−05 | 1.7 |

TABLE 6-continued

Genes overexpressed in malignant thyroid tumors identified by microarray analysis.

| Description | UG cluster | Gene symbol* | Parametric P value | Ratio† M/B |
|---|---|---|---|---|
| Hypothetical protein MGC9712 | Hs.592174 | MGC9712 | 6.39e−05 | 1.7 |
| Interleukin 1 receptor accessory protein, transcript variant 1 | Hs.478673 | IL1RAP | 9.68e−05 | 1.7 |
| Laminin, β3, transcript variant 1 | Hs.497636 | LAMB3 | 0.0001874 | 1.7 |
| Protease, serine, 3 (mesotrypsin)‡ | Hs.128013 | PRSS3 | 6.50e−06 | 1.7 |
| Low density lipoprotein receptor-related protein 4 | Hs.4930 | LRP4 | 0.0001359 | 1.6 |
| Sparc/osteonectin, cwcv and kazal-like‡ domains proteoglycan (testican) 1 | Hs.124611 | SPOCK1 | 0.0001704 | 1.6 |
| Phosphodiesterase 5 A, cGMP-specific, transcript variant 3‡ | Hs.370661 | PDE5A | 2.07e−05 | 1.6 |
| Hypothetical protein FLJ37078 | Hs.511025 | FLJ37078 | 0.000106 | 1.6 |
| Fibrillin 3 | Hs.370362 | FBN3 | 0.0007772 | 1.6 |
| DIRAS family, GTP-binding RAS-like 3 | Hs.194695 | DIRAS3 | 0.0001982 | 1.6 |
| Protease, serine, 1 (trypsin 1) | Hs.511522 | PRSS1 | 0.0002246 | 1.6 |
| Calcium/calmodulin-dependent protein kinase II inhibitor 1 | Hs.197922 | CAMK2N1 | 0.0005162 | 1.6 |
| SNAP25-interacting protein | Hs.448872 | SNIP | 0.0001026 | 1.6 |
| Potassium inwardly-rectifying channel, subfamily J, member 2 | Hs.1547 | KCNJ2 | 0.0001192 | 1.6 |
| Stratifin | Hs.523718 | SFN | 3.23e−05 | 1.5 |
| UDP-N-acetyl-α-D-galactosamine:polypeptide N-acetylgalactosaminyltransferase 7 | Hs.127407 | GALNT7 | 0.0002068 | 1.5 |
| Transforming growth factor, α | Hs.170009 | TGFA | 0.0003326 | 1.5 |
| BAI1-associated protein 3 | Hs.458427 | BAIAP3 | 4.13e−05 | 1.5 |
| Potassium channel, subfamily K, member 15 | Hs.528664 | KCNK15 | 0.0001188 | 1.5 |

*HUGO abbreviations used in Locus Link.
†The ratio between Geo mean expression values of malignant to benign thyroid tumors (P ≤ 0.001).
‡Genes validated by real-time RT-PCR.

TABLE 7

Genes underexpressed in malignant thyroid tumors identified by microarray analysis.

| Description | UG cluster | Gene symbol* | Parametric P value | Ratio† M/B |
|---|---|---|---|---|
| Recombination activating gene 2‡ | Hs.159376 | RAG2 | 1.32e−05 | 0.41 |
| Citrate lyase β-like, transcript variant 1 | Hs.130690 | CLYBL | 1.43e−05 | 0.44 |
| Nebulin | Hs.588655 | NEB | 0.0002811 | 0.53 |
| Tumor necrosis factor receptor superfamily, member 11b (osteoprotegerin) | Hs.81791 | TNFRSF11B | 4.50e−06 | 0.54 |
| Guanine nucleotide binding protein (G protein), α inhibiting activity polypeptide 1 | Hs.134587 | GNAI1 | 4.33e−05 | 0.55 |
| Angiotensin II receptor, type 1, transcript variant 5‡ | Hs.477887 | AGTR1 | 4.28e−05 | 0.56 |
| Hepatic leukemia factor | Hs.196952 | HLF | 1.40e−06 | 0.57 |
| Solute carrier family 26, member 4 | Hs.571246 | SLC26A4 | 1.00e−07 | 0.58 |
| Metallothionein 1A (functional) | Hs.643532 | MT1A | 0.0004668 | 0.59 |
| Fatty acid binding protein 4, adipocyte | Hs.391561 | FABP4 | 4.38e−05 | 0.60 |
| Low density lipoprotein-related protein 1B (deleted in tumors) | Hs.470117 | LRP1B | 0.0003571 | 0.60 |
| Solute carrier family 4, sodium bicarbonate cotransporter, member 4 | Hs.5462 | SLC4A4 | 0.0002522 | 0.61 |
| PREDICTED: similar to programmed cell death 6 interacting protein, transcript variant 2 | Hs.597835 | LOC646278 | 0.0001965 | 0.61 |
| Mannosidase, α, class 1C, member 1 | Hs.197043 | MAN1C1 | 9.46e−05 | 0.61 |
| Kv channel interacting protein 3, calsenilin, transcript variant 2 | Hs.437376 | KCNIP3 | 1.12e−05 | 0.62 |
| DnaJ (Hsp40) homologue, subfamily B, member 9 | Hs.6790 | DNAJB9 | 5.10e−06 | 0.62 |
| Ubiquitin protein ligase E3 component n-recognin 1 | Hs.591121 | UBR1 | 0.000166 | 0.62 |
| Hydroxysteroid (17-β) dehydrogenase 6 | Hs.524513 | HSD17B6 | 0.0002557 | 0.62 |
| Solute carrier family 33 (acetyl-CoA transporter), member 1 | Hs.478031 | SLC33A1 | 2.49e−05 | 0.63 |
| Cadherin 16, KSP-cadherin | Hs.513660 | CDH16 | 0.0007068 | 0.63 |
| TBC1 (tre-2/USP6, BUB2, cdc16) domain family, member 1 | Hs.176503 | TBC1D1 | 8.00e−07 | 0.63 |
| Solute carrier family 26, member 7, transcript variant 1 | Hs.354013 | SLC26A7 | 2.18e−05 | 0.63 |
| Chromosome 11 open reading frame 74 | Hs.406726 | C11orf74 | 1.40e−06 | 0.63 |
| Phospholipase A2 receptor 1, 180 kDa | Hs.410477 | PLA2R1 | 0.0001771 | 0.64 |
| Pituitary tumor-transforming 3 on chromosome 8. | | PTTG3 | 5.00e−07 | 0.64 |
| EGF-containing fibulin-like extracellular matrix protein 1, transcript variant 3 | Hs.76224 | EFEMP1 | 1.17e−05 | 0.64 |

TABLE 7-continued

Genes underexpressed in malignant thyroid tumors identified by microarray analysis.

| Description | UG cluster | Gene symbol* | Parametric P value | Ratio[†] M/B |
|---|---|---|---|---|
| Zinc finger, matrin type 4 | Hs.591850 | ZMAT4 | 7.03e−05 | 0.64 |
| STEAP family member 3 | Hs.642719 | STEAP3 | 0.0002097 | 0.64 |
| Deiodinase, iodothyronine, type I, transcript variant 4 | Hs.251415 | DIO1 | 0.0007362 | 0.64 |
| v-Kit Hardy-Zuckerman 4 feline sarcoma viral oncogene homologue | Hs.479754 | KIT | 8.16e−05 | 0.65 |
| Thyroid peroxidase, transcript variant 5[‡] | Hs.467554 | TPO | 9.70e−06 | 0.65 |
| Pituitary tumor-transforming 1 | Hs.350966 | PTTG1 | 6.00e−07 | 0.65 |
| Leucine-rich repeat LGI family, member 3 | Hs.33470 | LGI3 | 4.00e−05 | 0.65 |
| Transmembrane protein 38B | Hs.411925 | TMEM38B | 0.0001833 | 0.65 |
| SLIT and NTRK-like family, member 4 | Hs.272284 | SLITRK4 | 7.75e−05 | 0.65 |
| Von Hippel-Lindau binding protein 1 | Hs.436803 | VBP1 | 7.04e−05 | 0.65 |
| Collagen, type IX, α 3 | Hs.126248 | COL9A3 | 0.0009987 | 0.65 |
| Insulin receptor substrate 1 | Hs.471508 | IRS1 | 6.00e−06 | 0.66 |
| START domain containing 13, transcript variant γ | Hs.507704 | STARD13 | 0.0001052 | 0.66 |
| PREDICTED: similar to glycine cleavage system H protein, mitochondrial precursor, variant 1 | | LOC654085 | 9.60e−06 | 0.66 |
| Ribosomal protein S3A | Hs.356572 | RPS3A | 0.0004627 | 0.66 |
| SPARC-like 1 (mast9, hevin) | Hs.62886 | SPARCL1 | 7.61e−05 | 0.66 |

*HUGO abbreviations used in locus Link.
[†]The ratio between Geo mean expression values of malignant to benign thyroid tumors (P ≤ 0.001).
[‡]Genes validated by real-time RT-PCR.

TABLE 8

Summary of class performance indicating sensitivity, specificity, and positive predictive values obtained from seven classification methods.

| Methods | Mean percent of correct classification | Benign Tumors | | | Malignant Tumors | | |
|---|---|---|---|---|---|---|---|
| | | Sensitivity | Specificity | PPV[†] | Sensitivity | Specificity | PPV[‡] |
| Compound Covariate Predictor | 74 | 0.8 | 0.682 | 0.741 | 0.682 | 0.8 | 0.75 |
| Diagonal Liner Descriminant Analysis | 76 | 0.8 | 0.705 | 0.755 | 0.705 | 0.8 | 0.756 |
| 1-Nearest Neighbor* | 78 | 0.82 | 0.727 | 0.774 | 0.727 | 0.82 | 0.78 |
| 3-Nearest Neighbor | 71 | 0.72 | 0.705 | 0.735 | 0.705 | 0.72 | 0.689 |
| Nearest Centroid | 73 | 0.78 | 0.682 | 0.736 | 0.682 | 0.78 | 0.732 |
| Support Vector Machines | 77 | 0.76 | 0.773 | 0.792 | 0.773 | 0.76 | 0.739 |
| Bayesian Compound Covariate predictor | 74 | 0.8 | 0.682 | 0.741 | 0.682 | 0.8 | 0.75 |

Abbreviation: PPV, positive predictor value
*Highest percent of correct classification was determined by using 1-Nearest Neighbor method
[†]the probability that a sample predicted as 'Benign' actually belongs to 'Benign subtype'
[‡]the probability that a sample predicted as 'Malignant' actually belongs to 'Malignant subtype'

TABLE 9

Immunohistochemical evaluation of HMGA2 in thyroid tumors.

| | Total | HMGA2 positive | | | HMGA2 negative* |
|---|---|---|---|---|---|
| | | High[†] | Moderate[‡] | Low[§] | |
| Tissue array samples | 87 | | | | |
| Normal thyroid | 19 | — | — | 2 | 17 |
| Follicular adenoma | 14 | — | — | 1 | 13 |
| Lymphocytic thyroiditis nodule | 11 | — | — | 6 | 5 |
| Follicular carcinoma | 14 | 3 | 2 | 5 | 4 |
| Follicular variant of papillary thyroid carcinoma | 9 | 4 | 2 | 1 | 2 |
| Papillary thyroid carcinoma | 20 | 7 | 7 | 4 | 2 |
| Nonarrayed samples | 38 | | | | |
| Follicular adenoma | 11 | — | — | 2 | 9 |
| Adenomatoid nodule | 10 | — | 1 | 1 | 8 |
| Follicular variant of papillary thyroid carcinoma | 7 | 4 | 1 | 1 | 1 |
| Papillary thyroid carcinoma | 10 | 5 | 2 | 1 | 2 |

*No significant expression.
[†]Expressed in >66% of cell population.
[‡]Expressed in 33% to 66% of cell population.
[§]Expressed in <33% of cell population.

What is claimed is:

1. A method of treating a patient with a thyroid tumor comprising:
   a) providing a tumor sample from a thyroid tumor of a patient;
   b) combining nucleic acids from cells of the tumor sample with primer pairs specific for the HMGA2, MRC2 and SFN genes and performing a quantitative reverse transcriptase polymerase chain reaction (RT-PCR) assay to detect the expression levels of the HMGA2, MRC2 and SFN genes in cells of the tumor sample;
   c) comparing the expression levels of the HMGA2, MRC2 and SFN genes detected in b) to reference levels characteristic of the expression levels of the HMGA2, MRC2 and SFN genes in benign and malignant thyroid tumors;
   d) classifying the thyroid tumor of the patient as benign or malignant based on the comparison in c); and
   e) treating the patient by performing a surgical thyroid lobectomy on the patient if the thyroid tumor is classified as benign in step d) or performing a surgical thyroidectomy on the patient if the thyroid tumor is determined to be malignant in step d).

2. The method of claim 1, wherein the patient is further treated with an anti-cancer treatment selected from the group consisting of surgery, chemotherapy, radiotherapy, immunotherapy or any combination thereof.

3. The method of claim 1, wherein the thyroid tumor is selected from the group consisting of: papillary thyroid carcinoma, follicular variant of papillary thyroid carcinoma, follicular carcinoma, Hurthle cell tumor, anaplastic thyroid cancer, medullary thyroid cancer, thyroid lymphoma, poorly differentiated thyroid cancer and thyroid angiosarcoma.

4. The method of claim 3, wherein the thyroid tumor is selected from the group consisting of: a follicular adenoma, adenomatoid nodule, Hurthle cell adenoma, lymphocytic thyroiditis nodule, hyperplastic nodule, papillary adenoma, thyroiditis nodule and multinodular goiter.

5. The method of claim 1, wherein the thyroid tumor of the patient is also analyzed by fine needle aspiration (FNA) biopsy.

6. The method of claim 5, wherein FNA biopsy identifies an indeterminate or suspicious lesion.

* * * * *